(12) United States Patent
Kunz et al.

(10) Patent No.: US 8,138,211 B2
(45) Date of Patent: Mar. 20, 2012

(54) ISOTHIAZOLYLOXYPHENYLAMIDINES AND THEIR USE AS FUNGICIDES

(75) Inventors: Klaus Kunz, Düsseldorf (DE); Kerstin Ilg, Köln (DE); Jörg Nico Greul, Leichlingen (DE); Pierre Cristau, Köln (DE); Sebastian Hoffmann, Neuss (DE); Thomas Seitz, Langenfeld (DE); Oswald Ort, Leverkusen (DE); Ulrich Heinemann, Leichlingen (DE); Jürgen Benting, Leichlingen (DE); Peter Dahmen, Neuss (DE); Ulrike Wachendorff-Neumann, Neuwied (DE); Marcel Calleja, St. Genis les Ollieres (FR); Hiroyuki Hadano, Tochigi (JP)

(73) Assignee: Bayer Cropscience AG, Monheim (DE)

( * ) Notice: Subject to any disclaimer, the term of this patent is extended or adjusted under 35 U.S.C. 154(b) by 152 days.

(21) Appl. No.: 12/697,211

(22) Filed: Jan. 30, 2010

(65) Prior Publication Data
US 2011/0130282 A1 Jun. 2, 2011

(30) Foreign Application Priority Data

Feb. 2, 2009 (EP) .................................. 09151856

(51) Int. Cl.
*A61K 31/425* (2006.01)
*C07D 275/02* (2006.01)
(52) U.S. Cl. ..................... 514/372; 548/206; 548/213
(58) Field of Classification Search ............... 548/206, 548/213; 514/372
See application file for complete search history.

(56) References Cited

U.S. PATENT DOCUMENTS

| | | | |
|---|---|---|---|
| 3,840,665 | A | 10/1974 | O'Brien et al. |
| 4,245,432 | A | 1/1981 | Dannelly |
| 4,272,417 | A | 6/1981 | Barke et al. |
| 4,808,430 | A | 2/1989 | Kouno |
| 5,338,856 | A | 8/1994 | Ricks et al. |
| 5,876,739 | A | 3/1999 | Turnblad et al. |
| 6,893,650 | B1 * | 5/2005 | Charles et al. ............... 424/405 |
| 2003/0176428 | A1 | 9/2003 | Schneidersmann et al. |

FOREIGN PATENT DOCUMENTS

| | | |
|---|---|---|
| DE | 2231098 | 1/1974 |
| DE | 2434922 | 1/1975 |
| DE | 102008000872 | 11/2008 |
| EP | 129408 | 12/1984 |
| EP | 0129408 | 12/1984 |
| EP | 0327981 | 8/1989 |
| EP | 327981 | 8/1989 |
| EP | 1344774 | 9/2003 |
| JP | 2056473 | 2/1990 |
| JP | 06236057 | 8/1994 |
| JP | 2002/003410 | 1/2002 |
| WO | 96/33270 | 10/1996 |
| WO | 00/46184 | 8/2000 |
| WO | 0046184 | 8/2000 |
| WO | 02/28186 | 4/2002 |
| WO | 0228186 | 4/2002 |
| WO | 02/080675 | 10/2002 |
| WO | 02080675 | 10/2002 |
| WO | 03/024219 | 3/2003 |
| WO | 03024219 | 3/2003 |
| WO | 03/093224 | 11/2003 |
| WO | 03093224 | 11/2003 |
| WO | 2004/037239 | 5/2004 |
| WO | 2004037239 | 5/2004 |
| WO | 2007/024782 | 3/2007 |
| WO | 2007/027777 | 3/2007 |
| WO | 2007/031513 | 3/2007 |
| WO | 2007027777 | 3/2007 |
| WO | 2007031513 | 3/2007 |

OTHER PUBLICATIONS

Krebs; "Thienoisothiazoles. III. The Synthesis and Reactions of 3-Phenyl-5-Alkylthioisothiazole-4-Carbonit Riles and 3-Phenylthieno(3,2-D) Isothiazoles" Australian Journal of Chemistry, Csiro, AU, BD. 42, Nr. 8, Jan. 1, 1989, pp. 1291-1306.

Stocks et al.; "Isothiazoles. Part XIV. 5-Alkoxy- and Hydroxyisothiazoles" Journal of the Chemical Society, Section C: Organic Chemistry, Chemical Society. Letchworth, GB, Jan. 1, 1971, pp. 1314-1317.

Davis et al.; "The Chemistry of 2,1-Benzisothiazoles. IX* The Reaction of 3-Chloro-Substituted 2,1-Benzisothiazoles With Nucleophiles and the Preparation of (2,1-Benzisothiazol-3-Yl)Acetic Acid"; Australian Journal of Chemistry, 1975, 28, pp. 2051-2055.

(Continued)

*Primary Examiner* — Golam M M Shameem
(74) *Attorney, Agent, or Firm* — Baker, Donelson, Bearman, Caldwell & Berkowitz, PC

(57) ABSTRACT

The present invention relates to isothiazolyloxyphenylamidines of the general formula (I), to a process for their preparation, to the use of the amidines according to the invention for controlling unwanted microorganisms, and also to a composition for this purpose which comprises the isothiazolyloxyphenylamidines according to the invention. Furthermore, the invention relates to a method for controlling unwanted microorganisms by applying the compounds according to the invention to the microorganisms and/or in their habitat.

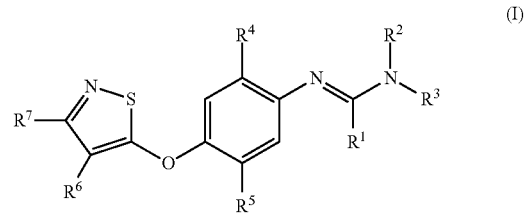

6 Claims, No Drawings

OTHER PUBLICATIONS

Perronet, et al.; "Action Des Isocyanates Sur Les Benzisothiazol-2, 1 Ones-3(1H) et Sur Les Thiadiazol-1, 2, 4 Ones-5: Un Nouveau Rearrangement Avec Extrusion De L'Atome De Soufre"; Journal of Heterocyclic Chemistry, BD. 17, 1980, pp. 673-678.

Cohgi et al.; "Sintesi E Attivita Fitotossica De Acidi 2, 1-Benzisotiazol-3-Ilacetici BZ-Sostituiti E Di Loro Esteri" Acta Naturalia De L'Ateneo Parmense, Parma, IT, BD. 22, Jan. 1, 1986, pp. 41-46.

Arriau; "Etude Theorique De La Tautomerie D'Heterocycles a Cinq Chainons Contenants 1 Ou 2 Heteroatomes Dans Le Cycle"; Anales De Quimica, Serie C, Quimica Organica Y Bioquimica, Real Sociedad Espanola De Quimica, Madrid, ES, BD. 77, Jan. 1, 1981, pp. 105-111.

Mille et al; "Etude Des Spectres De Vibration Des Derives Monosubstitues En Position 5 De L'Isothiazole" Canadian Journal of Chemistry; BD. 53, 1975, pp. 1642-1646.

Naito et al.; Studies on Isothiazoles, I. 3-Arylisothiazole-4-Carboxylic Acids Chemical and Pharmaceutical Society of Japan, Tokyo, JP, BD. 16, Nr. 1, Jan. 1, 1968, pp. 148-164.

Kislitsyn et al.; "Unusual Oxidative Dehydration of Vic-[Alkyl(Aryl)Thio]-Substituted Aromatic (Heteroaromatic) Carboxamides" Russian Chemical Bulletin, International Edition, BD. 53, Nr. 4, 2004, pp. 916-924.

Draber et al.; Chemie Der Pflanzenschutz- Und Schaedlingsgekaempfungsmittel; BD. 2, Springer Verlag, 1970, S. 401-412.

Carvalho, et al.; "Synthesis of Novel 6-Enaminopurines"; Org. Biomol. Chem., 2004, 2340-2345.

Hodgson et al.; "Nitrosation of Phenols. Part III. Nitrosation of 4-Halogeno-O and -M-Cresols and Oximation of the 4-Halogeno-2: 5-Toluquinones"; Journal of the Chemical Society 1926, pp. 2036.

Pavlik et al.; "Phototransposition Chemistry of Phenylisothiazoles and Phenylthiazoles. 1. Interconversions in Benzene Solution1"; Journal of The American Chemical Society; 1994, 116, pp. 2292-2300.

Wagnat; "Novel Synthesis of 1,3,4-Thiadiazine Derivatives and Their Cycloaddition Reactions"; Arch. Pharm. Chem. Life Sci. 2006, pp. 608-615.

Barker et al.; "The Synthesis and Chemistry of Thieno[3,2-C]Isothiazole and Some of Its Derivatives"; Journal of Chemical Research, Synopses, 1989, 2, 29.

Galat et al.; "The Interaction of Amides With Amines: A General Method of Acylation1"; JACS, 65, 1566 (1943).

Kraybill et al.; "Inhibitor Scaffolds as New Allele Specific Kinase Substrates"; JACS, 2002, pp. 12118-12128.

Yevich et al.; "Synthesis and Biological Evaluation of 1-(1,2-Benzisothiazol-3-Yl)- and (1,2-Benzisoxazol-3-Yl) Piperazine Derivatives as Potential Antipsychotic Agents"; J.F Med. Chem, 1986, 29, pp. 359-369.

Hatchard; "The Synthesis of Isothiazoles. I. 3,5-Dichloro-4-Isothiazolecarbonitrile and Its Derivatives"; J. Org. Chem., 1964, 29, 660.

Hackler et al.; "The Syntheses of 5-Amino-3-T-Butylisothiazole and 3-Amino-5-T-Butyllisothiazole"; J. Heterocyclic Chem, 1989, 1575.

Albert et al.; "The Synthesis and Reactions of Certain 3-Substituted-2,1-Benzisothiazoles"; J. Heterocyclic Chem, 1978, 15, pp. 529-536.

Albert et al.; "Synthesis of 3-Hydroxy-2,1-Benziothiazole (1)"; J. Heterocyclic Chem, 1973, 10, 413.

HTTP://WWW.LIFESCI.SUSSEX.AC.UK/HOME/NEIL__CRICKMORE/BT/.

Ohkata et al.; "Chlorination of 5-[2-(N-Silylamino)Vinyl]-Isothiazole and Related Derivatives With N-Chlorosuccinimide. Inhibition of Ring-Transformation (Bond Switch) by Steric Hindrance"; Heterocycles, 1994, 37, pp. 859-867.

Ji et al.; "Isothiazolopyrimidines and Isoxazolopyrimidines as Novel Multi-Targeted Inhibitors of Receptor Tyrosine Kinases"; Bioorg. Med. Chem. Lett., 2006, pp. 4326-4330.

European Search Report Based on European Application No. 09151856 Dated Jul. 7, 2009.

International Search Report Based on PCT/EP2010/000353 Dated Apr. 15, 2010.

* cited by examiner

ISOTHIAZOLYLOXYPHENYLAMIDINES AND THEIR USE AS FUNGICIDES

The present invention relates to isothiazolyloxyphenylamidines of the general formula (I), to a process for their preparation, to the use of the amidines according to the invention for controlling unwanted microorganisms, and also to a composition for this purpose which comprises the isothiazolyloxyphenylamidines according to the invention. Furthermore, the invention relates to a method for controlling unwanted microorganisms by applying the compounds according to the invention to the microorganisms and/or in their habitat.

WO-A-00/046 184 discloses the use of amidines as fungicides.

WO-A-03/093 224 discloses the use of arylamidine derivatives as fungicides.

WO-A-03/024 219 discloses fungicide compositions comprising at least one N2-phenylamidine derivative in combination with a further selected known active compound.

WO-A-04/037 239 discloses antifungicidal medicaments based on N2-phenylamidine derivatives.

WO-A-07/031,513 discloses thiadiazolyl-substituted phenylamidines and their preparation and use as fungicides.

The activity of the amidines described in the prior art is good; however, it is sometimes unsatisfactory.

Accordingly, the present invention is based on the object of providing amidines having improved fungicidal activity.

Surprisingly, this object was achieved by isothiazolyloxyphenylamidines of the formula (I)

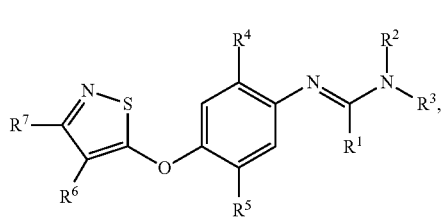

in which $R^1$ is selected from the group consisting of hydrogen; straight-chain or branched $C_{1-12}$-alkyl, $C_{2-12}$-alkenyl, $C_{2-12}$-alkinyl and cyclic $C_{3-8}$-alkyl, $C_{4-8}$-alkenyl and $C_{4-8}$-alkinyl groups, where in the ring systems of all of the cyclic groups mentioned above one or more carbon atoms may be replaced by heteroatoms selected from the group consisting of C, N, O, P and S and all of the groups mentioned above may be substituted by one or more groups selected from the group consisting of —R', —X, —OR', —SR', —NR'$_2$, —SiR'$_3$, —COOR', —CN and —CONR$_2$', where R' is hydrogen or a $C_{1-12}$-alkyl group and X is a halogen atom selected from the group consisting of F, Cl, Br and I;

$R^2$ is selected from the group consisting of straight-chain and branched $C_{1-12}$-alkyl, $C_{2-12}$-alkenyl, $C_{2-12}$-alkinyl, cyclic $C_{3-8}$-alkyl, $C_{4-8}$-alkenyl, $C_{4-8}$-alkinyl or $C_{5-18}$-aryl, $C_{7-19}$-aralkyl and $C_{7-19}$-alkaryl groups, where in the ring systems of all of the cyclic groups mentioned above one or more carbon atoms may be replaced by heteroatoms selected from the group consisting of C, N, O, P and S and all of the groups mentioned above may be substituted by one or more groups selected from the group consisting of —R', —X, —OR', —SR', —NR'$_2$, —SiR'$_3$, —COOR', —CN and —CONR$_2$', where R' and X have the above meanings;

$R^3$ is selected from the group consisting of —CN, —SH, —SR", —OR", —(C=O)—R", where R" has the above meanings; straight-chain and branched $C_{1-12}$-alkyl, $C_{2-12}$-alkenyl, $C_{2-12}$-alkinyl, cyclic $C_{3-8}$-alkyl, $C_{4-8}$-alkenyl, $C_{4-8}$-alkinyl and $C_{5-18}$-aryl, $C_{7-19}$-aralkyl and $C_{7-19}$-alkaryl groups, where in the ring systems of all of the cyclic groups mentioned above one or more carbon atoms may be replaced by heteroatoms selected from the group consisting of C, N, O, P and S and all of the groups mentioned above may be substituted by one or more groups selected from the group consisting of —R', —X, —OR', —SR', —NR'$_2$, —SiR'$_3$, —COOR', —CN and —CONR$_2$', wherein R' and X have the above meanings;

or in which $R^2$ and $R^3$, $R^2$ and $R^1$ or $R^1$ and $R^3$ together with the atoms to which they are attached or with further atoms selected from the group consisting of C, N, O, P and S may form a four- to seven-membered ring which may be substituted by R', OR', SR', NR'$_2$, SiR'$_3$ groups, where R' has the above meanings;

$R^4$ is selected from the group consisting of hydrogen, —X, —CN, —SH, —SR", —OR", —(C=O)—R", where R" has the above meanings; straight-chain and branched $C_{1-12}$-alkyl, $C_{2-12}$-alkenyl, $C_{2-12}$-alkinyl, cyclic $C_{3-8}$-alkyl, $C_{4-8}$-alkenyl, $C_{4-8}$-alkinyl or $C_{5-18}$-aryl, $C_{7-19}$-aralkyl or $C_{7-19}$-alkaryl groups, where in the ring systems of all of the cyclic groups mentioned above one or more carbon atoms may be replaced by heteroatoms selected from the group consisting of N, O, P and S and all of the groups mentioned above may be substituted by one or more groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide (—CONR$_2$') groups, where R' and X have the above meanings;

$R^5$ is selected from the group consisting of hydrogen, —X, —CN, —SH, —SR", —OR", —(C=O)—R", where R" has the above meanings; straight-chain and branched $C_{1-12}$-alkyl, $C_{2-12}$-alkenyl, $C_{2-12}$-alkinyl, cyclic $C_{3-8}$-alkyl, $C_{4-8}$-alkenyl, $C_{4-8}$-alkinyl or $C_{5-18}$-aryl, $C_{7-19}$-aralkyl or $C_{7-19}$-alkaryl groups, where in the ring systems of all of the cyclic groups mentioned above one or more carbon atoms may be replaced by heteroatoms selected from the group consisting of N, O, P and S and all of the groups mentioned above may be substituted by one or more groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide (—CONR$_2$') groups, where R' and X have the above meanings;

$R^6$ is selected from the group consisting of hydrogen, halogen (—X), alkoxy (—OR'), thioether or mercapto (—SR'), amino (—NR'$_2$), nitro (—NO$_2$), silyl (—SiR'$_3$), carboxyl (—COOR'), cyano (—CN) and amide (—CONR$_2$') groups, straight-chain and branched $C_{1-12}$-alkyl, $C_{2-12}$-alkenyl, $C_{2-12}$-alkinyl, cyclic $C_{3-12}$-alkyl, $C_{4-12}$-alkenyl, $C_{4-12}$-alkinyl or $C_{5-18}$-aryl, $C_{7-19}$-aralkyl or $C_{7-19}$-alkaryl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide (—CONR$_2$') groups, where R' and X have the above meanings;

R$^7$ is selected from the group consisting of hydrogen, straight-chain and branched C$_{1-12}$-alkyl, C$_{2-12}$-alkenyl, C$_{2-12}$-alkinyl, cyclic C$_{3-12}$-alkyl, C$_{4-12}$-alkenyl, C$_{4-12}$-alkinyl or cyclic groups mentioned above one or more carbon atoms may be replaced by heteroatoms selected from the group consisting of N, O, P and S and all of the groups mentioned above may be substituted by one or more groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide (—CONR$_2$') groups, where R' and X have the above meanings;

R$^6$ and R$^7$ together with the atoms to which they are attached or with further atoms selected from the group consisting of C, N, O, P and S may form a four- to seven-membered ring which may be substituted by R'—, X—, —OR', —SR', —NR'$_2$, —SiR'$_3$, —COOR', —CN and NR$_2$'CO— groups, where R' has the above meanings and which may have one, two or three unsaturated bonds;

and their salts.

GENERAL DEFINITIONS

In the context of the present invention, the term halogens (X) comprises, unless defined otherwise, elements selected from the group consisting of fluorine, chlorine, bromine and iodine, with fluorine, chlorine and bromine being used preferably and fluorine and chlorine being used particularly preferably.

Optionally substituted groups may be mono- or polysubstituted, where in the case of polysubstitution the substituents may be identical or different.

Alkyl groups substituted by one or more halogen atoms (—X) are, for example, selected from the group consisting of trifluoromethyl (CF$_3$), difluoromethyl (CHF$_2$), CF$_3$CH$_2$, ClCH$_2$, CF$_3$CCl$_2$.

In the context of the present invention, alkyl groups are, unless defined otherwise, straight-chain, branched or cyclic hydrocarbon groups which may optionally have one, two or more singly or doubly unsaturated bonds or one, two or more heteroatoms selected from the group consisting of O, N, P and S. Moreover, the alkyl groups according to the invention may optionally be substituted by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a C$_{1-12}$-alkyl group, preferably a C$_{2-10}$-alkyl group, particularly preferably a C$_{3-8}$-alkyl group, which may have one or more heteroatoms selected from the group consisting of N, O, P and S.

The definition C$_1$-C$_{12}$-alkyl comprises the greatest range defined herein for an alkyl group. Specifically, this definition comprises, for example, the meanings methyl, ethyl, n-, iso-propyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

In the context of the present invention, alkenyl groups are, unless defined otherwise, straight-chain, branched or cyclic hydrocarbon groups having at least one singly unsaturated bond (double bond) and optionally one, two or more singly or doubly unsaturated bonds or one, two or more heteroatoms selected from the group consisting of O, N, P and S. Moreover, the alkenyl groups according to the invention may optionally be substituted by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a C$_{1-12}$-alkyl group, preferably a C$_{2-10}$-alkyl group, particularly preferably a C$_{3-8}$-alkyl group, which may have one or more heteroatoms selected from the group consisting of N, O, P and S.

The definition C$_2$-C$_{12}$-alkenyl comprises the greatest range defined herein for an alkenyl group. Specifically, this definition comprises, for example, the meanings vinyl; allyl (2-propenyl), isopropenyl (1-methylethenyl); but-1-enyl (crotyl), but-2-enyl, but-3-enyl; hex-1-enyl, hex-2-enyl, hex-3-enyl, hex-4-enyl, hex-5-enyl; hept-1-enyl, hept-2-enyl, hept-3-enyl, hept-4-enyl, hept-5-enyl, hept-6-enyl; oct-1-enyl, oct-2-enyl, oct-3-enyl, oct-4-enyl, oct-5-enyl, oct-6-enyl, oct-7-enyl; non-1-enyl, non-2-enyl, non-3-enyl, non-4-enyl, non-5-enyl, non-6-enyl, non-7-enyl, non-8-enyl; dec-1-enyl, dec-2-enyl, dec-3-enyl, dec-4-enyl, dec-5-enyl, dec-6-enyl, dec-7-enyl, dec-8-enyl, dec-9-enyl; undec-1-enyl, undec-2-enyl, undec-3-enyl, undec-4-enyl, undec-5-enyl, undec-6-enyl, undec-7-enyl, undec-8-enyl, undec-9-enyl, undec-10-enyl; dodec-1-enyl, dodec-2-enyl, dodec-3-enyl, dodec-4-enyl, dodec-5-enyl, dodec-6-enyl, dodec-7-enyl, dodec-8-enyl, do dec-9-enyl, do dec-10-enyl, do dec-11-enyl; buta-1,3-dienyl, penta-1,3-dienyl.

In the context of the present invention, alkinyl groups are, unless defined otherwise, straight-chain, branched or cyclic hydrocarbon groups having at least one doubly unsaturated bond (triple bond) and optional one, two or more singly or doubly unsaturated bonds or one, two or more heteroatoms selected from the group consisting of O, N, P and S. Moreover, the alkinyl groups according to the invention may optionally be substituted by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a straight-chain, branched or cyclic C$_{1-12}$-alkyl group which may have one or more heteroatoms selected from the group consisting of N, O, P and S.

The definition C$_2$-C$_{12}$-alkinyl comprises the greatest range defined herein for an alkinyl group. Specifically, this definition comprises, for example, the meanings ethinyl (acetylenyl); prop-1-inyl and prop-2-inyl.

The definition C$_3$-C$_8$-cycloalkyl comprises monocyclic saturated hydrocarbon groups having 3 to 8 ring members, such as cyclopropyl, cyclobutyl, cyclopentyl, cyclohexyl, cycloheptyl and cyclooctyl.

In the context of the present invention, aryl groups are, unless defined otherwise, aromatic hydrocarbon groups which may have one, two or more heteroatoms selected from the group consisting of O, N, P and S and may optionally be substituted by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a C$_{1-12}$-alkyl group, preferably a C$_{2-10}$-alkyl group, particularly preferably a C$_{3-8}$-alkyl group, which may have one or more heteroatoms selected from the group consisting of N, O, P and S.

The definition C$_{5-18}$-aryl comprises the greatest range defined herein for an aryl group having 5 to 18 skeleton atoms, where the carbon atoms may be replaced by heteroatoms. Specifically, this definition comprises, for example, the meanings cyclopentadienyl, phenyl, cycloheptatrienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

In the context of the present invention, arylalkyl groups (aralkyl groups) are, unless defined otherwise, alkyl groups which are substituted by alkyl groups and may have a $C_{1-8}$-alkylene chain and may be substituted in the aryl skeleton or the alkylene chain by one or more heteroatoms selected from the group consisting of O, N, P and S and optionally by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may have one or more heteroatoms selected from the group consisting of N, O, P and S.

The definition $C_{7-19}$-aralkyl group comprises the greatest range defined herein for an arylalkyl group having a total of 7 to 19 atoms in the skeleton and the alkylene chain. Specifically, this definition comprises, for example, the meanings benzyl and phenylethyl.

In the context of the present invention, alkylaryl groups (alkaryl groups) are, unless defined otherwise, aryl groups which are substituted by alkyl groups and which may have a $C_{1-8}$-alkylene chain and may be substituted in the aryl skeleton or the alkylene chain by one or more heteroatoms selected from the group consisting of O, N, P and S and optionally by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may have one or more heteroatoms selected from the group consisting of N, O, P and S.

The definition $C_{7-19}$-alkylaryl group comprises the greatest range defined herein for an alkylaryl group having a total of 7 to 19 atoms in the skeleton and the alkylene chain. Specifically, this definition comprises, for example, the meanings tolyl-, 2,3-, 2,4-, 2,5-, 2,6-, 3,4- or 3,5-dimethylphenyl.

The alkyl, alkenyl, alkinyl, aryl, alkaryl and aralkyl groups may additionally have one or more heteroatoms which—unless defined otherwise—are selected from the group consisting of N, O, P and S. Here, the heteroatoms replace the carbon atoms indicated.

The compounds according to the invention may, if appropriate, be present as mixtures of various possible isomeric forms, in particular stereoisomers such as, for example, E and Z, threo and erythro, and also optical isomers, and, if appropriate, also of tautomers. What is disclosed and claimed are both the E and the Z isomers, and also the threo and erythro, and also the optical isomers, any mixtures of these isomers, and also the possible tautomeric forms.

The amidines according to the invention are compounds of the formula (I)

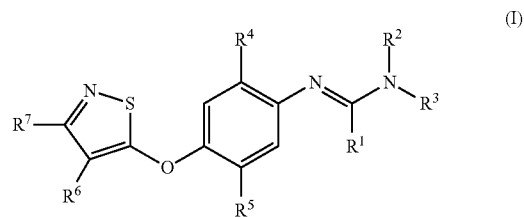

or their salts, N-oxides, metal complexes and their stereoisomers.

In formula (I), the groups have the meanings defined below. The given definitions likewise apply to all intermediates:

$R^1$ is selected from the group consisting of hydrogen; straight-chain or branched $C_{1-12}$-alkyl, $C_{2-12}$-alkenyl, $C_{2-12}$-alkinyl and cyclic $C_{3-8}$-alkyl, $C_{4-8}$-alkenyl and $C_{4-8}$-alkinyl groups, where in the ring systems of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR$_2$', where R' is hydrogen or a $C_{1-12}$-alkyl group and X is a halogen atom selected from the group consisting of F, Cl, Br and I;

$R^2$ is selected from the group consisting of straight-chain and branched $C_{1-12}$-alkyl, $C_{2-12}$-alkenyl, $C_{2-12}$-alkinyl, cyclic $C_{3-8}$-alkyl, $C_{4-8}$-alkenyl, $C_{4-8}$-alkinyl or $C_{5-18}$-aryl, $C_{7-19}$-aralkyl and $C_{7-19}$-alkaryl groups, where in the ring systems of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR$_2$', where R' and X have the above meanings;

$R^3$ is selected from the group consisting of —CN, —SH, —SR'', —OR'', —(C=O)—R'', where R'' has the above meanings; straight-chain and branched $C_{1-12}$-alkyl, $C_{2-12}$-alkenyl, $C_{2-12}$-alkinyl, cyclic $C_{3-8}$-alkyl, $C_{4-8}$-alkenyl, $C_{4-8}$-alkinyl and $C_{5-18}$-aryl, $C_{7-19}$-aralkyl and $C_{7-19}$-alkaryl groups, where in the ring systems of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR$_2$', wherein R' and X have the above meanings.

In an alternative embodiment according to the invention, $R^2$ and $R^3$, $R^2$ and $R^1$ or $R^1$ and $R^3$ together with the atoms to which they are attached or with further atoms selected from the group consisting of N, O, P and S may form a four- to seven-membered ring which may be substituted by R', OR', SR', NR'$_2$, SiR'$_3$ groups, where R' has the above meanings;

$R^4$ is selected from the group consisting of hydrogen, —X, —CN, —SH, —SR'', —OR'', —(C=O)—R'', where R'' has the above meanings; straight-chain and branched $C_{1-12}$-alkyl, $C_{2-12}$-alkenyl, $C_{2-12}$-alkinyl, cyclic $C_{3-8}$-alkyl, $C_{4-8}$-alkenyl, $C_{4-8}$-alkinyl or $C_{5-18}$-aryl, $C_{7-19}$-aralkyl or $C_{7-19}$-alkaryl groups, where in the ring systems of all of the cyclic groups mentioned above one or more carbon atoms may be replaced by heteroatoms selected from the group consisting of N, O, P and S and all of the groups mentioned above may be substituted by one or more groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide (—CONR$_2$') groups, where R' and X have the above meanings;

$R^5$ is selected from the group consisting of hydrogen, —X, —CN, —SH, —SR'', —OR'', —(C=O)—R'', where R'' has the above meanings; straight-chain and branched $C_{1-12}$-alkyl, $C_{2-12}$-alkenyl, $C_{2-12}$-alkinyl, cyclic $C_{3-8}$-alkyl, $C_{4-8}$-alkenyl, $C_{4-8}$-alkinyl or $C_{5-18}$-aryl, $C_{7-19}$-aralkyl or $C_{7-19}$-alkaryl groups, where in the ring systems of all of the cyclic groups mentioned above one or more carbon atoms may be replaced by heteroatoms selected from the group consisting of N, O, P and S and all of the groups mentioned above may be substituted by one or more groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide (—CONR$_2$') groups, where R' and X have the above meanings;

$R^6$ is selected from the group consisting of hydrogen, halogen (—X), alkoxy (—OR'), thioether or mercapto (—SR'), amino (—NR'$_2$), nitro (—NO$_2$), silyl (—SiR'$_3$), carboxyl (—COOR'), cyano (—CN) and amide (—CONR$_2$') groups, straight-chain and branched $C_{1-12}$-alkyl, $C_{2-12}$-alkenyl, $C_{2-12}$-alkinyl, cyclic $C_{3-12}$-alkyl, $C_{4-12}$-alkenyl, $C_{4-12}$-alkinyl or $C_{5-18}$-aryl, $C_{7-19}$-aralkyl or $C_{7-19}$-alkaryl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', halogen-(—X), alkoxy (—OR'), thioether or mercapto (—SR'), amino (—NR'$_2$), silyl (—SiR'$_3$), carboxyl (—COOR'), cyano (—CN) and amide (—CONR$_2$') groups, where R' and X have the above meanings;

$R^7$ is selected from the group consisting of hydrogen, straight-chain and branched $C_{1-12}$-alkyl, $C_{2-12}$-alkenyl, $C_{2-12}$-alkinyl, cyclic $C_{3-12}$-alkyl, $C_{4-12}$-alkenyl, $C_{4-12}$-alkinyl or cyclic groups mentioned above one or more carbon atoms may be replaced by heteroatoms selected from the group consisting of N, O, P and S and all of the groups mentioned above may be substituted by one or more groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide (—CONR$_2$') groups, where R' and X have the above meanings;

$R^6$ and $R^7$ together with the atoms to which they are attached or with further atoms selected from the group consisting of C, N, O, P and S may form a four- to seven-membered ring which may be substituted by R'—, X—, —OR', —SR', —NR'$_2$, —SiR'$_3$, —COOR', —CN and NR$_2$'CO— groups, where R' and X have the above meanings;

or their salts, N-oxides, metal complexes and their stereoisomers.

In formula (I), the groups have the preferred meanings defined below. The definitions given as being preferred likewise apply to all intermediates:

$R^1$ is selected from the group consisting of hydrogen, a mercapto group (—SH) and $C_{1-8}$-alkyl groups;

$R^2$ is selected from straight-chain and branched $C_{1-8}$-alkyl groups;

$R^3$ is selected from straight-chain, branched and alicyclic $C_{1-8}$-alkyl groups.

In an alternative preferred embodiment according to the invention, $R^2$ and $R^3$ together with the nitrogen atom to which they are attached or with further atoms selected from the group consisting of N and O may form a five- or six-membered ring which may be substituted by one or more $C_{1-12}$-alkyl groups;

$R^4$ is selected from the group consisting of —X (halogen), straight-chain and branched $C_{1-12}$-alkyl groups and $C_{1-5}$-haloalkyl groups;

$R^5$ is selected from the group consisting of —X (halogen), straight-chain and branched $C_{1-12}$-alkyl groups and $C_{1-5}$-haloalkyl groups;

$R^6$ is selected from the group consisting of hydrogen, —X (halogen), cyano and straight-chain $C_{1-8}$-alkyl groups;

$R^7$ is selected from the group consisting of hydrogen, straight-chain and branched $C_{1-12}$-alkyl groups and phenyl groups, wherein the phenyl groups may be substituted by halogen atoms and/or by straight-chain or branched $C_{1-12}$-alkyl groups;

$R^6$ and $R^7$ together with the atoms to which they are attached form a fused-on five- or six-membered ring which may have one, two or three unsaturated bonds;

or their salts, N-oxides, metal complexes and their stereoisomers.

In formula (I), the radicals have the particularly preferred meanings defined below. The definitions given as being particularly preferred likewise apply to all intermediates:

$R^1$ is selected from the group consisting of hydrogen, mercapto and methyl;

$R^2$ is selected from the group consisting of methyl and ethyl;

$R^3$ is selected from the group consisting of methyl, ethyl and isopropyl.

In an alternative particularly preferred embodiment according to the invention, $R^2$ and $R^3$, together with the nitrogen atom to which they are attached form a piperidinyl, piperidyl, pyrrolidinyl, pyrrolidyl or 2,6-dimethylmorpholinyl radical;

$R^4$ is selected from the group consisting of a Cl atom and a methyl group;

$R^5$ is selected from the group consisting of a Cl-atom and a methyl group;

$R^6$ is selected from the group consisting of hydrogen, halogen atoms and a cyano group;

$R^7$ is selected from the group consisting of tert-butyl, ethyl, phenyl and benzyl groups, where the phenyl groups may be substituted in the 3- or 4-position by halogen atoms or by a tert-butyl or methyl group;

$R^6$ and $R^7$ together with the atoms to which they are attached may form a phenyl ring;

or their salts, N-oxides, metal complexes and their stereoisomers.

In addition, the present invention also relates to the salts, N-oxides, metal complexes of the compounds described above and their stereoisomers.

Depending on the nature of the substituents defined above, the compounds of the formula (I) have acidic or basic properties and can form salts, if appropriate also inner salts or adducts, with inorganic or organic acids or with bases or with metal ions.

Suitable metal ions are in particular the ions of the elements of the second main group, in particular calcium and magnesium, of the third and fourth main group, in particular aluminium, tin and lead, and also of the first to eighth transition group, in particular chromium, manganese, iron, cobalt, nickel, copper, zinc and others. Particular preference is given to the metal ions of the elements of the fourth period. Here, the metals may be present in the various valences that they can assume.

If the compounds of the formula (I) carry hydroxyl, carboxyl or other groups which induce acidic properties, these compounds can be reacted with bases to give salts.

Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having ($C_1$-$C_4$)-alkyl groups, mono-, di- and trialkanolamines of ($C_1$-$C_4$)-alkanols, choline and also chlorocholine.

If the compounds of the formula (I) carry amino, alkylamino or other groups which induce basic properties, these compounds can be reacted with acids to give salts.

Examples of inorganic acids are hydrohalic acids, such as hydrogen fluoride, hydrogen chloride, hydrogen bromide and hydrogen iodide, sulphuric acid, phosphoric acid and nitric acid and acidic salts, such as $NaHSO_4$ and $KHSO_4$.

Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulphonic acids (sulphonic acids having straight-chain or branched alkyl groups of 1 to 20 carbon atoms), arylsulphonic acids or -disulphonic acids (aromatic groups, such as phenyl and naphthyl, which carry one or two sulphonic acid groups), alkylphosphonic acids (phosphonic acids having straight-chain or branched alkyl groups of 1 to 20 carbon atoms), arylphosphonic acids or -diphosphonic acids (aromatic radicals, such as phenyl and naphthyl, which carry one or two phosphonic acid groups), where the alkyl or aryl groups may carry further substituents, for example p-toluene sulphonic acid, salicylic acid, p-aminosalicylic acid, 2-phenoxybenzoic acid, 2-acetoxybenzoic acid, saccharin, etc.

The salts which can be obtained in this manner also have fungicidal properties.

Amidines which are particularly preferred in the context of the present invention are selected from the group consisting of: N'-{4-[(4-cyano-3-ethyl-1,2-thiazol-5-yl)oxy]-2,5-dimethylphenyl}-N-ethyl-N-methylimidoformamide (1), 5-(2,5-dimethyl-4-{[(E)-piperidin-1-ylmethylidene]amino}phenoxy)-3-ethyl-1,2-thiazole-4-carbonitrile (2), N'-{4-[(4-cyano-3-ethyl-1,2-thiazol-5-yl)oxy]-2,5-dimethylphenyl}-N-methyl-N-propylimidoformamide (3), N'-{4-[(3-tert-butyl-4-cyano-1,2-thiazol-5-yl) oxy]-2,5-dimethylphenyl}-N-methyl-N-propylimidoformamide (4), N'-{4-[(3-tert-butyl-4-cyano-1,2-thiazol-5-yl)oxy]-2,5-dimethylphenyl}-N-methyl-N-prop-2-en-1-ylimidoformamide (5), N'-{4-[(3-tert-butyl-4-cyano-1,2-thiazol-5-yl)oxy]-2,5-dimethylphenyl}-N-ethyl-N-methylimidoformamide (6), 3-tert-butyl-5-(2,5-dimethyl-4-{[(E)-piperidin-1-ylmethylidene]amino}phenoxy)-1,2-thiazole-4-carbonitrile (7), N'-{4-[(3-tert-butyl-4-cyano-1,2-thiazol-5-yl)oxy]-2,5-dimethylphenyl}-N,N-dimethylimidoformamide (8), N'-{2-chloro-4-[(4-cyano-3-ethyl-1,2-thiazol-5-yl)oxy]-5-methylphenyl}-N-ethyl-N-methylimidoformamide (9), N'-{4-[(3-tert-butyl-4-cyano-1,2-thiazol-5-yl)oxy]-2-chloro-5-methylphenyl}-N-ethyl-N-methylimidoformamide (10), N'-{5-chloro-4-[(4-cyano-3-phenyl-1,2-thiazol-5-yl)oxy]-2-methylphenyl}-N,N-dimethylimidoformamide (11), N'-{5-chloro-4-[(4-cyano-3-phenyl-1,2-thiazol-5-yl)oxy]-2-methylphenyl}-N-ethyl-N-methylimido formamide (12), N'-{5-chloro-4-[(4-cyano-3-phenyl-1,2-thiazol-5-yl)oxy]-2-methylphenyl}-N-methyl-N-propylimidoformamide (13), N'-{4-[(4-cyano-3-phenyl-1,2-thiazol-5-yl)oxy]-2,5-dimethylphenyl}-N,N-dimethylimidoformamide (14), N'-{4-[(4-cyano-3-phenyl-1,2-thiazol-5-yl)oxy]-2,5-dimethylphenyl}-N-ethyl-N-methylimidoformamide (15), N'-{4-[(4-cyano-3-phenyl-1,2-thiazol-5-yl)oxy]-2,5-dimethylphenyl}-N-methyl-N-propylimidoformamide (16), N'-{2-chloro-4-[(4-cyano-3-phenyl-1,2-thiazol-5-yl)oxy]-5-methylphenyl}-N,N-dimethylimidoformamide (17), N'-{2-chloro-4-[(4-cyano-3-phenyl-1,2-thiazol-5-yl)oxy]-5-methylphenyl}-N-ethyl-N-methylimidoformamide (18), N'-{2-chloro-4-[(4-cyano-3-phenyl-1,2-thiazol-5-yl)oxy]-5-methylphenyl}-N-methyl-N-propylimidoformamide (19), 3-(4-chlorophenyl)-5-(2,5-dimethyl-4-{[(E)-piperidin-1-ylmethylidene]amino}phenoxy)-1,2-thiazole-4-carbonitrile (20), N'-(4-{[3-(4-chlorophenyl)-4-cyano-1,2-thiazol-5-yl]oxy}-2,5-dimethylphenyl)-N-methyl-N-propylimidoformamide (21), N'-(4-{[3-(4-chlorophenyl)-4-cyano-1,2-thiazol-5-yl]oxy}-2,5-dimethylphenyl)-N-ethyl-N-methylimidoformamide (22), N'-(4-{[3-(4-chlorophenyl)-4-cyano-1,2-thiazol-5-yl]oxy}-2,5-dimethylphenyl)-N,N-dimethylimidoformamide (23), N'-(4-{[4-cyano-3-(3-methylphenyl)-1,2-thiazol-5-yl]oxy}-2,5-dimethylphenyl)-N,N-dimethylimidoformamide (24), N'-(4-{[4-cyano-3-(3-methylphenyl)-1,2-thiazol-5-yl]oxy}-2,5-dimethylphenyl)-N-ethyl-N-methylimidoformamide (25), N'-(4-{[4-cyano-3-(3-methylphenyl)-1,2-thiazol-5-yl]oxy}-2,5-dimethylphenyl)-N-methyl-N-propylimidoformamide (26), N'-(4-{[3-(4-chlorobenzyl)-4-cyano-1,2-thiazol-5-yl]oxy}-2,5-dimethylphenyl)-N-ethyl-N-methylimidoformamide (27), N'-(4-{[3-(4-tert-butylphenyl)-4-cyano-1,2-thiazol-5-yl]oxy}-2,5-dimethylphenyl)-N-ethyl-N-methylimidoformamide (28), N'-(4-{[3-(4-tert-butylphenyl)-4-cyano-1,2-thiazol-5-yl]oxy}-2,5-dimethylphenyl)-N-methyl-N-propylimido formamide (29), N'-(4-{[3-(4-tert-butylphenyl)-4-cyano-1,2-thiazol-5-yl]oxy}-2,5-dimethylphenyl)-N-methyl-N-prop-2-en-1-ylimidoformamide (30), N'-(4-{[4-cyano-3-(4-fluorophenyl)-1,2-thiazol-5-yl]oxy}-2,5-dimethylphenyl)-N,N-dimethylimidoformamide (31), N'-(4-{[4-cyano-3-(4-fluorophenyl)-1,2-thiazol-5-yl]oxy}-2,5-dimethylphenyl)-N-ethyl-N-methylimidoformamide (32), N'-(4-{[4-cyano-3-(4-fluorophenyl)-1,2-thiazol-5-yl]oxy}-2,5-dimethylphenyl)-N-methyl-N-propylimidoformamide (33), N'-{4-[(4-bromo-3-phenyl-1,2-thiazol-5-yl)oxy]-2,5-dimethylphenyl}-N-ethyl-N-methylimidoformamide (34), N'-(2-chloro-4-{[4-cyano-3-(4-fluorophenyl)-1,2-thiazol-5-yl]oxy}-5-methylphenyl)-N-methyl-N-propylimidoformamide (35), N'-(5-chloro-4-{[4-cyano-3-(4-fluorophenyl)-1,2-thiazol-5-yl]oxy}-2-methylphenyl)-N,N-dimethylimidoformamide (36), N'-(5-chloro-4-{[4-cyano-3-(4-fluorophenyl)-1,2-thiazol-5-yl]oxy}-2-methylphenyl)-N-ethyl-N-methylimidoformamide (37), N'-(5-chloro-4-{[4-cyano-3-(4-fluorophenyl)-1,2-thiazol-5-yl]oxy}-2-methylphenyl)-N-methyl-N-propylimidoformamide (38), N'-(5-chloro-4-{[4-cyano-3-(3-methylphenyl)-1,2-thiazol-5-yl]oxy}-2-methylphenyl)-N,N-dimethylimidoformamide (39), N'-(5-chloro-4-{[4-cyano-3-(3-methylphenyl)-1,2-thiazol-5-yl]oxy}-2-methylphenyl)-N-ethyl-N-methylimidoformamide (40), N'-(5-chloro-4-{[4-cyano-3-(3-methylphenyl)-1,2-thiazol-5-yl]oxy}-2-methylphenyl)-N-methyl-N-propylimidoformamide (41), N'-{2,5-dimethyl-4-[(3-phenyl-1,2-thiazol-5-yl)oxy]phenyl}-N,N-dimethylimidoformamide (42), N'-{2,5-dimethyl-4-[(3-phenyl-1,2-thiazol-5-yl)oxy]phenyl}-N-ethyl-N-methylimidoformamide (43), N'-{2,5-dimethyl-4-[(3-phenyl-1,2-thiazol-5-yl)oxy]phenyl}-N-methyl-N-propylimidoformamide (44), N'-{2-chloro-5-methyl-4-[(3-phenyl-1,2-thiazol-5-yl)oxy]phenyl}-N,N- dimethylimidoformamide (45), N'-{2-chloro-5-methyl-4-[(3-phenyl-1,2-thiazol-5-yl)oxy]phenyl}-N-ethyl-N-methylimidoformamide (46), N'-{2-chloro-5-methyl-4-[(3-phenyl-1,2-thiazol-5-yl)oxy]phenyl}-N-methyl-N-propylimidoformamide (47), N'-{4-[(4-chloro-3-phenyl-1,2-thiazol-5-yl)oxy]-2,5-dimethylphenyl}-N-ethyl-N-methylimidoformamide (48), N'-{4-[(4-chloro-3-phenyl-1,2-thiazol-5-yl)oxy]-2,5-dimethylphenyl}-N-methyl-N-propan-2-ylimidoformamide (49), 4-[(4-chloro-3-phenyl-1,2-thiazol-5-yl)oxy]-2,5-dimethyl-N-[(E)-piperidin-1-ylmethylidene]aniline (50), N'-{5-chloro-4-[(4-chloro-3-phenyl-1,2-thiazol-5-yl)oxy]-2-methylphenyl}-N-ethyl-N-methylimido formamide (51), N'-{5-chloro-4-[(4-chloro-3-phenyl-1,2-thiazol-5-yl)oxy]-2-methylphenyl}-N-methyl-N-propan-2-ylimidoformamide (52), 5-chloro-4-[(4-chloro-3-phenyl-1,2-thiazol-5-yl)oxy]-2-methyl-N-[(E)-piperidin-1-ylmethylidene]aniline (53), N'-{4-[(4-bromo-3-phenyl-1,2-thiazol-5-yl)oxy]-5-chloro-2-methylphenyl}-N-ethyl-N-methylimidoformamide (54), N'-{4-[(4-bromo-3-phenyl-1,2-thiazol-5-yl)oxy]-5-chloro-2-methylphenyl}-N-methyl-N-propan-2-ylimidoformamide (55), 4-[(4-bromo-3-phenyl-1,2-thiazol-5-yl)oxy]-5-chloro-2-methyl-N-[(E)-piperidin-1-ylmethylidene]aniline (56), N'-(2-chloro-4-{[4-cyano-3-(4-fluorophenyl)-1,2-thiazol-5-yl]oxy}-5-methylphenyl)-N,N-dimethylimidoformamide (57), N'-(2-chloro-4-{[4-cyano-3-(4-fluorophenyl)-1,2-thiazol-5-yl]oxy}-5-methylphenyl)-N-ethyl-N-methylimidoformamide (58), N'-[4-(2,1-benzothiazol-3-yloxy)-2,5-dimethylphenyl]-N-ethyl-N-methylimidoformamide (59), N'-[4-(2,1-benzothiazol-3-yloxy)-2,5-dimethylphenyl]-N,N-dimethylimidoformamide (60), N'-[4-(2,1-benzothiazol-3-yloxy)-2,5-dimethylphenyl]-N-methyl-N-propylimidoformamide (61), 4-(2,1-benzothiazol-3-yloxy)-2,5-dimethyl-N-[(E)-piperidin-1-ylmethylidene]aniline (62), 4-(2,1-benzothiazol-3-yloxy)-2,5-dimethyl-N-[(E)-pyrrolidin-1-ylmethylidene]aniline (63), N'-{4-[(3-tert-butyl-4-chloro-1,2-thiazol-5-yl)oxy]-2,5-dimethylphenyl}-N-ethyl-N-methylimidoformamide (64), N'-{4-[(3-tert-butyl-4-chloro-1,2-thiazol-5-yl)oxy]-2,5-dimethylphenyl}-N-methyl-N-propan-2-ylimidoformamide (65), 4-[(3-tert-butyl-4-chloro-1,2-thiazol-5-yl)oxy]-2,5-dimethyl-N-[(E)-piperidin-1-ylmethylidene]aniline (66), N'-{4-[(3-tert-butyl-4-chloro-1,2-thiazol-5-yl)oxy]-2-chloro-5-methylphenyl}-N-ethyl-N-methylimidoformamide (67), N'-{4-[(3-tert-butyl-4-chloro-1,2-thiazol-5-yl)oxy]-2-chloro-5-methylphenyl}-N-methyl-N-propan-2-ylimidoformamide (68), 4-[(3-tert-butyl-4-chloro-1,2-thiazol-5-yl)oxy]-2-chloro-5-methyl-N-[(E)-piperidin-1-ylmethylidene]aniline (69), N'-{4-[(3-tert-butyl-4-chloro-1,2-thiazol-5-yl)oxy]-5-chloro-2-methylphenyl}-N-ethyl-N-methylimidoformamide (70), N'-{4-[(3-tert-butyl-4-chloro-1,2-thiazol-5-yl)oxy]-5-chloro-2-methylphenyl}-N-methyl-N-propan-2-ylimidoformamide (71), 4-[(3-tert-butyl-4-chloro-1,2-thiazol-5-yl)oxy]-5-chloro-2-methyl-N-[(E)-piperidin-1-ylmethylidene]aniline (72), N'-{4-[(3-tert-butyl-1,2-thiazol-5-yl)oxy]-2,5-dimethylphenyl}-N,N-dimethylimidoformamide (73), N'-{4-[(3-tert-butyl-1,2-thiazol-5-yl)oxy]-2,5-dimethylphenyl}-N-ethyl-N-methylimidoformamide (74), N'-{4-[(3-tert-butyl-1,2-thiazol-5-yl)oxy]-2,5-dimethylphenyl}-N-methyl-N-propylimidoformamide (75), N'-(4-{[4-cyano-3-(3-fluorophenyl)-1,2-thiazol-5-yl]oxy}-2,5-dimethylphenyl)-N,N-dimethylimidoformamide (76), N'-(4-{[4-cyano-3-(3-fluorophenyl)-1,2-thiazol-5-yl]oxy}-2,5-dimethylphenyl)-N-methyl-N-propan-2-ylimidoformamide (77), N'-(4-{[4-cyano-3-(3-fluorophenyl)-1,2-thiazol-5-yl]oxy}-2,5-dimethylphenyl)-N-ethyl-N-methylimidoformamide (78), N'-(4-{[4-cyano-3-(2-methylphenyl)-1,2-thiazol-5-yl]oxy}-2,5-dimethylphenyl)-N,N-dimethylimidoformamide (79), N'-(4-{[4-cyano-3-(2-methylphenyl)-1,2-thiazol-5-yl]oxy}-2,5-dimethylphenyl)-N-methyl-N-propan-2-ylimidoformamide (80), N'-(4-{[4-cyano-3-(2-methylphenyl)-1,2-thiazol-5-yl]oxy}-2,5-dimethylphenyl)-N-ethyl-N-methylimidoformamide (81), N'-{4-[(3-tert-butyl-4-cyano-1,2-thiazol-5-yl)oxy]-2,5-difluorophenyl}-N-ethyl-N-methylimidoformamide (82), N'-{4-[(4-chloro-3-methyl-1,2-thiazol-5-yl)oxy]-2,5-dimethylphenyl}-N-ethyl-N-methylimidoformamide (83), 4-[(4-chloro-3-methyl-1,2-thiazol-5-yl)oxy]-2,5-dimethyl-N-[(E)-piperidin-1-ylmethylidene]aniline (84), N'-{5-chloro-4-[(4-chloro-3-methyl-1,2-thiazol-5-yl)oxy]-2-methylphenyl}-N-ethyl-N-methylimidoformamide (85), 5-chloro-4-[(4-chloro-3-methyl-1,2-thiazol-5-yl)oxy]-2-methyl-N-[(E)-piperidin-1-ylmethylidene]aniline (86), N'-{2-chloro-4-[(4-chloro-3-methyl-1,2-thiazol-5-yl)oxy]-5-methylphenyl}-N-ethyl-N-methylimidoformamide (87), 2-chloro-4-[(4-chloro-3-methyl-1,2-thiazol-5-yl)oxy]-5-methyl-N-[(E)-piperidin-1-ylmethylidene]aniline (88), N'-(2-chloro-4-{[4-cyano-3-(3-fluorophenyl)-1,2-thiazol-5-yl]oxy}-5-methylphenyl)-N-ethyl-N-methylimidoformamide (89), N'-(2-chloro-4-{[3-(2-chlorophenyl)-4-cyano-1,2-thiazol-5-yl]oxy}-5-methylphenyl)-N,N-dimethylimidoformamide (90), N'-(2-chloro-4-{[3-(2-chlorophenyl)-4-cyano-1,2-thiazol-5-yl]oxy}-5-methylphenyl)-N-ethyl-N-methylimidoformamide (91), N'-(2-chloro-4-{[3-(2-chlorophenyl)-4-cyano-1,2-thiazol-5-yl]oxy}-5-methylphenyl)-N-methyl-N-propan-2-ylimidoformamide (92), N'-(5-chloro-4-{[4-cyano-3-(2-methylphenyl)-1,2-thiazol-5-yl]oxy}-2-methylphenyl)-N,N-dimethylimidoformamide (93), N'-(5-chloro-4-{[4-cyano-3-(2-methylphenyl)-1,2-thiazol-5-yl]oxy}-2-methylphenyl)-N-methyl-N-propan-2-ylimidoformamide (94), N'-(5-chloro-4-{[4-cyano-3-(2-methylphenyl)-1,2-thiazol-5-yl]oxy}-2-methylphenyl)-N-ethyl-N-methylimidoformamide (95), N'-(4-{[4-cyano-3-(2,2-dimethylpropyl)-1,2-thiazol-5-yl]oxy}-2,5-dimethylphenyl)-N,N-dimethylimidoformamide (96), N'-(4-{[4-cyano-3-(2,2-dimethylpropyl)-1,2-thiazol-5-yl]oxy}-2,5-dimethylphenyl)-N-methyl-N-propan-2-ylimidoformamide (97), N'-(4-{[4-cyano-3-(2,2-dimethylpropyl)-1,2-thiazol-5-yl]oxy}-2,5-dimethylphenyl)-N-ethyl-N-methylimidoformamide (98), N'-(4-{[3-(1-chlorocyclopropyl)-4-cyano-1,2-thiazol-5-yl]oxy}-2,5-dimethylphenyl)-N,N-dimethylimidoformamide (99), N'-(4-{[3-(1-chlorocyclopropyl)-4-cyano-1,2-thiazol-5-yl)oxy}-2,5-dimethylphenyl)-N-ethyl-N-methylimidoformamide (100), N'-(4-{[3-(1-chlorocyclopropyl)-4-cyano-1,2-thiazol-5-yl]oxy}-2,5-dimethylphenyl)-N-methyl-N-propan-2-ylimidoformamide (101), N'-(5-chloro-4-{[4-cyano-3-(2,2-dimethylpropyl)-1,2-thiazol-5-yl]oxy}-2-methylphenyl)-N,N-dimethylimidoformamide (102), N'-{4-[(4-bromo-3-methyl-1,2-thiazol-5-yl)oxy]-2,5-dimethylphenyl}-N-ethyl-N-methylimidoformamide (103), N'-(2-chloro-4-{[4-cyano-3-(3-fluorophenyl)-1,2-thiazol-5-yl]oxy}-5-methylphenyl)-N,N-dimethylimidoformamide (104), N'-(2-chloro-4-{[4-cyano-3-(3-fluorophenyl)-1,2-thiazol-5-yl]oxy}-5-methylphenyl)-N-methyl-N-propan-2-ylimidoformamide (105), N'-{4-[(3-tert-butyl-4-cyano-1,2-thiazol-5-yl)oxy]-2,5-difluorophenyl}-N-methyl-N-propan-2-ylimidoformamide (106), 4-[(4-bromo-3-methyl-1,2-thiazol-5-yl)oxy]-2,5-dimethyl-N-[(E)-piperidin-1-ylmethylidene]aniline (107), N'-{4-[(4-bromo-3-methyl-1,2-thiazol-5-yl)oxy]-5-chloro-2-methylphenyl}-N-ethyl-N-methylimidoformamide (108), 4-[(4-bromo-3-methyl-1,2-thiazol-5-yl)oxy]-5-chloro-2-methyl-N-[(E)-piperidin-1-ylmethylidene]aniline (109), N'-{4-[(4-bromo-3-methyl-1,2-thiazol-5-yl)oxy]-2-chloro-5-methylphenyl}-N-ethyl-N- methylimidoformamide (110), 4-[(4-bromo-3-methyl-1,2-thiazol-5-yl)oxy]-2-chloro-5-methyl-N-[(E)-piperidin-1-ylmethylidene]aniline (111), N'-(5-chloro-4-{[4-cyano-3-(2,2-dimethylpropyl)-1,2-thiazol-5-yl]oxy}-2-methylphenyl)-N-methyl-N-propan-2-ylimidoformamide (112), N'-(5-chloro-4-{[4-cyano-3-(2,2-dimethylpropyl)-1,2-thiazol-5-yl]oxy}-2-methylphenyl)-N-ethyl-N-methylimidoformamide (113), N'-(5-chloro-4-{[4-cyano-3-(3-fluorophenyl)-1,2-thiazol-5-yl]oxy}-2-methylphenyl)-N,N-dimethylimidoformamide (114), N'-(2-chloro-4-{[4-cyano-3-(2-methylphenyl)-1,2-thiazol-5-yl]oxy}-5-methylphenyl)-N,N-dimethylimidoformamide (115), N'-(2-chloro-4-{[4-cyano-3-(2-methylphenyl)-1,2-thiazol-5-yl]oxy}-5-methylphenyl)-N-methyl-N-propan-2-ylimidoformamide (116), N'-(2-chloro-4-{[4-cyano-3-(2,2-dimethylpropyl)-1,2-thiazol-5-yl]oxy}-5-methylphenyl)-N,N-dimethylimidoformamide (117), N'-(2-chloro-4-{[4-cyano-3-(2,2-dimethylpropyl)-1,2-thiazol-5-yl]oxy}-5-methylphenyl)-N-methyl-N-propan-2-ylimidoformamide (118), N'-(2-chloro-4-{[4-cyano-3-(2,2-dimethylpropyl)-1,2-thiazol-5-yl]oxy}-5-methylphenyl)-N-ethyl-N-methylimidoformamide (119), N'-(4-{[4-cyano-3-(2-phenylpropan-2-yl)-1,2-thiazol-5-yl]oxy}-2,5-dimethylphenyl)-N,N-dimethylimidoformamide (120), N'-(4-{[4-cyano-3-(2-phenylpropan-2-yl)-1,2-thiazol-5-yl]oxy}-2,5-dimethylphenyl)-N-methyl-N-propan-2-ylimidoformamide (121), N'-(4-{[4-cyano-3-(2-phenylpropan-2-yl)-1,2-thiazol-5-yl]oxy}-2,5-dimethylphenyl)-N-ethyl-N-methylimidoformamide (122), N'-(4-{[3-(2-chlorophenyl)-4-cyano-1,2-thiazol-5-yl]oxy}-2,5-dimethylphenyl)-N,N-dimethylimidoformamide (123), N'-(4-{[3-(2-chlorophenyl)-4-cyano-1,2-thiazol-5-yl]oxy}-2,5-dimethylphenyl)-N-methyl-N-propan-2-ylimidoformamide (124), N'-(4-{[3-(2-chlorophenyl)-4-cyano-1,2-thiazol-5-yl]oxy}-2,5-dimethylphenyl)-N-ethyl-N-methylimidoformamide (125), N'-(5-chloro-4-{[3-(2-chlorophenyl)-4-cyano-1,2-thiazol-5-yl]oxy}-2-methylphenyl)-N,N-dimethylimidoformamide (126), N'-(4-{[4-cyano-3-(2-fluorophenyl)-1,2-thiazol-5-yl]oxy}-2,5-dimethylphenyl)-N,N-dimethylimidoformamide (127), N'-(4-{[4-cyano-3-(2-fluorophenyl)-1,2-thiazol-5-yl]oxy}-2,5-dimethylphenyl)-N-methyl-N-propan-2-ylimidoformamide (128), N'-(4-{[4-cyano-3-(2-fluorophenyl)-1,2-thiazol-5-yl]oxy}-2,5-dimethylphenyl)-N-ethyl-N-methylimidoformamide (129), N'-(5-chloro-4-{[4-cyano-3-(3-fluorophenyl)-1,2-thiazol-5-yl]oxy}-2-methylphenyl)-N-ethyl-N-methylimidoformamide (130), N'-(2-chloro-4-{[4-cyano-3-(2-methylphenyl)-1,2-thiazol-5-yl]oxy}-5-methylphenyl)-N-ethyl-N-methylimidoformamide (131), N'-(5-chloro-4-{[3-(2-chlorophenyl)-4-cyano-1,2-thiazol-5-yl]oxy}-2-methylphenyl)-N-ethyl-N-methylimidoformamide (132), N'-(2-chloro-4-{[4-cyano-3-(2-fluorophenyl)-1,2-thiazol-5-yl]oxy}-5-methylphenyl)-N,N-dimethylimidoformamide (133), N'-(5-chloro-4-{[3-(2-chlorophenyl)-4-cyano-1,2-thiazol-5-yl]oxy}-2-methylphenyl)-N-methyl-N-propan-2-ylimidoformamide (134), N'-(2-chloro-4-{[4-cyano-3-(2-fluorophenyl)-1,2-thiazol-5-yl]oxy}-5-methylphenyl)-N-methyl-N-propan-2-ylimidoformamide (135), N'-(2-chloro-4-{[4-cyano-3-(2-fluorophenyl)-1,2-thiazol-5-yl]oxy}-5-methylphenyl)-N-ethyl-N-methylimidoformamide (136), N'-(5-chloro-4-{[4-cyano-3-(2-fluorophenyl)-1,2-thiazol-5-yl]oxy}-2-methylphenyl)-N,N-dimethylimidoformamide (137), N'-(5-chloro-4-{[4-cyano-3-(2-fluorophenyl)-1,2-thiazol-5-yl]oxy}-2-methylphenyl)-N-methyl-N-propan-2-ylimidoformamide (138), N'-(5-chloro-4-{[4-cyano-3-(2-fluorophenyl)-1,2-thiazol-5-yl]oxy}-2-methylphenyl)-N-ethyl-N-methylimidoformamide (139), N'-(2-chloro-4-{[3-(1-chlorocyclopropyl)-4-cyano-1,2-thiazol-5-yl]oxy}-5-methylphenyl)-N,N-dimethylimidoformamide (140), N'-(2-chloro-4-{[3-(1-chlorocyclopropyl)-4-cyano-1,2-thiazol-5-yl]oxy}-5-methylphenyl)-N-methyl-N-propan-2-ylimidoformamide (141), N'-(2-chloro-4-{[3-(1-chlorocyclopropyl)-4-cyano-1,2-thiazol-5-yl]oxy}-5-methylphenyl)-N-ethyl-N-methylimidoformamide (142), N'-(5-chloro-4-{[3-(1-chlorocyclopropyl)-4-cyano-1,2-thiazol-5-yl]oxy}-2-methylphenyl)-N,N-dimethylimidoformamide (143), ethyl 5-(2,5-dimethyl-4-{[(E)-piperidin-1-ylmethylidene]amino}phenoxy)-3-methyl-1,2-thiazole-4-carboxylate (144), ethyl 5-[4-({(E)-[ethyl(methyl)amino]methylidene}amino)-2,5-dimethylphenoxy]-3-methyl-1,2-thiazole-4-carboxylate (145), ethyl 5-[2,5-dimethyl-44{(E)-[methyl(propan-2-yl)amino]-methylidene}amino)phenoxy]-3-methyl-1,2-thiazole-4-carboxylate (146), ethyl 5-[5-chloro-4-({(E)-[ethyl(methyl)amino]methylidene}amino)-2-methylphenoxy]-3-methyl-1,2-thiazole-4-carboxylate (147), ethyl 5-[5-chloro-2-methyl-44{(E)-[methyl(propan-2-yl)amino]-methylidene}amino)phenoxy]-3-methyl-1,2-thiazole-4-carboxylate (148), ethyl 5-(2-chloro-5-methyl-4-{[(E)-piperidin-1-ylmethylidene]amino}phenoxy)-3-methyl-1,2-thiazole-4-carboxylate (149), ethyl 5-[2-chloro-4-({(E)-[ethyl(methyl)amino]methylidene}amino)-5-methylphenoxy]-3-methyl-1,2-thiazole-4-carboxylate (150), ethyl 5-[2-chloro-5-methyl-4-({(E)-[methyl(propan-2-yl)amino]methylidene}amino)phenoxy]-3-methyl-1,2-thiazole-4-carboxylate (151), ethyl 5-(5-chloro-2-methyl-4-{[(E)-piperidin-1-ylmethylidene]-amino}phenoxy)-3-methyl-1,2-thiazole-4-carboxylate (152), N'-(5-chloro-4-{[3-(1-chlorocyclopropyl)-4-cyano-1,2-thiazol-5-yl]oxy}-2-methylphenyl)-N-ethyl-N-methylimidoformamide (153), N'-(5-chloro-4-{[3-(1-chlorocyclopropyl)-4-cyano-1,2-thiazol-5-yl]oxy}-2-methylphenyl)-N-methyl-N-propan-2-ylimidoformamide (154), N-[(E)-({4-[(3-tert-butyl-4-cyano-1,2-thiazol-5-yl)oxy]-2,5-dimethylphenyl}imino)methyl]-N-methylethanaminium chloride (155), N-[(E)-({4-[(3-tert-butyl-4-cyano-1,2-thiazol-5-yl)oxy]-2,5-dimethylphenyl}imino)methyl]-N-methylethanaminium bromide (156), N'-{4-[(3-tert-butyl-4-cyano-1,2-thiazol-5-yl)oxy]-2,5-dimethylphenyl}-N-ethyl-N-methylimidoformamide-1,2-benzothiazol-3(2H)-one 1,1-dioxide (1:1) (157), N-ethyl-N'-{4-[(4-iodo-3-methyl-1,2-thiazol-5-yl)oxy]-2,5-dimethylphenyl}-N-methylimidoformamide (158), N'-(4-{[4-cyano-3-(4-methylphenyl)-1,2-thiazol-5-yl]oxy}-2,5-dimethylphenyl)-N-ethyl-N-methylimidoformamide (159), N'-(4-{[4-cyano-3-(4-methylphenyl)-1,2-thiazol-5-yl]oxy}-2,5-dimethylphenyl)-N,N-dimethylimidoformamide (160), N'-(5-chloro-4-{[4-cyano-3-(4-methylphenyl)-1,2-thiazol-5-yl]oxy}-2-methylphenyl)-N,N-dimethylimidoformamide (161), N'-(5-chloro-4-{[4-cyano-3-(4-methylphenyl)-1,2-thiazol-5-yl]oxy}-2-methylphenyl)-N-methyl-N-propan-2-ylimidoformamide (162), N'-{4-[(3,4-dimethyl-1,2-thiazol-5-yl)oxy]-2,5-dimethylphenyl}-N-ethyl-N-methylimidoformamide (163), N'-(4-{[4-cyano-3-(2,3-dimethylbutan-2-yl)-1,2-thiazol-5-yl]oxy}-2,5-dimethylphenyl)-N,N-dimethylimidoformamide (164), N'-(4-{[4-cyano-3-(2,3-dimethylbutan-2-yl)-1,2-thiazol-5-yl]oxy}-2,5-dimethylphenyl)-N-methyl-N-propan-2-ylimidoformamide (165), N'-(4-{[4-cyano-3-(2,3-dimethylbutan-2-yl)-1,2-thiazol-5-yl]oxy}-2,5-dimethylphenyl)-N-ethyl-N-methylimidoformamide (166), N'-{4-[(3-tert-butyl-4-cyano-1,2-thiazol-5-yl)oxy]-5-chloro-2-methylphenyl}-N-ethyl-N-methylimidoformamide (167), N'-{5-tert-butyl-4-[(3-tert-butyl-4-cyano-1,2-thiazol-5-yl)oxy]-2-methylphenyl}-N-ethyl-N-methylimidoformamide (168), N'-{5-bromo-4-[(3-tert-butyl-4-cyano-1,2-thiazol-5-yl)oxy]-2-methylphenyl}-N-ethyl-N-methylimido formamide (169), N'-[4-(2,1-benzothiazol-3-yloxy)-5-chloro-2-methylphenyl]-N-ethyl-N-methylimidoformamide (170), N'-[4-(2,1-benzothiazol-3-yloxy)-5-chloro-2-methylphenyl]-N,N-dimethylimidoformamide (171), N'-[4-(2,1-benzothiazol-3-yloxy)-5-chloro-2-methylphenyl]-N-methyl-N-propan-2-ylimidoformamide (172), N'-(2-chloro-4-{[4-cyano-3-(1-phenylethyl)-1,2-thiazol-5-yl]oxy}-5-methylphenyl)-N-ethyl-N-methylimidoformamide (173), N'-(4-{[4-cyano-3-(1-phenylethyl)-1,2-thiazol-5-yl]oxy}-2,5-dimethylphenyl)-N-ethyl-N-methylimidoformamide (174), N'-[4-(2,1-benzothiazol-3-yloxy)-2-chloro-5-methylphenyl]-N-ethyl-N-methylimidoformamide (175), N'-(2-chloro-4-{[4-cyano-3-(1-phenylethyl)-1,2-thiazol-5-yl]oxy}-5-methylphenyl)-N-methyl-N-propan-2-ylimidoformamide (176), N'-(4-{[4-cyano-3-(1-methylcyclopropyl)-1,2-thiazol-5-yl]oxy}-2,5-dimethylphenyl)-N,N-dimethylimidoformamide (177), N'-(4-{[4-cyano-3-(1-methylcyclopropyl)-1,2-thiazol-5-yl]oxy}-2,5-dimethylphenyl)-N-methyl-N-propan-2-ylimidoformamide (178), N'-(4-{[4-cyano-3-(1-methylcyclopropyl)-1,2-thiazol-5-yl]oxy}-2,5-dimethylphenyl)-N-ethyl-N-methylimidoformamide (179), N'-(4-{[4-cyano-3-(2-methylbutan-2-yl)-1,2-thiazol-5-yl]oxy}-2,5-dimethylphenyl)-N-methyl-N-propan-2-ylimidoformamide (180), N'-(4-{[4-cyano-3-(2-methylbutan-2-yl)-1,2-thiazol-5-yl]oxy}-2,5-dimethylphenyl)-N-ethyl-N-methylimidoformamide (181), N'-{4-[(3-benzyl-4-cyano-1,2-thiazol-5-yl)oxy]-2,5-dimethylphenyl}-N-ethyl-N-methylimidoformamide (182), N'-(4-{[4-cyano-3-(2-methylbutan-2-yl)-1,2-thiazol-5-yl]oxy}-2,5-dimethylphenyl)-N,N-dimethylimidoformamide (183), N'-{4-[(3-tert-butyl-4-cyano-1,2-thiazol-5-yl)oxy]-5-fluoro-2-methylphenyl}-N-ethyl-N-methylimido formamide (184), N'-(5-chloro-4-{[4-cyano-3-(3-methylpentan-3-yl)-1,2-thiazol-5-yl]oxy}-2-methylphenyl)-N,N-dimethylimidoformamide (185), N'-(5-chloro-4-{[4-cyano-3-(3-methylpentan-3-yl)-1,2-thiazol-5-yl]oxy}-2-methylphenyl)-N-ethyl-N-methylimidoformamide (186), N'-(5-chloro-4-{[4-cyano-3-(3-methylpentan-3-yl)-1,2-thiazol-5-yl]oxy}-2-methylphenyl)-N-methyl-N-propan-2-ylimidoformamide (187), N'-(4-{[4-cyano-3-(3-methylpentan-3-yl)-1,2-thiazol-5-yl]oxy}-2,5-dimethylphenyl)-N,N-dimethylimidoformamide (188), N'-(4-{[4-cyano-3-(3-methylpentan-3-yl)-1,2-thiazol-5-yl]oxy}-2,5-dimethylphenyl)-N-ethyl-N-methylimidoformamide (189), N'-(4-{[4-cyano-3-(3-methylpentan-3-yl)-1,2-thiazol-5-yl]oxy}-2,5-dimethylphenyl)-N-methyl-N-propan-2-ylimidoformamide (190), N'-(2-chloro-4-{[3-(4-chlorobenzyl)-4-cyano-1,2-thiazol-5-yl]oxy}-5-methylphenyl)-N-ethyl-N-methylimidoformamide (191), N'-(2-chloro-4-{[4-cyano-3-(3-methylpentan-3-yl)-1,2-thiazol-5-yl]oxy}-5-methylphenyl)-N,N-dimethylimidoformamide (192), N'-(2-chloro-4-{[4-cyano-3-(3-methylpentan-3-yl)-1,2-thiazol-5-yl]oxy}-5-methylphenyl)-N-ethyl-N-methylimidoformamide (193), N'-{4-[(3-tert-butyl-4-cyano-1,2-thiazol-5-yl)oxy]-5-cyano-2-methylphenyl}-N-ethyl-N-methylimido formamide (194), N'-(4-{[4-cyano-3-(1-methylcyclohexyl)-1,2-thiazol-5-yl]oxy}-2,5-dimethylphenyl)-N-ethyl-N-methylimidoformamide (195), N'-(2-chloro-4-{[4-cyano-3-(1-phenylethyl)-1,2-thiazol-5-yl]oxy}-5-methylphenyl)-N,N-dimethylimidoformamide (196), N'-(4-{[4-cyano-3-(1-methylcyclohexyl)-1,2-thiazol-5-yl]oxy}-2,5-dimethylphenyl)-N,N-dimethylimido formamide (197), N'-(4-{[4-cyano-3-(1-methylcyclohexyl)-1,2-thiazol-5-yl]oxy}-2,5-dimethylphenyl)-N-methyl-N-propan-2-ylimidoformamide (198), N'-(5-chloro-4-{[4-cyano-3-(2-methylbutan-2-yl)-1,2-thiazol-5-yl]oxy}-2-methylphenyl)-N-ethyl-N-methylimidoformamide (199), N'-(5-chloro-4-{[4-cyano-3-(2-methylbutan-2-yl)-1,2-thiazol-5-yl]oxy}-2-methylphenyl)-N-methyl-N-propan-2-ylimidoformamide (200), N'-(5-chloro-4-{[4-cyano-3-(2-methylbutan-2-yl)-1,2-thiazol-5-yl]oxy}-2-methylphenyl)-N,N-dimethylimidoformamide (201), N'-{4-[(3,4-dichloro-1,2-thiazol-5-yl)oxy]-2,5-dimethylphenyl}-N-ethyl-N-methylimidoformamide (202), N'-{2,5-dimethyl-4-[(3-methyl-1,2-thiazol-5-yl)oxy]phenyl}-N-ethyl-N-methylimidoformamide (203), N'-{4-[(3-tert-butyl-4-cyano-1,2-thiazol-5-yl)oxy]-2-chloro-5-methylphenyl}-N-ethyl-N-methylimidoformamide hydrochloride (1:1) (204), N'-(2-chloro-4-{[4-cyano-3-(2,4-dichlorophenyl)-1,2-thiazol-5-yl]oxy}-5-methylphenyl)-N,N-dimethylimidoformamide (205), N'-(2-chloro-4-{[4-cyano-3-(2,4-dichlorophenyl)-1,2-thiazol-5-yl]oxy}-5-methylphenyl)-N-ethyl-N-methylimidoformamide (206), N'-(2-chloro-4-{[4-cyano-3-(2,4-dichlorophenyl)-1,2-thiazol-5-yl]oxy}-5-methylphenyl)-N-methyl-N-propan-2-ylimidoformamide (207), N'-[4-({4-cyano-3-[(3S,5S,7S)-tricyclo[3.3.1.1$^{3,7}$]dec-1-yl]-1,2-thiazol-5-yl}oxy)-2,5-dimethylphenyl]-N-ethyl-N-methylimidoformamide (208), N'-[4-({4-cyano-3-[(3S,5S,7S)-tricyclo[3.3.1.1$^{3,7}$]dec-1-yl]-1,2-thiazol-5-yl}oxy)-2,5-dimethylphenyl]-N-methyl-N-propan-2-ylimidoformamide (209), N'-(4-{[4-cyano-3-(2,4-dichlorophenyl)-1,2-thiazol-5-yl]oxy}-2,5-dimethylphenyl)-N-ethyl-N-methylimidoformamide (210), N'-(4-{[4-cyano-3-(2,4-dichlorophenyl)-1,2-thiazol-5-yl]oxy}-2,5-dimethylphenyl)-N,N-dimethylimidoformamide (211), N'-(4-{[4-cyano-3-(2,4-dichlorophenyl)-1,2-thiazol-5-yl]oxy}-2,5-dimethylphenyl)-N-methyl-N-propan-2-ylimidoformamide (212), N'-[4-({4-cyano-3-[(3S,5S,7S)-tricyclo[3.3.1.1$^{3,7}$]dec-1-yl]-1,2-thiazol-5-yl}oxy)-2,5-dimethylphenyl]-N,N-dimethylimidoformamide (213), N'-{4-[(4-chloro-2,1-benzothiazol-3-yl)oxy]-2,5-dimethylphenyl}-N-ethyl-N-methylimidoformamide (214), N'-(4-{[4-cyano-3-(2-fluoropropan-2-yl)-1,2-thiazol-5-yl]oxy}-2,5-dimethylphenyl)-N,N-dimethylimidoformamide (215), N'-(4-{[4-cyano-3-(2-fluoropropan-2-yl)-1,2-thiazol-5-yl]oxy}-2,5-dimethylphenyl)-N-ethyl-N-methylimidoformamide (216), N'-(5-chloro-4-{[4-cyano-3-(2,4-dichlorophenyl)-1,2-thiazol-5-yl]oxy}-2-methylphenyl)-N,N-dimethylimidoformamide (217), N'-[2-chloro-4-({4-cyano-3-[4-(trifluoromethyl)phenyl]-1,2-thiazol-5-yl}oxy)-5-methylphenyl]-N,N-dimethylimidoformamide (218), N'-[2-chloro-4-({4-cyano-3-[4-(trifluoromethyl)phenyl]-1,2-thiazol-5-yl}oxy)-5-methylphenyl]-N-methyl-N-propan-2-ylimidoformamide (219), N'-[2-chloro-4-({4-cyano-3-[4-(trifluoromethyl)phenyl]-1,2-thiazol-5-yl}oxy)-5-methylphenyl]-N-ethyl-N-methylimidoformamide (220), N'-(4-{[4-cyano-3-(propan-2-yl)-1,2-thiazol-5-yl]oxy}-2,5-dimethylphenyl)-N-ethyl-N-methylimidoformamide (221), N'-[5-chloro-4-({4-cyano-3-[4-(trifluoromethyl)phenyl]-1,2-thiazol-5-yl}oxy)-2-methylphenyl]-N,N-dimethylimidoformamide (222), N'-[5-chloro-4-({4-cyano-3-[4-(trifluoromethyl)phenyl]-1,2-thiazol-5-yl}oxy)-2-methylphenyl]-N-methyl-N-propan-2-ylimidoformamide (223), N'-[5-chloro-4-({4-cyano-3-[4-(trifluoromethyl)phenyl]-1,2-thiazol-5-yl}oxy)-2-methylphenyl]-N-ethyl-N-methylimidoformamide (224), N'-(5-chloro-4-{[4-cyano-3-(2,4-dichlorophenyl)-1,2-thiazol-5-yl]oxy}-2-methylphenyl)-N-methyl-N-propan-2-ylimidoformamide (225), N'-(2-chloro-4-{[4-cyano-3-(propan-2-yl)-1,2-thiazol-5-yl]oxy}-5-methylphenyl)-N,N-dimethylimidoformamide (226), N'-(2-chloro-4-{[4-cyano- 3-(propan-2-yl)-1,2-thiazol-5-yl]oxy}-5-methylphenyl)-N-methyl-N-propan-2-ylimidoformamide (227), N'-(2-chloro-4-{[4-cyano-3-(propan-2-yl)-1,2-thiazol-5-yl]oxy}-5-methylphenyl)-N-ethyl-N-methylimidoformamide (228), N'-(4-{[4-cyano-3-(propan-2-yl)-1,2-thiazol-5-yl]oxy}-2,5-dimethylphenyl)-N,N-dimethylimidoformamide (229), N'-(2-chloro-4-{[4-cyano-3-(2-fluoropropan-2-yl)-1,2-thiazol-5-yl]oxy}-5-methylphenyl)-N,N-dimethylimidoformamide (230), N'-(5-chloro-4-{[4-cyano-3-(2-fluoropropan-2-yl)-1,2-thiazol-5-yl]oxy}-2-methylphenyl)-N-ethyl-N-methylimidoformamide (231), N'-(5-chloro-4-{[4-cyano-3-(2-fluoropropan-2-yl)-1,2-thiazol-5-yl]oxy}-2-methylphenyl)-N-methyl-N-propan-2-ylimidoformamide (232), N'-(4-{[4-cyano-3-(2-fluoropropan-2-yl)-1,2-thiazol-5-yl]oxy}-2,5-dimethylphenyl)-N-methyl-N-propan-2-ylimidoformamide (233), N'-(5-chloro-4-{[4-cyano-3-(propan-2-yl)-1,2-thiazol-5-yl]oxy}-2-methylphenyl)-N,N-dimethylimidoformamide (234), N'-(5-chloro-4-{[4-cyano-3-(propan-2-yl)-1,2-thiazol-5-yl]oxy}-2-methylphenyl)-N-methyl-N-propan-2-ylimidoformamide (235), N'-(5-chloro-4-{[4-cyano-3-(propan-2-yl)-1,2-thiazol-5-yl]oxy}-2-methylphenyl)-N-ethyl-N-methylimidoformamide (236), N'-(4-{[4-cyano-3-(propan-2-yl)-1,2-thiazol-5-yl]oxy}-2,5-dimethylphenyl)-N-methyl-N-propan-2-ylimidoformamide (237), N'-(2-chloro-4-{[4-cyano-3-(2-fluoropropan-2-yl)-1,2-thiazol-5-yl]oxy}-5-methylphenyl)-N-methyl-N-propan-2-ylimidoformamide (238), N'-(2-chloro-4-{[3-(2-chloro-4-fluorophenyl)-4-cyano-1,2-thiazol-5-yl]oxy}-5-methylphenyl)-N-ethyl-N-methylimidoformamide (239), N'-(2-chloro-4-{[3-(2-chloro-4-fluorophenyl)-4-cyano-1,2-thiazol-5-yl]oxy}-5-methylphenyl)-N-methyl-N-propan-2-ylimidoformamide (240), N'-(5-chloro-4-{[4-cyano-3-(2,4-dichlorophenyl)-1,2-thiazol-5-yl]oxy}-2-methylphenyl)-N-ethyl-N-methylimidoformamide (241), N'-[4-({3-[2-(4-chlorophenyl)propan-2-yl]-4-cyano-1,2-thiazol-5-yl}oxy)-2,5-dimethylphenyl]-N-ethyl-N-methylimidoformamide (242), N'-(5-chloro-4-{[3-(2-chloro-4-fluorophenyl)-4-cyano-1,2-thiazol-5-yl]oxy}-2-methylphenyl)-N-ethyl-N-methylimidoformamide (243), N'-(5-chloro-4-{[3-(2-chloro-4-fluorophenyl)-4-cyano-1,2-thiazol-5-yl]oxy}-2-methylphenyl)-N-methyl-N-propan-2-ylimidoformamide (244), N'-(5-chloro-4-{[3-(2-chloro-4-fluorophenyl)-4-cyano-1,2-thiazol-5-yl]oxy}-2-methylphenyl)-N,N-dimethylimidoformamide (245), N'-(4-{[4-cyano-3-(2-methoxyphenyl)-1,2-thiazol-5-yl]oxy}-2,5-dimethylphenyl)-N-ethyl-N-methylimidoformamide (246), N'-(4-{[4-cyano-3-(2-methoxyphenyl)-1,2-thiazol-5-yl]oxy}-2,5-dimethylphenyl)-N-methyl-N-propan-2-ylimidoformamide (247), N'-(2-chloro-4-{[4-cyano-3-(4-methoxyphenyl)-1,2-thiazol-5-yl]oxy}-5-methylphenyl)-N-ethyl-N-methylimidoformamide (248), N'-(4-{[4-cyano-3-(2-methoxyphenyl)-1,2-thiazol-5-yl]oxy}-2,5-dimethylphenyl)-N,N-dimethylimidoformamide (249), N'-(4-{[4-cyano-3-(2,2-dichloro-1-ethyl-3-methylcyclopropyl)-1,2-thiazol-5-yl]oxy}-2,5-dimethylphenyl)-N-ethyl-N-methylimidoformamide (250), N'-(4-{[4-cyano-3-(4-methoxyphenyl)-1,2-thiazol-5-yl]oxy}-2,5-dimethylphenyl)-N-ethyl-N-methylimidoformamide (251), N'-(2-chloro-4-{[3-(2-chloro-4-fluorophenyl)-4-cyano-1,2-thiazol-5-yl]oxy}-5-methylphenyl)-N,N-dimethylimidoformamide (252), N'-(2-chloro-4-{[4-cyano-3-(4-methoxyphenyl)-1,2-thiazol-5-yl]oxy}-5-methylphenyl)-N-methyl-N-propan-2-ylimidoformamide (253), N'-(2-chloro-4-{[4-cyano-3-(4-methoxyphenyl)-1,2-thiazol-5-yl]oxy}-5-methylphenyl)-N,N-dimethylimidoformamide (254), N'-(5-chloro-4-{[4-cyano-3-(4-methoxyphenyl)-1,2-thiazol-5-yl]oxy}-2-methylphenyl)-N-ethyl-N-methylimidoformamide (255), N'-(5-chloro-4-{[4-cyano-3-(4-methoxyphenyl)-1,2-thiazol-5-yl]oxy}-2-methylphenyl)-N-methyl-N-propan-2-ylimidoformamide (256), N'-(5-chloro-4-{[4-cyano-3-(4-methoxyphenyl)-1,2-thiazol-5-yl]oxy}-2-methylphenyl)-N,N-dimethylimidoformamide (257), N'-(2-chloro-4-{[4-cyano-3-(2,2-dichloro-1-ethyl-3-methylcyclopropyl)-1,2-thiazol-5-yl]oxy}-5-methylphenyl)-N-ethyl-N-methylimidoformamide (258), N'-(2-chloro-4-{[4-cyano-3-(2,2-dichloro-1-ethyl-3-methylcyclopropyl)-1,2-thiazol-5-yl]oxy}-5-methylphenyl)-N,N-dimethylimidoformamide (259), N'-(5-chloro-4-{[4-cyano-3-(2,2-dichloro-1-ethyl-3-methylcyclopropyl)-1,2-thiazol-5-yl]oxy}-2-methylphenyl)-N-ethyl-N-methylimidoformamide (260), N'-(5-chloro-4-{[4-cyano-3-(2,2-dichloro-1-ethyl-3-methylcyclopropyl)-1,2-thiazol-5-yl]oxy}-2-methylphenyl)-N-methyl-N-propan-2-ylimidoformamide (261), N'-(5-chloro-4-{[4-cyano-3-(2,2-dichloro-1-ethyl-3-methylcyclopropyl)-1,2-thiazol-5-yl]oxy}-2-methylphenyl)-N,N-dimethylimidoformamide (262), N'-(5-chloro-4-{[4-cyano-3-(3-methoxyphenyl)-1,2-thiazol-5-yl]oxy}-2-methylphenyl)-N-ethyl-N-methylimidoformamide (263), N'-{4-[(4,7-dichloro-2,1-benzothiazol-3-yl)oxy]-2,5-dimethylphenyl}-N-ethyl-N-methylimidoformamide (264), N'-{4-[(4,7-dichloro-2,1-benzothiazol-3-yl)oxy]-2,5-dimethylphenyl}-N-methyl-N-propan-2-ylimidoformamide (265), N'-{4-[(4,7-dichloro-2,1-benzothiazol-3-yl)oxy]-2,5-dimethylphenyl}-N,N-dimethylimidoformamide (266), N'-(2-chloro-4-{[4-cyano-3-(2,2-dichloro-1-ethyl-3-methylcyclopropyl)-1,2-thiazol-5-yl]oxy}-5-methylphenyl)-N-methyl-N-propan-2-ylimidoformamide (267), N'-{4-[(4-chloro-2,1-benzothiazol-3-yl)oxy]-2,5-dimethylphenyl}-N-methyl-N-propan-2-ylimidoformamide (268), N'-{4-[(4-chloro-2,1-benzothiazol-3-yl)oxy]-2,5-dimethylphenyl}-N,N-dimethylimidoformamide (269), N'-(4-{[4-cyano-3-(4-methoxyphenyl)-1,2-thiazol-5-yl]oxy}-2,5-dimethylphenyl)-N,N-dimethylimidoformamide (270), N'-(4-{[4-cyano-3-(3-methoxyphenyl)-1,2-thiazol-5-yl]oxy}-2,5-dimethylphenyl)-N-ethyl-N-methylimidoformamide (271), N'-(4-{[4-cyano-3-(4-methoxyphenyl)-1,2-thiazol-5-yl]oxy}-2,5-dimethylphenyl)-N-methyl-N-propan-2-ylimidoformamide (272), N'-(4-{[4-cyano-3-(2,2-dichloro-1-ethyl-3-methylcyclopropyl)-1,2-thiazol-5-yl]oxy}-2,5-dimethylphenyl)-N,N-dimethylimidoformamide (273), N'-(5-chloro-4-{[4-cyano-3-(2-fluoropropan-2-yl)-1,2-thiazol-5-yl]oxy}-2-methylphenyl)-N,N-dimethylimidoformamide (274), N'-(2-chloro-4-{[4-cyano-3-(2-fluoropropan-2-yl)-1,2-thiazol-5-yl]oxy}-5-methylphenyl)-N-ethyl-N-methylimidoformamide (275), N'-(4-{[4-cyano-3-(2,2-dichloro-1-ethyl-3-methylcyclopropyl)-1,2-thiazol-5-yl]oxy}-2,5-dimethylphenyl)-N-methyl-N-propan-2-ylimidoformamide (276), N'-{2-chloro-4-[(4-chloro-2,1-benzothiazol-3-yl)oxy]-5-methylphenyl}-N-ethyl-N-methylimidoformamide (277), N'-{2-chloro-4-[(4,7-dichloro-2,1-benzothiazol-3-yl)oxy]-5-methylphenyl}-N-ethyl-N-methylimidoformamide (278), N'-{2-chloro-4-[(4,7-dichloro-2,1-benzothiazol-3-yl)oxy]-5-methylphenyl}-N-methyl-N-propan-2-ylimidoformamide (279), N'-{2-chloro-4-[(4-chloro-2,1-benzothiazol-3-yl)oxy]-5-methylphenyl}-N-methyl-N-propan-2-ylimidoformamide (280), N'-{2-chloro-4-[(4-chloro-2,1-benzothiazol-3-yl)oxy]-5-methylphenyl}-N,N-dimethylimido formamide (281), N'-{2-chloro-4-[(4,7-dichloro-2,1-benzothiazol-3-yl)oxy]-5-methylphenyl}-N,N-dimethylimidoformamide (282), N'-(4-{[3-(2-chloro-4-fluorophenyl)-4-cyano-1,2-thiazol-5-yl]oxy}-2,5-dimethylphenyl)-N-ethyl-N-methylimidoformamide (283), N'-(4-{[4-chloro-3-(propan-2-yl)-1,2-thiazol-5-yl]oxy}-2,5-dimethylphenyl)-N,N-dimethylimidoformamide (284), N'-

(4-{[4-chloro-3-(propan-2-yl)-1,2-thiazol-5-yl]oxy}-2,5-dimethylphenyl)-N-methyl-N-propan-2-ylimidoformamide (285), N'-(4-{[4-chloro-3-(propan-2-yl)-1,2-thiazol-5-yl]oxy}-2,5-dimethylphenyl)-N-ethyl-N-methylimidoformamide (286), N'-(2-chloro-4-{[4-chloro-3-(propan-2-yl)-1,2-thiazol-5-yl]oxy}-5-methylphenyl)-N-ethyl-N-methylimidoformamide (287), N'-{4-[(3-bromo-4-cyano-1,2-thiazol-5-yl)oxy]-2,5-dimethylphenyl}-N-ethyl-N-methylimidoformamide (288), N'-(4-{[4-bromo-3-(propan-2-yl)-1,2-thiazol-5-yl]oxy}-2,5-dimethylphenyl)-N-ethyl-N-methylimidoformamide (289), N'-{2-bromo-4-[(4-chloro-3-methyl-1,2-thiazol-5-yl)oxy]-5-methoxyphenyl}-N-ethyl-N-methylimidoformamide (290), N'-{2-chloro-4-[(4-chloro-3-methyl-1,2-thiazol-5-yl)oxy]-5-methoxyphenyl}-N-ethyl-N-methylimidoformamide (291), N'-{4-[(3-benzyl-4-chloro-1,2-thiazol-5-yl)oxy]-2,5-dimethylphenyl}-N-ethyl-N-methylimidoformamide (292), N'-(4-{[4-chloro-3-(4-chlorobenzyl)-1,2-thiazol-5-yl]oxy}-2,5-dimethylphenyl)-N-ethyl-N-methylimidoformamide (293), N'-{4-[(4-cyano-3-cyclohexyl-1,2-thiazol-5-yl)oxy]-2,5-dimethylphenyl}-N-ethyl-N-methylimidoformamide (294), N'-{4-[(4-cyano-3-cyclohexyl-1,2-thiazol-5-yl)oxy]-2,5-dimethylphenyl}-N,N-dimethylimidoformamide (295), N'-{4-[(4-cyano-3-cyclohexyl-1,2-thiazol-5-yl)oxy]-2,5-dimethylphenyl}-N-methyl-N-propan-2-ylimidoformamide (296), N'-{4-[(3-tert-butyl-1,2-thiazol-5-yl)oxy]-2-chloro-5-methylphenyl}-N-ethyl-N-methylimidoformamide (297), N'-(4-{[4-cyano-3-(1-fluoro-2-methylpropan-2-yl)-1,2-thiazol-5-yl]oxy}-2,5-dimethylphenyl)-N-methyl-N-propan-2-ylimidoformamide (298), N'-(4-{[4-cyano-3-(1-fluoro-2-methylpropan-2-yl)-1,2-thiazol-5-yl]oxy}-2,5-dimethylphenyl)-N,N-dimethylimidoformamide (299), N'-(2,5-dimethyl-4-{[3-(propan-2-yl)-1,2-thiazol-5-yl]oxy}phenyl)-N-ethyl-N-methylimidoformamide (300), N'-(4-{[4-cyano-3-(1-fluoro-2-methylpropan-2-yl)-1,2-thiazol-5-yl]oxy}-2,5-dimethylphenyl)-N-ethyl-N-methylimidoformamide (301), N'-[4-({3-[2-(4-chlorophenyl)propan-2-yl]-4-cyano-1,2-thiazol-5-yl}oxy)-2,5-dimethylphenyl]-N-methyl-N-propan-2-ylimidoformamide (302), N'-(4-{[4-bromo-3-(propan-2-yl)-1,2-thiazol-5-yl]oxy}-2-chloro-5-methylphenyl)-N-ethyl-N-methylimidoformamide (303), N'-(2-chloro-4-{[4-iodo-3-(propan-2-yl)-1,2-thiazol-5-yl]oxy}-5-methylphenyl)-N-ethyl-N-methylimidoformamide (304), N'-[4-({3-[2-(4-chlorophenyl)propan-2-yl]-4-cyano-1,2-thiazol-5-yl}oxy)-2,5-dimethylphenyl]-N,N-dimethylimidoformamide (305), N'-{2-chloro-4-[(4-cyano-3-cyclohexyl-1,2-thiazol-5-yl)oxy]-5-methylphenyl}-N-ethyl-N-methylimidoformamide (306), N'-{4-[(4-cyano-3-cyclopropyl-1,2-thiazol-5-yl)oxy]-2,5-dimethylphenyl}-N-ethyl-N-methylimidoformamide (307), N'-{4-[(4-cyano-3-cyclopropyl-1,2-thiazol-5-yl)oxy]-2,5-dimethylphenyl}-N,N-dimethylimidoformamide (308), N'-{4-[(4-cyano-3-cyclopropyl-1,2-thiazol-5-yl)oxy]-2,5-dimethylphenyl}-N-methyl-N-propan-2-ylimidoformamide (309), N'-{4-[(7-chloro-2,1-benzothiazol-3-yl)oxy]-2,5-dimethylphenyl}-N-ethyl-N-methylimidoformamide (310), N'-{4-[(7-chloro-2,1-benzothiazol-3-yl)oxy]-2,5-dimethylphenyl}-N,N-dimethylimidoformamide (311), N'-{4-[(7-chloro-2,1-benzothiazol-3-yl)oxy]-2,5-dimethylphenyl}-N-methyl-N-propan-2-ylimidoformamide (312), N'-(4-{[4-bromo-3-(propan-2-yl)-1,2-thiazol-5-yl]oxy}-2,5-dimethylphenyl)-N,N-dimethylimidoformamide (313) or their salts, N-oxides, metal complexes and their stereoisomers.

Preparation of the Amidines According to the Invention

The amidines according to the invention can be obtained by the process shown in schemes (Ia) and (Ib) below:

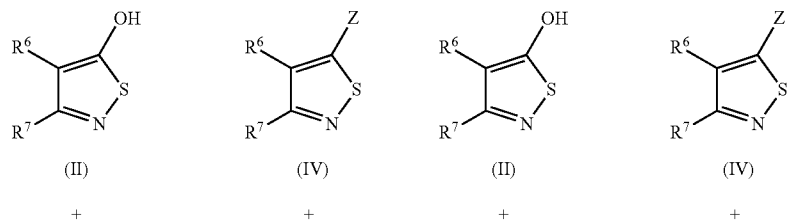

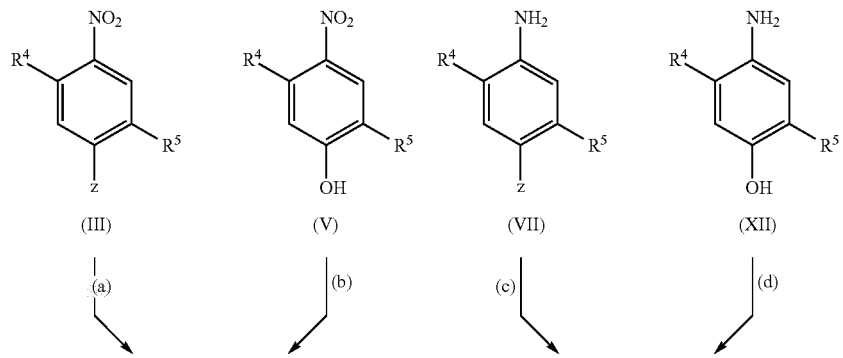

-continued
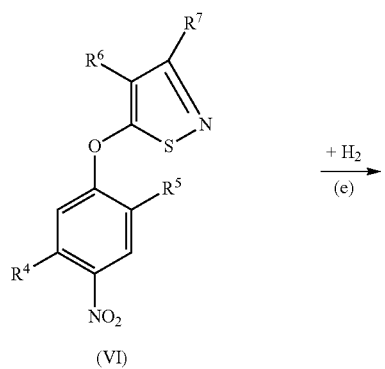 (VI)
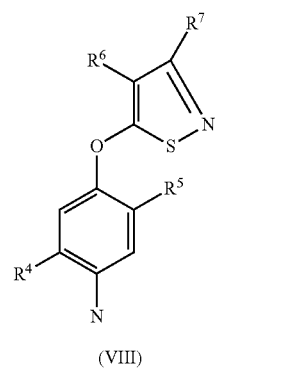 (VIII)
Scheme (Ib)
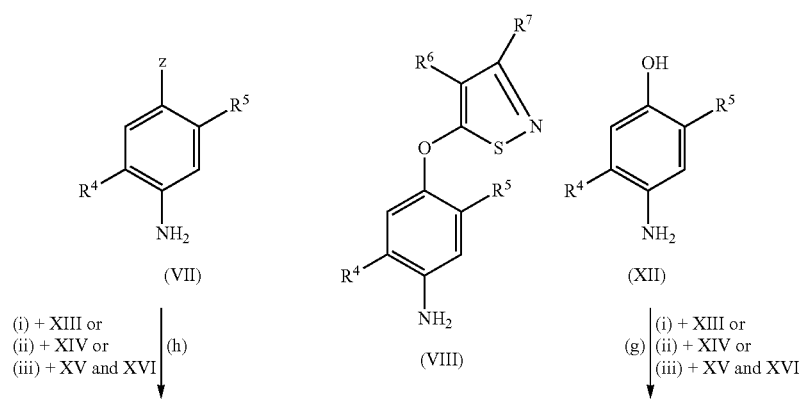
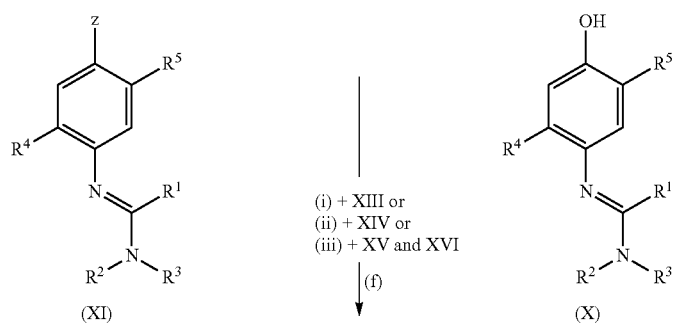

-continued

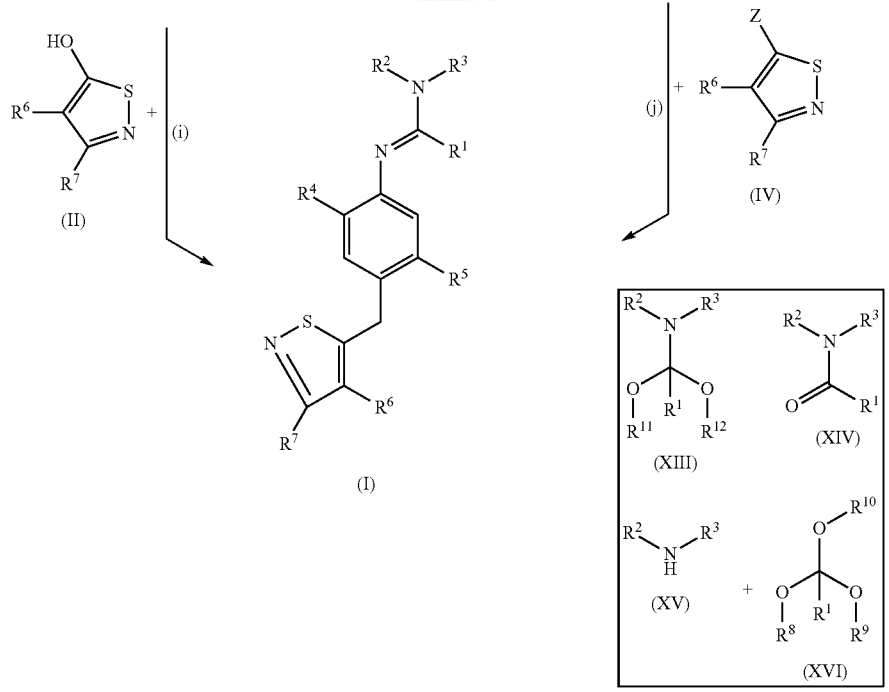

Step (a)

In one embodiment according to the invention, nitrobenzene derivates of the formula (III) are reacted with isothiazolyl alcohols of the formula (II) or the alkoxides prepared therefrom according to the reaction scheme below to give nitrophenyl ethers of the formula (VI):

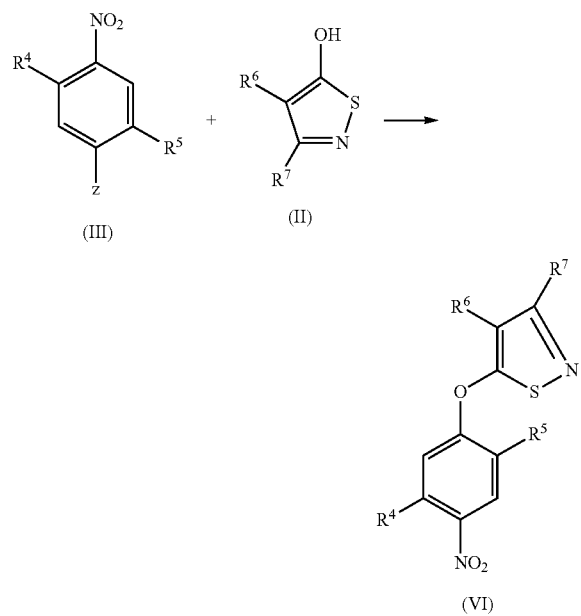

Suitable leaving groups Z are all substituents which, at the prevailing reaction conditions, are sufficiently nucleofugic. Examples which may be mentioned as suitable leaving groups are halogens, triflate, mesylate, tosylate or $SO_2Me$.

The nitrobenzene derivates of the formula (III) can be obtained according to Journal of the Chemical Society 1926, 2036. The reaction is preferably carried out in the presence of a base.

Suitable bases are organic and inorganic bases customarily used in such reactions. Preference is given to using bases selected, by way of example, from the group consisting of hydrides, hydroxides, amides, alkoxides, acetates, fluorides, phosphates, carbonates and bicarbonates of alkali metals or alkaline earth metals. Particular preference is given here to sodium amide, sodium hydride, lithium diisopropylamide, sodium methoxide, potassium-tert-butoxide, sodium hydroxide, potassium hydroxide, sodium acetate, sodium phosphate, potassium phosphate, potassium fluoride, caesium fluoride, sodium carbonate, potassium carbonate, potassium bicarbonate, sodium bicarbonate and caesium carbonate. Preference is furthermore given to tertiary amines, such as, for example, trimethylamine, triethylamine, tributylamine, N,N-dimethylaniline, N,N-dimethylbenzylamine, pyridine, N-methylpiperidine, N-methylpyrrolidone, N,N-dimethylaminopyridine, diazabicyclooctane (DABCO), diazabicyclononene (DBN) and diazabicycloundecene (DBU).

If appropriate, a catalyst selected from the group consisting of palladium, copper and their salts or complexes may be used.

The reaction of the nitrobenzene derivative with the hydroxyl compound can be carried out in the absence or in the presence of a solvent; preferably, the reaction is carried out in a solvent selected from customary solvents which are inert at the prevailing reaction conditions.

Preference is given to aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as, for example, diethyl ether, diisopropyl ether, methyl tert-butyl ether (MTBE), methyl tert-amyl ether, dioxane, tetrahydrofuran, 1,2-dimethoxyethane, 1,2-diethoxyethane or anisol; nitriles, such as, for example, acetonitrile, propionitrile, n- or iso-butyronitrile or benzonitrile; amides, such as, for example, N,N-dimethylformamide (DMF), N,N-dimethylacetamide, N-methylformanilide, N-methylpyrrolidone (NMP) or hexamethylenphosphoric triamide; or mixtures of these with water and also pure water.

The reaction can be carried our under reduced pressure, at atmospheric pressure or under superatmospheric pressure and at temperatures of from −20 to 200° C.; preferably, the reaction is carried out at atmospheric pressure and temperatures of from 50 to 150° C.

Step (b)

In an alternative embodiment according to the invention, nitrophenol derivates of the formula (V) or the phenolates prepared therefrom are reacted with isothiazolyl derivates of the formula (IV) according to the reaction scheme below to give nitrophenyl ethers of the formula (VI):

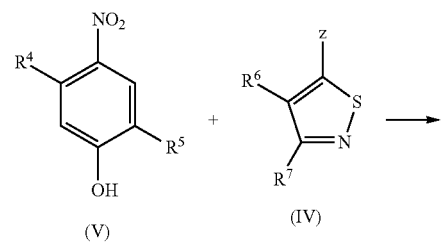

The nitrophenol derivates of the formula (V) can be obtained according to the Journal of the Chemical Society 1926, 2036.

With respect to reaction conditions, solvents, catalysts and suitable leaving groups, reference is made to step (a).

Step (c)

In a further alternative embodiment according to the invention, anilines of the formula (VII) are reacted with isothiazolyl alcohols of the formula (II) or the alkoxides prepared therefrom according to the reaction scheme below to give aminophenyl ethers of the formula (VIII):

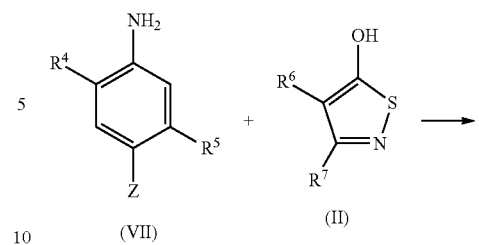

With respect to reaction conditions, solvents, catalysts and suitable leaving groups, reference is made to step (a).

Step (d)

In a further alternative embodiment according to the invention, aminophenols of the formula (XII) are reacted with isothiazolyl derivatives of the formula (IV) according to the reaction scheme below to give aminophenyl ethers of the formula (VIII):

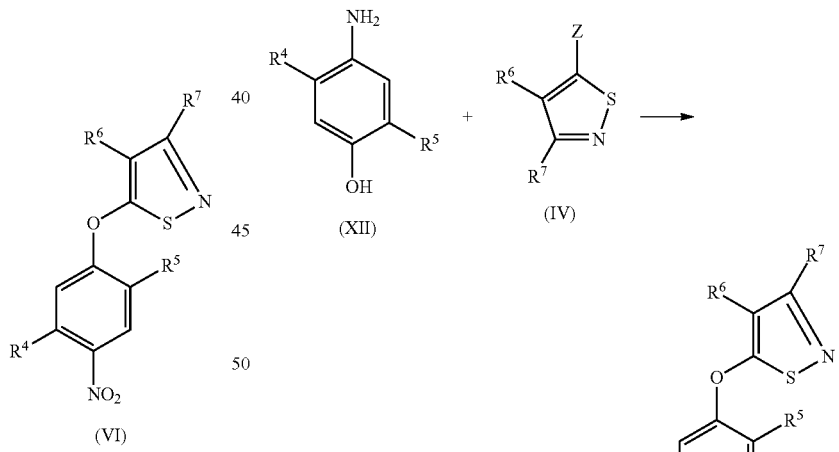

With respect to reaction conditions, solvents, catalysts and suitable leaving groups, reference is made to steps (a) and (c).

Step (e)

The nitrophenyl ethers of the formula (VI) obtained in steps (a) and (b) can be reduced according to the reaction scheme below to give the aniline ethers of the formula (VIII):

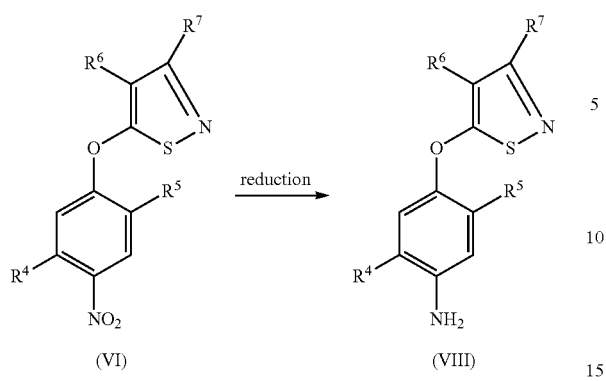

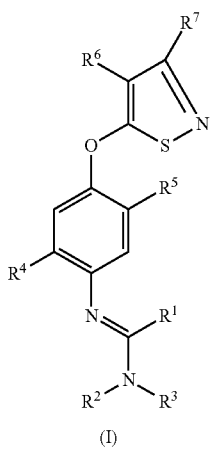

The reduction according to step (e) can be carried out by any of the methods for reducing nitro groups described in the prior art.

Preferably, the reduction is carried out using tin chloride and concentrated hydrochloric acid as described in WO-A-0 046 184. However, alternatively, the reduction can also be carried out using hydrogen gas, if appropriate in the presence of suitable hydrogenation catalysts, such as, for example, Raney Nickel or Pd/C. The reaction conditions have been described in the prior art and are familiar to the person skilled in the art.

If the reduction is carried out in liquid phase, the reaction should take place in a solvent inert towards the prevailing reaction conditions. One such solvent is, for example, toluene.

Step (f)

The conversion of the aniline ethers of the formula (VIII) into the amidines of the formula (I) according to the invention according to step (f) can, as shown above in the scheme (Ib), be carried out by various alternative methods using (i) Aminoacetals of the formula (XIII) or (ii) Amides of the formula (XIV) or (iii) Amines of the formula (XV) in the presence of orthoesters of the formula (XVI) according to the reaction scheme below:

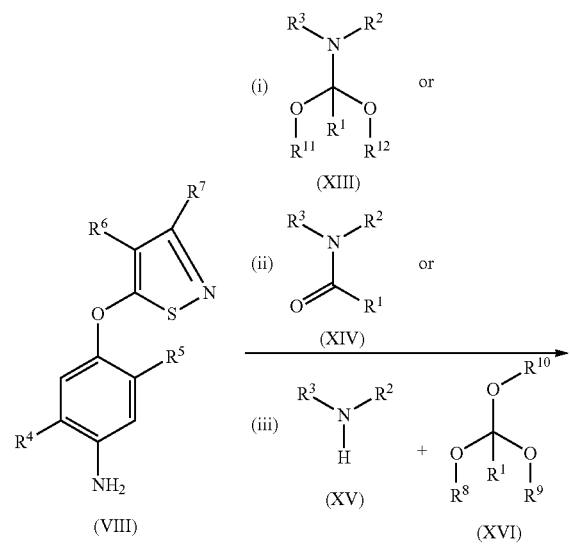

The individual alternative embodiments (i) to (iii) of the process according to the invention are briefly illustrated below:

(i) According to one embodiment according to the invention shown in scheme (Ib) as step (i), the aniline ethers of the formula (VIII) are reacted with aminoacetals of the formula (XIII) in which $R^1$, $R^2$ and $R^3$ are defined as described above and $R^{11}$ and $R^{12}$ are selected from $C_{1-8}$-alkyl groups, preferably from $C_{2-6}$-alkyl groups, particularly preferably from $C_{3-5}$-alkyl groups, and together with the oxygen atoms to which they are attached may form a five- or six-membered ring, to give the isothiazolyloxyphenylamidines of the formula (I) according to the invention.

The aminoacetals of the formula (XIII) are obtainable from the formamides described in JACS, 65, 1566 (1943), by reaction with alkylating agents, such as, for example, dimethyl sulphate.

(ii) In an alternative embodiment according to the invention shown in scheme (Ib) as step (ii), the aniline ethers of the formula (VIII) are reacted with amides of the formula (XIV) in which the groups $R^1$, $R^2$ and $R^3$ are as defined above, to give the isothiazolyloxyphenylamidines according to the invention.

The reaction according to step (ii) is, if appropriate, carried out in the presence of a halogenating agent. Suitable halogenating agents are selected, for example, from the group consisting of $PCl_5$, $PCl_3$, $POCl_3$ and $SOCl_2$.

Moreover, the reaction may alternatively be carried out in the presence of a condensing agent.

Suitable condensing agents are those which are customarily used for forming amide bonds, acid halide formers, such as, for example, phosgene, phosphorus tribromide, phosphorus trichloride, phosphorus pentachloride, phosphorus trichloride oxide or thionyl chloride; anhydride formers, such as, for example, chloroformate, methyl chloroformate, isopropyl chloroformate, isobutyl chloroformate or methansulphonyl chloride; carbodiimines such as, for example, N,N'-dicyclohexylcarbodimine (DCC) or other customary condensing agents, such as, for example, phosphorus pentoxide, polyphosphoric acid, N,N'-carbodiimidazole, 2-ethoxy-N-ethoxycarbonyl-1,2-dihydroquinoline (EEDQ), triphenylphosphine/carbon tetrachloride or bromotripyrrolidinophosphonium hexafluorophosphate.

The reaction according to step (ii) is preferably carried out in a solvent selected from the customary solvents which are inert at the prevailing reaction conditions. Preference is given to using aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as, for example, diethyl ether, diisopropyl ether, methyl tert-butyl ether (MTBE), methyl tert-amyl ether, dioxane, tetrahydrofuran, 1,2-dimethoxyethane, 1,2-diethoxyethane or anisol; nitriles, such as, for example, acetonitrile, propionitrile, n- or isobutyronitrile or benzonitrile; amides, such as, for example, N,N-dimethylformamide (DMF), N,N-dimethylacetamide, N-methylformanilide, N-methylpyrrolidone (NMP) or hexamethylenephosphoric triamide; esters, such as, for example, methyl acetate or ethyl acetate; sulphoxides, such as, for example, dimethyl sulphoxide (DMSO); sulphones, such as, for example, sulpholane; alcohols, such as, for example, methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether or mixtures of these.

(iii) According to a further alternative embodiment according to the invention shown in scheme (Ib) as step (iii), the aniline ethers of the formula (VIII) are reacted with amines of the formula (XV) in which the groups $R^2$ and $R^3$ are as defined above, in the presence of orthoesters of the formula (XVI), in which $R^1$ is hydrogen and $R^8$ to $R^{10}$ independently of one another are selected from $C_{1-8}$-alkyl groups, preferably from $C_{2-6}$-alkyl groups, particularly preferably from $C_{3-5}$-alkyl groups, or $R^8$ and $R^{10}$, $R^9$ and $R^{10}$ or $R^8$ and $R^9$ together with the oxygen atoms to which they are attached may form a five- or six-membered ring, to give the isothiazolyloxyphenylamidines according to the invention.

The reaction according to step (iii) is preferably carried out in a solvent selected from the customary solvents which are inert at the prevailing reaction conditions. Preference is given to using aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as, for example, diethyl ether, diisopropyl ether, methyl tert-butyl ether (MTBE), methyl tert-amyl ether, dioxane, tetrahydrofuran, 1,2-dimethoxyethane, 1,2-diethoxyethane or anisol; nitriles, such as, for example, acetonitrile, propionitrile, n- or isobutyronitrile or benzonitrile; amides, such as, for example, N,N-dimethylformamide (DMF), N,N-dimethylacetamide, N-methylformanilide, N-methylpyrrolidone (NMP) or hexamethylenephosphoric triamide; esters, such as, for example, methyl acetate or ethyl acetate; sulphoxides, such as, for example, dimethyl sulphoxide (DMSO); sulphones, such as, for example, sulpholane; alcohols, such as, for example, methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether; or mixtures of these with water, and also pure water.

The reaction according to step (iii) is preferably carried out in the presence of an acid.

Suitable acids are selected, for example, from the group consisting of organic and inorganic acids, with p-toluenesulphonic acid, methanesulphonic acid, hydrochloric acid (gaseous, aqueous or in organic solution) or sulphuric acid.

Step (g)

In an alternative embodiment according to the invention, the aminophenols of the formula (XII) can be reacted (i) with aminoacetals of the formula (XIII) or ii) with amides of the formula (XIV) or (iii) with amines of the formula (XV) in the presence of orthoesters of the formula (XVI) according to the reaction scheme below to give amidines of the formula (X):

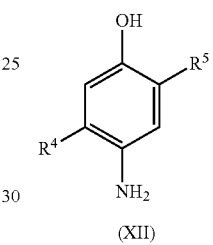

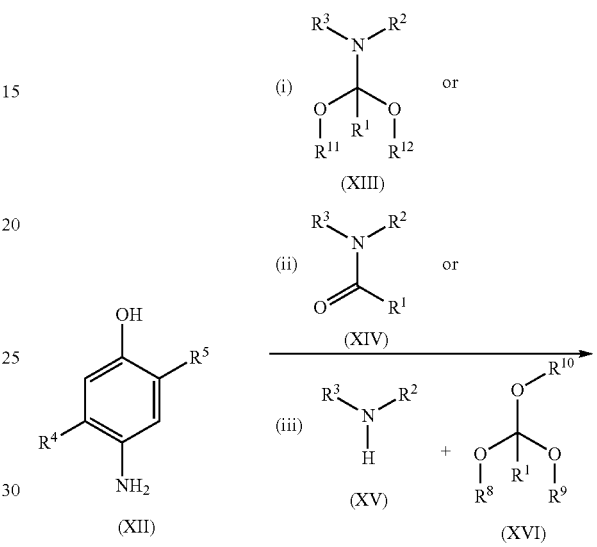

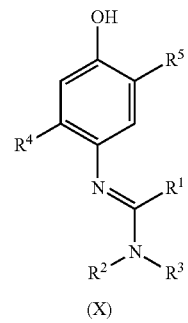

For reaction conditions, solvents and catalysts, reference is made to step (f).

The further reaction of the amidines of the formula (X) to the target molecules of the formula (I) according to the invention can be carried out, for example, as described in step (j).

Step (h)

In an alternative embodiment according to the invention, the aminophenyl derivates of the formula (VII) can be reacted (i) with amino acetals of the formula (XIII) or (ii) with amides of the formula (XIV) or (iii) with amines of the formula (XV) in the presence of orthoesters of the formula (XVI) according to the reaction scheme below to give amidines of the formula (XI):

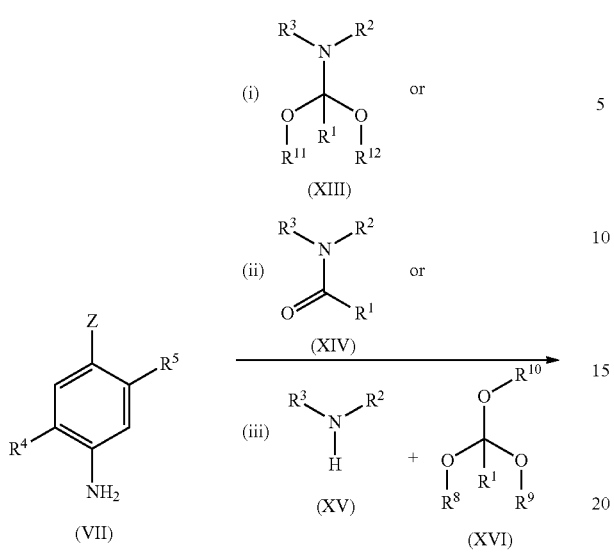
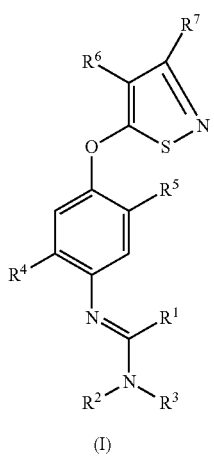

For reaction conditions, solvents and catalysts, reference may be made to step (a).

Step (j)

According to a further embodiment according to the invention, the amidines of the formula (X) obtainable from step (g) can be reacted with isothiazolyl derivatives of the formula (IV) to give the target molecules of the formula (I) according to the invention, according to the reaction scheme below:

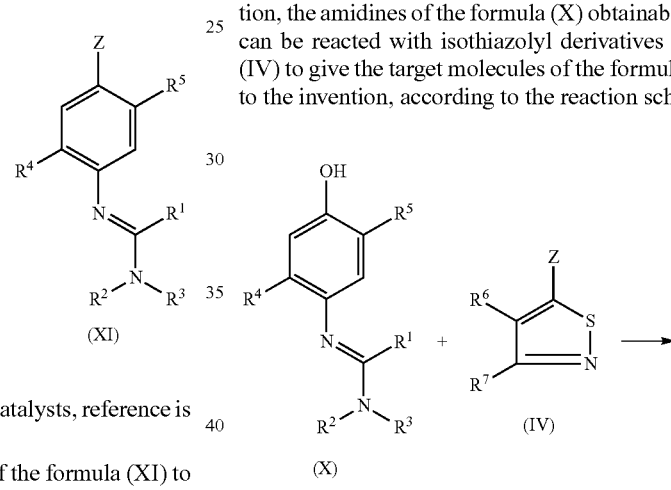

For reaction conditions, solvents and catalysts, reference is made to step (a).

The further reaction of the amidines of the formula (XI) to the target molecules of the formula (I) according to the invention can be carried out, for example, as described in step (i).

Step (i)

According to a further embodiment according to the invention, the amidines of the formula (XI) obtainable from step (h) can be reacted with isothiazolyl alcohols of the formula (II) or the alkoxides formed therefrom to give the target molecules of the formula (I) according to the invention, according to the reaction scheme below:

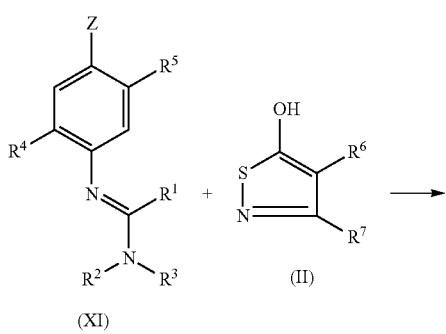
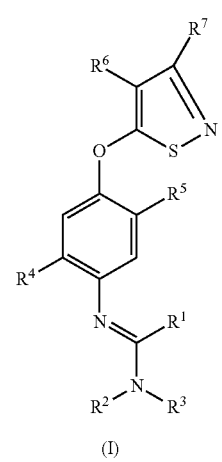

For reaction conditions, solvents and catalysts, reference is made to step (f).

In the context with the processes according to the invention for preparing the amidines of the formula (I), the following combinations of reaction steps are to be considered advantageous: steps (a), (e) and (f); steps (b), (e) and (f); steps (c) and (f); steps (d) and (f); steps (h) and (i) and/or steps (g) and (j).

If appropriate, the preparation of the isothiazolyloxyphenylamidines according to the invention is carried out without intermediate isolation of the intermediates.

The final purification of the isothiazolyloxyphenylamidines can, if appropriate, be carried out by customary purification methods. Preferably, the purification is carried out by crystallization.

The isothiazolyl derivates, used in steps (b), (d) and (j) of the process described above, of the formula IVa in which Z is a chlorine atom can be obtained, for example, according to processes described in Journal of Chemical Research, Synopses, 1989, 2, 29 and the Japanese Patent JP 2002/003410 and illustrated below, by reacting the isothiazolylamines of the formula (XVII).

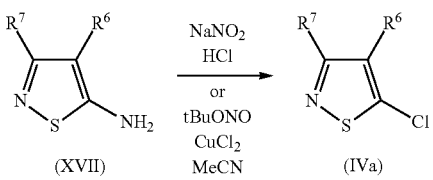

Synthesis options for $R^7$=Cl, Br and Z=Cl, Br are described in J. Org. Chem. 1964, 29, 660. Trichloroisothiazole can be obtained according to Tet. Lett. 1970, 42, 3719 or DE2231098.

If $R^6$ and $R^7$ form an aromatic ring, the derivates can be prepared from the appropriate hydroxy precursors using $POCl_3$. The hydroxy precursors are obtained from isatoic anhydrides, for example by reaction with $H_2S$ or KHS and subsequent reaction with $H_2O_2$, as described in *Acta Naturalia de l'Ateneo Parmense,* 1986, 22, 41-6; *J. Heterocycl. Chem.* 1978, 15, 529-36; *J.f Med. Chem.* 1986, 29, 359-69; *J. Heterocycl. Chem.* 1973, 10, 413; and in *J. Heterocycl. Chem.* 1978, 15, 529-36.

The isothiazolylamines of the formula (XVII) used can be obtained by the routes described in scheme (II) below.

Step (k): Preparation of the Alcohols According to Formula (XX):

The alcohols according to formula (XX) can be obtained, for example, by condensation of malononitrile (XIX) with carbonyl chlorides (XVIII) in the presence of bases, as shown in step (k) and described, for example, in *JACS,* 2002, 12118-12128 or *Bioorg. Med. Chem. Lett.,* 2006, 4326-4330.

Suitable bases are organic and inorganic bases customarily used in such reactions. Preference is given to using bases selected, by way of example, from the group consisting of hydrides, hydroxides, amides, alkoxides, acetates, fluorides, phosphates, carbonates and biocarbonates of alkali metals or alkaline earth metals. Preference is given here to sodium amide, sodium hydride, lithium diisopropylamide, sodium methoxide, potassium tert-butoxide, sodium hydroxide, potassium hydroxide, sodium acetate, sodium phosphate, potassium phosphate, potassium fluoride, caesium fluoride, sodium carbonate, potassium carbonate, potassium bicarbonate, sodium bicarbonate and caesium carbonate. Moreover, particular preference is given to tertiary amines, such as, for example, trimethylamine, triethylamine, tributylamine, N,N-dimethylaniline, N,N-dimethylbenzylamine, pyridine, N-methylpiperidine, N-methylpyrrolidone, N,N-dimethylaminopyridine, diazabicyclooctane (DABCO), diazabicyclononene (DBN) and diazabicycloundecene (DBU).

The reaction of the acid chloride (XVIII) with the malononitrile (XIX) is carried out in a solvent selected from customary solvents inert at the prevailing reaction conditions.

Preference is given to aliphatic, alicyclic or aromatic hydrocarbons such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as, for example, diethyl ether, diisopropyl ether, methyl tert-butyl ether (MTBE), methyl tert-amyl ether, dioxane, tetrahydrofuran, 1,2-dimethoxyethane, 1,2-diethoxyethane or anisol; nitriles, such as, for example, acetonitrile, propionitrile, n- or isobutyronitrile or benzonitrile; amides, such as, for example, N,N-dimethylformamide (DMF), N,N-dimethylacetamide, N-methylformanilide, N-methylpyrrolidone (NMP) or hexamethylenephosphoric triamide; or mixtures of these with water and also pure water.

The reaction can be carried out under reduced pressure, at atmospheric pressure or under superatmospheric pressure and at temperatures of from −20 to 200° C.; preferably, the reaction is carried out at atmospheric pressure and temperatures of from −10 to 20° C.

Step (l): Alkylation of the Alcohols of the Formula (XX)

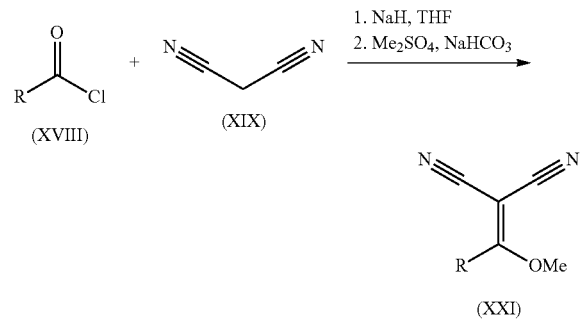

The alkylation of the hydroxyl function of the alcohols of the formula (XX) is carried out in a solvent selected from customary solvents inert at the prevailing reaction conditions.

Preference is given to aliphatic, alicyclic or aromatic hydrocarbons such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as, for example, diethyl ether, diisopropyl ether, methyl tert-butyl ether (MTBE), methyl tert-amyl ether, dioxane, tetrahydrofuran, 1,2-dimethoxyethane, 1,2-diethoxyethane or anisol; nitriles, such as, for example, acetonitrile, propionitrile, n- or isobutyronitrile or benzonitrile; amides, such as, for example, N,N-dimethylformamide (DMF), N,N-dimethylacetamide, N-methylformanilide, N-methylpyrrolidone (NMP) or hexamethylenephosphoric triamide; or mixtures of these with water and also pure water.

Suitable for use as alkylating agents are, for example dialkyl sulphates, alkyl halides, alkyl mesylates, alkyl tosylates or alkyl triflates. Preference is given to dialkyl sulphates.

For suitable bases, reference is made to step (k). Particular preference is given to $NaHCO_3$ or sodium hydride.

The reaction can be carried out under reduced pressure, at atmospheric pressure or under superatmospheric pressure and at temperatures of from −20 to 200° C.; preferably, the reaction is carried out at atmospheric pressure and temperatures of from 50 to 150° C.

In a subsequent step (1), the alcohols of the formula (XX) are converted into alkoxydinitriles of the formula (XXI), as described in *JACS,* 2002, 12118-12128.

Step (m): Preparation of the Aminodinitriles of the Formula (XXII)

The subsequent reaction with ammonia according to step (m) can be carried out both with the alkoxydinitriles (XXI) and the halodinitriles (XXVI), as described in *Bioorg. Med. Chem. Lett.*, 2006, 4326-4330.

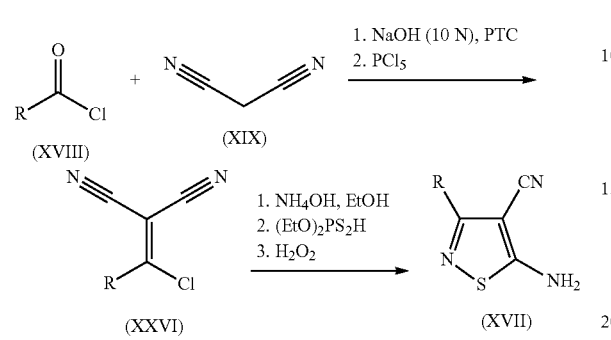

The conversion of the alkoxydinitriles (XXI) into the aminodinitriles (XXII) is carried out in a solvent selected from customary solvents inert at the prevailing reaction conditions.

Preference is given to aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as, for example, diethyl ether, diisopropyl ether, methyl tert-butyl ether (MTBE), methyl tert-amyl ether, dioxane, tetrahydrofuran, 1,2-dimethoxyethane, 1,2-diethoxyethane or anisol; nitriles, such as, for example, acetonitrile, propionitrile, n- or isobutyronitrile or benzonitrile; amides, such as, for example, N,N-dimethylformamide (DMF), N,N-dimethylacetamide, N-methylformanilide, N-methylpyrrolidone (NMP) or hexamethylenephosphoric triamide; or mixtures of these with water, and also pure water. Particular preference is given to alcohols, such as, for example, methanol, ethanol, isopropanol or n-butanol.

Instead of ammonia, it is also possible to use other sources of ammonia, such as, for example, urotropin.

The reaction can be carried out under reduced pressure, at atmospheric pressure or under superatmospheric pressure and temperatures of from −20 to 200° C.; preferably, the reaction is carried out at atmospheric pressure and temperatures of from 0 to 30° C.

Alternatively, the aminodinitriles of the formula (XXII) in which the radical $R^7$ corresponds to the group

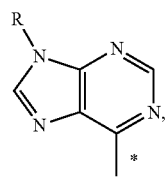

where * denotes the point of attachment of the substituent, can also be obtained according to the procedure in *Org. Biomol. Chem.*, 2004, 2340-2345. Here, imino esters of the formula (XXIV) are condensed with malononitrile (XIX) according to the scheme below:

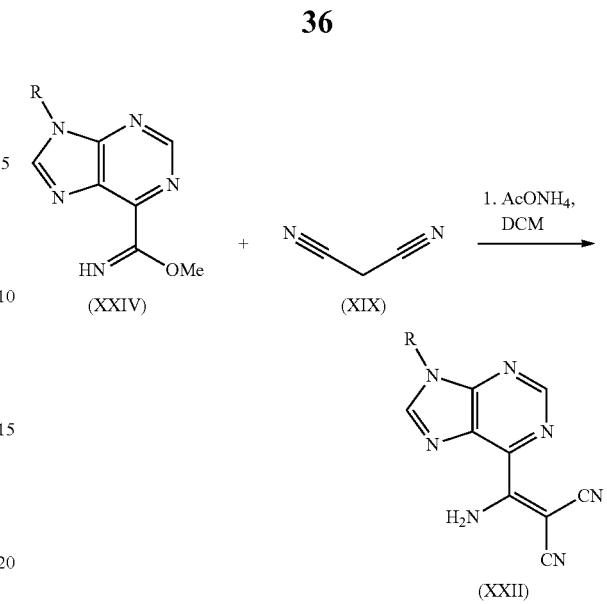

EP 1 344 774 A1 teaches a synthesis of the aminodinitriles of the formula (XXII) starting with malononitrile (XIX) and carbonyl chlorides (XVIII), according to the reaction scheme below:

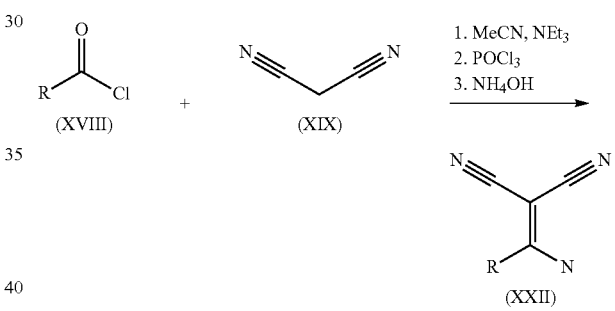

Furthermore, isothiazolylamines of the formula (XVII) in which $R^7$ corresponds to the group

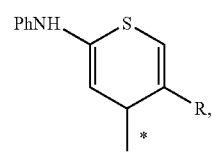

where * denotes the point of attachment of the substituent, can be prepared according to a procedure from *Arch. Pharm. Chem. Life Sci.* 2006, 608-615:

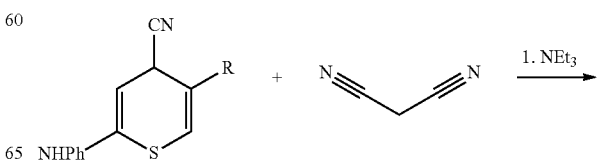

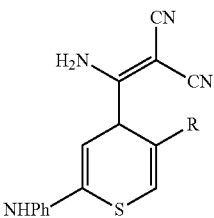

EP-A-327 981 describes the synthesis of aminodinitriles of the formula (XXII), likewise starting with nitriles (XXV), by reaction with malononitrile (XIX) and, if appropriate, isolation of the imino esters (XXIV) as intermediates.

Step (n): Preparation of the Thioamides of the Formula (XXIII)

The transformation of the nitriles of the formula (XXII) into the thioamides of the formula (XXIII) can be carried out in a mixture of organic bases, as described in DE-A-2 434 922.

Preference is given to tertiary amines, such as, for example, trimethylamine, triethylamine, tributylamine, N,N-dimethylaniline, N,N-dimethylbenzylamine, pyridine, N-methylpiperidine, N-methylpyrrolidone, N,N-dimethylaminopyridine, diazabicyclooctane (DABCO), diazabicyclononene (DBN) and diazabicycloundecene (DBU) in various mixtures.

Instead of the gaseous hydrogen sulphide preferably used, it is also possible to employ other sources of hydrogen sulphide, such as, for example, $P_2S_5$, Lawesson's reagent, thioacetamide, thioacetic acid, diphenylphosphinodithionic acid, O,O-dialkyl dithiophosphoric acid or trimethylsilanthio late.

The reaction can be carried out under reduced pressure, at atmospheric pressure or under superatmospheric pressure and at temperatures of from −20 to 200° C.; preferably, the reaction is carried out at atmospheric pressure and temperatures of from 0 to 30° C.

Step (o): Synthesis of Aminoisothiazoles of the Formula (XVII)

The synthesis of aminoisothiazoles of the formula (XVII) where $R^6$=H by oxidative cyclization of 3-iminothioacetamides of the formula (XXIII) according to step (O) has been described, for example, in Journal of the American Chemical Society, 1994, 116, 2292-300; in EP-A-129 408, in *J. Heterocyclic Chem.* 1989, 1575 or in DE-A-2 434 922 for $R^6$=H. *Bioorg. Med. Chem. Lett.*, 2006, 4326-4330 describes the oxidative cyclization of compounds where $R^6 \neq H$.

The oxidative cyclization to the aminoisothiazole is carried out in a solvent selected from customary solvents inert at the prevailing reaction conditions.

Preference is given to aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as, for example, diethyl ether, diisopropyl ether, methyl tert-butyl ether (MTBE), methyl tert-amyl ether, dioxane, tetrahydrofuran, 1,2-dimethoxyethane, 1,2-diethoxyethane or anisol; nitriles, such as, for example, acetonitrile, propionitrile, n- or isobutyronitrile or benzonitrile; amides, such as, for example, N,N-dimethylformamide (DMF), N,N-dimethylacetamide, N-methylformanilide, N-methylpyrrolidone (NMP) or hexamethylenephosphoric triamide; or mixtures of these with water, and also pure water. Particular preference is given to alcohols, such as, for example, methanol, ethanol, isopropanol or n-butanol.

Suitable for use as oxidizing agents are, for example, hydrogen peroxide or iodine. Preference is given to using hydrogen peroxide.

The reaction can be carried out under reduced pressure, at atmospheric pressure or under superatmospheric pressure and at temperatures of from −20 to 200° C.; preferably, the reaction is carried out at atmospheric pressure and temperatures of from −10 to 80° C.

The synthesises of the 4-haloaminoisothiazole intermediates of the formula (XVII) where $R^6$=halogen can be carried out by halogenation of the 4-position, which is still free, of the corresponding aminoisothiazoles analogously to *heterocycles*, 1994, 37, 859-67.

The preparation of hydroxyisothiazoles from thioalkyl derivates is described in Australian Journal of Chemistry 1989, 42, 1291-306.

According to Australian Journal of Chemistry 1975, 28, 2051-5, hydroxyisothiazoles are accessible from halodinitriles (XXVI).

Step (p): Preparation of the Chlorodinitriles of the Formula (XXVI)

In an alternative embodiment shown in step (p), the alcohols of the formula (XX) can be reacted with suitable chlorinating agents, such as, for example, $PCl_5$, to give the chlorodinitriles of the formula (XXVI). A corresponding process is described in *Bioorg. Med. Chem. Lett.*, 2006, 4326-4330.

Scheme (II)

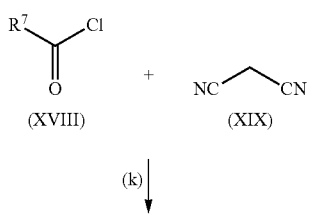

(k)

-continued
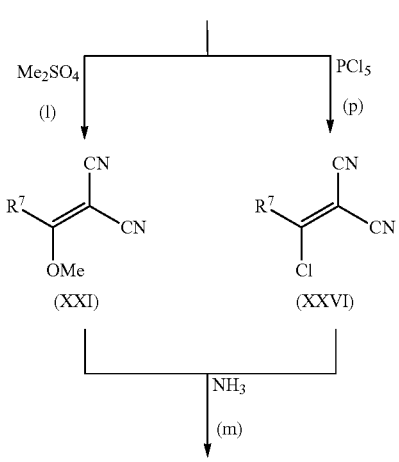
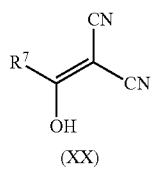
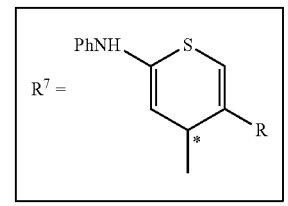
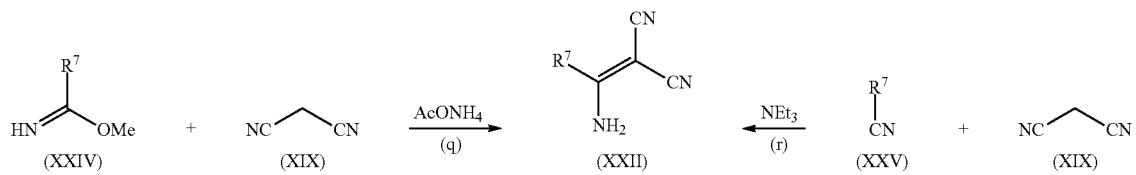
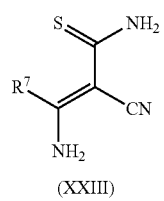
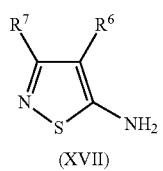

Step (q): Derivatization of the Anilines

In a further alternative embodiment according to the invention, aminophenol ethers of the formula (VIIIa) can be converted by halogenation into aminophenyl ethers of the formula (VIII):

$R^4$ = Br, Cl, I

In addition to chlorine and bromine in the presence of Lewis acids, it is also possible to use N-halosuccinimide derivates as halogenating agents. Preference is given to using N-bromo- and N-chlorosuccinimide The halogenation of the aminophenol ether can be carried out in the absence or presence of a solvent; preferably, the reaction is carried out in a solvent selected from customary solvents inert at the prevailing reaction conditions.

Preference is given to aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as, for example, diethyl ether, diisopropyl ether, methyl tert-butyl ether (MTBE), methyl tert-amyl ether, dioxane, tetrahydrofuran, 1,2-dimethoxyethane, 1,2-diethoxyethane or anisol; nitriles, such as, for example, acetonitrile, propionitrile, n- or isobutyronitrile or benzonitrile; amides, such as, for example, N,N-dimethylformamide (DMF), N,N-dimethylacetamide, N-methylformanilide, N-methylpyrrolidone (NMP) or hexamethylenephosphoric triamide; or mixtures of these with water, and also pure water.

The reaction can be carried out under reduced pressure, at atmospheric pressure or under superatmospheric pressure and at temperatures from −20 to 200° C.; preferably, the reaction is carried out at atmospheric pressure and room temperature.

Controlling of Unwanted Microorganisms

The amidines according to the invention exhibit a strong microbicidal action and can be used for controlling unwanted microorganisms, such as fungi and bacteria, in plant protection and in material protection.

Plant Protection

Fungicides can be used in plant protection for controlling Plasmodiophoromycetes, Oomycetes, Chytridiomycetes, Zygomycetes, Ascomycetes, Basidiomycetes and Deuteromycetes.

Bactericides can be used in plant protection for controlling Pseudomonadaceae, Rhizobiaceae, Enterobacteriaceae, Corynebacteriaceae and Streptomycetaceae.

Mention may be made, by way of example but without limitation, of some pathogens of fungal and bacterial diseases which come under the generic terms listed above:

diseases caused by pathogens of powdery mildew, such as, for example,
*Blumeria* species, such as, for example, *Blumeria graminis*;
*Podosphaera* species, such as, for example, *Podosphaera leucotricha*;
*Sphaerotheca* species, such as, for example, *Sphaerotheca fuliginea*;
*Uncinula* species, such as, for example, *Uncinula necator*;
diseases caused by rust pathogens, such as, for example,
*Gymnosporangium* species, such as, for example, *Gymnosporangium sabinae*;
*Hemileia* species, such as, for example, *Hemileia vastatrix*;
*Phakopsora* species, such as, for example, *Phakopsora pachyrhizi* and *Phakopsora meibomiae*;
*Puccinia* species, such as, for example, *Puccinia recondita*;
*Uromyces* species, such as, for example, *Uromyces appendiculatus*;
diseases caused by pathogens of the Oomycetes group, such as, for example,
*Bremia* species, such as, for example, *Bremia lactucae*;
*Peronospora* species, such as, for example, *Peronospora pisi* or *P. brassicae*;
*Phytophthora* species, such as, for example, *Phytophthora infestans*;
*Plasmopara* species, such as, for example, *Plasmopara viticola*;
*Pseudoperonospora* species, such as, for example, *Pseudoperonospora humuli* or
*Pseudoperonospora cubensis*;
*Pythium* species, such as, for example, *Pythium ultimum*;
leaf spot diseases and leaf wilts caused by, for example,
*Alternaria* species, such as, for example, *Alternaria solani*;
*Cercospora* species, such as, for example, *Cercospora beticola*;
*Cladosporium* species, such as, for example, *Cladosporium cucumerinum*;
*Cochliobolus* species, such as, for example, *Cochliobolus sativus*
(conidial form: *Drechslera*, syn: *Helminthosporium*);
*Colletotrichum* species, such as, for example, *Colletotrichum lindemuthanium*;
*Cycloconium* species, such as, for example, *Cycloconium oleaginum*;
*Diaporthe* species, such as, for example, *Diaporthe citri*;
*Elsinoe* species, such as, for example, *Elsinoe fawcettii*;
*Gloeosporium* species, such as, for example, *Gloeosporium laeticolor*;
*Glomerella* species, such as, for example, *Glomerella cingulata*;
*Guignardia* species, such as, for example, *Guignardia bidwelli*;

*Leptosphaeria* species, such as, for example, *Leptosphaeria maculans*;
*Magnaporthe* species, such as, for example, *Magnaporthe grisea*;
*Mycosphaerella* species, such as, for example, *Mycosphaerella graminicola* and *Mycosphaerella fijiensis*;
*Phaeosphaeria* species, such as, for example, *Phaeosphaeria nodorum*;
*Pyrenophora* species, such as, for example, *Pyrenophora teres*;
*Ramularia* species, such as, for example, *Ramularia collocygni*;
*Rhynchosporium* species, such as, for example, *Rhynchosporium secalis*;
*Septoria* species, such as, for example, *Septoria apii*;
*Typhula* species, such as, for example, *Typhula incarnata*;
*Venturia* species, such as, for example, *Venturia inaequalis*;
root and stalk diseases caused by, for example,
*Corticium* species, such as, for example, *Corticium graminearum*;
*Fusarium* species, such as, for example, *Fusarium oxysporum*;
*Gaeumannomyces* species, such as, for example, *Gaeumannomyces graminis*;
*Rhizoctonia* species, such as, for example, *Rhizoctonia solani*;
*Tapesia* species, such as, for example, *Tapesia acuformis*;
*Thielaviopsis* species, such as, for example, *Thielaviopsis basicola*;
ear and panicle diseases (including maize cobs) caused by, for example,
*Alternaria* species, such as, for example, *Alternaria* spp.;
*Aspergillus* species, such as, for example, *Aspergillus flavus*;
*Cladosporium* species, such as, for example, *Cladosporium cladosporioides*;
*Claviceps* species, such as, for example, *Claviceps purpurea*;
*Fusarium* species, such as, for example, *Fusarium culmorum*;
*Gibberella* species, such as, for example, *Gibberella zeae*;
*Monographella* species, such as, for example, *Monographella nivalis*;
diseases caused by smuts, such as, for example,
*Sphacelotheca* species, such as, for example, *Sphacelotheca reiliana*;
*Tilletia* species, such as, for example, *Tilletia caries*;
*Urocystis* species, such as, for example, *Urocystis occulta*;
*Ustilago* species, such as, for example, *Ustilago nuda*;
fruit rot caused by, for example,
*Aspergillus* species, such as, for example, *Aspergillus flavus*;
*Botrytis* species, such as, for example, *Botrytis cinerea*;
*Penicillium* species, such as, for example, *Penicillium expansum* and *Penicillium purpurogenum*;
*Sclerotinia* species, such as, for example, *Sclerotinia sclerotiorum*;
*Verticilium* species, such as, for example, *Verticilium alboatrum*;
seed- and soil-borne rots and wilts, and seedling diseases, caused by, for example,
*Alternaria* species, such as, for example, *Alternaria brassicicola*
*Aphanomyces* species, such as, for example, *Aphanomyces euteiches*
*Ascochyta* species, such as, for example, *Ascochyta lentis*
*Aspergillus* species, such as, for example, *Aspergillus flavus*
*Cladosporium* species, such as, for example, *Cladosporium herbarum*
*Cochliobolus* species, such as, for example, *Cochliobolus sativus* (conidial form: *Drechslera, Bipolaris* syn: *Helminthosporium*);
*Colletotrichum* species, such as, for example, *Colletotrichum coccodes*;
*Fusarium* species, such as, for example, *Fusarium culmorum*;
*Gibberella* species, such as, for example, *Gibberella zeae*;
*Macrophomina* species, such as, for example, *Macrophomina phaseolina*
*Monographella* species, such as, for example, *Monographella nivalis*;
*Penicillium* species, such as, for example, *Penicillium expansum*
*Phoma* species, such as, for example, *Phoma lingam*
*Phomopsis* species, such as, for example, *Phomopsis sojae*;
*Phytophthora* species, such as, for example, *Phytophthora cactorum*;
*Pyrenophora* species, such as, for example, *Pyrenophora graminea*
*Pyricularia* species, such as, for example, *Pyricularia oryzae*;
*Pythium* species, such as, for example, *Pythium ultimum*;
*Rhizoctonia* species, such as, for example, *Rhizoctonia solani*;
*Rhizopus* species, such as, for example, *Rhizopus oryzae*
*Sclerotium* species, such as, for example, *Sclerotium rolfsii*;
*Septoria* species, such as, for example, *septoria nodorum*;
*Typhula* species, such as, for example, *Typhula incarnata*;
*Verticillium* species, such as, for example, *Verticillium dahliae* cankers, galls and witches' broom disease caused by, for example,
*Nectria* species, such as, for example, *Nectria galligena*;
wilts caused by, for example,
*Monilinia* species, such as, for example, *Monilinia laxa*;
deformations of leaves, flowers and fruits caused by, for example,
*Taphrina* species, such as, for example, *Taphrina deformans*;
degenerative diseases of woody plants caused by, for example,
*Esca* species, such as, for example, *Phaeomoniella chlamydospora, Phaeoacremonium aleophilum* and *Fomitiporia mediterranea*;
flower and seed diseases caused by, for example,
*Botrytis* species, such as, for example, *Botrytis cinerea*;
diseases of plant tubers caused by, for example,
*Rhizoctonia* species, such as, for example, *Rhizoctonia solani*;
*Helminthosporium* species, such as, for example, *Helminthosporium solani*;
diseases caused by bacterial pathogens, such as, for example,
*Xanthomonas* species, such as, for example, *Xanthomonas campestris* pv. *oryzae*;
*Pseudomonas* species, such as, for example, *Pseudomonas syringae* pv. *lachrymans*;
*Erwinia* species, such as, for example, *Erwinia amylovora*.
Preferably, the following diseases of soybeans can be controlled:
fungal diseases on leaves, stalks, pods and seeds caused by, for example,
alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*)

fungal diseases on roots and the stem base caused by, for example, black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active compounds according to the invention also exhibit a strong strengthening activity in plants. They are accordingly suitable for mobilizing intrinsic defences of plants against attack by unwanted microorganisms.

In the present context, plant-strengthening (resistance-inducing) compounds are to be understood as meaning those materials which are capable of stimulating the defence system of plants such that the treated plants, on subsequent inoculation with unwanted microorganisms, exhibit extensive resistance to these microorganisms.

In the present case, unwanted microorganisms are to be understood as meaning phytopathogenic fungi, bacteria and viruses. The substances according to the invention can thus be used to protect plants from attack by the harmful pathogens mentioned for a certain period of time after the treatment. The period of time for which protection is brought about generally ranges from 1 to 10 days, preferably 1 to 7 days, after the treatment of the plants with the active compounds.

The fact that the active compounds are well tolerated by plants in the concentrations necessary for controlling plant diseases makes possible treatment of above ground plant parts, of plant propagation material and seed, and of the soil.

In this connection, the active compounds according to the invention can be used particularly successfully in controlling cereal diseases, such as, e.g., *Puccinia* species, and diseases in viticulture and in the cultivation of fruit and vegetables, such as, e.g., *Botrytis, Venturia* or *Alternaria* species.

The active compounds according to the invention are also suitable for increasing the crop yield. In addition, they are of lower toxicity and are well tolerated by plants.

The active compounds according to the invention can also optionally be used, in specific concentrations and application amounts, as herbicides, for affecting plant growth and for controlling animal pests. They can optionally also be used as intermediates and precursors for the synthesis of additional active compounds.

All plants and plant parts can be treated according to the invention. In this connection, plants are to be understood as meaning all plants and plant populations, such as desirable and unwanted wild plants or cultivated plants (including naturally occurring cultivated plants). Cultivated plants can be plants which can be obtained by conventional breeding and optimization methods or by biotechnological and genetic engineering methods or combinations of these methods, including transgenic plants and including plant varieties which may or may not be protected by laws on variety certification. Plant parts should be understood as meaning all above ground and subsoil parts and organs of plants, such as shoot, leaf, flower and root, examples which are listed being leaves, needles, stalks, stems, flowers, fruiting bodies, fruits and seeds, and also roots, tubers and rhizomes. Plant parts also include harvested crops, and also vegetative and generative propagation material, for example cuttings, tubers, rhizomes, slips and seeds.

The treatment according to the invention of the plants and plant parts with the active compounds is carried out directly or by acting on the environment, habitat or storage area thereof using conventional treatment methods, e.g. by dipping, spraying, evaporating, atomizing, scattering, spreading and, with propagation material, in particular with seeds, furthermore by coating with one or more layers.

Mycotoxins

In addition, it is possible, by the treatment according to the invention, to reduce the mycotoxin content in harvested crops and the foodstuffs and feedstuffs prepared therefrom. In this connection, mention may in particular but not exclusively be made of the following mycotoxins: deoxynivalenol (DON), nivalenol, 15-Ac-DON, 3-Ac-DON, T2 and HT2 toxin, fumonisins, zearalenone, moniliformin, fusarin, diacetoxyscirpenol (DAS), beauvericin, enniatin, fusaroproliferin, fusarenol, ochratoxins, patulin, ergot alkaloids and aflatoxins, which can be caused, for example, by the following fungi: *Fusarium* spec., such as *Fusarium* acuminatum, *F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, and others, and also by *Aspergillus* spec., *Penicillium* spec., *Claviceps purpurea, Stachybotrys* spec., and others.

Material Protection

In material protection, the substances according to the invention can be used for the protection of industrial materials from attack and destruction by unwanted microorganisms.

Industrial materials are to be understood in the present context as meaning nonliving materials which have been prepared for use in industry. For example, industrial materials which are to be protected by active compounds according to the invention from microbial change or destruction can be adhesives, sizes, paper and board, textiles, leather, wood, paints and plastic articles, cooling lubricants and other materials which can be attacked or destroyed by microorganisms. In the context of the materials to be protected, mention may also be made of parts of production plants, for example cooling water circuits, which can be detrimentally affected by proliferation of microorganisms. In the context of the present invention, mention may preferably be made, as industrial materials, of adhesives, sizes, papers and boards, leather, wood, paints, cooling lubricants and heat-transfer liquids, particularly preferably of wood.

Examples which may be mentioned of microorganisms which can decompose or modify industrial materials are bacteria, fungi, yeasts, algae and slime organisms. The active compounds according to the invention are preferably active against fungi, in particular molds, wood-discoloring and wood-destroying fungi (Basidiomycetes), and against slime organisms and algae.

Mention may be made, by way of example, of microorganisms of the following genera:
*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*,
*Staphylococcus*, such as *Staphylococcus aureus*.
Formulations The present invention relates to a composition for controlling unwanted microorganisms, comprising at least one of the isothiazolyloxyphenylamidines according to the invention.

The isothiazolyloxyphenylamidines according to the invention can for this, depending on their respective physical and/or chemical properties, be converted into the standard formulations, such as solutions, emulsions, suspensions, powders, foams, pastes, granules, aerosols, very fine encapsulations in polymeric substances and in coating materials for seed, and also ULV cold- and hot-fogging formulations.

These formulations are prepared in a known way, e.g. by mixing the active compounds with extenders, that is liquid solvents, liquefied gases under pressure and/or solid carriers, optionally with the use of surface-active agents, that is emulsifiers and/or dispersants and/or foaming agents. In the case of the use of water as extender, use may also be made, e.g., of organic solvents as cosolvents. Possible liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, e.g. petroleum fractions, alcohols, such as butanol or glycol, and the ethers and esters thereof, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are to be understood as meaning those liquids which are in the gas form at standard temperature and at standard pressure, e.g. aerosol propellants, such as halogenated hydrocarbons and also butane, propane, nitrogen and carbon dioxide. Possible solid carriers are, e.g., ground natural minerals, such as kaolins, argillaceous earths, talc, chalk, quartz, attapulgite, montmorillonite or diatomaceous earth, and ground synthetic minerals, such as highly dispersed silica, aluminium oxide and silicates. Possible solid carriers for granules are, e.g., broken and fractionated natural rocks, such as calcite, pumice, marble, sepiolite or dolomite, and also synthetic granules formed from inorganic and organic dusts, and also granules formed from organic material, such as sawdust, coconut shells, maize cobs and tobacco stalks. Possible emulsifiers and/or foaming agents are, e.g., nonionic and anionic emulsifiers, such as polyoxyethylene fatty acid esters, polyoxyethylene fatty alcohol ethers, e.g. alkylaryl polyglycol ethers, alkylsulphonates, alkyl sulphates, arylsulphonates, and also protein hydrolyzates. Possible dispersants are, e.g., lignosulphite waste liquors and methylcellulose.

Use may be made, in the formulations, of stickers, such as carboxymethylcellulose, natural and synthetic polymers in the powder, granule or latex form, such as gum arabic, polyvinyl alcohol, polyvinyl acetate, and also natural phospholipids, such as cephalins and lecithins, and synthetic phospholipids. Other possible additives are mineral and vegetable oils.

Use may also be made of colorants, such as inorganic pigments, e.g. iron oxide, titanium oxide, Prussian blue, and organic colorants, such as alizarin dyes, azo dyes and metal phthalocyanine dyes, and trace elements, such as salts of iron, manganese, boron, copper, cobalt, molybdenum and zinc.

The formulations generally comprise between 0.1 and 95% by weight of active compound, preferably between 0.5 and 90%.

The formulations described above can be used in a method according to the invention for controlling unwanted microorganisms, in which the isothiazolyloxyphenylamidines according to the invention are applied to the microorganisms and/or to the habitat thereof.

Seed Treatment

The controlling of phytopathogenic fungi by the treatment of the seed of plants has been known for a long time and is the subject matter of continuous improvements. Nevertheless, a series of problems arises in the treatment of seed, which problems may not always be satisfactorily solved. Thus, it is desirable to develop methods for protecting the seed and the germinating plant which render superfluous or at least markedly reduce the additional application of plant protection compositions after sowing or after emergence of the plants. It is furthermore desirable to optimize the amount of the active compound used, so that the seed and the germinating plant are given the best possible protection against attack by phytopathogenic fungi but without the plant itself being damaged by the active compound used. In particular, methods for the treatment of seed should also include the intrinsic fungicidal properties of transgenic plants in order to achieve optimum protection of the seed and the germinating plant with a minimum expenditure of plant protection compositions.

The present invention therefore also relates in particular to a method for the protection of seed and germinating plants from attack by phytopathogenic fungi, by treating the seed with a composition according to the invention.

The invention likewise relates to the use of the compositions according to the invention for the treatment of seed to protect the seed and the germinating plant from phytopathogenic fungi.

Furthermore, the invention relates to seed which has been treated with a composition according to the invention in order to protect from phytopathogenic fungi.

One of the advantages of the present invention is that, because of the particular systemic properties of the compositions according to the invention, the treatment of the seed with these compositions not only protects the seed itself from phytopathogenic fungi but also protects the plants resulting therefrom after emergence from phytopathogenic fungi. In this way, the immediate treatment of the crop at the time of sowing or shortly thereafter can be dispensed with.

It is likewise to be regarded as advantageous that the mixtures according to the invention can in particular also be used with transgenic seed.

The compositions according to the invention are suitable for the protection of seed of any plant variety used in agriculture, in the greenhouse, in forests or in horticulture. The seed concerned in this connection is in particular seed of cereals (such as wheat, barley, rye, millet and oats), maize, cotton, soya, rice, potatoes, sunflowers, beans, coffee, beet (e.g., sugarbeet and forage beet), peanuts, vegetables (such as tomatoes, cucumbers, onions and lettuce), lawns and ornamental plants. The treatment of the seed of cereals (such as wheat, barley, rye and oats), maize and rice is of particular importance.

In the context of the present invention, the composition according to the invention is applied to the seed alone or in a suitable formulation. Preferably, the seed is treated in a condition sufficiently stable for no damage to occur during the treatment. In general, the treatment of the seed can be carried out at any point in time between harvesting and sowing. Use is usually made of seed which has been separated from the plant and freed from pods, shells, stalks, skins, hairs or fruit flesh. Thus, it is possible, for example, to use seed which has been harvested, cleaned and dried up to a moisture content of less than 15% by weight. Alternatively, it is also possible to use seed which, after drying, has been treated, e.g. with water, and then dried again.

In general, care must be taken, in the treatment of the seed, that the amount of the composition according to the invention and/or of additional additives applied to the seed is chosen so that the germination of the seed is not impaired or that the plant resulting therefrom is not damaged. This is to be taken into consideration in particular with active compounds which may show phytotoxic effects at certain application rates.

The compositions according to the invention can be applied immediately, thus without comprising additional components and without having been diluted. It is generally preferable to apply the compositions to the seed in the form of a suitable formulation. Suitable formulations and methods for seed treatment are known to a person skilled in the art and are described, e.g., in the following documents: U.S. Pat. Nos. 4,272,417 A, 4,245,432 A, 4,808,430 A, 5,876,739 A, US 2003/0176428 A1, WO 2002/080675 A1, WO 2002/028186 A2.

The active compound combinations which can be used according to the invention can be converted into the usual seed dressing formulations, such as solutions, emulsions, suspensions, powders, foams, slurries or other coating materials for seed, and also ULV formulations.

These formulations are prepared in a known way by mixing the active compounds or active compound combinations with conventional additives, such as, for example, conventional extenders and also solvents or diluents, colorants, wetting agents, dispersants, emulsifiers, antifoaming agents, preservatives, secondary thickeners, adhesives, gibberellins and also water.

Suitable colorants which may be present in the seed dressing formulations which can be used according to the invention comprise all colorants conventional for such purposes. In this connection, use may be made both of pigments, which are sparingly soluble in water, and dyes, which are soluble in water. Mention may be made, as examples, of the colorants known under the descriptions Rhodamine B, C.I. Pigment Red 112 and C.I. Solvent Red 1.

Possible wetting agents which can be present in the seed dressing formulations which can be used according to the invention comprise all substances which promote wetting and are conventional in the formulation of agrochemical active compounds. Use may preferably be made of alkylnaphthalenesulphonates, such as diisopropyl- or diisobutylnaphthalenesulphonates.

Suitable dispersants and/or emulsifiers which may be present in the seed dressing formulations which can be used according to the invention comprise all nonionic, anionic and cationic dispersants conventional in the formulation of agrochemical active compounds. Use may preferably be made of nonionic or anionic dispersants or mixtures of nonionic or anionic dispersants. Mention may in particular be made, as suitable nonionic dispersants, of ethylene oxide/propylene oxide block polymers, alkylphenol polyglycol ethers and also tristyrylphenol polyglycol ethers, and the phosphated or sulphated derivatives thereof. Suitable anionic dispersants are in particular lignosulphonates, polyacrylic acid salts and arylsulphonate/formaldehyde condensates.

Antifoaming agents which may be present in the seed dressing formulations which can be used according to the invention comprise all foam-inhibiting substances conventional in the formulation of agrochemical active compounds. Use may preferably be made of silicone defoaming agents and magnesium stearate.

Preservatives which may be present in the seed dressing formulations which can be used according to the invention comprise all substances which can be used in agrochemical compositions for such purposes. Mention may be made, by way of example, of dichlorophen and benzyl alcohol hemiformal.

Possible secondary thickeners which may be present in the seed dressing formulations which can be used according to the invention comprise all substances which can be used in agrochemical compositions for such purposes. Preferably suitable are cellulose derivatives, acrylic acid derivatives, xanthan, modified clays and highly dispersed silica.

Possible adhesives which may be present in the seed dressing formulations which can be used according to the invention comprise all conventional binders which can be used in seed dressings. Mention may preferably be made of polyvinylpyrrolidone, polyvinyl acetate, polyvinyl alcohol and tylose.

Possible gibberellins which may be present in the seed dressing formulations which can be used according to the invention preferably comprise the gibberellins A1, A3 (=gibberellic acid), A4 and A7; particular preference is given to using gibberellic acid. The gibberellins are known (cf. R. Wegler, "Chemie der Pflanzenschutz- and Schadlingsbekampfungsmittel" [Chemistry of Plant Protection and Pest Control Agents], Vol. 2, Springer Verlag, 1970, pp. 401-412).

The seed dressing formulations which can be used according to the invention can be used, either directly or after prior diluting with water, for the treatment of seed of the most varied species. Thus, the concentrates or the preparations which can be obtained therefrom by diluting with water can be used for the dressing of the seed of cereals, such as wheat, barley, rye, oats and triticale, and also the seed of maize, rice, rape, peas, beans, cotton, sunflowers and beet, or also of vegetable seed of the most varied natures. The seed dressing formulations which can be used according to the invention or the diluted preparations thereof can also be used for the dressing of seed of transgenic plants. In this connection, additional synergistic effects may also occur in interaction with the substances formed by expression.

All mixing devices which can be conventionally used for dressing are suitable for the treatment of seed with the seed dressing formulations which can be used according to the invention or the preparations prepared therefrom by addition of water. Specifically, the dressing procedure is such that the seed is introduced into a mixer, the amount of seed dressing formulation desired each time is added, either as such or after prior dilution with water, and mixing is carried out until the formulation is uniformly distributed over the seed. If appropriate, a drying operation follows.

The application rate of the seed dressing formulations which can be used according to the invention can be varied within a relatively wide range. It depends on the respective content of the active compounds in the formulations and on the seed. The application rates of active compound combination are generally between 0.001 and 50 g per kilogram of seed, preferably between 0.01 and 15 g per kilogram of seed.

Mixture with Known Fungicides, Bactericides, Acaricides, Nematicides or Insecticides The amidines according to the invention can be used, as such or in their formulations, also in a mixture with known fungicides, bactericides, acaricides, nematicides or insecticides in order, in this way, to broaden the activity spectrum or to prevent the development of resistance.

A mixture with other known active compounds, such as herbicides, or with fertilizers and growth regulators, safeners or semiochemicals is also possible.

In addition, the compounds of the formula (I) according to the invention also exhibit very good antimycotic activities. They have a very broad spectrum of antimycotic activity, in particular against dermatophytes and budding fungi, molds and diphasic fungi (e.g. against *Candida* species, such as *Candida albicans, Candida glabrata*), and also *Epidermophyton floccosum, Aspergillus* species, such as *Aspergillus niger* and *Aspergillus fumigatus, Trichophyton* species, such as *Trichophyton mentagrophytes, Microsporon* species, such as *Microsporon canis* and *audouinii*. The enumeration of these fungi does not represent in any way a limitation on the mycotic spectrum which can be included but has only an illustrative nature.

The isothiazolyloxyphenylamidines according to the invention can thus be used both in medicinal and in nonmedicinal applications.

The active compounds can be applied as such, in the form of their formulations or in the form of the application forms prepared therefrom, such as ready-to-use solutions, suspensions, sprayable powders, pastes, soluble powders, dusts and granules. Application takes place in standard fashion, e.g. by pouring, spraying, atomizing, scattering, dusting, foaming, spreading, and the like. It is furthermore possible to apply the active compounds by the ultra-low-volume method or to inject the active compound preparation or the active compound itself into the soil.

The seed of the plants can also be treated.

When the isothiazolyloxyphenylamidines according to the invention are used as fungicides, the application rates can be varied within a relatively wide range depending on the type of application. In the treatment of plant parts, the application rates of active compound are generally between 0.1 and 10 000 g/ha, preferably between 10 and 1000 g/ha. In seed treatment, the application rates of active compound are generally between 0.001 and 50 g per kilogram of seed, preferably between 0.01 and 10 g per kilogram of seed. In soil treatment, the application rates of active compound are generally between 0.1 and 10 000 g/ha, preferably between 1 and 5000 g/ha.

GMOs

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNA interference—RNAi technology). A heterologous gene that is located in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, also those substances or combinations of substances which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case unwanted phytopathogenic fungi and/or microorganisms and/or viruses are to be understood as phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant varieties which are preferably to be treated according to the invention include all plants which have genetic material which imparts particularly advantageous, useful traits to these plants (whether obtained by breeding and/or biotechnological means).

Plants and plant varieties which are also preferably to be treated according to the invention are resistant against one or more biotic stresses, i.e. said plants have a better defence against animal and microbial pests, such as against nematodes, insects, mites, phytopathogenic fungi, bacteria, viruses and/or viroids.

Plants and plant varieties which may also be treated according to the invention are those plants which are resistant to one or more abiotic stresses. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which may also be treated according to the invention are those plants characterized by enhanced yield characteristics Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid vigour, which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in the hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male sterile plants can also be obtained by plant biotechnology methods such as genetic engineering. A particularly useful means of obtaining male sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the abovementioned genes.

Other herbicide-resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase are described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which parahydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme of prephenate dehydrogenase in addition to a gene encoding an HPPD-tolerant enzyme.

Further herbicide-resistant plants are plants that are made tolerant to acetolactate synthase (ALS) inhibitors. Known ALS inhibitors include, for example, sulphonylurea, imidazolinone, triazolopyrimidines, pyrimidinyloxy(thio)benzoates, and/or sulphonylaminocarbonyltriazolinone herbicides. Different mutations in the ALS enzyme (also known as acetohydroxyacid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Other plants tolerant to imidazolinone and/or sulphonylurea can be obtained by induced mutagenesis, selection in cell cultures in the presence of the herbicide or mutation breeding.

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

The term "insect-resistant transgenic plant", as used herein, includes any plant containing at least one transgene comprising a coding sequence encoding:
1) an insecticidal crystal protein from *Bacillus thuringiensis* or an insecticidal portion thereof, such as the insecticidal crystal proteins listed online at: http://www.lifesci.sussex.ac.uk/Home/Neil_Crickmore/Bt/, or insecticidal portions thereof, e.g. proteins of the Cry protein classes Cry1Ab, Cry1Ac, Cry1F, Cry2Ab, Cry3Ae, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or 3) a hybrid insecticidal protein comprising parts of two different insecticidal crystal proteins from *Bacillus thuringiensis*, such as a hybrid of the proteins of 1) above or a hybrid of the proteins of 2) above, e.g. the Cry1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation, such as the Cry3Bb 1 protein in corn events MON863 or MON88017, or the Cry3A protein in corn event MIR 604;

5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Crickmore/Bt/vip.html, e.g. proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins; or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of the poly(ADP-ribose) polymerase (PARP) gene in the plant cells or plants.

b. plants which contain a stress tolerance-enhancing transgene capable of reducing the expression and/or the activity of the PARG-encoding genes of the plants or plant cells.

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant varieties (obtained by plant biotechnology methods such as genetic engineering) which may also be treated according to the invention show altered quantity, quality and/or storage stability of the crop product and/or altered properties of specific ingredients of the crop product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesized starch in wild type plant cells or plants, so that this modified starch is better suited for special applications.

2) transgenic plants which synthesize non-starch carbohydrate polymers or which synthesize non-starch carbohydrate polymers with altered properties in comparison to wild type plants without genetic modification. Examples are plants which produce polyfructose, especially of the inulin and levan type, plants which produce alpha-1,4-glucans, plants which produce alpha-1,6 branched alpha-1,4-glucans, and plants producing alternan.

3) transgenic plants which produce hyaluronan.

Plants or plant varieties (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:

a) plants, such as cotton plants which contain an altered form of cellulose synthase genes, b) plants, such as cotton plants which contain an altered form of rsw2 or rsw3 homologous nucleic acids;

c) plants, such as cotton plants, with an increased expression of sucrose phosphate synthase;

d) plants, such as cotton plants, with an increased expression of sucrose synthase;

e) plants, such as cotton plants, wherein the timing of the plasmodesmatal gating at the basis of the fibre cell is altered, e.g. through downregulation of fibre-selective (3-1,3-glucanase;

f) plants, such as cotton plants, which have fibres with altered reactivity, e.g. through the expression of the N-acetylglucosaminetransferase gene including nodC and chitin synthase genes.

Plants or plant varieties (obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:

a) plants, such as oilseed rape plants, which produce oil having a high oleic acid content;

b) plants, such as oilseed rape plants, which produce oil having a low linolenic acid content;

c) plants, such as oilseed rape plants, which produce oil having a low level of saturated fatty acids.

Particularly useful transgenic plants which may be treated according to the invention are plants which comprise one or more genes which encode one or more toxins and are the following which are sold under the trade names YIELD GARD® (for example maize, cotton, soya beans), Knock-Out® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinothricin, for example oilseed rape), IMF) (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, that are listed for example in the databases for various national or regional regulatory agencies (see for example http://gmoinfo.jrc.it/gmp_browse.aspx and http://www.agbios.com/dbase.php).

PREPARATION EXAMPLES

| Ex. | $R^1$ | $R^2$ | $R^3$ / $R^2 + R^3$ | $R^4$ | $R^5$ | $R^6$ | $R^7$ / $R^6 + R^7$ | NMR |
|---|---|---|---|---|---|---|---|---|
| 1 | H | CH₃ | ethyl | CH₃ | CH₃ | cyano | ethyl | δ = 7.64 (b, 1H), 7.12 (s, 1H), 6.76 (s, 1H), 3.39 (q, 2H), 2.99 (s, 3H), 2.77 (q, 2H), 2.15 (s, 6H), 1.25 (t, 3H), 1.16 (t, 3H) |
| 2 | H | | pentane-1,5-diyl | CH₃ | CH₃ | cyano | ethyl | δ = 7.61 (b, 1H), 7.18 (s, 1H), 6.77 (s, 1H), 3.50 (m, 4H), 2.78 (q, 2H), 2.15 (s, 6H), 1.67-1.45 (m, 6H) |
| 3 | H | CH₃ | propyl | CH₃ | CH₃ | cyano | ethyl | δ = 7.66 (b, 1H), 7.12 (s, 1H), 6.75 (s, 1H), 3.20 (m, 2H), 2.97 (s, 3H), 2.79 (q, 2H), 2.15 (s, 3H), 2.14 (s, 3H), 1.60 (m, 2H), 1.25 (t, 3H), 0.89 (t, 3H) |
| 4 | H | CH₃ | propyl | CH₃ | CH₃ | cyano | tert-butyl | δ = 7.66 (b, 1H), 7.12 (s, 1H), 6.75 (s, 1H), 3.21 (m, 2H), 2.98 (s, 3H), 2.15 (s, 6H), 1.60 (m, 2H), 1.30 (s, 9H), 0.88 (t, 3H) |
| 5 | H | CH₃ | prop-2-en-1-yl | CH₃ | CH₃ | cyano | tert-butyl | δ = 7.70 (b, 1H), 7.14 (s, 1H), 6.77 (s, 1H), 5.86 (m, 1H), 5.21 (m, 2H), 2.97 (m, 2H), 2.98 (s, 3H), 2.14 (s, 6H), 1.40 (s, 9H) |
| 6 | H | CH₃ | ethyl | CH₃ | CH₃ | cyano | tert-butyl | δ = 7.65 (b, 1H), 7.13 (s, 1H), 6.76 (s, 1H), 3.38 (m, 2H), 2.95 (s, 3H), 2.15 (s, 3H), 2.14 (s, 3H), 1.40 (s, 9H), 1.14 (t, 3H) |
| 7 | H | | pentane-1,5-diyl | CH₃ | CH₃ | cyano | tert-butyl | δ = 7.62 (b, 1H), 7.12 (s, 1H), 6.77 (s, 1H), 3.45 (m, 4H), 1.14 (s, 6H), 1.40 (s, 9H) |
| 8 | H | CH₃ | CH₃ | CH₃ | CH₃ | cyano | tert-butyl | δ = 7.63 (b, 1H), 7.14 (s, 1H), 6.76 (s, 1H), 2.97 (s, 6H), 2.15 (s, 3H), 2.14 (s, 3H), 1.65-1.52 (m, 6H), 1.39 (s, 9H) |
| 9 | H | CH₃ | ethyl | chloro | CH₃ | cyano | ethyl | δ = 7.51 (b, 1H), 6.99 (s, 1H), 3.40 (q, 2H), 2.99 (s, 3H), 2.77 (q, 2H), 2.17 (s, 3H), 1.24 (t, 3H), 1.13 (t, 3H) |
| 10 | H | CH₃ | ethyl | chloro | CH₃ | cyano | tert-butyl | δ = 7.52 (b, 1H), 7.00 (s, 1H), 3.39 (m, 2H), 2.98 (s, |

-continued

| | | | | | | | | |
|---|---|---|---|---|---|---|---|---|
| 11 | H | CH$_3$ | CH$_3$ | CH$_3$ | chloro | cyano | phenyl | 3H), 2.17 (s, 3H), 1.40 (s, 9H), 1.16 (t, 3H)<br>δ = 7.90-7.94 (m, 2H), 7.77 (s, 1 H), 7.55-7.59 (m, 3H), 7.47 (s, 1H), 7.10 (s, 1H), 3.00 (s, 6H), 2.21 (s, 3H) |
| 12 | H | ethyl | CH$_3$ | CH$_3$ | chloro | cyano | phenyl | δ = 7.90-7.93 (m, 2H), 7.79 (s, 1H), 7.55-7.59 (m, 3H), 7.47 (s, 1H), 7.11 (s, 1H), 3.42 (q, 2H), 2.98 (s, 3H), 2.21 (s, 3H), 1.16 (t, 3H) |
| 13 | H | propyl | CH$_3$ | CH$_3$ | chloro | cyano | phenyl | δ = 7.91-7.93 (m, 2H), 7.80 (s, 1 H), 7.56-7.58 (m, 3H), 7.47 (s, 1H), 7.09 (s, 1H), 3.34 (brt, 2H), 2.98 (s, 3H), 2.21 (s, 3H), 1.58-1.64 (m, 2H), 0.88 (t, 3H) |
| 14 | H | CH$_3$ | CH$_3$ | CH$_3$ | CH$_3$ | cyano | phenyl | δ = 7.91-7.93 (m, 2H), 7.66 (s, 1 H), 7.54-7.58 (m, 3H), 7.20 (s, 1H), 6.80 (s, 1H), 2.99 (s, 6H), 2.19 (s, 3H), 2.18 (s, 3H) |
| 15 | H | ethyl | CH$_3$ | CH$_3$ | CH$_3$ | cyano | phenyl | δ = 7.91-7.94 (m, 2H), 7.67 (s, 1H), 7.54-7.58 (m, 3H), 7.20 (s, 1H), 6.80 (s, 1H), 3.40 (q, 2H), 2.97 (s, 3H), 2.20 (s, 3H), 2.18 (s, 3H), 1.54 (t, 3H) |
| 16 | H | propyl | CH$_3$ | CH$_3$ | CH$_3$ | cyano | phenyl | δ = 7.90-7.94 (m, 2H), 7.68 (s, 1 H), 7.54-7.58 (m, 3H), 7.20 (s, 1H), 6.78 (s, 1H), 3.32 (brt, 2H), 2.96 (s, 3H), 2.19 (s, 3H), 2.18 (s, 3H), 1.56-1.65 (m, 2H), 0.89 (t, 3H) |
| 17 | H | CH$_3$ | CH$_3$ | chloro | CH$_3$ | cyano | phenyl | δ = 7.91-7.93 (m, 2H), 7.75 (s, 1H), 7.56-7.59 (m + s, 4H), 7.03 (s, 1H), 3.01 (s, 6H), 2.22 (s,3H) |
| 18 | H | ethyl | CH$_3$ | chloro | CH$_3$ | cyano | phenyl | δ = 7.91-7.93 (m, 2H), 7.76 (s, 1H), 7.56-7.59 (m + s, 4H), 7.03 (s, 1H), 3.42 (q, 2H), 2.99 (s, 3H), 2.21 (s, 3H), 1.17 (t, 3H) |
| 19 | H | propyl | CH$_3$ | chloro | CH$_3$ | cyano | phenyl | δ = 7.91-7.93 (m, 2H), 7.77 (s, 1 H), 7.56-7.59 (m + s, 4H), 7.02 (s, 1H), 3.33 (brt, 2H), 2.98 (s, 3H), 2.22 (s, 3H), 1.60-1.65 (m, 2H), 0.88 (t, 3H) |
| 20 | H | pentane-1,5-diyl | CH$_3$ | CH$_3$ | CH$_3$ | cyano | 4-chloro-phenyl | δ = 7.94 (d, 2H), 7.64 (s, 1 H), 7.63 (d, 2H), 7.20 (s, 1H), 6.80 (s, 1H), 3.42-3.50 (m, 4H), 2.19 (s, 3H), 2.17 (s, 3H), 1.52-1.68 (m, 6H) |
| 21 | H | propyl | CH$_3$ | CH$_3$ | CH$_3$ | cyano | 4-chloro-phenyl | δ = 7.94 (d, 2H), 7.68 (s, 1 H), 7.63 (d, 2H), 7.20 (s, 1H), 6.79 (s, 1H), 3.32 (brt, 2H), 2.96 (s, 3H), 2.19 (s, 3H), 2.17 (s, 3H), 1.60-1.65 (m, 2H), 0.88 (t, 3H) |
| 22 | H | ethyl | CH$_3$ | CH$_3$ | CH$_3$ | cyano | 4-chloro-phenyl | δ = 7.95 (d, 2H), 7.68 (s, 1H), 7.63 (d, 2H), 7.20 (s, 1H), 6.81 (s, 1H), 3.40 (q, 2H), 2.97 (s, 3H), 2.19 (s, 3H), 2.18 (s, 3H), 1.56 (t, 3H) |
| 23 | H | CH$_3$ | CH$_3$ | CH$_3$ | CH$_3$ | cyano | 4-chloro-phenyl | δ = 7.94 (d, 2H), 7.65 (s, 1H), 7.62 (d, 2H), 7.20 (s, 1H), 6.79 (s, 6H), 2.98 (s, 6H), 2.18 (s, 3H), 2.19 (s, 3H) |
| 24 | H | CH$_3$ | CH$_3$ | CH$_3$ | CH$_3$ | cyano | 3-methyl-phenyl | δ = 7.69-7.74 (m, 2H), 7.65 (s, 1 H), 7.34-7.48 (m, 2H), 7.20 (s, 1H), 6.79 (s, 1H), 2.98 (s, 6H), 2.40 (s, |

| | | | | | | | | |
|---|---|---|---|---|---|---|---|---|
| | | | | | | | | 3H), 2.19 (s, 3H), 2.18 (s, 3H) |
| 25 | H | ethyl | CH₃ | CH₃ | CH₃ | cyano | 3-methyl-phenyl | δ = 7.69-7.75 (m, 2H), 7.67 (s, 1H), 7.34-7.48 (m, 2H), 7.20 (s, 1H), 6.80 (s, 1H), 3.39 (q, 2H), 2.96 (s, 3H), 2.18 (s, 3H), 1.15 (t, 3H) |
| 26 | H | propyl | CH₃ | CH₃ | CH₃ | cyano | 3-methyl-phenyl | δ = 7.69-7.75 (m, 2H), 7.68 (s, 1 H), 7.35-7.48 (m, 2H), 7.20 (s, 1H), 6.78 (s, 1H), 3.32 (brt, 2H), 2.96 (s, 3H), 2.40 (s, 3H), 2.19 (s, 3H), 2.18 (s, 3H), 1.55-1.67 (m, 2H), 0.89 (t, 3H) |
| 27 | H | ethyl | CH₃ | CH₃ | CH₃ | cyano | 4-chloro-benzyl | δ = 7.64 (s, 1H), 7.38 (d, 2H), 7.30 (d, 2H), 7.13 (s, 1H), 6.76 (s, 1H), 4.14 (s, 2H), 3.38 (q, 2H), 2.95 (s, 3H), 2.15 (s, 3H), 2.13 (s, 3H), 1.14 (t, 3H) |
| 28 | H | ethyl | CH₃ | CH₃ | CH₃ | cyano | 4-tert-butyl-phenyl | δ = 7.86 (d, 2H), 7.67 (s, 1H), 7.58 (d, 2H), 7.20 (s, 1H), 6.80 (s, 1H), 3.38 (q, 2H), 2.96 (s, 3H), 2.19 (s, 3H), 2.17 (s, 3H), 1.34 (s, 9H), 1.15 (t, 3H) |
| 29 | H | propyl | CH₃ | CH₃ | CH₃ | cyano | 4-tert-butyl-phenyl | δ = 7.86 (d, 2H), 7.68 (s, 1H), 7.58 (d, 2H), 7.20 (s, 1H), 6.78 (s, 1H), 3.32 (brt, 2H), 2.96 (s, 3H), 2.19 (s, 3H), 2.17 (s, 3H), 1.53-1.64 (m, 2H), 1.33 (s, 9H), 0.88 (t, 3H) |
| 30 | H | prop-2-en-1-yl | CH₃ | CH₃ | CH₃ | cyano | 4-tert-butyl-phenyl | δ = 7.86 (d, 2H), 7.71 (s, 1H), 7.58 (d, 2H), 7.21 (s, 1H), 6.80 (s, 1H), 5.81-5.95 (m, 1H), 5.19-5.25 (m, 2H), 3.97 (brd, 2H), 2.95 (s, 3H), 2.19 (s, 3H), 2.18 (s, 3H), 1.33 (s, 9H) |
| 31 | H | CH₃ | CH₃ | CH₃ | CH₃ | cyano | 4-fluoro-phenyl | δ = 7.80-7.95 (m, 2H), 7.65 (s, 1 H), 7.36-7.41 (m, 2H), 7.20 (s, 1H), 6.79 (s, 1H), 2.98 (s, 6H), 2.19 (s, 3H), 2.18 (s, 3H) |
| 32 | H | ethyl | CH₃ | CH₃ | CH₃ | cyano | 4-fluoro-phenyl | δ = 7.95-8.00 (m, 2H), 7.67 (s, 1H), 7.36-7.42 (m, 2H), 7.19 (s, 1H), 6.80 (s, 1H), 3.39 (q, 2H), 2.97 (s, 3H), 2.19 (s, 3H), 2.17 (s, 3H), 1.15 (t, 3H) |
| 33 | H | propyl | CH₃ | CH₃ | CH₃ | cyano | 4-fluoro-phenyl | δ = 7.93-8.01 (m, 2H), 7.68 (s, 1H), 7.35-7.43 (m, 2H), 7.20 (s, 1H), 6.78 (s, 1H), 3.13 (brt, 2H), 2.96 (s, 3H), 1.55-1.65 (m, 2H), 0.88 (t, 3H) |
| 34 | H | CH₃ | ethyl | CH₃ | CH₃ | bromo | phenyl | δ = 7.78-7.82 (m, 2H), 7.65 (s, 1 H), 7.49-7.52 (m, 3H), 7.09 (s, 1H), 6.77 (s, 1H), 3.38 (q, 2H), 2.95 (s, 3H), 2.17 (s, 6H), 1.15 (t, 3H) |
| 35 | H | propyl | CH₃ | chloro | CH₃ | cyano | 4-fluoro-phenyl | δ = 7.96-8.00 (m, 2H), 7.77 (brs, 1 H), 7.58 (s, 1H), 7.38-7.42 (m, 2H), 7.02 (s, 1H), 3.32 (brt, 2H), 2.98 (s, 3H), 2.21(s, 3H), 1.55-1.67 (m, 2H), 0.88 (t, 3H) |
| 36 | H | CH₃ | CH₃ | CH₃ | chloro | cyano | 4-fluoro-phenyl | δ = 7.95-8.01 (m, 2H), 7.77 (s, 1H), 7.46 (s, 1H), 7.37-7.43 (m, 2H), 7.10 (s, 1H), 3.01 (s, 6H), 2.21 (s, 3H) |
| 37 | H | ethyl | CH₃ | CH₃ | chloro | cyano | 4-fluoro-phenyl | δ = 7.96-8.00 (m, 2H), 7.79 (brs, 1H), 7.46 (s, 1H), 7.33-7.42 (m, 2H), 7.11 (s, 1H), 3.42 (q, 2H), |

| | | | | | | | |
|---|---|---|---|---|---|---|---|
| | | | | | | | 2.98 (s, 3H), 2.21 (s, 3H), 1.16 (t, 3H) |
| 38 | H | propyl | CH₃ | CH₃ | chloro | cyano | 4-fluoro-phenyl | δ = 7.95-8.01 (m, 2H), 7.80 (s, 1 H), 7.47 (s, 1H), 7.37-7.42 (m, 2H), 7.09 (s, 1H), 3.33 (brt, 2H), 2.98 (s, 3H), 2.21 (s, 3H), 1.57-1.68 (m, 2H), 0.88 (t, 3H) |
| 39 | H | CH₃ | CH₃ | CH₃ | chloro | cyano | 3-methyl-phenyl | δ = 7.77 (s, 1H), 7.69-7.74 (m, 2H), 7.47 (s, 1H), 7.37-7.45 (m, 2H), 7.10 (s, 1H), 3.00 (s, 6H), 2.40 (s, 3H), 2.21 (s, 3H) |
| 40 | H | ethyl | CH₃ | CH₃ | chloro | cyano | 3-methyl-phenyl | δ = 7.79 (s, 1H), 7.69-7.74 (m, 2H), 7.47 (s, 1H), 7.37-7.46 (m, 2H), 7.11 (s, 1H), 3.42 (q, 2H), 2.98 (s, 3H), 2.40 (s, 3H), 2.21 (s, 3H), 1.16 (t, 3H) |
| 41 | H | propyl | CH₃ | CH₃ | chloro | cyano | 3-methyl-phenyl | δ = 7.80 (s, 1H),7.69-7.74 (m, 2H), 7.47 (s, 1H), 7.37-7.45 (m, 2H), 7.09 (s, 1H), 3.34 (brt, 2H), 2.99 (s, 3H), 2.40 (s, 3H), 2.20 (s, 3H), 1.55-1.65 (m, 2H), 0.88 (t, 3H) |
| 42 | H | CH₃ | CH₃ | CH₃ | CH₃ | H | phenyl | δ = 7.92 (d, 2H), 7.63 (s, 1H), 7.40-7.48 (m, 3H), 7.29 (s, 1H), 7.04 (s, 1H), 6.74 (s, 1H), 2.98 (s, 6H), 2.17 (s, 6H) |
| 43 | H | ethyl | CH₃ | CH₃ | CH₃ | H | phenyl | δ = 7.91 (d, 2H), 7.64 (s, 1H), 7.40-7.48 (m, 3H), 7.28 (s, 1H), 7.04 (s, 1H), 6.74 (s, 1H), 3.38 (q, 2H), 2.95 (s, 3H), 2.16 (s, 6H), 1.15 (t, 3H) |
| 44 | H | propyl | CH₃ | CH₃ | CH₃ | H | phenyl | δ = 7.91 (d, 2H), 7.65 (s, 1H), 7.39-7.47 (m, 3H), 7.28 (s, 1H), 7.04 (s, 1H), 6.73 (s, 1H), 3.31 (brt, 2H), 2.96 (s, 3H), 2.16 (s, 6H), 1.55-1.64 (m, 2H), 0.88 (t, 3H) |
| 45 | H | CH₃ | CH₃ | chloro | CH₃ | H | phenyl | δ = 7.93 (d, 2H), 7.73 (s, 1H), 7.40-7.47 (m, 3H), 7.35 (s, 1H), 7.33 (s, 1H), 6.98 (s, 1H), 3.01 (brt, 2H), 2.96 (s, 3H), 2.16 (s, 6H), 2.19 (s, 3H) |
| 46 | H | ethyl | CH₃ | chloro | CH₃ | H | phenyl | δ = 7.93 (d, 2H), 7.73 (s, 1H), 7.40-7.48 (m, 3H), 7.35 (s, 1H), 7.33 (s, 1H), 6.98 (s, 1H), 3.40 (q, 2H), 2.98 (s, 3H), 2.19 (s, 3H), 1.16 (t, 3H) |
| 47 | H | propyl | CH₃ | chloro | CH₃ | H | phenyl | δ = 7.93 (d, 2H), 7.74 (s, 1H), 7.40-7.47 (m, 3H), 7.34 (s, 1H), 7.33 (s, 1H), 6.96 (s, 1H), 3.32 (brt, 2H), 2.98 (s, 3H), 2.19 (s, 3H), 1.57-1.66 (m, 2H), 0.89 (t, 3H) |
| 48 | H | CH₃ | ethyl | CH₃ | CH₃ | chloro | phenyl | δ = 7.80-7.84 (m, 2H), 7.65 (s, 1 H), 7.49-7.54 (m, 3H), 7.10 (s, 1H), 6.76 (s, 1H), 3.38 (q, 2H), 2.95 (s, 3H), 2.17 (s, 6H), 1.15 (t, 3H) |
| 49 | H | CH₃ | propan-2-yl | CH₃ | CH₃ | chloro | phenyl | δ = 7.81-7.84 (m, 2H), 7.69 (s, 1 H), 7.49-7.53 (m, 3H), 7.10 (s, 1H), 6.76 (s, 1H), 2.86 (s, 3H), 2.17 (s, 6H), 1.20 (d, 6H) |
| 50 | H | pentane-1,5-diyl | CH₃ | CH₃ | chloro | phenyl | δ = 7.80-7.84 (m, 2H), 7.62 (s, 1 H), 7.49-7.54 (m, 3H), 7.10 (s, 1H), 6.77 (s, 1H), 3.45 (m, 4H), 2.17 (s, 3H), 2.16 (s, 3H), 1.51-1.67 (m, 6H) |

-continued

| Ex. | R¹ | R² | R³ | R⁴ | R⁵ | R⁶ | R⁷ | NMR |
|---|---|---|---|---|---|---|---|---|
| 51 | H | CH₃ | ethyl | CH₃ | chloro | chloro | phenyl | δ = 7.80-7.84 (m, 2H), 7.76 (s, 1 H), 7.50-7.54 (m, 3H), 7.34 (s, 1H), 7.06 (s, 1H), 3.40 (q, 2H), 2.97 (s, 3H), 2.19 (s, 6H), 1.15 (t, 3H) |
| 52 | H | CH₃ | propan-2-yl | CH₃ | chloro | chloro | phenyl | δ = 7.80-7.84 (m, 3H), 7.50-7.54 (m, 3H), 7.34 (s, 1H), 7.07 (s, 1H), 2.88 (s, 3H), 2.19 (s, 3H), 1.20 (d, 6H) |
| 53 | H | pentane-1,5-diyl | | CH₃ | chloro | chloro | phenyl | δ = 7.80-7.84 (m, 2H), 7.73 (s, 1 H), 7.50-7.54 (m, 3H), 7.34 (s, 1H), 7.07 (s, 1H), 3.48 (m, 4H), 2.18 (s, 3H), 1.52-1.67 (m, 6H) |
| 54 | H | CH₃ | ethyl | CH₃ | chloro | chloro | phenyl | δ = 7.76-7.84 (m, 3H), 7.49-7.54 (m, 3H), 7.34 (s, 1H), 7.07 (s, 1H), 3.40 (q, 2H), 2.97 (s, 3H), 2.20 (s, 3H), 1.15 (t, 3H) |
| 55 | H | CH₃ | propan-2-yl | CH₃ | chloro | bromo | phenyl | δ = 7.76-7.84 (m, 3H), 7.50-7.53 (m, 3H), 7.34 (s, 1H), 7.07 (s, 1H), 2.88 (s, 3H), 2.19 (s, 3H), 1.20 (d, 6H) |
| 56 | H | pentane-1,5-diyl | | CH₃ | chloro | bromo | phenyl | δ = 7.80-7.84 (m, 2H), 7.73 (s, 1 H), 7.49-7.54 (m, 3H), 7.34 (s, 1H), 7.07 (s, 1H), 3.48 (m, 4H), 2.19 (s, 3H), 1.52-1.67 (m, 6H) |
| 57 | H | CH₃ | CH₃ | chloro | CH₃ | cyano | 4-fluoro-phenyl | δ = 7.95-8.00 (m, 2H), 7.45 (s, 1H), 7.59 (s, 1H), 7.37-7.43 (m, 2H), 7.03 (s, 1H), 3.01 (s, 6H), 2.22 (s, 3H) |
| 58 | H | ethyl | CH₃ | chloro | CH₃ | cyano | 4-fluoro-phenyl | δ = 7.96-8.00 (m, 2H), 7.77 (brs, 1H), 7.58 (s, 1H), 7.37-7.42 (m, 2H), 7.04 (s, 1H), 3.41 (q, 2H), 2.99 (s, 3H), 2.22 (s, 3H), 1.17 (t, 3H) |
| 59 | ethyl | CH₃ | CH₃ | CH₃ | (1Z,3Z)-buta-1,3-diene-1,4-diyl | | | δ = 7.72 (d, 1H), 7.66 (s, 1H), 7.49 (d, 1H), 7.40-7.44 (m, 1H), 7.10-7.14 (m, 2H), 6.79 (s, 1H), 3.39 (brq, 2H), 2.96 (s, 3H), 2.17 (s, 3H), 2.15 (s, 3H), 1.15 (t, 3H) |
| 60 | CH₃ | CH₃ | CH₃ | CH₃ | (1Z,3Z)-buta-1,3-diene-1,4-diyl | | | δ = 7.72 (d, 1H), 7.65 (s, 1H), 7.50 (d, 1H), 7.39-7.44 (m, 1H), 7.10-7.14 (m, 2H), 6.79 (s, 1H), 2.98 (s, 6H), 2.17 (s, 3H), 2.15 (s, 3H) |

| Ex. | R¹ | R² / R² + R³ | R³ | R⁴ | R⁵ | R⁶ / R⁶ + R⁷ | R⁷ |
|---|---|---|---|---|---|---|---|
| 61 | H | CH₃ | propyl | CH₃ | CH₃ | (1Z,3Z)-buta-1,3-diene-1,4-diyl | |
| 62 | H | pentane-1,5-diyl | | CH₃ | CH₃ | (1Z,3Z)-buta-1,3-diene-1,4-diyl | |
| 63 | H | butylene | | CH₃ | CH₃ | (1Z,3Z)-buta-1,3-diene-1,4-diyl | |
| 64 | H | CH₃ | ethyl | CH₃ | CH₃ | chloro | tert-butyl |
| 65 | H | CH₃ | propan-2-yl | CH₃ | CH₃ | chloro | tert-butyl |
| 66 | H | pentane-1,5-diyl | | CH₃ | CH₃ | chloro | tert-butyl |
| 67 | H | CH₃ | ethyl | chloro | CH₃ | chloro | tert-butyl |
| 68 | H | CH₃ | propan-2-yl | chloro | CH₃ | chloro | tert-butyl |
| 69 | H | pentane-1,5-diyl | | chloro | CH₃ | chloro | tert-butyl |
| 70 | H | CH₃ | ethyl | CH₃ | chloro | chloro | tert-butyl |
| 71 | H | CH₃ | propan-2-yl | CH₃ | chloro | chloro | tert-butyl |
| 72 | H | pentane-1,5-diyl | | CH₃ | chloro | chloro | tert-butyl |
| 73 | H | CH₃ | CH₃ | CH₃ | CH₃ | H | tert-butyl |
| 74 | H | ethyl | CH₃ | CH₃ | CH₃ | H | tert-butyl |
| 75 | H | propyl | CH₃ | CH₃ | CH₃ | H | tert-butyl |
| 76 | H | CH₃ | CH₃ | CH₃ | CH₃ | cyano | 3-fluorophenyl |
| 77 | H | CH₃ | propan-2-yl | CH₃ | CH₃ | cyano | 3-fluorophenyl |

-continued

| | | | | | | | |
|---|---|---|---|---|---|---|---|
| 78 | H | CH$_3$ | ethyl | CH$_3$ | CH$_3$ | cyano | 3-fluorophenyl |
| 79 | H | CH$_3$ | CH$_3$ | CH$_3$ | CH$_3$ | cyano | 2-methylphenyl |
| 80 | H | propan-2-yl | CH$_3$ | CH$_3$ | CH$_3$ | cyano | 2-methylphenyl |
| 81 | H | CH$_3$ | ethyl | CH$_3$ | CH$_3$ | cyano | 2-methylphenyl |
| 82 | H | CH$_3$ | ethyl | fluoro | fluoro | cyano | tert-butyl |
| 83 | H | CH$_3$ | ethyl | CH$_3$ | CH$_3$ | chloro | CH$_3$ |
| 84 | H | pentane-1,5-diyl | | CH$_3$ | CH$_3$ | chloro | CH$_3$ |
| 85 | H | CH$_3$ | ethyl | CH$_3$ | chloro | chloro | CH$_3$ |
| 86 | H | pentane-1,5-diyl | | CH$_3$ | chloro | chloro | CH$_3$ |
| 87 | H | CH$_3$ | ethyl | chloro | CH$_3$ | chloro | CH$_3$ |
| 88 | H | pentane-1,5-diyl | | chloro | CH$_3$ | chloro | CH$_3$ |
| 89 | H | ethyl | CH$_3$ | chloro | CH$_3$ | cyano | 3-fluorophenyl |
| 90 | H | CH$_3$ | CH$_3$ | chloro | CH$_3$ | cyano | 2-chlorophenyl |
| 91 | H | ethyl | CH$_3$ | chloro | CH$_3$ | cyano | 2-chlorophenyl |
| 92 | H | propan-2-yl | CH$_3$ | chloro | CH$_3$ | cyano | 2-chlorophenyl |
| 93 | H | CH$_3$ | CH$_3$ | CH$_3$ | chloro | cyano | 2-methylphenyl |
| 94 | H | propan-2-yl | CH$_3$ | CH$_3$ | chloro | cyano | 2-methylphenyl |
| 95 | H | CH$_3$ | ethyl | CH$_3$ | chloro | cyano | 2-methylphenyl |
| 96 | H | CH$_3$ | CH$_3$ | CH$_3$ | CH$_3$ | cyano | 2,2-dimethylpropyl |
| 97 | H | propan-2-yl | CH$_3$ | CH$_3$ | CH$_3$ | cyano | 2,2-dimethylpropyl |
| 98 | H | ethyl | CH$_3$ | CH$_3$ | CH$_3$ | cyano | 2,2-dimethylpropyl |
| 99 | H | CH$_3$ | CH$_3$ | CH$_3$ | CH$_3$ | cyano | 1-chlorocyclopropyl |
| 100 | H | ethyl | CH$_3$ | CH$_3$ | CH$_3$ | cyano | 1-chlorocyclopropyl |
| 101 | H | propan-2-yl | CH$_3$ | CH$_3$ | CH$_3$ | cyano | 1-chlorocyclopropyl |
| 102 | H | CH$_3$ | CH$_3$ | CH$_3$ | chloro | cyano | 2,2-dimethylpropyl |
| 103 | H | CH$_3$ | ethyl | CH$_3$ | CH$_3$ | bromo | CH$_3$ |
| 104 | H | CH$_3$ | CH$_3$ | chloro | CH$_3$ | cyano | 3-fluorophenyl |
| 105 | H | CH$_3$ | propan-2-yl | chloro | CH$_3$ | cyano | 3-fluorophenyl |
| 106 | H | CH$_3$ | propan-2-yl | fluoro | fluoro | cyano | tert-butyl |
| 107 | H | pentane-1,5-diyl | | CH$_3$ | CH$_3$ | bromo | CH$_3$ |
| 108 | H | CH$_3$ | ethyl | CH$_3$ | chloro | bromo | CH$_3$ |
| 109 | H | pentane-1,5-diyl | | CH$_3$ | chloro | bromo | CH$_3$ |
| 110 | H | CH$_3$ | ethyl | chloro | CH$_3$ | bromo | CH$_3$ |
| 111 | H | pentane-1,5-diyl | | chloro | CH$_3$ | bromo | CH$_3$ |
| 112 | H | propan-2-yl | CH$_3$ | CH$_3$ | chloro | cyano | 2,2-dimethylpropyl |
| 113 | H | ethyl | CH$_3$ | CH$_3$ | chloro | cyano | 2,2-dimethylpropyl |
| 114 | H | CH$_3$ | CH$_3$ | CH$_3$ | chloro | cyano | 3-fluorophenyl |
| 115 | H | CH$_3$ | CH$_3$ | chloro | CH$_3$ | cyano | 2-methylphenyl |
| 116 | H | propan-2-yl | CH$_3$ | chloro | CH$_3$ | cyano | 2-methylphenyl |
| 117 | H | CH$_3$ | CH$_3$ | chloro | CH$_3$ | cyano | 2,2-dimethylpropyl |
| 118 | H | propan-2-yl | CH$_3$ | chloro | CH$_3$ | cyano | 2,2-dimethylpropyl |
| 119 | H | ethyl | CH$_3$ | chloro | CH$_3$ | cyano | 2,2-dimethylpropyl |
| 120 | H | CH$_3$ | CH$_3$ | CH$_3$ | CH$_3$ | cyano | 2-phenylpropan-2-yl |
| 121 | H | propan-2-yl | CH$_3$ | CH$_3$ | CH$_3$ | cyano | 2-phenylpropan-2-yl |
| 122 | H | CH$_3$ | CH$_3$ | CH$_3$ | CH$_3$ | cyano | 2-phenylpropan-2-yl |
| 123 | H | CH$_3$ | CH$_3$ | CH$_3$ | CH$_3$ | cyano | 2-chlorophenyl |
| 124 | H | propan-2-yl | CH$_3$ | CH$_3$ | CH$_3$ | cyano | 2-chlorophenyl |
| 125 | H | ethyl | CH$_3$ | CH$_3$ | CH$_3$ | cyano | 2-chlorophenyl |
| 126 | H | CH$_3$ | CH$_3$ | CH$_3$ | chloro | cyano | 2-chlorophenyl |
| 127 | H | CH$_3$ | CH$_3$ | CH$_3$ | CH$_3$ | cyano | 2-fluorophenyl |
| 128 | H | CH$_3$ | propan-2-yl | CH$_3$ | CH$_3$ | cyano | 2-fluorophenyl |
| 129 | H | ethyl | CH$_3$ | CH$_3$ | CH$_3$ | cyano | 2-fluorophenyl |
| 130 | H | ethyl | CH$_3$ | CH$_3$ | chloro | cyano | 3-fluorophenyl |
| 131 | H | ethyl | CH$_3$ | chloro | CH$_3$ | cyano | 2-methylphenyl |
| 132 | H | ethyl | CH$_3$ | CH$_3$ | chloro | cyano | 2-chlorophenyl |
| 133 | H | CH$_3$ | CH$_3$ | chloro | CH$_3$ | cyano | 2-chlorophenyl |
| 134 | H | propan-2-yl | CH$_3$ | CH$_3$ | chloro | cyano | 2-chlorophenyl |
| 135 | H | propan-2-yl | CH$_3$ | chloro | CH$_3$ | cyano | 2-fluorophenyl |
| 136 | H | ethyl | CH$_3$ | chloro | CH$_3$ | cyano | 2-fluorophenyl |
| 137 | H | CH$_3$ | CH$_3$ | chloro | CH$_3$ | cyano | 2-fluorophenyl |
| 138 | H | propan-2-yl | CH$_3$ | CH$_3$ | chloro | cyano | 2-fluorophenyl |
| 139 | H | ethyl | CH$_3$ | CH$_3$ | chloro | cyano | 2-fluorophenyl |
| 140 | H | CH$_3$ | CH$_3$ | chloro | CH$_3$ | cyano | 1-chlorocyclopropyl |

-continued

| | | | | | | | |
|---|---|---|---|---|---|---|---|
| 141 | H | propan-2-yl | CH$_3$ | chloro | CH$_3$ | cyano | 1-chlorocyclopropyl |
| 142 | H | ethyl | CH$_3$ | chloro | CH$_3$ | cyano | 1-chlorocyclopropyl |
| 143 | H | CH$_3$ | CH$_3$ | CH$_3$ | chloro | cyano | 1-chlorocyclopropyl |
| 144 | H | pentane-1,5-diyl | | CH$_3$ | CH$_3$ | ethoxycarbonyl | CH$_3$ |
| 145 | H | CH$_3$ | ethyl | CH$_3$ | CH$_3$ | ethoxycarbonyl | CH$_3$ |
| 146 | H | CH$_3$ | propan-2-yl | CH$_3$ | CH$_3$ | ethoxycarbonyl | CH$_3$ |
| 147 | H | CH$_3$ | ethyl | chloro | CH$_3$ | ethoxycarbonyl | CH$_3$ |
| 148 | H | CH$_3$ | propan-2-yl | chloro | CH$_3$ | ethoxycarbonyl | CH$_3$ |
| 149 | H | pentane-1,5-diyl | | CH$_3$ | chloro | ethoxycarbonyl | CH$_3$ |
| 150 | H | CH$_3$ | ethyl | CH$_3$ | chloro | ethoxycarbonyl | CH$_3$ |
| 151 | H | CH$_3$ | propan-2-yl | CH$_3$ | chloro | ethoxycarbonyl | CH$_3$ |
| 152 | H | pentane-1,5-diyl | | chloro | CH$_3$ | ethoxycarbonyl | CH$_3$ |
| 153 | H | ethyl | CH$_3$ | CH$_3$ | chloro | cyano | 1-chlorocyclopropyl |
| 154 | H | propan-2-yl | CH$_3$ | CH$_3$ | chloro | cyano | 1-chlorocyclopropyl |
| 158 | H | CH$_3$ | ethyl | CH$_3$ | CH$_3$ | iodo | CH$_3$ |
| 159 | H | ethyl | CH$_3$ | CH$_3$ | CH$_3$ | cyano | 4-methylphenyl |
| 160 | H | CH$_3$ | CH$_3$ | CH$_3$ | CH$_3$ | cyano | 4-methylphenyl |
| 161 | H | CH$_3$ | CH$_3$ | CH$_3$ | chloro | cyano | 4-methylphenyl |
| 162 | H | CH$_3$ | propan-2-yl | CH$_3$ | chloro | cyano | 4-methylphenyl |
| 163 | H | CH$_3$ | ethyl | CH$_3$ | CH$_3$ | CH$_3$ | CH$_3$ |
| 164 | H | CH$_3$ | CH$_3$ | CH$_3$ | CH$_3$ | cyano | 2,3-dimethylbutan-2-yl |
| 165 | H | CH$_3$ | propan-2-yl | CH$_3$ | CH$_3$ | cyano | 2,3-dimethylbutan-2-yl |
| 166 | H | ethyl | CH$_3$ | CH$_3$ | CH$_3$ | cyano | 2,3-dimethylbutan-2-yl |
| 167 | H | CH$_3$ | ethyl | CH$_3$ | chloro | cyano | tert-butyl |
| 168 | H | CH$_3$ | ethyl | CH$_3$ | tert-butyl | cyano | tert-butyl |
| 169 | H | CH$_3$ | ethyl | CH$_3$ | bromo | cyano | tert-butyl |
| 170 | H | ethyl | CH$_3$ | CH$_3$ | chloro | (1Z,3Z)-buta-1,3-diene-1,4-diyl | |
| 171 | H | CH$_3$ | CH$_3$ | CH$_3$ | chloro | (1Z,3Z)-buta-1,3-diene-1,4-diyl | |
| 172 | H | CH$_3$ | propan-2-yl | CH$_3$ | chloro | (1Z,3Z)-buta-1,3-diene-1,4-diyl | |
| 173 | H | ethyl | CH$_3$ | chloro | CH$_3$ | cyano | 1-phenylethyl |
| 174 | H | ethyl | CH$_3$ | CH$_3$ | CH$_3$ | cyano | 1-phenylethyl |
| 175 | H | ethyl | CH$_3$ | chloro | CH$_3$ | (1Z,3Z)-buta-1,3-diene-1,4-diyl | |
| 176 | H | CH$_3$ | propan-2-yl | chloro | CH$_3$ | cyano | 1-phenylethyl |
| 177 | H | CH$_3$ | CH$_3$ | CH$_3$ | CH$_3$ | cyano | 1-methylcyclopropyl |
| 178 | H | propan-2-yl | CH$_3$ | CH$_3$ | CH$_3$ | cyano | 1-methylcyclopropyl |
| 179 | H | ethyl | CH$_3$ | CH$_3$ | CH$_3$ | cyano | 1-methylcyclopropyl |
| 180 | H | propan-2-yl | CH$_3$ | CH$_3$ | CH$_3$ | cyano | 2-methylbutan-2-yl |
| 181 | H | ethyl | CH$_3$ | CH$_3$ | CH$_3$ | cyano | 2-methylbutan-2-yl |
| 182 | H | CH$_3$ | ethyl | CH$_3$ | CH$_3$ | cyano | benzyl |
| 183 | H | CH$_3$ | CH$_3$ | CH$_3$ | CH$_3$ | cyano | 2-methylbutan-2-yl |
| 184 | H | CH$_3$ | ethyl | CH$_3$ | fluoro | cyano | tert-butyl |
| 185 | H | CH$_3$ | CH$_3$ | CH$_3$ | chloro | cyano | 3-methylpentan-3-yl |
| 186 | H | ethyl | CH$_3$ | CH$_3$ | chloro | cyano | 3-methylpentan-3-yl |
| 187 | H | propan-2-yl | CH$_3$ | CH$_3$ | chloro | cyano | 3-methylpentan-3-yl |
| 188 | H | CH$_3$ | CH$_3$ | CH$_3$ | CH$_3$ | cyano | 3-methylpentan-3-yl |
| 189 | H | CH$_3$ | ethyl | CH$_3$ | CH$_3$ | cyano | 3-methylpentan-3-yl |
| 190 | H | propan-2-yl | CH$_3$ | CH$_3$ | CH$_3$ | cyano | 3-methylpentan-3-yl |
| 191 | H | CH$_3$ | ethyl | chloro | CH$_3$ | cyano | 4-chlorobenzyl |
| 192 | H | CH$_3$ | CH$_3$ | chloro | CH$_3$ | cyano | 3-methylpentan-3-yl |
| 193 | H | ethyl | CH$_3$ | chloro | CH$_3$ | cyano | 3-methylpentan-3-yl |
| 194 | H | CH$_3$ | ethyl | CH$_3$ | cyano | cyano | tert-butyl |
| 195 | H | ethyl | CH$_3$ | CH$_3$ | CH$_3$ | cyano | 1-methylcyclohexyl |
| 196 | H | CH$_3$ | CH$_3$ | chloro | CH$_3$ | cyano | 1-phenylethyl |
| 197 | H | CH$_3$ | CH$_3$ | CH$_3$ | CH$_3$ | cyano | 1-methylcyclohexyl |
| 198 | H | propan-2-yl | CH$_3$ | CH$_3$ | CH$_3$ | cyano | 1-methylcyclohexyl |
| 199 | H | ethyl | CH$_3$ | CH$_3$ | chloro | cyano | 2-methylbutan-2-yl |
| 200 | H | propan-2-yl | CH$_3$ | CH$_3$ | chloro | cyano | 2-methylbutan-2-yl |
| 201 | H | CH$_3$ | CH$_3$ | CH$_3$ | chloro | cyano | 2-methylbutan-2-yl |
| 202 | H | ethyl | CH$_3$ | CH$_3$ | CH$_3$ | chloro | chloro |
| 203 | H | CH$_3$ | CH$_3$ | CH$_3$ | CH$_3$ | H | CH$_3$ |
| 204 | H | CH$_3$ | ethyl | chloro | CH$_3$ | cyano | tert-butyl |
| 205 | H | CH$_3$ | CH$_3$ | chloro | CH$_3$ | cyano | 2,4-dichlorophenyl |
| 206 | H | ethyl | CH$_3$ | chloro | CH$_3$ | cyano | 2,4-dichlorophenyl |
| 207 | H | propan-2-yl | CH$_3$ | chloro | CH$_3$ | cyano | 2,4-dichlorophenyl |

-continued

| | | | | | | |
|---|---|---|---|---|---|---|
| 208 | H | CH$_3$ | ethyl | CH$_3$ | CH$_3$ | cyano | (3S,5S,7S)-tricyclo-[3.3.1.1$^{3,7}$]dec-1-yl |
| 209 | H | propan-2-yl | CH$_3$ | CH$_3$ | CH$_3$ | cyano | (3S,5S,7S)-tricyclo-[3.3.1.1$^{3,7}$]dec-1-yl |
| 210 | H | ethyl | CH$_3$ | CH$_3$ | CH$_3$ | cyano | 2,4-dichlorophenyl |
| 211 | H | CH$_3$ | CH$_3$ | CH$_3$ | CH$_3$ | cyano | 2,4-dichlorophenyl |
| 212 | H | propan-2-yl | CH$_3$ | CH$_3$ | CH$_3$ | cyano | 2,4-dichlorophenyl |
| 213 | H | CH$_3$ | CH$_3$ | CH$_3$ | CH$_3$ | cyano | (3S,5S,7S)-tricyclo-[3.3.1.1$^{3,7}$]dec-1-yl |
| 214 | H | CH$_3$ | ethyl | CH$_3$ | CH$_3$ | C(Cl)=CH—CH=CH; CH=CH—CH=C(Cl) | |
| 215 | H | CH$_3$ | CH$_3$ | CH$_3$ | CH$_3$ | cyano | 2-fluoropropan-2-yl |
| 216 | H | CH$_3$ | ethyl | CH$_3$ | CH$_3$ | cyano | 2-fluoropropan-2-yl |
| 217 | H | CH$_3$ | CH$_3$ | CH$_3$ | chloro | cyano | 2,4-dichlorophenyl |
| 218 | H | CH$_3$ | CH$_3$ | chloro | CH$_3$ | cyano | 4-(trifluoromethyl)phenyl |
| 219 | H | CH$_3$ | propan-2-yl | chloro | CH$_3$ | cyano | 4-(trifluoromethyl)phenyl |
| 220 | H | CH$_3$ | ethyl | chloro | CH$_3$ | cyano | 4-(trifluoromethyl)phenyl |
| 221 | H | CH$_3$ | ethyl | CH$_3$ | CH$_3$ | cyano | propan-2-yl |
| 222 | H | CH$_3$ | CH$_3$ | CH$_3$ | chloro | cyano | 4-(trifluoromethyl)phenyl |
| 223 | H | CH$_3$ | propan-2-yl | CH$_3$ | chloro | cyano | 4-(trifluoromethyl)phenyl |
| 224 | H | CH$_3$ | ethyl | CH$_3$ | chloro | cyano | 4-(trifluoromethyl)phenyl |
| 225 | H | CH$_3$ | propan-2-yl | CH$_3$ | chloro | cyano | 2,4-dichlorophenyl |
| 226 | H | CH$_3$ | CH$_3$ | chloro | CH$_3$ | cyano | propan-2-yl |
| 227 | H | CH$_3$ | propan-2-yl | chloro | CH$_3$ | cyano | propan-2-yl |
| 228 | H | CH$_3$ | ethyl | chloro | CH$_3$ | cyano | propan-2-yl |
| 229 | H | CH$_3$ | CH$_3$ | CH$_3$ | CH$_3$ | cyano | propan-2-yl |
| 230 | H | CH$_3$ | CH$_3$ | chloro | CH$_3$ | cyano | 2-fluoropropan-2-yl |
| 231 | H | CH$_3$ | ethyl | CH$_3$ | chloro | cyano | 2-fluoropropan-2-yl |
| 232 | H | propan-2-yl | CH$_3$ | CH$_3$ | chloro | cyano | 2-fluoropropan-2-yl |
| 233 | H | propan-2-yl | CH$_3$ | CH$_3$ | CH$_3$ | cyano | 2-fluoropropan-2-yl |
| 234 | H | CH$_3$ | CH$_3$ | CH$_3$ | chloro | cyano | propan-2-yl |
| 235 | H | CH$_3$ | propan-2-yl | CH$_3$ | chloro | cyano | propan-2-yl |
| 236 | H | CH$_3$ | ethyl | CH$_3$ | chloro | cyano | propan-2-yl |
| 237 | H | CH$_3$ | propan-2-yl | CH$_3$ | CH$_3$ | cyano | propan-2-yl |
| 238 | H | propan-2-yl | CH$_3$ | chloro | CH$_3$ | cyano | 2-fluoropropan-2-yl |
| 239 | H | CH$_3$ | ethyl | chloro | CH$_3$ | cyano | 2-chloro-4-fluorophenyl |
| 240 | H | CH$_3$ | propan-2-yl | chloro | CH$_3$ | cyano | 2-chloro-4-fluorophenyl |
| 241 | H | CH$_3$ | ethyl | CH$_3$ | chloro | cyano | 2,4-dichlorophenyl |
| 242 | H | CH$_3$ | ethyl | CH$_3$ | CH$_3$ | cyano | 2-(4-chlorophenyl)propan-2-yl |
| 243 | H | CH$_3$ | ethyl | chloro | CH$_3$ | cyano | 2-chloro-4-fluorophenyl |
| 244 | H | CH$_3$ | propan-2-yl | CH$_3$ | chloro | cyano | 2-chloro-4-fluorophenyl |
| 245 | H | CH$_3$ | CH$_3$ | CH$_3$ | chloro | cyano | 2-chloro-4-fluorophenyl |
| 246 | H | CH$_3$ | ethyl | CH$_3$ | CH$_3$ | cyano | 2-methoxyphenyl |
| 247 | H | CH$_3$ | propan-2-yl | CH$_3$ | CH$_3$ | cyano | 2-methoxyphenyl |
| 248 | H | CH$_3$ | ethyl | chloro | CH$_3$ | cyano | 4-methoxyphenyl |
| 249 | H | CH$_3$ | CH$_3$ | CH$_3$ | CH$_3$ | cyano | 2-methoxyphenyl |
| 250 | H | CH$_3$ | ethyl | CH$_3$ | CH$_3$ | cyano | 2,2-dichloro-1-ethyl-3-methylcyclopropyl |
| 251 | H | CH$_3$ | ethyl | CH$_3$ | CH$_3$ | cyano | 4-methoxyphenyl |
| 252 | H | CH$_3$ | CH$_3$ | chloro | CH$_3$ | cyano | 2-chloro-4-fluorophenyl |
| 253 | H | CH$_3$ | propan-2-yl | chloro | CH$_3$ | cyano | 4-methoxyphenyl |
| 254 | H | CH$_3$ | CH$_3$ | chloro | CH$_3$ | cyano | 4-methoxyphenyl |
| 255 | H | CH$_3$ | ethyl | CH$_3$ | chloro | cyano | 4-methoxyphenyl |
| 256 | H | CH$_3$ | propan-2-yl | CH$_3$ | chloro | cyano | 4-methoxyphenyl |
| 257 | H | CH$_3$ | CH$_3$ | CH$_3$ | chloro | cyano | 4-methoxyphenyl |
| 258 | H | CH$_3$ | ethyl | chloro | CH$_3$ | cyano | 2,2-dichloro-1-ethyl-3-methylcyclopropyl |
| 259 | H | CH$_3$ | CH$_3$ | chloro | CH$_3$ | cyano | 2,2-dichloro-1-ethyl-3-methylcyclopropyl |
| 260 | H | CH$_3$ | ethyl | CH$_3$ | chloro | cyano | 2,2-dichloro-1-ethyl-3-methylcyclopropyl |
| 261 | H | CH$_3$ | propan-2-yl | CH$_3$ | chloro | cyano | 2,2-dichloro-1-ethyl-3-methylcyclopropyl |
| 262 | H | CH$_3$ | CH$_3$ | CH$_3$ | chloro | cyano | 2,2-dichloro-1-ethyl-3-methylcyclopropyl |
| 263 | H | CH$_3$ | ethyl | CH$_3$ | chloro | cyano | 3-methoxyphenyl |

-continued

| No. | | | | | | | |
|---|---|---|---|---|---|---|---|
| 264 | H | CH₃ | ethyl | CH₃ | CH₃ | C(Cl)=CH—CH=C(Cl) | |
| 265 | H | CH₃ | propan-2-yl | CH₃ | CH₃ | C(Cl)=CH—CH=C(Cl) | |
| 266 | H | CH₃ | CH₃ | CH₃ | CH₃ | C(Cl)=CH—CH=C(Cl) | |
| 267 | H | CH₃ | propan-2-yl | chloro | CH₃ | cyano | 2,2-dichloro-1-ethyl-3-methylcyclopropyl |
| 268 | H | CH₃ | propan-2-yl | CH₃ | CH₃ | C(Cl)=CH—CH=CH; CH=CH—CH=C(Cl) | |
| 269 | H | CH₃ | CH₃ | CH₃ | CH₃ | C(Cl)=CH—CH=CH; CH=CH—CH=C(Cl) | |
| 270 | H | CH₃ | CH₃ | CH₃ | CH₃ | cyano | 4-methoxyphenyl |
| 271 | H | CH₃ | ethyl | CH₃ | CH₃ | cyano | 3-methoxyphenyl |
| 272 | H | CH₃ | propan-2-yl | CH₃ | CH₃ | cyano | 4-methoxyphenyl |
| 273 | H | CH₃ | CH₃ | CH₃ | CH₃ | cyano | 2,2-dichloro-1-ethyl-3-methylcyclopropyl |
| 274 | H | CH₃ | CH₃ | CH₃ | chloro | cyano | 2-fluoropropan-2-yl |
| 275 | H | CH₃ | ethyl | chloro | CH₃ | cyano | 2-fluoropropan-2-yl |
| 276 | H | CH₃ | propan-2-yl | CH₃ | CH₃ | cyano | 2,2-dichloro-1-ethyl-3-methylcyclopropyl |
| 277 | H | ethyl | CH₃ | chloro | CH₃ | C(Cl)=CH—CH=CH; CH=CH—CH=C(Cl) | |
| 278 | H | ethyl | CH₃ | chloro | CH₃ | C(Cl)=CH—CH=C(Cl) | |
| 279 | H | CH₃ | propan-2-yl | chloro | CH₃ | C(Cl)=CH—CH=C(Cl) | |
| 280 | H | propan-2-yl | CH₃ | chloro | CH₃ | C(Cl)=CH—CH=CH; CH=CH—CH=C(Cl) | |
| 281 | H | CH₃ | CH₃ | chloro | CH₃ | C(Cl)=CH—CH=CH; CH=CH—CH=C(Cl) | |
| 282 | H | CH₃ | CH₃ | chloro | CH₃ | C(Cl)=CH—CH=C(Cl) | |
| 283 | H | CH₃ | ethyl | CH₃ | CH₃ | cyano | 2-chloro-4-fluorophenyl |
| 284 | H | CH₃ | CH₃ | CH₃ | CH₃ | chloro | propan-2-yl |
| 285 | H | CH₃ | propan-2-yl | CH₃ | CH₃ | chloro | propan-2-yl |
| 286 | H | CH₃ | ethyl | CH₃ | CH₃ | chloro | propan-2-yl |
| 287 | H | CH₃ | ethyl | chloro | CH₃ | chloro | propan-2-yl |
| 288 | H | CH₃ | ethyl | CH₃ | CH₃ | cyano | bromo |
| 289 | H | CH₃ | ethyl | CH₃ | CH₃ | bromo | propan-2-yl |
| 290 | H | ethyl | CH₃ | bromo | methoxy | chloro | CH₃ |
| 291 | H | ethyl | CH₃ | chloro | methoxy | chloro | CH₃ |
| 292 | H | CH₃ | ethyl | CH₃ | CH₃ | chloro | benzyl |
| 293 | H | CH₃ | ethyl | CH₃ | CH₃ | chloro | 4-chlorobenzyl |
| 294 | H | CH₃ | ethyl | CH₃ | CH₃ | cyano | cyclohexyl |
| 295 | H | CH₃ | CH₃ | CH₃ | CH₃ | cyano | cyclohexyl |
| 296 | H | CH₃ | propan-2-yl | CH₃ | CH₃ | cyano | cyclohexyl |
| 297 | H | CH₃ | ethyl | chloro | CH₃ | H | tert-butyl |
| 298 | H | CH₃ | propan-2-yl | CH₃ | CH₃ | cyano | 1-fluoro-2-methylpropan-2-yl |
| 299 | H | CH₃ | CH₃ | CH₃ | CH₃ | cyano | 1-fluoro-2-methylpropan-2-yl |
| 300 | H | CH₃ | ethyl | CH₃ | CH₃ | H | propan-2-yl |
| 301 | H | CH₃ | ethyl | CH₃ | CH₃ | cyano | 1-fluoro-2-methylpropan-2-yl |
| 302 | H | CH₃ | propan-2-yl | CH₃ | CH₃ | cyano | 2-(4-chlorophenyl)propan-2-yl |
| 303 | H | CH₃ | ethyl | chloro | CH₃ | bromo | propan-2-yl |
| 304 | H | CH₃ | ethyl | chloro | CH₃ | iodo | propan-2-yl |
| 305 | H | CH₃ | CH₃ | CH₃ | CH₃ | cyano | 2-(4-chlorophenyl)propan-2-yl |
| 306 | H | CH₃ | ethyl | chloro | CH₃ | cyano | cyclohexyl |
| 307 | H | CH₃ | ethyl | CH₃ | CH₃ | cyano | cyclopropyl |
| 308 | H | CH₃ | CH₃ | CH₃ | CH₃ | cyano | Cyclopropyl |
| 309 | H | CH₃ | propan-2-yl | CH₃ | CH₃ | cyano | cyclopropyl |
| 310 | H | CH₃ | ethyl | CH₃ | CH₃ | C(Cl)=CH—CH=CH; CH=CH—CH=C(Cl) | |
| 311 | H | CH₃ | CH₃ | CH₃ | CH₃ | C(Cl)=CH—CH=CH; CH=CH—CH=C(Cl) | |
| 312 | H | CH₃ | propan-2-yl | CH₃ | CH₃ | C(Cl)=CH—CH=CH; CH=CH—CH=C(Cl) | |
| 313 | H | CH₃ | CH₃ | CH₃ | CH₃ | bromo | propan-2-yl |

List of NMR Data Peaks:

The NMR data of examples 61 to 313 are listed in the form of peak lists, where for each signal peak the δ in ppm and the signal intensity are listed in the form of a pair of numbers (delta; intensity). Except for broad signals, the intensities of the signals correspond roughly to the height of the signals in a printed copy of an NMR spectrum in cm and indicate the real relative signal height ratios. For broad signals, it is possible to determine a plurality of peak values or the centre of the signal and their relative intensity to the highest signal in the spectrum.

Ex. 61:
(7.975; 0.40), (7.734; 1.78), (7.731; 2.72), (7.728; 1.75), (7.712; 2.00), (7.709; 2.96), (7.707; 1.90), (7.673; 4.61), (7.516; 1.30), (7.514; 2.39), (7.511; 1.29), (7.493; 2.46), (7.491; 4.07), (7.489; 2.17), (7.438; 1.97), (7.435; 2.00), (7.422; 2.26), (7.419; 2.09), (7.415; 1.23), (7.412; 1.15), (7.399; 1.40), (7.396; 1.31), (7.141; 2.30), (7.139; 2.95), (7.134; 4.94), (7.125; 2.06), (7.123; 1.89), (7.120; 1.92), (7.117; 1.84), (7.104; 1.64), (7.101; 1.52), (6.775; 5.01), (3.329; 1.17), (3.315; 1.82), (3.116; 474.30), (2.963; 12.84), (2.662; 0.59), (2.657; 0.76), (2.653; 0.55), (2.527; 2.42), (2.510; 2.31), (2.498; 42.37), (2.493; 84.64), (2.488; 116.37), (2.484; 80.42), (2.479; 37.87), (2.324; 0.33), (2.320; 0.49), (2.315; 0.72), (2.311; 0.65), (2.167; 15.65), (2.154; 16.00), (1.698; 0.35), (1.660; 0.85), (1.649; 0.60), (1.630; 1.72), (1.612; 2.85), (1.594; 2.72), (1.576; 1.60), (1.558; 0.36), (1.404; 0.87), (1.298; 0.33), (1.296; 0.47), (1.245; 0.58), (1.203; 0.39), (1.195; 0.35), (1.174; 0.34), (1.159; 0.46), (1.132; 0.43), (0.959; 0.38), (0.955; 0.39), (0.906; 5.06), (0.887; 9.83), (0.869; 4.51), (−0.000; 3.27)

Ex. 62:
(7.73; 0.39), (7.71; 0.46), (7.63; 0.97), (7.51; 0.37), (7.49; 0.64), (7.42; 0.34), (7.42; 0.36), (7.14; 0.33), (7.13; 0.86), (7.12; 0.41), (7.12; 0.36), (7.10; 0.39), (6.79; 0.80), (3.65; 0.33), (3.64; 0.34), (3.63; 0.65), (3.62; 0.35), (3.60; 0.35), (3.56; 0.38), (3.46; 1.02), (3.40; 0.48), (3.35; 0.46), (2.93; 3.59), (2.89; 2.160), (2.82; 16.00), (2.73; 0.78), (2.71; 0.41), (2.70; 0.37), (2.66; 0.48), (2.66; 0.52), (2.65; 0.48), (2.65; 0.41), (2.57; 0.34), (2.53; 0.68), (2.50; 13.34), (2.49; 25.95), (2.49; 35.40), (2.48; 25.38), (2.48; 13.07), (2.39; 2.85), (2.32; 0.98), (2.32; 0.99), (2.31; 0.98), (2.29; 0.84), (2.22; 0.46), (2.18; 0.35), (2.16; 2.71), (2.15; 2.73), (1.64; 4.15), (1.55; 4.64), (1.53; 4.48), (1.52; 4.37), (1.49; 4.38), (1.40; 6.52)

Ex. 63:
(7.85; 0.55), (7.73; 0.30), (7.71; 0.33), (7.51; 0.33), (7.49; 0.50), (7.44; 0.23), (7.44; 0.23), (7.42; 0.25), (7.42; 0.23), (7.14; 0.22), (7.13; 0.67), (7.12; 0.27), (7.12; 0.24), (6.79; 0.55), (4.65; 0.30), (4.60; 0.38), (4.57; 0.43), (4.38; 1.32), (4.30; 1.68), (4.29; 1.68), (4.26; 1.63), (3.97; 0.35), (3.94; 0.30), (3.89; 0.25), (3.86; 0.21), (3.48; 0.34), (3.46; 0.68), (3.22; 16.00), (3.18; 0.24), (3.04; 3.80), (2.89; 1.55), (2.88; 0.30), (2.87; 0.29), (2.77; 0.22), (2.74; 1.29), (2.72; 0.26), (2.71; 0.26), (2.67; 0.39), (2.66; 0.43), (2.66; 0.42), (2.65; 0.42), (2.64; 0.53), (2.61; 0.89), (2.54; 2.41), (2.53; 2.26), (2.52; 1.86), (2.50; 6.62), (2.50; 11.93), (2.49; 15.97), (2.49; 11.60), (2.48; 6.08), (2.46; 0.56), (2.31; 0.25), (2.29; 0.34), (2.18; 1.74), (2.15; 1.74), (1.90; 0.52), (1.89; 1.16), (1.88; 0.67), (1.87; 0.79), (1.79; 5.05), (1.70; 2.79), (1.64; 1.07)

Ex. 64:
(7.629; 0.41), (7.016; 0.78), (6.727; 0.78), (3.385; 0.33), (3.367; 0.33), (3.121; 78.31), (2.944; 2.75), (2.506; 0.33), (2.498; 4.40), (2.493; 8.99), (2.489; 12.55), (2.484; 8.74), (2.479; 4.14), (2.142; 2.60), (2.125; 2.58), (1.392; 16.00), (1.158; 1.19), (1.140; 2.62), (1.123; 1.14), (−0.000; 1.15)

Ex. 65:
(7.014; 0.80), (6.730; 0.78), (3.122; 44.25), (2.856; 4.63), (2.499; 2.31), (2.494; 4.75), (2.489; 6.69), (2.484; 4.69), (2.480; 2.26), (2.142; 2.65), (2.126; 2.65), (1.392; 16.00), (1.200; 4.00), (1.183; 3.94), (−0.000; 0.67)

Ex. 66:
(7.599; 1.10), (7.016; 0.81), (6.734; 0.84), (3.446; 0.61), (3.119; 60.64), (2.498; 3.68), (2.493; 7.53), (2.489; 10.54), (2.484; 7.36), (2.479; 3.50), (2.298; 0.51), (2.134; 2.73), (2.125; 2.70), (1.640; 0.37), (1.629; 0.34), (1.546; 0.66), (1.532; 0.88), (1.519; 0.44), (1.391; 16.00), (1.382; 0.37), (−0.000; 0.93)

Ex. 67:
(7.326; 1.02), (6.966; 0.67), (3.126; 193.23), (2.969; 1.02), (2.527; 0.49), (2.511; 0.38), (2.507; 0.56), (2.499; 7.87), (2.494; 16.13), (2.489; 22.65), (2.484; 15.84), (2.480; 7.57), (2.153; 3.02), (1.396; 16.00), (1.386; 0.45), (1.172; 0.95), (1.155; 2.03), (1.137; 0.94), (−0.000; 2.35)

Ex. 68:
(7.323; 1.06), (6.970; 0.68), (3.122; 62.68), (2.882; 3.48), (2.498; 3.22), (2.494; 6.62), (2.489; 9.30), (2.484; 6.50), (2.480; 3.12), (2.154; 3.05), (1.396; 16.00), (1.212; 1.98), (1.196; 1.91), (−0.000; 0.87)

Ex. 69:
(7.701; 1.08), (7.324; 1.07), (6.978; 0.84), (6.977; 0.83), (3.128; 76.11), (2.499; 3.10), (2.494; 6.33), (2.490; 8.87), (2.485; 6.18), (2.480; 2.94), (2.154; 3.09), (1.648; 0.36), (1.636; 0.33), (1.557; 0.58), (1.553; 0.58), (1.543; 0.77), (1.529; 0.41), (1.396; 16.00), (1.386; 0.71), (−0.000; 0.99)

Ex. 70:
(7.268; 0.78), (7.266; 0.76), (7.029; 0.66), (3.126; 156.03), (2.965; 1.12), (2.511; 0.36), (2.507; 0.54), (2.499; 7.22), (2.494; 14.77), (2.489; 20.70), (2.484; 14.44), (2.480; 6.88), (2.197; 0.33), (2.173; 2.95), (1.396; 16.00), (1.392; 2.94), (1.166; 0.92), (1.148; 1.92), (1.131; 0.87), (−0.000; 1.54),

Ex. 71:
(7.264; 0.84), (7.263; 0.84), (7.032; 0.76), (3.116; 32.86), (3.092; 0.51), (2.875; 3.20), (2.865; 0.66), (2.498; 2.62), (2.493; 5.41), (2.489; 7.63), (2.484; 5.36), (2.479; 2.58), (2.298; 0.66), (2.193; 0.40), (2.171; 3.05), (1.396; 16.00), (1.391; 3.04), (1.207; 2.24), (1.201; 1.09), (1.190; 2.20), (1.184; 0.98), (−0.000; 0.45)

Ex. 72:
(7.714; 1.06), (7.266; 0.83), (7.265; 0.82), (7.170; 0.33), (7.032; 1.25), (3.469; 0.40), (3.135; 0.36), (3.116; 54.93), (3.092; 0.82), (2.506; 0.36), (2.498; 4.52), (2.493; 9.20), (2.488; 12.86), (2.484; 8.94), (2.479; 4.24), (2.298; 1.35), (2.185; 0.40), (2.163; 3.10), (1.643; 0.39), (1.632; 0.37), (1.553; 0.67), (1.540; 0.83), (1.526; 0.45), (1.396; 16.00), (1.391; 2.89), (−0.000; 0.61)

-continued

Ex. 73:
(7.642; 1.13), (7.018; 0.84), (6.808; 1.90), (6.719; 0.87), (3.348; 94.10), (3.324; 4.38), (3.003; 0.40),
(2.926; 0.40), (2.524; 0.29), (2.521; 0.36), (2.518; 0.37), (2.509; 8.38), (2.506; 18.16), (2.503; 24.76),
(2.500; 17.73), (2.497; 8.03), (2.136; 2.52), (2.115; 2.52), (2.077; 0.47), (1.245; 13.50), (−0.000; 7.02)
Ex. 74:
(7.618; 0.33), (6.970; 0.67), (6.705; 2.20), (3.567; 0.42), (3.382; 0.42), (3.365; 0.45), (3.205; 0.39),
(3.168; 1.16), (3.124; 628.58), (3.101; 8.31), (2.942; 2.47), (2.663; 0.37), (2.658; 0.50), (2.653; 0.38),
(2.527; 0.98), (2.511; 1.50), (2.506; 2.21), (2.498; 28.29), (2.494; 57.43), (2.489; 80.14), (2.484; 56.01),
(2.479; 26.74), (2.320; 0.36), (2.316; 0.46), (2.311; 0.34), (2.139; 2.39), (2.122; 2.44), (2.040; 0.32),
(1.392; 1.34), (1.262; 0.99), (1.249; 16.00), (1.158; 1.13), (1.140; 2.43), (1.122; 1.08), (0.008; 0.45), (−0.000;
12.47), (−0.008; 0.47)
Ex. 75:
(6.975; 0.54), (6.707; 1.70), (6.700; 0.36), (3.302; 0.36), (3.119; 202.55), (2.948; 1.68), (2.527; 0.56),
(2.511; 0.84), (2.506; 1.26), (2.498; 15.96), (2.493; 32.44), (2.488; 45.25), (2.484; 31.60), (2.479; 15.09),
(2.137; 2.25), (2.123; 2.40), (1.600; 0.41), (1.582; 0.44), (1.392; 1.33), (1.249; 16.00), (0.895; 0.90),
(0.877; 1.69), (0.858; 0.77), (−0.000; 7.94)
Ex. 76:
(7.792; 1.18), (7.790; 1.36), (7.786; 1.25), (7.773; 1.33), (7.769; 1.82), (7.766; 1.52), (7.700; 0.84),
(7.694; 1.03), (7.690; 0.81), (7.676; 0.97), (7.669; 1.08), (7.665; 0.98), (7.655; 5.56), (7.640; 1.02),
(7.635; 1.52), (7.620; 1.49), (7.615; 0.91), (7.600; 0.95), (7.428; 0.61), (7.425; 0.64), (7.418; 0.61),
(7.404; 1.02), (7.399; 0.95), (7.385; 0.60), (7.382; 0.60), (7.378; 0.58), (7.202; 3.49), (6.798; 3.60),
(3.302; 0.40), (3.282; 2.94), (3.246; 0.50), (3.235; 0.52), (3.125; 1828.34), (3.085; 1.57), (3.066; 0.54),
(2.985; 15.80), (2.889; 1.29), (2.733; 1.01), (2.667; 0.54), (2.663; 1.06), (2.658; 1.44), (2.653; 1.04),
(2.648; 0.59), (2.554; 0.35), (2.546; 0.37), (2.527; 5.48), (2.511; 3.82), (2.507; 5.49), (2.498; 82.81),
(2.494; 171.25), (2.489; 241.42), (2.484; 168.18), (2.480; 79.87), (2.325; 0.56), (2.320; 1.01), (2.316; 1.39),
(2.311; 1.09), (2.307; 0.50), (2.191; 11.50), (2.181; 11.45), (2.041; 1.08), (2.037; 0.76), (1.974; 1.03),
(1.404; 16.00), (1.361; 0.32), (1.307; 0.61), (1.299; 0.65), (1.296; 0.64), (1.245; 0.92), (1.177; 0.65),
(1.082; 0.36), (0.008; 1.14), (−0.000; 33.61), (−0.009; 0.99)
Ex. 77:
(7.975; 0.42), (7.788; 0.94), (7.786; 0.79), (7.773; 0.84), (7.769; 1.15), (7.710; 0.55), (7.701; 0.77),
(7.695; 0.78), (7.691; 0.60), (7.675; 0.64), (7.670; 0.70), (7.655; 0.64), (7.640; 0.55), (7.635; 0.88),
(7.620; 0.88), (7.615; 0.70), (7.600; 0.51), (7.426; 0.44), (7.421; 0.41), (7.404; 0.58), (7.399; 0.59),
(7.382; 0.40), (7.378; 0.39), (7.198; 2.01), (6.803; 2.00), (3.636; 0.35), (3.316; 0.32), (3.300; 0.49),
(3.282; 3.23), (3.252; 0.44), (3.246; 0.46), (3.186; 0.99), (3.121; 1727.91), (3.079; 0.83), (3.051; 0.34),
(2.888; 1.26), (2.874; 11.23), (2.860; 0.58), (2.734; 1.00), (2.662; 1.15), (2.658; 1.66), (2.653; 1.23),
(2.648; 0.61), (2.638; 0.34), (2.545; 0.59), (2.527; 6.08), (2.511; 4.32), (2.506; 6.16), (2.498; 88.06),
(2.493; 181.81), (2.489; 256.37), (2.484; 178.58), (2.479; 84.86), (2.325; 0.61), (2.320; 1.00), (2.316; 1.50),
(2.311; 1.00), (2.306; 0.64), (2.193; 6.55), (2.179; 6.60), (2.041; 0.34), (2.040; 0.75), (2.037; 0.79),
(1.901; 0.45), (1.404; 16.00), (1.360; 0.32), (1.307; 0.74), (1.296; 0.81), (1.245; 1.27), (1.211; 8.88),
(1.195; 8.95), (1.184; 0.65), (1.157; 0.50), (1.140; 0.40), (1.082; 0.41), (1.049; 0.38), (0.895; 0.34),
(0.008; 0.99), (−0.000; 26.60), (−0.008; 0.71)
Ex. 78:
(12.828; 0.49), (7.975; 1.95), (7.789; 1.34), (7.769; 1.84), (7.767; 1.48), (7.701; 0.96), (7.694; 1.15),
(7.676; 1.46), (7.665; 2.26), (7.655; 1.27), (7.640; 0.89), (7.635; 1.63), (7.620; 1.25), (7.615; 1.08),
(7.600; 0.92), (7.428; 0.73), (7.419; 0.70), (7.405; 1.04), (7.399; 1.02), (7.382; 0.75), (7.376; 0.69),
(7.200; 3.56), (6.801; 3.49), (5.689; 0.52), (3.741; 0.45), (3.620; 0.50), (3.511; 0.45), (3.429; 0.68),
(3.401; 1.47), (3.385; 1.48), (3.303; 0.85), (3.282; 4.96), (3.249; 1.06), (3.239; 1.01), (3.229; 1.18),
(3.122; 3140.76), (3.000; 0.46), (2.982; 0.50), (2.962; 10.04), (2.888; 0.70), (2.734; 0.45), (2.695; 0.60),
(2.667; 1.12), (2.663; 2.22), (2.658; 2.93), (2.653; 2.20), (2.648; 1.25), (2.527; 11.57), (2.511; 8.18),
(2.506; 11.90), (2.498; 168.81), (2.493; 348.34), (2.489; 490.70), (2.484; 341.40), (2.479; 162.00),
(2.325; 1.15), (2.320; 1.99), (2.315; 3.00), (2.311; 2.07), (2.306; 1.03), (2.298; 0.48), (2.192; 11.25),
(2.180; 11.04), (2.041; 1.73), (2.037; 1.61), (1.404; 16.00), (1.307; 0.80), (1.299; 1.42), (1.296; 1.34),
(1.245; 1.73), (1.170; 4.99), (1.152; 10.97), (1.135; 4.79), (1.082; 1.01), (1.062; 0.49), (0.895; 0.54),
(0.008; 1.97), (−0.000; 55.36), (−0.008; 1.67), (−3.553; 0.50)
Ex. 79:
(12.829; 1.58), (7.661; 1.88), (7.448; 1.24), (7.441; 1.61), (7.424; 2.47), (7.421; 2.77), (7.414; 2.13),
(7.386; 2.75), (7.365; 1.38), (7.357; 1.56), (7.334; 1.89), (7.319; 1.09), (7.228; 3.16), (6.804; 2.07),
(5.689; 1.79), (3.812; 1.02), (3.580; 0.98), (3.490; 1.01), (3.484; 1.06), (3.460; 1.18), (3.401; 1.01),
(3.386; 1.11), (3.371; 1.38), (3.367; 1.25), (3.360; 1.06), (3.319; 1.40), (3.303; 3.94), (3.294; 1.37),
(3.284; 1.54), (3.264; 3.03), (3.255; 2.04), (3.250; 1.93), (3.232; 1.90), (3.201; 2.84), (3.167; 6.43),
(3.160; 9.08), (3.121; 6657.33), (3.079; 2.68), (3.059; 1.32), (3.044; 1.19), (2.989; 14.10), (2.964; 0.94),
(2.888; 1.08), (2.695; 3.56), (2.662; 4.67), (2.658; 6.36), (2.653; 4.53), (2.648; 2.51), (2.636; 1.30),
(2.566; 2.12), (2.554; 2.42), (2.527; 24.13), (2.511; 16.96), (2.506; 23.90), (2.498; 340.52), (2.493; 706.01),
(2.489; 998.08), (2.484; 697.89), (2.479; 332.95), (2.447; 1.25), (2.327; 16.00), (2.320; 5.26), (2.315; 6.53),
(2.311; 4.49), (2.306; 1.86), (2.204; 12.41), (2.188; 12.13), (2.041; 6.74), (2.037; 2.10), (1.974; 0.94),
(1.901; 3.68), (1.404; 9.53), (1.298; 3.73), (1.296; 2.81), (1.245; 2.94), (1.082; 1.12), (0.895; 3.27),
(0.008; 1.07), (−0.000; 35.31), (−0.009; 1.32)
Ex. 80:
(7.722; 0.76), (7.444; 1.36), (7.440; 1.32), (7.430; 1.92), (7.425; 2.15), (7.421; 2.47), (7.414; 2.21),
(7.410; 1.15), (7.385; 2.48), (7.369; 1.10), (7.365; 1.02), (7.355; 1.36), (7.334; 1.39), (7.318; 0.66),
(7.222; 3.08), (6.806; 2.26), (5.690; 1.36), (3.812; 1.23), (3.491; 1.05), (3.303; 1.96), (3.284; 0.68),
(3.264; 2.04), (3.255; 0.94), (3.219; 0.76), (3.197; 0.99), (3.164; 2.04), (3.115; 2241.06), (2.887; 1.05),
(2.876; 16.00), (2.732; 0.86), (2.696; 1.90), (2.667; 1.30), (2.662; 2.50), (2.657; 3.33), (2.653; 2.51),
(2.648; 1.15), (2.638; 1.14), (2.566; 1.01), (2.554; 1.02), (2.547; 0.86), (2.536; 1.24), (2.526; 13.07),
(2.510; 8.98), (2.506; 12.58), (2.497; 183.40), (2.493; 379.83), (2.488; 535.98), (2.483; 374.33),
(2.479; 178.27), (2.327; 14.23), (2.320; 3.13), (2.315; 3.60), (2.310; 2.59), (2.305; 1.17), (2.257; 1.01),
(2.245; 0.98), (2.205; 11.58), (2.185; 11.20), (2.169; 0.79), (2.123; 0.89), (2.041; 3.64), (2.037; 1.21),
(1.901; 2.35), (1.404; 9.90), (1.298; 2.08), (1.296; 1.45), (1.245; 1.67), (1.213; 15.25), (1.196; 15.27),
(1.177; 0.98), (1.163; 0.62), (1.157; 1.46), (1.153; 0.72), (1.145; 0.73), (1.140; 1.59), (1.083; 0.80),
(1.072; 0.61), (1.054; 0.69), (0.895; 2.05), (−0.000; 18.41)

Ex. 81:
(7.974; 0.67), (7.669; 1.30), (7.451; 0.68), (7.444; 1.28), (7.440; 1.25), (7.431; 1.71), (7.425; 2.04),
(7.421; 2.15), (7.413; 2.01), (7.410; 0.82), (7.385; 2.03), (7.365; 0.98), (7.356; 1.24), (7.334; 1.20),
(7.319; 0.53), (7.223; 3.31), (6.801; 3.17), (5.690; 0.69), (3.812; 1.06), (3.700; 0.68), (3.491; 0.84),
(3.411; 0.76), (3.402; 1.29), (3.385; 1.24), (3.344; 0.41), (3.319; 0.46), (3.303; 1.00), (3.284; 0.45),
(3.279; 0.41), (3.264; 2.87), (3.255; 0.61), (3.250; 0.51), (3.174; 0.96), (3.114; 830.82), (2.963; 9.67),
(2.905; 0.95), (2.898; 0.47), (2.696; 1.03), (2.667; 0.67), (2.662; 1.14), (2.657; 1.73), (2.652; 1.24),
(2.648; 0.54), (2.566; 0.48), (2.555; 0.62), (2.526; 6.73), (2.510; 4.67), (2.505; 6.49), (2.497; 95.31),
(2.493; 197.17), (2.488; 277.91), (2.483; 193.60), (2.478; 91.75), (2.327; 12.88), (2.319; 1.73), (2.315; 2.00),
(2.310; 1.35), (2.305; 0.55), (2.257; 1.03), (2.245; 0.65), (2.203; 10.63), (2.185; 10.65), (2.168; 0.41),
(2.120; 0.81), (2.066; 0.45), (2.041; 2.00), (2.037; 0.92), (1.404; 16.00), (1.298; 1.20), (1.296; 0.72),
(1.244; 0.66), (1.171; 4.62), (1.153; 10.74), (1.135; 4.91), (1.117; 0.67), (1.083; 0.43), (0.959; 0.40),
(0.941; 0.61), (0.895; 1.05), (−0.000; 9.68)
Ex. 82:
(8.00; 1.430), (7.95; 7.880), (7.87; 3.830), (7.73; 2.680), (7.71; 2.880), (7.70; 3.590), (7.69; 2.620),
(7.32; 2.440), (7.30; 3.150), (7.29; 2.720), (7.28; 1.550), (7.27; 3.130), (7.24; 1.130), (5.75; 2.950),
(3.49; 1.340), (3.47; 3.470), (3.46; 12.000), (3.44; 2.020), (3.42; 2.650), (3.40; 9.890), (3.40; 10.270),
(3.39; 17.730), (3.36; 6356.810), (3.33; 34.860), (3.31; 3.870), (3.30; 5.980), (3.30; 5.790), (3.26; 1.660),
(3.25; 1.310), (3.21; 2.110), (3.18; 1.320), (3.16; 1.300), (3.15; 2.400), (3.12; 1.510), (3.03; 14.590),
(2.94; 34.920), (2.68; 1.350), (2.67; 1.890), (2.67; 1.400), (2.54; 2.600), (2.53; 6.080), (2.51; 99.400),
(2.51; 213.630), (2.50; 298.520), (2.50; 223.820), (2.49; 108.050), (2.33; 1.430), (2.33; 1.940), (2.33; 1.390),
(1.99; 1.510), (1.90; 1.560), (1.40; 196.350), (1.35; 6.900), (1.23; 1.790), (1.20; 1.190), (1.17; 8.640),
(1.16; 18.150), (1.14; 8.840), (1.13; 4.890), (1.11; 7.550), (1.09; 3.480), (0.01; 7.360), (−0.00; 208.060), (−0.01;
8.180)
Ex. 83:
(7.623; 1.23), (7.006; 2.31), (6.726; 2.35), (3.401; 0.35), (3.384; 0.93), (3.366; 0.93), (3.349; 0.36),
(3.122; 44.25), (2.944; 8.59), (2.499; 1.96), (2.495; 3.93), (2.490; 5.56), (2.485; 3.86), (2.480; 1.83),
(2.340; 16.00), (2.144; 7.76), (2.126; 7.72), (1.158; 3.68), (1.140; 8.06), (1.123; 3.55)
Ex. 84:
(7.595; 3.33), (7.008; 2.40), (6.734; 2.55), (3.445; 1.72), (3.122; 71.36), (2.499; 4.19), (2.494; 8.56),
(2.489; 12.02), (2.484; 8.37), (2.480; 3.98), (2.340; 16.00), (2.298; 0.92), (2.135; 8.16), (2.126; 8.11),
(1.657; 0.49), (1.653; 0.49), (1.648; 0.63), (1.640; 1.08), (1.628; 0.98), (1.619; 0.57), (1.613; 0.57),
(1.560; 0.93), (1.546; 1.86), (1.532; 2.56), (1.523; 1.11), (1.518; 1.25), (1.504; 0.51), (1.392; 0.63), (−0.000;
0.56)
Ex. 85:
(7.718; 0.34), (7.317; 3.00), (6.966; 1.97), (3.399; 0.47), (3.391; 0.47), (3.118; 62.49), (2.969; 2.92),
(2.506; 0.32), (2.498; 4.69), (2.493; 9.71), (2.489; 13.69), (2.484; 9.57), (2.479; 4.55), (2.354; 16.00),
(2.156; 8.97), (1.172; 2.87), (1.154; 6.11), (1.136; 2.77), (−0.000; 1.54)
Ex. 86:
(7.698; 3.33), (7.314; 3.28), (7.235; 0.40), (7.217; 0.39), (7.170; 0.46), (7.152; 0.34), (7.150; 0.33),
(6.978; 2.57), (6.977; 2.54), (3.476; 0.83), (3.136; 0.33), (3.118; 48.21), (2.498; 3.73), (2.494; 7.65),
(2.489; 10.76), (2.484; 7.50), (2.480; 3.55), (2.353; 16.00), (2.298; 1.88), (2.156; 9.49), (1.664; 0.49),
(1.660; 0.49), (1.655; 0.63), (1.646; 1.07), (1.635; 0.98), (1.626; 0.59), (1.620; 0.55), (1.570; 0.85),
(1.556; 1.73), (1.543; 2.31), (1.529; 1.19), (1.515; 0.46), (−0.000; 0.47)
Ex. 87:
(7.739; 0.48), (7.254; 2.39), (7.253; 2.38), (7.026; 2.49), (3.403; 0.57), (3.388; 0.59), (3.118; 62.72),
(2.964; 3.37), (2.951; 0.76), (2.507; 0.32), (2.498; 4.68), (2.494; 9.66), (2.489; 13.58), (2.484; 9.45),
(2.480; 4.49), (2.355; 16.00), (2.344; 0.80), (2.298; 0.42), (2.193; 0.46), (2.173; 9.22), (1.396; 2.28),
(1.166; 2.81), (1.160; 0.52), (1.148; 5.93), (1.142; 0.71), (1.130; 2.68), (−0.000; 0.41),
Ex. 88:
(7.709; 3.30), (7.253; 2.62), (7.251; 2.52), (7.032; 3.97), (3.473; 1.12), (3.136; 0.41), (3.118; 49.27),
(2.499; 3.76), (2.494; 7.72), (2.489; 10.84), (2.484; 7.55), (2.480; 3.58), (2.354; 16.00), (2.344; 0.84),
(2.298; 1.18), (2.185; 0.46), (2.164; 9.85), (1.660; 0.52), (1.656; 0.52), (1.650; 0.68), (1.642; 1.13),
(1.631; 1.05), (1.622; 0.63), (1.615; 0.59), (1.567; 0.90), (1.553; 1.85), (1.539; 2.46), (1.525; 1.28),
(1.511; 0.50), (1.396; 2.34), (−0.000; 1.23)
Ex. 89:
(7.795; 1.47), (7.792; 1.80), (7.791; 1.81), (7.788; 1.69), (7.775; 2.13), (7.773; 2.37), (7.771; 2.57),
(7.769; 2.25), (7.702; 1.15), (7.698; 1.16), (7.696; 1.32), (7.692; 1.08), (7.678; 1.11), (7.673; 1.20),
(7.671; 1.22), (7.667; 1.08), (7.660; 1.12), (7.646; 1.34), (7.640; 1.77), (7.625; 1.93), (7.620; 1.13),
(7.605; 1.04), (7.589; 5.50), (7.434; 0.76), (7.431; 0.83), (7.427; 0.74), (7.411; 1.20), (7.405; 1.11),
(7.037; 3.39), (3.873; 1.60), (3.730; 2.63), (3.410; 0.91), (3.354; 1.12), (3.282; 7.86), (3.269; 0.81),
(3.251; 1.02), (3.233; 1.46), (3.120; 29.30), (3.061; 1.78), (3.044; 0.96), (2.988; 4.39), (2.923; 1.64),
(2.908; 2.91), (2.866; 1.15), (2.719; 1.48), (2.718; 1.47), (2.670; 1.94), (2.542; 0.94), (2.526; 2.62),
(2.524; 1.30), (2.510; 1.76), (2.506; 2.69), (2.497; 33.84), (2.493; 69.55), (2.488; 97.68), (2.483; 67.86),
(2.479; 32.12), (2.243; 3.39), (2.220; 16.00), (2.083; 1.46), (2.059; 2.40), (2.058; 2.44), (1.404; 12.29),
(1.185; 4.59), (1.167; 9.87), (1.157; 0.86), (1.149; 4.68), (1.139; 1.39), (1.130; 1.56), (1.121; 2.32),
(1.112; 1.29), (1.103; 1.09), (1.094; 1.30), (1.086; 1.01), (1.076; 0.73), (1.068; 2.07), (1.061; 0.74),
(1.050; 0.92), (1.043; 1.25), (−0.000; 9.34)
Ex. 90:
(7.749; 5.36), (7.659; 1.48), (7.657; 1.45), (7.646; 0.83), (7.639; 2.64), (7.635; 2.75), (7.618; 5.66),
(7.609; 1.59), (7.605; 2.06), (7.600; 1.65), (7.595; 1.77), (7.593; 1.58), (7.588; 3.40), (7.585; 1.36),
(7.581; 3.73), (7.577; 3.07), (7.570; 2.67), (7.566; 0.88), (7.538; 2.42), (7.535; 2.48), (7.521; 1.60),
(7.517; 2.03), (7.501; 1.05), (7.498; 0.91), (7.456; 0.44), (7.446; 0.37), (7.035; 4.31), (3.767; 0.33),
(3.303; 0.48), (3.265; 4.99), (3.122; 843.55), (3.067; 0.47), (3.059; 0.44), (3.013; 5.83), (2.695; 0.47),
(2.663; 0.58), (2.658; 0.91), (2.653; 0.57), (2.527; 3.15), (2.511; 2.28), (2.506; 3.13), (2.498; 47.53),
(2.493; 98.54), (2.489; 139.23), (2.484; 97.14), (2.479; 46.26), (2.325; 0.37), (2.320; 0.63), (2.315; 0.88),
(2.311; 0.55), (2.222; 16.00), (2.040; 0.48), (1.901; 0.35), (1.404; 6.67), (1.299; 0.47), (1.296; 0.37),
(0.895; 0.32), (−0.000; 4.10)

Ex. 91:
(16.855; 1.42), (16.744; 1.37), (12.831; 1.84), (12.562; 1.58), (7.975; 4.12), (7.760; 1.52), (7.659; 1.74),
(7.639; 2.41), (7.635; 2.41), (7.616; 5.35), (7.605; 1.71), (7.601; 2.13), (7.588; 3.15), (7.581; 2.92),
(7.577; 2.43), (7.571; 2.44), (7.565; 1.40), (7.535; 2.60), (7.518; 2.19), (7.040; 3.70), (4.028; 1.40),
(3.567; 1.44), (3.422; 2.21), (3.400; 1.72), (3.303; 2.28), (3.265; 3.32), (3.250; 2.08), (3.218; 2.60),
(3.159; 7.91), (3.151; 9.63), (3.118; 6226.18), (3.032; 1.60), (3.018; 1.66), (2.990; 4.12), (2.970; 1.53),
(2.696; 1.38), (2.667; 2.27), (2.662; 5.38), (2.657; 7.12), (2.653; 5.33), (2.648; 2.69), (2.616; 1.43),
(2.527; 12.60), (2.511; 17.11), (2.506; 25.42), (2.498; 400.23), (2.493; 827.81), (2.488; 1168.39),
(2.484; 814.36), (2.479; 388.32), (2.325; 2.44), (2.320; 5.03), (2.315; 6.76), (2.311; 5.10), (2.306; 2.41),
(2.223; 14.65), (2.040; 2.98), (1.974; 4.23), (1.901; 1.80), (1.478; 1.38), (1.404; 16.00), (1.299; 1.85),
(1.245; 2.15), (1.195; 1.51), (1.185; 3.86), (1.177; 3.13), (1.168; 9.45), (1.150; 4.00), (0.895; 3.26), (−0.000;
42.65), (−0.008; 2.18)
Ex. 92:
(7.976; 1.38), (7.658; 1.35), (7.646; 0.79), (7.639; 2.46), (7.635; 2.65), (7.612; 5.23), (7.605; 2.23),
(7.600; 1.74), (7.595; 1.83), (7.593; 1.58), (7.588; 3.23), (7.581; 3.42), (7.577; 2.81), (7.571; 2.53),
(7.566; 1.06), (7.538; 2.21), (7.535; 2.41), (7.521; 1.64), (7.517; 1.97), (7.502; 1.10), (7.498; 0.95),
(7.458; 0.84), (7.046; 2.99), (3.852; 2.45), (3.609; 0.99), (3.479; 2.79), (3.380; 0.94), (3.303; 1.18),
(3.265; 4.51), (3.255; 0.84), (3.233; 0.80), (3.224; 0.84), (3.215; 1.15), (3.191; 1.84), (3.129; 2764.84),
(3.089; 2.20), (3.086; 1.75), (3.075; 0.98), (3.066; 0.87), (2.902; 16.00), (2.888; 0.83), (2.866; 1.19),
(2.761; 1.87), (2.697; 0.99), (2.663; 1.43), (2.658; 1.73), (2.654; 1.38), (2.639; 4.06), (2.638; 3.93),
(2.528; 7.06), (2.512; 4.91), (2.507; 7.14), (2.499; 103.80), (2.494; 214.78), (2.489; 303.02), (2.485; 211.65),
(2.480; 100.65), (2.326; 0.82), (2.321; 1.86), (2.316; 1.74), (2.312; 1.47), (2.224; 15.04), (2.207; 0.79),
(2.149; 1.60), (2.040; 1.11), (1.901; 0.85), (1.404; 15.10), (1.299; 1.02), (1.296; 0.80), (1.245; 1.25),
(1.225; 7.78), (1.208; 8.00), (1.195; 1.96), (1.177; 1.45), (1.157; 6.78), (1.140; 6.65), (1.072; 2.35),
(1.055; 2.41), (0.895; 0.89), (−0.000; 8.92)
Ex. 93:
(17.592; 0.60), (12.824; 1.43), (7.975; 1.17), (7.770; 5.42), (7.579; 1.06), (7.493; 4.17), (7.491; 4.24),
(7.460; 0.78), (7.456; 0.84), (7.440; 3.58), (7.422; 4.95), (7.392; 2.42), (7.374; 1.29), (7.363; 1.55),
(7.344; 1.90), (7.322; 0.90), (7.104; 6.55), (6.883; 0.93), (6.818; 1.03), (5.688; 0.69), (3.951; 0.73),
(3.766; 5.57), (3.473; 0.63), (3.381; 0.97), (3.320; 0.58), (3.303; 1.31), (3.285; 0.95), (3.264; 7.28),
(3.255; 0.81), (3.243; 1.16), (3.223; 1.29), (3.208; 1.43), (3.193; 1.76), (3.166; 4.33), (3.155; 6.65),
(3.126; 3525.94), (3.082; 1.92), (3.064; 1.45), (3.057; 1.15), (3.040; 1.03), (3.007; 6.35), (2.976; 0.88),
(2.941; 5.29), (2.927; 0.61), (2.734; 0.57), (2.697; 1.57), (2.668; 1.05), (2.663; 1.80), (2.658; 2.68),
(2.654; 1.97), (2.649; 0.93), (2.591; 0.58), (2.567; 0.94), (2.556; 0.79), (2.527; 9.95), (2.511; 6.78),
(2.507; 10.00), (2.499; 150.93), (2.494; 312.50), (2.489; 441.37), (2.484; 308.08), (2.480; 146.83),
(2.351; 0.66), (2.323; 16.00), (2.316; 3.57), (2.311; 2.65), (2.257; 1.80), (2.242; 0.80), (2.218; 15.33),
(2.165; 3.41), (2.137; 0.56), (2.040; 1.48), (2.037; 0.77), (1.901; 1.76), (1.299; 1.41), (1.296; 1.26),
(1.245; 1.13), (1.164; 0.59), (0.895; 1.32), (−0.000; 11.52)
Ex. 94:
(14.909; 0.74), (9.705; 0.73), (7.837; 0.74), (7.490; 3.85), (7.457; 1.11), (7.441; 3.75), (7.422; 4.61),
(7.395; 2.80), (7.361; 1.80), (7.346; 1.82), (7.327; 1.17), (7.121; 2.19), (5.687; 1.15), (3.880; 0.79),
(3.794; 1.27), (3.693; 0.83), (3.651; 1.33), (3.647; 1.61), (3.638; 1.07), (3.578; 0.78), (3.569; 0.77),
(3.545; 1.05), (3.505; 0.75), (3.473; 1.06), (3.431; 0.77), (3.422; 0.79), (3.398; 1.00), (3.370; 1.04),
(3.345; 1.32), (3.323; 1.09), (3.303; 1.75), (3.264; 2.74), (3.240; 2.13), (3.223; 2.85), (3.210; 3.51),
(3.187; 5.11), (3.132; 4694.75), (3.075; 1.92), (3.028; 0.72), (2.896; 12.78), (2.697; 1.66), (2.659; 2.94),
(2.654; 2.00), (2.637; 0.82), (2.583; 0.89), (2.565; 1.05), (2.528; 9.35), (2.499; 208.70), (2.494; 375.32),
(2.490; 458.46), (2.485; 305.16), (2.480; 133.20), (2.355; 1.15), (2.324; 16.00), (2.317; 3.52), (2.259; 0.97),
(2.218; 14.50), (2.189; 1.06), (2.174; 1.19), (2.140; 1.03), (2.040; 1.85), (1.902; 1.82), (1.404; 4.90),
(1.299; 1.54), (1.277; 0.79), (1.246; 2.04), (1.221; 10.15), (1.204; 10.46), (1.164; 0.91), (1.156; 1.00),
(1.136; 0.80), (1.127; 0.83), (0.895; 1.38), (−0.000; 9.40), (−1.477; 0.70), (−2.374; 0.68), (−2.696; 0.69), (−3.701;
0.84)
Ex. 95:
(12.830; 0.64), (7.975; 3.03), (7.792; 1.01), (7.492; 4.34), (7.490; 4.17), (7.457; 1.02), (7.441; 3.51),
(7.422; 4.49), (7.394; 2.30), (7.374; 1.13), (7.361; 1.43), (7.344; 1.59), (7.322; 0.66), (7.111; 3.66),
(6.884; 0.78), (6.822; 0.68), (5.689; 2.04), (4.775; 0.62), (3.766; 5.21), (3.619; 0.81), (3.566; 0.61),
(3.545; 0.63), (3.474; 0.63), (3.405; 1.35), (3.396; 1.21), (3.370; 0.97), (3.363; 0.92), (3.340; 1.05),
(3.321; 0.83), (3.310; 0.95), (3.303; 1.68), (3.285; 0.93), (3.270; 0.95), (3.255; 1.13), (3.245; 1.11),
(3.226; 1.25), (3.217; 3.54), (3.119; 2861.12), (2.983; 4.56), (2.921; 1.94), (2.888; 0.71), (2.696; 1.49),
(2.662; 2.15), (2.658; 3.22), (2.653; 2.08), (2.648; 1.15), (2.566; 0.63), (2.555; 0.94), (2.527; 11.33),
(2.511; 7.89), (2.506; 10.83), (2.498; 169.43), (2.493; 351.39), (2.488; 496.18), (2.484; 346.57),
(2.479; 165.23), (2.324; 16.00), (2.315; 3.48), (2.310; 2.40), (2.257; 1.60), (2.217; 14.82), (2.191; 0.73),
(2.164; 3.26), (2.041; 2.93), (2.037; 1.24), (1.901; 1.52), (1.404; 14.92), (1.298; 1.80), (1.274; 0.75),
(1.256; 1.57), (1.245; 1.56), (1.179; 4.32), (1.161; 8.94), (1.153; 4.74), (1.124; 2.60), (1.107; 1.11),
(1.026; 0.63), (0.895; 1.75), (−0.000; 28.60), (−0.008; 1.19)
Ex. 96:
(7.974; 0.43), (7.636; 0.89), (7.147; 0.79), (6.763; 0.77), (3.201; 0.40), (3.181; 0.40), (3.153; 0.90),
(3.119; 450.70), (2.975; 4.11), (2.656; 3.07), (2.527; 2.02), (2.506; 2.07), (2.498; 30.00),
(2.493; 61.92), (2.488; 87.05), (2.484; 60.51), (2.479; 28.74), (2.320; 0.39), (2.315; 0.56), (2.311; 0.35),
(2.160; 3.00), (2.136; 2.91), (2.040; 0.33), (1.901; 0.45), (1.404; 0.59), (1.247; 0.33), (0.998; 16.00),
(0.977; 0.44), (−0.000; 3.17)
Ex. 97:
(7.141; 0.93), (6.766; 0.84), (3.303; 0.36), (3.160; 0.65), (3.118; 579.98), (2.863; 4.99), (2.696; 0.34),
(2.662; 0.67), (2.656; 3.07), (2.648; 0.38), (2.527; 2.60), (2.511; 1.86), (2.506; 2.58), (2.498; 37.50),
(2.493; 77.52), (2.488; 109.31), (2.484; 76.21), (2.479; 36.31), (2.320; 0.45), (2.315; 0.69), (2.310; 0.47),
(2.157; 2.94), (2.137; 2.93), (2.041; 0.90), (1.298; 0.43), (1.246; 0.46), (1.203; 4.07), (1.186; 3.99),
(1.026; 0.50), (1.019; 0.49), (0.998; 16.00), (0.974; 0.66), (0.967; 0.45), (0.956; 0.37), (−0.000; 7.76)
Ex. 98:
(7.645; 0.40), (7.144; 0.89), (6.764; 0.82), (3.393; 0.39), (3.375; 0.40), (3.303; 0.47), (3.200; 0.41),
(3.114; 487.45), (2.951; 2.72), (2.695; 0.47), (2.666; 0.44), (2.662; 0.82), (2.656; 3.25), (2.648; 0.46),
(2.554; 0.37), (2.526; 3.53), (2.510; 2.41), (2.505; 3.48), (2.497; 48.90), (2.493; 100.95), (2.488; 142.15),

-continued (2.483; 98.97), (2.478; 46.94), (2.319; 0.64), (2.315; 0.87), (2.310; 0.57), (2.158; 2.94), (2.136; 3.07),
(2.041; 0.62), (2.037; 0.37), (1.298; 0.51), (1.296; 0.40), (1.245; 0.49), (1.162; 1.37), (1.144; 2.97),
(1.126; 1.30), (1.027; 0.38), (1.019; 0.35), (0.998; 16.00), (0.976; 0.52), (0.974; 0.32), (0.967; 0.35),
(0.956; 0.36), (0.008; 0.35), (−0.000; 10.73)
Ex. 99:
(7.975; 0.53), (7.638; 4.55), (7.157; 3.59), (7.148; 0.46), (6.898; 0.39), (6.773; 3.67), (3.816; 2.20),
(3.463; 2.17), (3.378; 0.53), (3.303; 0.41), (3.221; 6.30), (3.190; 0.57), (3.162; 1.13), (3.122; 759.00),
(2.975; 16.00), (2.697; 0.34), (2.662; 0.50), (2.658; 0.71), (2.653; 0.72), (2.527; 2.49), (2.511; 1.92),
(2.506; 2.73), (2.498; 39.55), (2.493; 81.65), (2.489; 115.05), (2.484; 80.28), (2.479; 38.19), (2.320; 0.50),
(2.316; 0.73), (2.311; 0.55), (2.165; 1.83), (2.156; 12.64), (2.150; 12.88), (2.116; 1.18), (1.617; 1.70),
(1.602; 2.67), (1.599; 2.63), (1.595; 3.10), (1.592; 2.39), (1.582; 2.89), (1.541; 0.48), (1.534; 0.43),
(1.493; 2.96), (1.483; 2.39), (1.479; 3.13), (1.476; 2.68), (1.473; 2.62), (1.458; 1.69), (1.444; 0.46),
(1.442; 0.36), (1.439; 0.42), (1.431; 0.70), (1.419; 0.43), (1.404; 14.77), (1.397; 0.73), (1.390; 0.40),
(1.387; 0.36), (1.383; 0.43), (1.373; 0.32), (1.365; 0.35), (1.363; 0.35), (1.298; 0.36), (1.296; 0.35),
(1.246; 0.34), (−0.000; 6.35)
Ex. 100:
(7.729; 0.71), (7.218; 3.59), (7.189; 0.50), (6.924; 0.46), (6.811; 0.79), (6.787; 0.35), (5.764; 0.76),
(3.813; 2.32), (3.458; 0.38), (3.446; 0.40), (3.435; 0.38), (3.344; 68.12), (3.320; 2.02), (3.225; 0.69),
(2.994; 0.89), (2.922; 2.24), (2.615; 0.35), (2.524; 0.71), (2.521; 0.93), (2.518; 1.10), (2.506; 45.54),
(2.503; 60.98), (2.500; 45.28), (2.387; 0.34), (2.166; 1.71), (2.148; 16.00), (2.109; 1.71), (1.609; 1.09),
(1.599; 2.52), (1.597; 2.47), (1.595; 2.81), (1.586; 1.56), (1.505; 1.66), (1.496; 2.76), (1.493; 2.62),
(1.492; 2.59), (1.482; 1.02), (1.426; 0.44), (1.375; 0.41), (1.147; 0.90), (1.136; 1.94), (1.125; 1.55),
(0.005; 0.61), (0.000; 14.14), (−0.005; 0.54)
Ex. 101:
(7.715; 0.60), (7.703; 0.59), (7.159; 2.15), (7.148; 0.77), (6.899; 0.79), (6.786; 1.25), (3.816; 3.74),
(3.723; 0.73), (3.463; 3.17), (3.303; 0.92), (3.286; 0.58), (3.251; 0.64), (3.233; 0.62), (3.221; 4.49),
(3.213; 0.87), (3.206; 0.93), (3.197; 1.03), (3.193; 1.07), (3.188; 1.23), (3.151; 4.26), (3.123; 1997.86),
(3.085; 1.37), (3.081; 1.19), (3.062; 0.56), (2.868; 10.47), (2.696; 1.00), (2.667; 0.68), (2.662; 1.23),
(2.658; 1.70), (2.653; 1.11), (2.649; 0.73), (2.639; 0.94), (2.567; 0.60), (2.555; 0.68), (2.527; 6.79),
(2.511; 5.05), (2.506; 7.14), (2.498; 99.63), (2.493; 206.02), (2.489; 290.77), (2.484; 202.71), (2.479; 96.24),
(2.325; 0.62), (2.320; 1.13), (2.316; 1.64), (2.311; 1.22), (2.165; 2.73), (2.155; 16.00), (2.116; 1.89),
(2.076; 0.64), (2.040; 0.62), (2.037; 0.61), (1.901; 0.87), (1.617; 1.44), (1.602; 2.29), (1.599; 2.33),
(1.595; 2.58), (1.592; 2.05), (1.582; 2.28), (1.494; 2.56), (1.484; 2.20), (1.480; 2.63), (1.476; 2.35),
(1.474; 2.24), (1.459; 1.43), (1.430; 0.67), (1.419; 0.66), (1.404; 9.18), (1.373; 0.58), (1.362; 0.63),
(1.298; 0.98), (1.296; 0.84), (1.245; 0.94), (1.205; 12.00), (1.188; 11.81), (1.157; 1.50), (1.140; 1.35),
(1.055; 0.71), (0.895; 0.74), (−0.000; 14.41)
Ex. 102:
(7.749; 1.16), (7.420; 0.94), (7.418; 0.98), (7.066; 1.37), (3.765; 0.68), (3.259; 0.47), (3.226; 0.34),
(3.213; 0.45), (3.201; 1.67), (3.178; 0.76), (3.122; 608.86), (3.098; 24.13), (2.997; 1.52), (2.940; 0.66),
(2.888; 1.95), (2.815; 0.47), (2.734; 1.63), (2.733; 1.57), (2.698; 0.37), (2.671; 2.93), (2.663; 0.69),
(2.658; 0.81), (2.653; 0.59), (2.535; 0.52), (2.527; 1.19), (2.511; 2.03), (2.506; 3.00), (2.498; 44.49),
(2.493; 92.27), (2.489; 130.19), (2.484; 90.78), (2.479; 43.17), (2.320; 0.56), (2.315; 0.82), (2.311; 0.51),
(2.298; 0.54), (2.243; 0.66), (2.192; 3.53), (2.165; 0.42), (2.040; 0.72), (1.404; 0.78), (1.245; 0.45),
(1.056; 0.51), (0.997; 16.00), (0.990; 1.93), (0.976; 2.25), (0.974; 3.55), (0.961; 1.87), (0.952; 0.47),
(0.903; 0.78), (0.008; 0.33), (−0.000; 10.00), (−0.008; 0.34)
Ex. 103:
(7.626; 1.35), (7.007; 2.51), (6.729; 2.60), (3.402; 0.44), (3.384; 1.11), (3.367; 1.12), (3.349; 0.44),
(3.124; 300.57), (3.099; 12.27), (2.944; 9.39), (2.527; 0.54), (2.511; 0.79), (2.506; 1.14), (2.498; 16.76),
(2.494; 34.58), (2.489; 48.75), (2.484; 33.95), (2.480; 16.10), (2.368; 16.00), (2.340; 2.82), (2.144; 8.82),
(2.119; 7.72), (2.041; 0.36), (1.158; 4.17), (1.140; 9.16), (1.122; 4.03), (−0.000; 2.54)
Ex. 104:
(7.975; 0.67), (7.952; 0.55), (7.794; 1.51), (7.790; 1.73), (7.775; 1.73), (7.771; 2.05), (7.768; 1.92),
(7.749; 5.59), (7.702; 1.18), (7.698; 1.26), (7.692; 1.01), (7.677; 1.07), (7.671; 1.28), (7.667; 1.17),
(7.661; 1.15), (7.640; 1.79), (7.625; 1.99), (7.620; 1.03), (7.604; 1.05), (7.591; 5.52), (7.538; 0.70),
(7.431; 0.98), (7.425; 0.89), (7.409; 1.12), (7.404; 1.14), (7.389; 0.75), (7.382; 0.77), (7.034; 4.59),
(6.636; 0.57), (3.835; 0.84), (3.447; 0.53), (3.382; 0.61), (3.361; 0.62), (3.354; 2.78), (3.338; 0.83),
(3.319; 0.74), (3.303; 1.10), (3.282; 11.55), (3.212; 2.16), (3.118; 714.37), (3.012; 6.72), (2.955; 1.52),
(2.938; 4.53), (2.904; 0.67), (2.887; 0.67), (2.695; 0.58), (2.667; 1.40), (2.662; 2.52), (2.657; 3.59),
(2.652; 2.47), (2.648; 1.48), (2.583; 0.58), (2.568; 0.72), (2.555; 0.88), (2.526; 5.89), (2.510; 8.58),
(2.506; 12.31), (2.497; 187.33), (2.493; 387.37), (2.488; 546.01), (2.483; 381.11), (2.479; 181.51),
(2.324; 1.19), (2.320; 2.33), (2.315; 3.32), (2.310; 2.60), (2.306; 1.27), (2.285; 2.80), (2.268; 0.53),
(2.219; 16.00), (2.136; 0.61), (2.070; 3.50), (2.040; 1.49), (1.404; 1.33), (1.299; 0.80), (1.245; 1.92),
(1.082; 0.53), (0.008; 1.67), (−0.000; 54.02), (−0.009; 1.72)
Ex. 105:
(7.796; 0.71), (7.793; 0.83), (7.792; 0.82), (7.790; 0.76), (7.776; 0.86), (7.774; 0.97), (7.772; 1.04),
(7.770; 0.89), (7.703; 0.53), (7.699; 0.56), (7.696; 0.61), (7.693; 0.51), (7.678; 0.55), (7.674; 0.59),
(7.671; 0.61), (7.668; 0.52), (7.659; 0.55), (7.644; 0.63), (7.639; 0.86), (7.624; 0.86), (7.619; 0.53),
(7.604; 0.50), (7.582; 2.55), (7.432; 0.36), (7.430; 0.38), (7.425; 0.33), (7.423; 0.33), (7.410; 0.55),
(7.403; 0.51), (7.042; 1.55), (6.874; 0.32), (5.689; 16.00), (3.730; 1.54), (3.609; 0.92), (3.282; 3.44),
(3.117; 3.27), (2.902; 8.06), (2.864; 0.71), (2.838; 1.62), (2.823; 0.46), (2.640; 0.35), (2.638; 0.35),
(2.546; 0.86), (2.499; 3.67), (2.494; 7.78), (2.489; 11.11), (2.484; 7.88), (2.480; 3.85), (2.320; 0.50),
(2.221; 7.29), (2.208; 0.62), (2.207; 0.60), (2.180; 0.41), (2.086; 0.86), (2.085; 0.86), (2.057; 0.32),
(1.225; 3.81), (1.209; 3.91), (1.188; 1.87), (1.180; 0.85), (1.171; 1.51), (1.164; 0.64), (1.158; 0.76),
(1.141; 0.68), (1.070; 0.55), (1.066; 0.98), (1.054; 0.57), (1.049; 0.96), (−0.000; 1.47)
Ex. 106:
(10.995; 0.01), (7.993; 0.01), (7.960; 0.03), (7.886; 0.00), (7.616; 0.07), (7.597; 0.07), (7.590; 0.07),
(7.571; 0.07), (7.516; 0.01), (7.497; 0.01), (7.489; 0.01), (7.470; 0.01), (7.360; 0.01), (7.344; 0.01),
(7.338; 0.03), (7.333; 0.01), (7.308; 0.02), (7.287; 0.01), (7.235; 0.04), (7.216; 0.04), (7.204; 0.04),
(7.185; 0.04), (7.163; 0.01), (7.152; 0.00), (7.132; 0.00), (5.688; 0.05), (4.727; 0.00), (4.703; 0.00),
(4.683; 0.00), (4.170; 0.01), (4.093; 0.04), (4.047; 0.01), (4.029; 0.01), (3.818; 0.02), (3.816; 0.02), (3.775; 0.01), (3.204; 0.03), (3.187; 0.01), (3.172; 0.01), (3.126; 16.00), (3.057; 0.01), (3.043; 0.01), (2.938; 0.00), (2.908; 0.02), (2.886; 0.27), (2.858; 0.01), (2.830; 0.01), (2.710; 0.00), (2.697; 0.00), (2.668; 0.00), (2.663; 0.01), (2.659; 0.01), (2.654; 0.01), (2.528; 0.02), (2.512; 0.03), (2.507; 0.04), (2.499; 0.68), (2.494; 1.42), (2.490; 2.00), (2.485; 1.40), (2.480; 0.67), (2.321; 0.01), (2.316; 0.01), (2.312; 0.01), (2.041; 0.01), (1.974; 0.03), (1.902; 0.01), (1.559; 0.01), (1.402; 4.11), (1.368; 0.03), (1.360; 0.02), (1.357; 0.05), (1.299; 0.01), (1.242; 0.04), (1.215; 0.18), (1.204; 0.19), (1.178; 0.07), (1.160; 0.03), (0.895; 0.01), (−0.000; 0.03)

Ex. 107:
(7.598; 3.61), (7.008; 2.63), (6.737; 2.81), (3.445; 2.01), (3.119; 232.78), (3.095; 3.51), (2.527; 0.61), (2.511; 0.80), (2.506; 1.15), (2.498; 16.24), (2.493; 33.47), (2.489; 47.06), (2.484; 32.74), (2.479; 15.50), (2.367; 16.00), (2.340; 2.69), (2.136; 9.15), (2.119; 8.02), (1.658; 0.57), (1.654; 0.57), (1.648; 0.73), (1.640; 1.27), (1.628; 1.14), (1.620; 0.67), (1.613; 0.65), (1.560; 1.06), (1.546; 2.15), (1.533; 2.97), (1.518; 1.43), (1.505; 0.57), (−0.000; 2.83)

Ex. 108:
(7.737; 0.56), (7.249; 2.52), (7.247; 2.43), (7.026; 2.88), (3.403; 0.66), (3.388; 0.67), (3.131; 125.37), (3.106; 1.42), (2.964; 3.90), (2.500; 4.32), (2.495; 8.90), (2.490; 12.54), (2.486; 8.75), (2.481; 4.16), (2.383; 16.00), (2.374; 0.33), (2.372; 0.35), (2.355; 2.65), (2.174; 10.42), (1.166; 3.22), (1.148; 6.84), (1.130; 3.10), (−0.000; 1.50)

Ex. 109:
(7.709; 3.64), (7.249; 2.59), (7.247; 2.59), (7.031; 4.30), (3.470; 1.26), (3.130; 294.43), (3.106; 3.15), (2.528; 0.32), (2.512; 0.52), (2.507; 0.72), (2.499; 10.11), (2.494; 29.20), (2.485; 20.32), (2.480; 9.66), (2.382; 16.00), (2.371; 0.63), (2.355; 2.50), (2.184; 0.40), (2.164; 10.88), (2.041; 0.39), (1.974; 0.66), (1.661; 0.57), (1.656; 0.58), (1.643; 1.23), (1.632; 1.16), (1.623; 0.69), (1.616; 0.64), (1.567; 1.00), (1.553; 2.03), (1.540; 2.71), (1.526; 1.39), (1.512; 0.53), (1.178; 0.38), (−0.000; 3.49)

Ex. 110:
(7.719; 0.43), (7.315; 0.72), (7.310; 3.08), (6.967; 2.37), (3.394; 0.59), (3.369; 0.37), (3.127; 89.59), (3.102; 1.10), (2.970; 3.69), (2.500; 3.46), (2.495; 7.08), (2.490; 9.94), (2.485; 6.90), (2.481; 3.27), (2.382; 16.00), (2.354; 2.78), (2.156; 2.20), (2.150; 9.34), (1.178; 0.47), (1.173; 3.49), (1.155; 7.41), (1.137; 3.36), (−0.000; 1.20)

Ex. 111:
(7.698; 3.63), (7.314; 0.63), (7.310; 3.22), (6.978; 2.90), (3.475; 0.98), (3.188; 0.37), (3.132; 406.41), (2.528; 0.46), (2.512; 0.67), (2.507; 0.97), (2.499; 13.87), (2.494; 28.53), (2.490; 40.11), (2.485; 27.88), (2.480; 13.21), (2.381; 16.00), (2.353; 2.46), (2.155; 2.03), (2.149; 9.49), (2.040; 0.35), (1.665; 0.55), (1.661; 0.55), (1.647; 1.22), (1.637; 1.12), (1.627; 0.67), (1.620; 0.63), (1.571; 0.97), (1.557; 1.98), (1.543; 2.64), (1.529; 1.36), (1.515; 0.52), (1.386; 0.58), (−0.000; 0.77)

Ex. 112:
(7.415; 1.02), (7.079; 0.73), (5.690; 1.17), (3.764; 0.65), (3.200; 0.47), (3.117; 395.89), (3.093; 6.82), (2.883; 3.33), (2.828; 0.52), (2.671; 2.91), (2.662; 0.50), (2.657; 0.59), (2.653; 0.37), (2.527; 1.17), (2.510; 1.50), (2.506; 2.10), (2.498; 30.81), (2.493; 63.89), (2.488; 90.32), (2.484; 63.59), (2.479; 30.81), (2.320; 0.43), (2.315; 0.55), (2.310; 0.41), (2.190; 3.50), (2.161; 0.41), (1.245; 0.75), (1.211; 2.16), (1.194; 2.15), (1.181; 0.66), (1.164; 0.55), (1.017; 0.32), (0.997; 16.00), (0.974; 1.58), (0.895; 0.34), (−0.000; 4.55)

Ex. 113:
(7.419; 0.92), (7.417; 0.89), (7.075; 0.71), (3.201; 0.77), (3.149; 0.80), (3.120; 186.62), (2.972; 1.04), (2.672; 2.94), (2.527; 0.56), (2.511; 0.72), (2.506; 1.02), (2.498; 12.97), (2.493; 26.53), (2.489; 37.27), (2.484; 26.06), (2.479; 12.45), (2.192; 3.48), (1.170; 0.97), (1.153; 2.10), (1.135; 1.03), (0.997; 16.00), (0.977; 1.46), (0.974; 0.70), (−0.000; 1.81)

Ex. 114:
(7.795; 1.35), (7.793; 1.64), (7.791; 1.64), (7.789; 1.53), (7.773; 7.54), (7.770; 2.76), (7.708; 1.09), (7.704; 1.13), (7.702; 1.26), (7.698; 1.06), (7.683; 1.09), (7.679; 1.15), (7.676; 1.22), (7.673; 1.06), (7.661; 1.12), (7.646; 1.33), (7.640; 1.81), (7.632; 0.38), (7.625; 2.00), (7.620; 1.19), (7.605; 1.09), (7.579; 1.12), (7.470; 4.46), (7.468; 4.40), (7.436; 0.81), (7.434; 0.85), (7.430; 0.74), (7.427; 0.77), (7.414; 1.22), (7.412; 1.18), (7.408; 1.12), (7.393; 0.72), (7.391; 0.71), (7.387; 0.64), (7.385; 0.60), (7.106; 6.79), (6.882; 0.70), (6.818; 1.00), (4.048; 0.40), (4.030; 0.39), (3.980; 0.73), (3.953; 0.62), (3.895; 0.96), (3.766; 4.88), (3.490; 0.92), (3.282; 8.65), (3.118; 69.57), (3.093; 1.83), (3.008; 6.33), (2.941; 4.40), (2.688; 0.33), (2.575; 0.46), (2.574; 0.45), (2.512; 0.38), (2.507; 0.54), (2.499; 7.96), (2.494; 16.47), (2.490; 23.18), (2.485; 16.14), (2.480; 7.65), (2.245; 0.68), (2.232; 0.34), (2.214; 16.00), (2.166; 2.84), (1.975; 1.84), (1.196; 0.54), (1.178; 1.06), (1.160; 0.53), (−0.000; 2.08)

Ex. 115:
(7.748; 5.60), (7.707; 0.53), (7.609; 5.48), (7.453; 0.61), (7.450; 1.01), (7.446; 1.56), (7.442; 1.73), (7.433; 2.13), (7.427; 2.57), (7.423; 2.81), (7.416; 2.62), (7.412; 1.38), (7.387; 2.69), (7.385; 2.26), (7.379; 0.59), (7.378; 0.62), (7.376; 0.57), (7.370; 1.16), (7.369; 1.13), (7.366; 1.07), (7.365; 1.01), (7.359; 1.50), (7.358; 1.50), (7.355; 1.25), (7.349; 0.50), (7.340; 1.44), (7.337; 1.20), (7.321; 0.80), (7.319; 0.71), (7.284; 0.33), (7.143; 0.42), (7.141; 0.41), (7.032; 4.48), (7.031; 4.37), (3.850; 0.41), (3.769; 2.54), (3.731; 0.78), (3.474; 0.34), (3.356; 1.02), (3.263; 5.14), (3.185; 4.23), (3.128; 4.03), (3.076; 0.40), (3.072; 0.47), (3.013; 6.48), (2.955; 0.59), (2.947; 0.92), (2.930; 0.56), (2.887; 0.42), (2.735; 0.34), (2.734; 0.33), (2.498; 3.04), (2.494; 6.22), (2.489; 8.67), (2.484; 6.01), (2.480; 2.85), (2.334; 16.00), (2.311; 0.49), (2.282; 1.53), (2.281; 1.49), (2.274; 0.77), (2.260; 2.82), (2.230; 15.83), (2.085; 0.43), (−0.000; 1.12)

Ex. 116:
(7.926; 0.55), (7.839; 0.54), (7.806; 0.56), (7.611; 4.36), (7.452; 1.11), (7.436; 2.21), (7.422; 3.19), (7.418; 3.08), (7.389; 3.05), (7.371; 1.33), (7.360; 1.68), (7.338; 1.71), (7.322; 0.90), (7.256; 0.54), (7.235; 0.62), (7.172; 0.66), (7.153; 0.93), (7.046; 2.87), (4.029; 0.54), (3.925; 0.78), (3.850; 1.62), (3.833; 0.57), (3.816; 0.63), (3.774; 0.56), (3.768; 2.49), (3.754; 1.45), (3.474; 1.53), (3.304; 0.63), (3.284; 0.76), (3.264; 3.50), (3.241; 0.75), (3.116; 1928.12), (3.074; 1.27), (3.052; 0.54), (2.903; 15.96), (2.888; 3.54), (2.760; 1.24), (2.732; 1.41), (2.696; 1.22), (2.667; 1.13), (2.662; 2.02), (2.657; 2.82), (2.652; 2.07), (2.648; 1.07), (2.637; 2.86), (2.526; 6.58), (2.510; 8.18), (2.506; 12.09), (2.497; 163.67), (2.493; 333.75), (2.488; 466.67), (2.483; 324.51), (2.479; 153.94), (2.332; 16.00), (2.320; 2.52), (2.315; 3.01), (2.310; 2.36), (2.306; 2.00), (2.298; 2.43), (2.283; 1.48), (2.259; 2.25), (2.232; 15.18), (2.212; 0.62), (2.149; 1.06), (2.101; 1.74), (2.041; 1.78), (1.974; 1.35), (1.404; 1.22), (1.296; 0.58),

-continued (1.245; 2.27), (1.226; 8.55), (1.209; 9.49), (1.177; 1.23), (1.157; 4.61), (1.140; 4.51), (1.072; 1.74),
(1.054; 1.67), (0.956; 1.19), (0.008; 0.83), (−0.000; 26.86)
Ex. 117:
(7.728; 1.24), (7.533; 1.17), (6.998; 0.99), (3.201; 1.41), (3.115; 76.15), (3.091; 2.09), (3.002; 1.32),
(2.663; 2.97), (2.535; 0.34), (2.510; 0.33), (2.506; 0.48), (2.498; 6.67), (2.493; 13.79), (2.488; 19.48),
(2.484; 13.66), (2.479; 6.55), (2.298; 0.63), (2.162; 3.55), (1.000; 16.00), (0.992; 1.48), (0.977; 1.87),
(0.962; 0.35), (−0.000; 1.73)
Ex. 118:
(7.528; 1.21), (7.006; 0.75), (3.201; 1.43), (3.120; 196.66), (3.095; 4.01), (2.891; 3.79), (2.760; 1.01),
(2.663; 2.98), (2.658; 0.46), (2.639; 1.99), (2.637; 2.01), (2.535; 0.38), (2.527; 0.52), (2.511; 0.61),
(2.506; 0.88), (2.498; 11.66), (2.493; 23.98), (2.489; 33.72), (2.484; 23.55), (2.479; 11.22), (2.164; 3.51),
(1.217; 1.93), (1.200; 1.92), (1.157; 3.39), (1.140; 3.30), (1.072; 1.23), (1.061; 0.33), (1.055; 1.23),
(1.001; 16.00), (0.992; 1.32), (0.976; 1.81), (0.962; 0.33), (0.951; 0.36), (−0.000; 2.35)
Ex. 119:
(7.531; 1.13), (7.002; 0.74), (3.402; 0.37), (3.269; 0.33), (3.251; 0.42), (3.201; 1.50), (3.118; 210.09),
(2.978; 0.96), (2.866; 0.58), (2.719; 0.76), (2.718; 0.78), (2.663; 3.01), (2.658; 0.54), (2.535; 0.45),
(2.527; 0.79), (2.511; 0.94), (2.506; 1.39), (2.498; 17.42), (2.493; 35.80), (2.488; 50.36), (2.484; 35.18),
(2.479; 16.78), (2.315; 0.32), (2.163; 3.47), (1.177; 1.05), (1.159; 2.21), (1.141; 1.07), (1.112; 0.37),
(1.094; 0.68), (1.076; 0.34), (1.015; 0.50), (1.001; 16.00), (0.992; 1.28), (0.977; 2.07), (0.962; 0.33),
(0.951; 0.45), (−0.000; 3.78)
Ex. 120:
(7.633; 2.43), (7.364; 0.47), (7.361; 0.70), (7.357; 0.33), (7.347; 0.48), (7.343; 1.72), (7.340; 1.03),
(7.328; 0.60), (7.324; 1.44), (7.270; 0.36), (7.266; 0.77), (7.263; 0.56), (7.248; 0.98), (7.243; 0.36),
(7.233; 0.35), (7.230; 0.98), (7.227; 1.87), (7.224; 2.04), (7.219; 0.49), (7.206; 1.44), (7.203; 1.14),
(7.136; 1.73), (6.755; 1.82), (5.688; 2.98), (3.142; 0.39), (3.123; 35.06), (3.099; 0.75), (2.973; 8.12),
(2.866; 0.36), (2.760; 0.33), (2.720; 0.48), (2.719; 0.47), (2.639; 0.66), (2.638; 0.66), (2.498; 2.44),
(2.493; 5.02), (2.489; 7.06), (2.484; 4.92), (2.479; 2.35), (2.158; 5.62), (2.113; 5.61), (1.713; 16.00),
(1.157; 1.11), (1.140; 1.09), (1.094; 0.39), (1.072; 0.41), (1.055; 0.40), (−0.000; 0.52)
Ex. 121:
(7.695; 0.41), (7.362; 0.69), (7.358; 0.35), (7.344; 1.69), (7.328; 0.61), (7.325; 1.44), (7.270; 0.42),
(7.267; 0.75), (7.264; 0.58), (7.253; 0.57), (7.249; 1.03), (7.243; 0.43), (7.234; 0.76), (7.227; 1.93),
(7.223; 2.09), (7.218; 1.02), (7.206; 1.43), (7.202; 1.19), (7.170; 0.69), (7.151; 0.51), (7.134; 1.86),
(6.760; 1.67), (3.142; 0.92), (3.116; 328.56), (3.092; 9.13), (2.760; 0.67), (2.662; 0.37),
(2.657; 0.46), (2.652; 0.36), (2.638; 1.27), (2.637; 1.28), (2.526; 1.10), (2.510; 1.32), (2.506; 1.81),
(2.497; 25.70), (2.493; 53.19), (2.488; 75.06), (2.483; 52.56), (2.479; 25.19), (2.320; 0.34), (2.315; 0.49),
(2.310; 0.38), (2.298; 2.78), (2.155; 5.52), (2.114; 5.59), (1.712; 16.00), (1.404; 0.91), (1.246; 0.39),
(1.203; 7.60), (1.186; 7.53), (1.157; 2.17), (1.140; 2.10), (1.072; 0.75), (1.055; 0.77), (−0.000; 4.77),
Ex. 122:
(7.647; 0.74), (7.362; 0.68), (7.358; 0.34), (7.344; 1.71), (7.341; 1.09), (7.328; 0.59), (7.325; 1.40),
(7.270; 0.35), (7.267; 0.76), (7.264; 0.53), (7.253; 0.38), (7.248; 0.98), (7.243; 0.38), (7.227; 1.85),
(7.223; 2.02), (7.218; 0.57), (7.205; 1.43), (7.203; 1.17), (7.136; 1.72), (6.759; 1.70), (3.392; 0.60),
(3.374; 0.63), (3.142; 0.81), (3.114; 265.00), (3.090; 7.99), (2.951; 5.11), (2.866; 0.34), (2.719; 0.48),
(2.662; 0.36), (2.657; 0.50), (2.652; 0.37), (2.526; 1.21), (2.510; 1.43), (2.505; 2.04), (2.497; 26.11),
(2.493; 53.58), (2.488; 75.40), (2.483; 52.66), (2.478; 25.09), (2.319; 0.33), (2.315; 0.48), (2.310; 0.33),
(2.298; 0.58), (2.156; 5.51), (2.114; 5.55), (2.040; 0.35), (1.712; 16.00), (1.245; 0.34), (1.161; 2.41),
(1.144; 5.32), (1.126; 2.30), (1.094; 0.39), (−0.000; 6.89)
Ex. 123:
(7.656; 5.84), (7.645; 0.62), (7.640; 0.75), (7.635; 2.28), (7.631; 2.19), (7.605; 1.02), (7.600; 2.59),
(7.594; 1.34), (7.588; 1.02), (7.583; 3.28), (7.580; 3.64), (7.576; 2.15), (7.566; 2.08), (7.561; 0.95),
(7.533; 2.05), (7.529; 1.98), (7.516; 1.48), (7.511; 1.97), (7.496; 0.86), (7.493; 0.87), (7.456; 0.60),
(7.446; 0.49), (7.227; 3.46), (7.217; 0.94), (7.170; 0.96), (7.153; 0.66), (6.801; 3.86), (3.813; 1.28),
(3.714; 0.65), (3.491; 1.26), (3.265; 4.92), (3.259; 1.22), (3.247; 0.51), (3.238; 0.63), (3.223; 0.59),
(3.200; 1.30), (3.189; 1.00), (3.162; 1.82), (3.116; 1392.38), (3.092; 13.53), (3.061; 0.51), (2.985; 16.00),
(2.888; 4.93), (2.734; 4.27), (2.732; 4.15), (2.696; 0.56), (2.667; 0.72), (2.662; 1.36), (2.657; 2.08),
(2.652; 1.41), (2.648; 0.77), (2.551; 0.60), (2.526; 4.93), (2.510; 5.89), (2.506; 8.35), (2.497; 111.91),
(2.493; 229.81), (2.488; 322.85), (2.483; 224.69), (2.479; 106.53), (2.324; 0.85), (2.320; 1.44), (2.315; 1.91),
(2.310; 1.41), (2.306; 0.87), (2.298; 3.86), (2.210; 0.91), (2.196; 11.64), (2.187; 11.51), (2.124; 0.73),
(2.041; 0.85), (1.974; 1.48), (1.404; 3.87), (1.245; 1.12), (1.195; 0.54), (1.177; 0.89), (0.895; 0.72),
(0.008; 0.86), (−0.000; 26.10), (−0.009; 0.80)
Ex. 124:
(8.077; 0.95), (7.975; 0.85), (7.925; 0.47), (7.715; 0.67), (7.656; 0.98), (7.646; 0.38), (7.636; 1.86),
(7.632; 1.78), (7.605; 0.89), (7.600; 2.12), (7.594; 1.06), (7.589; 0.79), (7.584; 2.66), (7.580; 3.02),
(7.576; 1.88), (7.567; 1.68), (7.562; 0.70), (7.533; 1.65), (7.530; 1.60), (7.517; 1.17), (7.512; 1.71),
(7.496; 0.68), (7.493; 0.77), (7.456; 0.37), (7.446; 0.44), (7.444; 0.52), (7.236; 0.32), (7.222; 2.99),
(7.191; 0.34), (7.170; 0.37), (6.807; 2.83), (4.387; 0.36), (3.833; 0.67), (3.813; 1.89), (3.798; 0.67),
(3.491; 1.55), (3.265; 3.44), (3.215; 0.75), (3.123; 986.63), (3.099; 7.22), (3.083; 0.73), (2.889; 0.42),
(2.874; 16.00), (2.760; 3.80), (2.667; 0.36), (2.662; 0.59), (2.657; 0.66), (2.649; 0.38),
(2.639; 7.55), (2.637; 7.36), (2.527; 1.97), (2.511; 2.35), (2.506; 3.43), (2.498; 47.48), (2.493; 97.70),
(2.489; 137.42), (2.484; 95.94), (2.479; 45.71), (2.320; 0.61), (2.316; 0.85), (2.311; 0.70), (2.306; 0.36),
(2.298; 1.23), (2.211; 1.15), (2.198; 9.49), (2.185; 9.40), (2.124; 0.93), (2.076; 0.66), (1.245; 0.49),
(1.212; 12.59), (1.195; 12.34), (1.157; 12.49), (1.140; 12.28), (1.072; 4.56), (1.055; 4.57), (−0.000; 8.89)
Ex. 125:
(7.669; 1.54), (7.656; 1.55), (7.646; 0.46), (7.640; 0.66), (7.636; 2.14), (7.632; 2.14), (7.605; 1.02),
(7.600; 2.66), (7.594; 1.33), (7.589; 0.90), (7.584; 3.11), (7.580; 3.75), (7.576; 2.11), (7.566; 1.92),
(7.562; 0.73), (7.533; 1.90), (7.530; 1.85), (7.516; 1.28), (7.511; 1.97), (7.496; 0.86), (7.493; 0.80),
(7.446; 0.46), (7.444; 0.45), (7.225; 3.43), (6.805; 3.47), (3.812; 1.44), (3.491; 1.27), (3.419; 0.64),
(3.403; 1.20), (3.385; 1.26), (3.374; 0.59), (3.265; 3.08), (3.251; 0.50), (3.239; 0.33), (3.234; 0.40),
(3.219; 0.43), (3.118; 857.86), (3.094; 14.44), (2.984; 0.33), (2.963; 10.16), (2.888; 0.33), (2.866; 0.45),
(2.733; 0.34), (2.720; 0.65), (2.718; 0.61), (2.667; 0.39), (2.662; 0.84), (2.657; 1.21), (2.653; 0.80),
(2.648; 0.41), (2.527; 2.64), (2.511; 3.37), (2.506; 4.53), (2.498; 61.95), (2.493; 128.00), (2.488; 180.59), -continued (2.484; 126.50), (2.479; 60.69), (2.459; 0.44), (2.324; 0.37), (2.320; 0.74), (2.315; 1.19), (2.311; 0.74),
(2.306; 0.35), (2.210; 0.99), (2.197; 11.46), (2.186; 11.37), (2.124; 0.69), (2.041; 0.39), (1.974; 0.39),
(1.901; 1.12), (1.404; 16.00), (1.245; 0.56), (1.171; 4.86), (1.153; 10.95), (1.135; 4.63), (1.094; 0.41),
(1.076; 0.35), (0.895; 0.85), (−0.000; 6.00)

Ex. 126:
(7.773; 5.50), (7.662; 1.36), (7.660; 1.36), (7.651; 0.57), (7.648; 0.59), (7.642; 2.57), (7.638; 2.60),
(7.613; 1.22), (7.608; 2.10), (7.606; 1.85), (7.600; 1.75), (7.596; 1.26), (7.591; 3.38), (7.586; 4.23),
(7.582; 3.24), (7.574; 2.17), (7.569; 0.75), (7.563; 0.45), (7.545; 0.34), (7.538; 2.23), (7.534; 2.17),
(7.528; 0.46), (7.521; 1.54), (7.518; 1.86), (7.516; 2.27), (7.499; 4.79), (7.497; 5.15), (7.459; 0.33),
(7.457; 0.37), (7.446; 0.48), (7.444; 0.59), (7.136; 0.37), (7.110; 6.58), (6.885; 0.47), (6.823; 0.53),
(5.690; 2.10), (3.941; 0.34), (3.881; 1.88), (3.812; 1.02), (3.767; 3.04), (3.476; 1.80), (3.265; 3.29),
(3.122; 93.46), (3.098; 1.44), (3.008; 6.52), (2.943; 2.84), (2.511; 0.36), (2.507; 0.51), (2.499; 7.16),
(2.494; 14.74), (2.489; 20.80), (2.484; 14.63), (2.480; 7.08), (2.416; 0.80), (2.238; 1.49), (2.218; 16.00),
(2.167; 1.86), (1.975; 0.90), (1.178; 0.52), (−0.000; 1.35)

Ex. 127:
(7.698; 0.73), (7.693; 0.87), (7.679; 1.24), (7.675; 1.77), (7.657; 5.56), (7.652; 0.91), (7.643; 0.59),
(7.638; 0.97), (7.636; 0.71), (7.634; 0.65), (7.631; 0.61), (7.623; 0.74), (7.620; 0.73), (7.617; 1.00),
(7.613; 0.57), (7.604; 0.63), (7.599; 0.51), (7.434; 0.96), (7.432; 1.09), (7.413; 0.96), (7.411; 1.10),
(7.407; 3.03), (7.388; 2.53), (7.386; 3.22), (7.370; 1.22), (7.367; 1.02), (7.228; 3.42), (6.800; 3.62),
(5.689; 1.90), (3.818; 0.68), (3.708; 0.61), (3.503; 0.60), (3.346; 0.76), (3.268; 0.78), (3.260; 0.34),
(3.122; 40.97), (2.986; 16.00), (2.941; 0.86), (2.697; 1.21), (2.507; 0.35), (2.499; 4.77), (2.494; 9.82),
(2.490; 13.78), (2.485; 9.59), (2.480; 4.54), (2.213; 0.54), (2.196; 11.31), (2.184; 11.22), (2.148; 0.33),
(2.126; 0.49), (2.042; 0.36), (−0.000; 1.17)

Ex. 128: (7.69; 1.280), (7.67; 2.170), (7.66; 1.280), (7.64; 1.150), (7.62; 1.310), (7.43; 1.460), (7.41; 3.620),
(7.39; 3.690), (7.37; 1.240), (7.37; 1.370), (7.23; 2.590), (6.81; 2.020), (5.69; 6.480), (3.82; 1.310),
(3.18; 2.220), (3.16; 3.100), (3.12; 3819.230), (3.08; 6.330), (3.04; 1.450), (2.89; 2.050), (2.88; 13.920),
(2.76; 3.310), (2.67; 1.400), (2.66; 2.880), (2.66; 4.420), (2.65; 3.190), (2.65; 1.450), (2.64; 6.400),
(2.64; 6.960), (2.55; 1.580), (2.53; 13.970), (2.51; 10.380), (2.51; 14.920), (2.50; 224.340), (2.49; 467.460),
(2.49; 661.210), (2.48; 463.050), (2.48; 221.510), (2.32; 2.950), (2.32; 4.220), (2.31; 3.050), (2.31; 1.450),
(2.20; 12.310), (2.18; 11.810), (2.04; 14.720), (1.90; 2.390), (1.40; 8.180), (1.30; 1.540), (1.24; 2.200),
(1.24; 1.300), (1.23; 1.170), (1.21; 16.000), (1.20; 15.940), (1.16; 11.580), (1.14; 11.230), (1.11; 6.800),
(1.09; 1.280), (1.07; 4.100), (1.07; 1.540), (1.05; 4.280), (1.05; 3.830), (1.03; 2.970), (0.89; 1.510),
(0.00; 28.030)

Ex. 129:
(8.006; 1.45), (7.697; 1.19), (7.693; 1.40), (7.679; 2.31), (7.674; 3.47), (7.669; 2.46), (7.662; 1.83),
(7.655; 2.23), (7.639; 1.55), (7.624; 1.34), (7.621; 1.26), (7.618; 1.54), (7.434; 1.62), (7.432; 1.76),
(7.411; 1.87), (7.407; 4.37), (7.389; 3.58), (7.387; 4.66), (7.370; 1.85), (7.367; 1.53), (7.226; 4.84),
(6.802; 4.79), (4.162; 1.69), (3.818; 1.54), (3.700; 5.35), (3.501; 1.42), (3.402; 1.94), (3.385; 2.01),
(3.366; 1.51), (3.343; 1.67), (3.338; 1.22), (3.287; 1.56), (3.269; 5.42), (3.251; 5.99), (3.233; 3.75),
(3.215; 1.45), (3.181; 1.29), (3.121; 657.40), (3.080; 3.22), (3.062; 2.50), (2.962; 14.71), (2.899; 5.16),
(2.866; 9.21), (2.720; 11.98), (2.718; 11.98), (2.670; 9.40), (2.527; 4.25), (2.511; 3.11), (2.506; 4.52),
(2.498; 54.83), (2.493; 111.80), (2.489; 156.46), (2.484; 109.38), (2.479; 52.32), (2.212; 1.43),
(2.196; 16.00), (2.181; 15.84), (2.135; 2.97), (2.126; 1.37), (2.065; 2.87), (2.037; 1.86), (1.235; 2.02),
(1.171; 6.93), (1.157; 3.12), (1.153; 15.47), (1.140; 2.39), (1.135; 7.45), (1.116; 4.08), (1.112; 5.88),
(1.098; 2.54), (1.094; 10.22), (1.076; 5.03), (1.072; 1.14), (1.061; 3.25), (1.043; 6.12), (1.033; 2.84),
(1.025; 3.14), (1.015; 5.23), (0.997; 2.61), (−0.000; 8.17)

Ex. 130:
(7.795; 2.04), (7.793; 2.40), (7.791; 2.42), (7.789; 2.28), (7.776; 2.47), (7.773; 2.64), (7.772; 2.79),
(7.769; 2.30), (7.708; 1.33), (7.704; 1.28), (7.702; 1.47), (7.698; 1.26), (7.683; 1.36), (7.679; 1.35),
(7.677; 1.45), (7.673; 1.24), (7.661; 1.36), (7.646; 1.54), (7.640; 2.11), (7.625; 2.52), (7.621; 1.56),
(7.606; 1.21), (7.469; 4.58), (7.467; 4.57), (7.437; 0.89), (7.434; 0.98), (7.430; 0.87), (7.428; 0.90),
(7.414; 1.43), (7.407; 1.39), (7.393; 0.83), (7.391; 0.84), (7.387; 0.79), (7.385; 0.73), (7.114; 4.02),
(7.079; 1.01), (6.895; 1.05), (6.856; 0.82), (3.849; 0.89), (3.772; 7.13), (3.695; 0.66), (3.414; 0.95),
(3.392; 0.81), (3.374; 0.81), (3.356; 0.68), (3.282; 2.40), (3.233; 1.10), (3.124; 144.14), (3.059; 0.69),
(2.984; 4.72), (2.955; 0.77), (2.935; 3.98), (2.919; 1.70), (2.901; 0.57), (2.546; 7.40), (2.528; 1.02),
(2.512; 0.85), (2.507; 1.17), (2.499; 15.66), (2.494; 32.27), (2.490; 45.38), (2.485; 31.53), (2.480; 14.89),
(2.260; 1.06), (2.213; 16.00), (2.172; 4.16), (2.084; 0.89), (1.403; 1.29), (1.264; 0.74), (1.257; 0.93),
(1.246; 0.67), (1.184; 2.05), (1.179; 4.60), (1.166; 4.14), (1.161; 9.77), (1.148; 3.22), (1.144; 4.47),
(1.131; 3.67), (1.114; 1.64), (−0.000; 1.56)

Ex. 131:
(7.771; 0.51), (7.763; 0.54), (7.611; 5.45), (7.455; 0.55), (7.451; 0.85), (7.444; 1.43), (7.440; 1.89),
(7.435; 1.96), (7.425; 2.11), (7.422; 3.11), (7.417; 2.93), (7.389; 2.70), (7.372; 1.15), (7.370; 1.18),
(7.366; 1.11), (7.330; 1.51), (7.351; 0.59), (7.341; 1.52), (7.339; 1.52), (7.322; 1.01), (7.287; 0.56),
(7.282; 0.64), (7.037; 3.40), (3.768; 2.28), (3.424; 0.86), (3.420; 0.92), (3.413; 0.92), (3.264; 12.81),
(3.217; 0.38), (3.117; 644.08), (2.988; 4.29), (2.662; 0.60), (2.657; 0.81), (2.653; 0.58), (2.648; 0.37),
(2.527; 2.95), (2.511; 2.46), (2.506; 3.34), (2.498; 44.81), (2.493; 92.75), (2.488; 130.55), (2.484; 90.84),
(2.479; 43.07), (2.332; 16.00), (2.320; 0.74), (2.315; 0.99), (2.310; 0.65), (2.306; 0.56), (2.281; 1.26),
(2.258; 3.97), (2.230; 15.72), (1.901; 0.78), (1.404; 3.72), (1.361; 0.56), (1.303; 0.33), (1.263; 0.47),
(1.245; 0.71), (1.186; 4.69), (1.168; 10.11), (1.158; 1.15), (1.150; 4.55), (1.140; 0.46), (0.895; 0.64), (−0.000;
3.70)

Ex. 132:
(7.798; 0.60), (7.662; 1.42), (7.660; 1.40), (7.651; 0.62), (7.648; 0.60), (7.642; 2.64), (7.639; 2.72),
(7.613; 1.36), (7.609; 2.26), (7.606; 1.86), (7.601; 1.81), (7.596; 1.31), (7.592; 3.45), (7.586; 3.88),
(7.582; 2.95), (7.575; 2.31), (7.570; 0.72), (7.538; 2.38), (7.535; 2.32), (7.529; 0.39), (7.522; 1.63),
(7.518; 1.85), (7.517; 2.25), (7.501; 4.93), (7.128; 2.73), (6.973; 0.40), (5.689; 1.45), (4.281; 0.43),
(3.813; 1.31), (3.808; 3.27), (3.476; 0.32), (3.457; 0.55), (3.438; 0.89), (3.423; 1.01), (3.219; 0.72),
(3.121; 114.01), (3.032; 0.87), (2.988; 4.61), (2.527; 0.65), (2.511; 0.56), (2.507; 0.78), (2.499; 10.25),
(2.494; 21.08), (2.489; 29.60), (2.484; 20.56), (2.480; 9.70), (2.416; 0.72), (2.220; 16.00), (2.041; 0.51),
(1.403; 1.06), (1.255; 0.39), (1.195; 0.76), (1.181; 4.43), (1.163; 8.94), (1.145; 4.01), (0.895; 0.33), (−0.000;
1.70)

-continued

Ex. 133:
(7.949; 0.88), (7.750; 5.58), (7.700; 0.87), (7.696; 1.08), (7.682; 1.49), (7.677; 2.18), (7.665; 0.56),
(7.662; 1.52), (7.658; 1.63), (7.648; 0.72), (7.643; 1.20), (7.641; 0.88), (7.639; 0.83), (7.636; 0.76),
(7.628; 1.35), (7.622; 6.69), (7.618; 1.13), (7.609; 0.87), (7.604; 0.68), (7.438; 1.19), (7.436; 1.44),
(7.417; 1.17), (7.415; 1.43), (7.411; 3.71), (7.394; 2.87), (7.391; 3.91), (7.388; 1.25), (7.375; 1.53),
(7.372; 1.30), (7.034; 4.39), (7.033; 4.42), (5.620; 0.38), (4.163; 1.27), (4.031; 0.38), (3.816; 0.33),
(3.791; 0.41), (3.732; 0.69), (3.367; 0.87), (3.355; 2.98), (3.268; 2.50), (3.260; 3.75), (3.157; 0.62),
(3.120; 49.13), (3.062; 0.61), (3.013; 5.98), (2.956; 1.14), (2.950; 0.94), (2.939; 0.53), (2.888; 9.98),
(2.866; 0.39), (2.760; 0.79), (2.734; 8.48), (2.733; 8.34), (2.720; 0.41), (2.719; 0.41), (2.697; 4.85),
(2.639; 1.41), (2.638; 1.36), (2.616; 0.82), (2.527; 0.68), (2.511; 0.57), (2.507; 0.79), (2.498; 10.88),
(2.494; 22.48), (2.489; 31.67), (2.484; 22.06), (2.480; 10.48), (2.287; 0.33), (2.222; 16.00), (2.137; 0.77),
(2.117; 0.49), (2.084; 0.43), (2.041; 0.60), (1.739; 0.80), (1.236; 2.72), (1.157; 2.32), (1.140; 2.29),
(1.072; 0.82), (1.055; 0.81), (−0.000; 3.29)
Ex. 134:
(7.663; 1.54), (7.661; 1.54), (7.651; 0.64), (7.649; 0.62), (7.643; 2.96), (7.639; 3.04), (7.614; 1.44),
(7.610; 2.44), (7.607; 2.08), (7.601; 1.84), (7.597; 1.39), (7.593; 3.82), (7.587; 4.35), (7.583; 3.16),
(7.575; 2.55), (7.571; 0.89), (7.539; 2.63), (7.536; 2.61), (7.530; 0.70), (7.522; 4.83), (7.520; 4.73),
(7.518; 4.13), (7.502; 1.16), (7.499; 1.06), (7.187; 0.99), (5.690; 4.27), (4.047; 0.43), (4.030; 0.46),
(3.851; 1.81), (3.820; 0.64), (3.120; 21.84), (3.101; 1.71), (3.059; 0.82), (2.919; 16.00), (2.905; 0.59),
(2.528; 0.41), (2.507; 0.44), (2.499; 6.77), (2.494; 14.09), (2.489; 19.92), (2.485; 13.92), (2.480; 6.67),
(2.423; 0.39), (2.279; 1.06), (2.233; 13.86), (2.042; 0.39), (1.975; 1.88), (1.403; 0.66), (1.292; 0.35),
(1.275; 1.56), (1.258; 1.75), (1.229; 8.71), (1.212; 8.55), (1.196; 1.17), (1.178; 1.26), (1.160; 0.63), (−0.000;
2.03)
Ex. 135:
(7.830; 0.38), (7.817; 0.35), (7.700; 0.80), (7.696; 1.08), (7.682; 1.38), (7.677; 2.07), (7.662; 1.49),
(7.658; 1.62), (7.648; 0.72), (7.644; 1.17), (7.641; 0.91), (7.636; 0.77), (7.629; 1.14), (7.622; 1.48),
(7.618; 5.80), (7.609; 0.98), (7.604; 0.73), (7.439; 1.19), (7.437; 1.49), (7.415; 1.43), (7.412; 3.51),
(7.394; 2.66), (7.391; 3.69), (7.375; 1.44), (7.373; 1.22), (7.365; 0.37), (7.043; 3.06), (5.689; 0.81),
(4.274; 0.56), (4.162; 2.51), (4.031; 0.64), (3.816; 0.70), (3.799; 0.38), (3.733; 0.49), (3.491; 0.43),
(3.366; 1.26), (3.268; 2.77), (3.153; 1.53), (3.115; 657.75), (2.901; 16.00), (2.887; 1.07), (2.863; 0.96),
(2.837; 0.58), (2.760; 0.78), (2.667; 0.47), (2.662; 0.75), (2.657; 0.96), (2.653; 0.89), (2.648; 0.37),
(2.639; 1.51), (2.637; 1.50), (2.527; 4.07), (2.511; 2.53), (2.506; 3.38), (2.498; 50.89), (2.493; 106.37),
(2.488; 150.98), (2.484; 105.36), (2.479; 50.13), (2.320; 0.61), (2.315; 0.91), (2.310; 0.65), (2.223; 14.76),
(2.154; 0.58), (2.037; 0.75), (1.419; 0.51), (1.252; 1.69), (1.235; 2.92), (1.225; 8.22), (1.208; 8.30),
(1.193; 1.65), (1.187; 1.34), (1.175; 0.79), (1.163; 0.48), (1.157; 2.69), (1.140; 2.91), (1.124; 0.68),
(1.072; 0.94), (1.055; 0.96), (−0.000; 5.49)
Ex. 136:
(8.005; 0.83), (7.700; 1.01), (7.696; 1.12), (7.682; 1.59), (7.677; 2.23), (7.662; 1.57), (7.658; 1.87),
(7.649; 0.79), (7.644; 1.33), (7.641; 0.98), (7.629; 1.40), (7.621; 6.01), (7.609; 0.96), (7.605; 0.73),
(7.439; 1.32), (7.437; 1.66), (7.418; 1.33), (7.412; 3.86), (7.394; 3.00), (7.392; 4.05), (7.376; 1.58),
(7.373; 1.37), (7.038; 3.45), (4.162; 2.95), (4.031; 0.74), (3.731; 3.16), (3.403; 0.99), (3.395; 0.88),
(3.385; 0.76), (3.366; 2.00), (3.354; 1.12), (3.287; 0.88), (3.268; 5.51), (3.259; 0.81), (3.251; 3.39),
(3.233; 2.12), (3.223; 0.83), (3.215; 0.78), (3.120; 632.16), (3.079; 0.88), (2.988; 4.53), (2.925; 1.94),
(2.866; 5.35), (2.720; 7.04), (2.718; 7.01), (2.670; 1.06), (2.662; 0.63), (2.658; 0.85), (2.653; 0.63),
(2.527; 3.43), (2.511; 2.43), (2.506; 3.53), (2.498; 43.95), (2.493; 90.04), (2.489; 126.30), (2.484; 88.25),
(2.479; 42.18), (2.315; 0.81), (2.222; 16.00), (2.084; 1.95), (2.041; 0.76), (2.037; 0.70), (1.738; 0.83),
(1.235; 2.93), (1.185; 4.82), (1.177; 1.03), (1.167; 10.11), (1.157; 1.59), (1.149; 5.27), (1.140; 1.43),
(1.131; 2.16), (1.123; 0.66), (1.112; 3.47), (1.094; 5.86), (1.076; 2.89), (1.043; 0.78), (1.033; 1.56),
(1.015; 3.02), (0.997; 1.51), (−0.000; 2.38)
Ex. 137:
(7.774; 5.54), (7.706; 0.88), (7.701; 1.09), (7.687; 1.57), (7.682; 2.00), (7.669; 0.81), (7.666; 1.11),
(7.665; 1.06), (7.663; 1.35), (7.653; 0.69), (7.648; 1.16), (7.645; 0.85), (7.643; 0.79), (7.641; 0.74),
(7.634; 0.85), (7.632; 0.83), (7.630; 0.85), (7.627; 1.23), (7.622; 0.70), (7.613; 0.79), (7.609; 0.63),
(7.585; 2.64), (7.500; 4.42), (7.499; 4.34), (7.442; 1.17), (7.440; 1.30), (7.421; 1.13), (7.419; 1.28),
(7.413; 3.28), (7.395; 4.44), (7.376; 1.47), (7.373; 1.26), (7.108; 6.72), (6.885; 2.24), (6.824; 2.75),
(5.690; 3.24), (3.767; 15.15), (3.268; 4.40), (3.116; 136.19), (3.076; 0.55), (3.008; 6.36), (2.983; 0.96),
(2.967; 0.56), (2.943; 13.28), (2.920; 0.37), (2.527; 0.75), (2.511; 0.66), (2.506; 0.91), (2.498; 13.05),
(2.493; 27.03), (2.489; 38.10), (2.484; 26.58), (2.479; 12.66), (2.215; 16.00), (2.167; 8.86), (−0.000; 3.31)
Ex. 138:
(8.079; 0.38), (7.836; 0.42), (7.706; 0.99), (7.701; 1.17), (7.687; 1.70), (7.683; 2.21), (7.669; 0.90),
(7.666; 1.30), (7.663; 1.53), (7.653; 0.90), (7.648; 1.53), (7.645; 1.30), (7.643; 1.33), (7.641; 1.36),
(7.634; 1.24), (7.632; 1.14), (7.630; 1.14), (7.627; 1.44), (7.622; 0.83), (7.614; 0.86), (7.609; 0.71),
(7.495; 4.77), (7.493; 4.64), (7.442; 1.25), (7.440; 1.43), (7.419; 1.41), (7.414; 3.58),
(7.395; 4.28), (7.377; 1.58), (7.374; 1.33), (7.121; 3.38), (6.884; 1.82), (6.826; 1.67), (5.689; 2.14),
(4.163; 0.47), (3.887; 0.34), (3.832; 0.40), (3.816; 0.45), (3.799; 0.36), (3.766; 12.08), (3.578; 0.34),
(3.268; 1.38), (3.122; 267.39), (2.895; 15.68), (2.857; 0.45), (2.832; 9.53), (2.823; 0.43), (2.760; 1.54),
(2.673; 0.33), (2.658; 0.33), (2.639; 3.03), (2.638; 3.00), (2.546; 0.57), (2.528; 0.83), (2.512; 0.85),
(2.507; 0.89), (2.499; 14.86), (2.494; 31.08), (2.489; 44.09), (2.485; 30.92), (2.480; 14.86), (2.213; 16.00),
(2.164; 7.08), (2.041; 0.34), (1.975; 0.45), (1.246; 0.44), (1.219; 9.57), (1.202; 9.63), (1.183; 10.14),
(1.166; 9.81), (1.157; 5.53), (1.140; 5.19), (1.072; 1.88), (1.066; 0.74), (1.064; 0.55), (1.055; 1.92),
(1.049; 0.72), (1.047; 0.52), (−0.000; 4.19)
Ex. 139:
(7.791; 0.67), (7.706; 0.96), (7.702; 1.15), (7.688; 1.68), (7.683; 2.12), (7.670; 0.86), (7.668; 0.98),
(7.666; 1.40), (7.664; 1.38), (7.653; 0.79), (7.648; 1.25), (7.645; 0.93), (7.643; 0.89), (7.641; 0.82),
(7.634; 0.92), (7.632; 0.90), (7.630; 0.95), (7.627; 1.31), (7.622; 0.78), (7.613; 0.85), (7.609; 0.73),
(7.589; 0.58), (7.497; 4.64), (7.496; 4.49), (7.442; 1.23), (7.440; 1.39), (7.421; 1.22), (7.419; 1.35),
(7.413; 3.43), (7.395; 4.59), (7.392; 3.00), (7.376; 1.54), (7.373; 1.30), (7.115; 4.04), (6.882; 1.01),
(6.819; 1.16), (5.690; 5.93), (3.766; 6.19), (3.639; 0.74), (3.622; 0.71), (3.438; 0.71), (3.410; 0.98),
(3.360; 0.61), (3.269; 2.78), (3.252; 1.24), (3.234; 0.80), (3.223; 3.50), (3.119; 55.60), (3.062; 0.56),
(2.984; 4.81), (2.942; 0.58), (2.919; 3.44), (2.867; 1.80), (2.721; 2.40), (2.720; 2.33), (2.671; 2.00),

-continued (2.499; 7.02), (2.494; 14.44), (2.490; 20.30), (2.485; 14.12), (2.480; 6.69), (2.215; 16.00), (2.165; 3.66),
(1.274; 0.82), (1.257; 1.78), (1.239; 0.90), (1.179; 4.47), (1.161; 9.48), (1.144; 4.57), (1.129; 0.58),
(1.123; 3.20), (1.112; 1.35), (1.105; 1.49), (1.094; 2.10), (1.077; 1.00), (1.061; 0.66), (1.044; 1.28),
(1.026; 0.63), (1.016; 1.03), (−0.000; 2.15)

Ex. 140:
(7.731; 5.52), (7.549; 5.33), (7.421; 0.49), (7.419; 0.48), (7.159; 0.68), (7.007; 4.42), (7.006; 4.28),
(5.689; 1.46), (3.862; 2.96), (3.731; 1.49), (3.440; 3.10), (3.355; 1.37), (3.221; 2.70), (3.123; 161.62),
(3.003; 5.34), (2.955; 0.69), (2.948; 1.40), (2.888; 0.33), (2.527; 0.52), (2.511; 0.45), (2.507; 0.65),
(2.499; 9.06), (2.494; 18.70), (2.489; 26.28), (2.484; 18.28), (2.480; 8.66), (2.177; 16.00), (2.149; 1.78),
(2.148; 1.76), (2.138; 0.37), (2.083; 0.81), (1.621; 2.01), (1.606; 2.95), (1.603; 3.03), (1.600; 3.49),
(1.599; 3.51), (1.596; 2.74), (1.586; 3.42), (1.545; 0.73), (1.542; 0.70), (1.501; 3.49), (1.492; 2.87),
(1.488; 3.54), (1.487; 3.47), (1.484; 3.10), (1.481; 2.89), (1.467; 1.98), (1.439; 0.41), (1.434; 0.46),
(1.431; 0.62), (1.429; 0.43), (1.420; 0.44), (1.387; 0.35), (1.381; 0.49), (1.373; 0.34), (1.370; 0.36),
(1.367; 0.42), (−0.000; 1.81)

Ex. 141:
(7.810; 0.33), (7.544; 5.28), (7.421; 0.59), (7.419; 0.60), (7.159; 0.84), (7.018; 3.14), (5.688; 1.94),
(3.862; 3.70), (3.852; 0.35), (3.742; 1.88), (3.568; 0.39), (3.441; 3.75), (3.221; 0.66), (3.120; 67.90),
(2.892; 16.00), (2.868; 1.25), (2.527; 0.35), (2.507; 0.39), (2.499; 6.30), (2.494; 13.19), (2.489; 18.70),
(2.484; 13.15), (2.480; 6.32), (2.179; 15.42), (2.149; 2.17), (2.148; 2.16), (2.094; 1.15), (1.974; 0.85),
(1.621; 1.92), (1.607; 2.85), (1.604; 2.94), (1.601; 3.39), (1.599; 3.43), (1.596; 2.68), (1.587; 3.26),
(1.546; 0.66), (1.543; 0.64), (1.502; 3.32), (1.492; 2.71), (1.488; 3.42), (1.487; 3.37), (1.485; 3.04),
(1.482; 2.85), (1.467; 1.88), (1.439; 0.38), (1.434; 0.53), (1.432; 0.56), (1.429; 0.46), (1.421; 0.55),
(1.403; 0.91), (1.381; 0.58), (1.373; 0.46), (1.370; 0.48), (1.367; 0.52), (1.363; 0.36), (1.217; 7.72),
(1.201; 8.95), (1.184; 1.92), (1.178; 0.93), (1.160; 0.39), (−0.000; 1.38)

Ex. 142:
(7.751; 0.51), (7.732; 0.44), (7.547; 5.34), (7.011; 3.36), (5.689; 0.58), (3.862; 0.50), (3.440; 0.85),
(3.405; 0.81), (3.221; 1.98), (3.175; 1.52), (3.120; 69.16), (2.978; 3.99), (2.527; 0.54), (2.511; 0.47),
(2.506; 0.65), (2.498; 8.84), (2.493; 18.22), (2.489; 25.60), (2.484; 17.83), (2.479; 8.47), (2.177; 16.00),
(2.148; 0.35), (1.621; 1.97), (1.606; 2.94), (1.603; 3.02), (1.600; 3.49), (1.599; 3.52), (1.596; 2.72),
(1.586; 3.32), (1.545; 0.70), (1.543; 0.69), (1.501; 3.43), (1.492; 2.84), (1.488; 3.53), (1.487; 3.49),
(1.484; 3.12), (1.481; 2.90), (1.467; 1.94), (1.241; 0.38), (1.223; 0.68), (1.206; 0.34), (1.176; 4.34),
(1.159; 9.17), (1.141; 4.19), (−0.000; 2.10)

Ex. 143:
(7.974; 0.53), (7.947; 1.41), (7.756; 4.16), (7.432; 3.30), (7.430; 3.15), (7.081; 4.70), (3.890; 1.60),
(3.766; 1.26), (3.439; 1.60), (3.380; 2.99), (3.285; 0.44), (3.259; 1.81), (3.242; 0.61), (3.221; 8.89),
(3.204; 0.73), (3.156; 2.37), (3.118; 1270.18), (3.094; 56.67), (3.030; 0.67), (2.998; 4.61), (2.951; 1.45),
(2.943; 1.16), (2.897; 0.40), (2.888; 16.00), (2.878; 0.45), (2.734; 13.42), (2.732; 13.20), (2.696; 0.56),
(2.667; 0.76), (2.662; 1.66), (2.657; 2.19), (2.653; 1.63), (2.648; 0.85), (2.615; 0.63), (2.559; 0.57),
(2.527; 2.74), (2.511; 5.96), (2.506; 8.24), (2.498; 119.23), (2.493; 246.01), (2.488; 346.64), (2.484; 241.68),
(2.479; 114.85), (2.325; 0.82), (2.320; 1.69), (2.315; 2.14), (2.310; 1.49), (2.305; 0.64), (2.189; 12.41),
(2.166; 0.94), (2.138; 0.83), (2.041; 2.31), (1.974; 0.97), (1.626; 1.37), (1.612; 2.24), (1.608; 2.38),
(1.605; 2.75), (1.601; 2.09), (1.592; 2.68), (1.550; 0.58), (1.506; 2.50), (1.496; 2.21), (1.492; 2.76),
(1.489; 2.17), (1.486; 2.39), (1.471; 1.27), (1.449; 0.47), (1.444; 0.50), (1.442; 0.58), (1.431; 0.76),
(1.404; 0.47), (1.397; 0.59), (1.390; 0.50), (1.384; 0.64), (1.245; 0.88), (1.177; 0.41), (0.895; 0.91),
(0.008; 0.75), (−0.000; 24.69), (−0.008; 0.84)

Ex. 144:
(7.603; 5.56), (7.038; 4.00), (6.749; 4.27), (4.328; 2.27), (4.310; 7.41), (4.292; 7.39), (4.275; 2.34),
(3.827; 0.62), (3.451; 2.81), (3.122; 326.44), (2.658; 0.33), (2.527; 1.10), (2.511; 1.00), (2.506; 1.45),
(2.498; 19.15), (2.494; 39.41), (2.489; 56.52), (2.484; 62.16), (2.480; 19.43), (2.320; 0.33), (2.316; 0.33),
(2.144; 13.18), (2.114; 13.00), (1.660; 0.79), (1.655; 0.80), (1.650; 1.04), (1.642; 1.76), (1.630; 1.62),
(1.622; 0.94), (1.615; 0.92), (1.563; 1.49), (1.549; 3.03), (1.535; 4.15), (1.521; 2.10), (1.507; 0.85),
(1.318; 7.60), (1.301; 16.00), (1.291; 0.39), (1.283; 7.40), (−0.000; 1.09)

Ex. 145:
(7.633; 1.99), (7.038; 4.00), (6.743; 4.34), (4.328; 2.31), (4.311; 7.33), (4.293; 7.46), (4.275; 2.35),
(3.828; 3.41), (3.407; 0.66), (3.389; 1.63), (3.371; 1.66), (3.354; 0.68), (3.188; 0.33), (3.121; 411.76),
(2.971; 0.34), (2.949; 14.61), (2.663; 0.32), (2.658; 0.45), (2.653; 0.32), (2.527; 1.47), (2.511; 1.37),
(2.506; 1.89), (2.498; 24.82), (2.493; 51.29), (2.489; 73.44), (2.484; 71.51), (2.479; 24.91), (2.321; 0.34),
(2.316; 0.46), (2.311; 0.36), (2.152; 14.21), (2.114; 13.13), (1.901; 0.46), (1.319; 7.55), (1.301; 16.00),
(1.291; 0.37), (1.283; 7.41), (1.244; 0.59), (1.161; 6.49), (1.143; 14.40), (1.125; 6.26), (−0.000; 4.62)

Ex. 146:
(7.681; 0.74), (7.036; 2.56), (6.744; 2.75), (4.329; 1.45), (4.311; 4.72), (4.293; 4.73), (4.275; 1.51),
(3.828; 2.40), (3.121; 168.59), (2.860; 16.00), (2.527; 0.60), (2.511; 0.55), (2.506; 0.75), (2.498; 10.60),
(2.494; 22.09), (2.489; 32.02), (2.484; 35.94), (2.480; 11.13), (2.298; 0.33), (2.151; 9.09), (2.115; 8.40),
(1.319; 4.79), (1.301; 10.29), (1.284; 4.68), (1.244; 0.32), (1.202; 13.44), (1.185; 13.26), (−0.000; 1.64)

Ex. 147:
(7.731; 0.64), (7.367; 5.10), (6.984; 3.50), (4.326; 2.32), (4.308; 7.29), (4.291; 7.48), (4.273; 2.34),
(3.828; 1.41), (3.397; 0.98), (3.302; 0.38), (3.261; 0.34), (3.252; 0.33), (3.226; 0.44), (3.221; 0.41),
(3.203; 0.60), (3.120; 583.60), (2.983; 2.25), (2.974; 4.97), (2.667; 0.41), (2.662; 0.78), (2.658; 1.24),
(2.653; 0.81), (2.648; 0.43), (2.527; 1.55), (2.511; 3.29), (2.506; 4.96), (2.498; 82.59), (2.493; 130.18),
(2.489; 181.47), (2.484; 126.29), (2.479; 59.99), (2.325; 0.40), (2.320; 0.72), (2.316; 1.27), (2.311; 0.80),
(2.306; 0.39), (2.143; 15.28), (2.041; 1.57), (1.313; 7.65), (1.295; 16.00), (1.278; 7.44), (1.245; 0.73),
(1.175; 5.00), (1.158; 10.63), (1.140; 4.77), (0.895; 0.38), (−0.000; 10.09), (−0.008; 0.36)

Ex. 148:
(7.790; 0.33), (7.364; 4.72), (6.988; 3.04), (5.690; 2.48), (4.327; 2.08), (4.309; 6.67), (4.292; 6.76),
(4.274; 2.12), (3.828; 0.83), (3.115; 61.10), (3.091; 5.76), (2.983; 0.75), (2.887; 16.00), (2.511; 0.59),
(2.498; 31.10), (2.493; 20.06), (2.489; 26.82), (2.484; 18.64), (2.479; 8.96), (2.317; 0.41), (2.145; 13.66),
(1.404; 1.40), (1.314; 6.87), (1.305; 0.34), (1.296; 14.57), (1.287; 0.46), (1.279; 6.73), (1.215; 8.35),
(1.198; 8.23), (1.171; 0.34), (−0.000; 1.38)

Ex. 149:
(7.718; 5.44), (7.277; 4.31), (7.276; 4.22), (7.235; 0.46), (7.216; 0.45), (7.174; 0.32), (7.169; 0.52), (7.152; 0.39), (7.150; 0.38), (7.045; 6.58), (4.329; 2.30), (4.311; 7.36), (4.293; 7.52), (4.276; 2.44), (4.261; 0.96), (4.243; 0.92), (3.767; 0.39), (3.625; 0.34), (3.590; 2.22), (3.477; 1.70), (3.210; 0.50), (3.196; 0.63), (3.190; 0.53), (3.182; 0.67), (3.173; 0.47), (3.155; 0.38), (3.137; 0.71), (3.122; 70.93), (2.746; 1.71), (2.501; 26.36), (2.495; 8.85), (2.490; 11.54), (2.486; 8.63), (2.481; 3.94), (2.345; 3.69), (2.298; 2.23), (2.263; 0.59), (2.192; 0.86), (2.172; 15.31), (2.157; 0.37), (1.975; 0.91), (1.724; 0.34), (1.676; 0.35), (1.671; 0.37), (1.662; 1.02), (1.658; 1.03), (1.645; 2.07), (1.634; 2.03), (1.624; 1.20), (1.618; 1.10), (1.604; 0.33), (1.591; 0.33), (1.570; 1.51), (1.556; 2.91), (1.543; 3.87), (1.529; 2.11), (1.515; 0.88), (1.386; 7.31), (1.314; 7.56), (1.308; 1.66), (1.296; 16.00), (1.290; 3.22), (1.279; 7.40), (1.272; 1.52), (1.242; 0.32), (1.179; 0.52), (−0.000; 0.46)
Ex. 150:
(7.749; 0.78), (7.279; 3.97), (7.277; 3.80), (7.040; 3.95), (5.689; 6.61), (4.330; 2.11), (4.312; 6.78), (4.294; 6.85), (4.277; 2.19), (3.831; 5.02), (3.591; 2.12), (3.409; 0.97), (3.395; 0.97), (3.173; 0.42), (3.155; 0.33), (3.118; 24.47), (3.093; 1.93), (2.970; 5.72), (2.934; 0.32), (2.747; 1.67), (2.501; 27.79), (2.495; 7.55), (2.490; 9.87), (2.486; 6.93), (2.481; 3.27), (2.263; 0.56), (2.182; 16.00), (1.403; 4.54), (1.387; 7.20), (1.315; 7.01), (1.308; 0.43), (1.297; 14.51), (1.291; 0.56), (1.287; 0.38), (1.279; 6.81), (1.170; 4.79), (1.152; 10.22), (1.141; 0.59), (1.134; 4.62), (−0.000; 0.57)
Ex. 151:
(7.796; 0.45), (7.278; 3.88), (7.277; 3.70), (7.046; 3.15), (5.689; 2.92), (4.329; 2.02), (4.311; 6.57), (4.293; 6.58), (4.276; 2.10), (3.830; 6.38), (3.589; 1.96), (3.173; 0.47), (3.154; 0.46), (3.119; 140.71), (3.096; 6.95), (2.879; 16.00), (2.745; 1.54), (2.511; 0.87), (2.500; 31.96), (2.493; 31.20), (2.489; 43.35), (2.484; 30.60), (2.479; 14.62), (2.462; 0.33), (2.262; 0.54), (2.180; 15.98), (2.041; 0.39), (1.404; 3.79), (1.385; 6.78), (1.314; 6.75), (1.308; 0.40), (1.296; 14.14), (1.290; 0.65), (1.278; 6.59), (1.272; 0.37), (1.209; 10.83), (1.192; 10.70), (1.169; 0.34), (0.895; 0.35), (−0.000; 1.77)
Ex. 152:
(7.707; 5.28), (7.365; 5.18), (7.235; 0.50), (7.217; 0.48), (7.172; 0.84), (7.154; 0.35), (7.152; 0.42), (7.150; 0.43), (6.995; 4.18), (6.994; 4.12), (4.362; 0.50), (4.344; 0.49), (4.326; 2.39), (4.308; 7.31), (4.290; 7.30), (4.273; 2.31), (3.835; 1.43), (3.827; 0.39), (3.730; 0.83), (3.575; 0.35), (3.483; 1.29), (3.136; 1.11), (3.118; 167.86), (2.983; 0.89), (2.527; 0.95), (2.511; 0.92), (2.506; 1.59), (2.497; 32.99), (2.493; 27.96), (2.489; 37.13), (2.484; 25.87), (2.479; 12.45), (2.317; 0.55), (2.298; 2.42), (2.178; 0.91), (2.144; 14.89), (1.974; 0.41), (1.676; 0.33), (1.666; 0.80), (1.662; 0.81), (1.657; 1.06), (1.649; 1.75), (1.638; 1.66), (1.629; 1.04), (1.622; 0.95), (1.574; 1.36), (1.560; 2.76), (1.546; 3.67), (1.532; 2.01), (1.518; 0.86), (1.404; 0.35), (1.366; 0.49), (1.348; 0.94), (1.331; 0.48), (1.313; 7.48), (1.305; 0.44), (1.295; 16.00), (1.277; 7.29), (1.243; 0.45), (−0.000; 1.89)
Ex. 153:
(7.771; 0.64), (7.598; 0.74), (7.426; 4.57), (7.425; 4.38), (7.087; 3.96), (6.885; 1.44), (6.827; 1.51), (5.688; 0.74), (3.891; 0.92), (3.768; 9.38), (3.592; 0.71), (3.574; 0.80), (3.568; 0.53), (3.441; 1.20), (3.398; 0.93), (3.383; 0.87), (3.364; 0.91), (3.346; 0.78), (3.222; 0.77), (3.176; 3.40), (3.120; 56.88), (2.974; 4.52), (2.947; 0.37), (2.923; 5.12), (2.499; 4.32), (2.494; 8.88), (2.490; 12.45), (2.485; 8.68), (2.480; 4.13), (2.191; 16.00), (2.167; 5.59), (1.975; 1.08), (1.628; 2.05), (1.613; 3.11), (1.610; 3.19), (1.607; 3.66), (1.606; 3.65), (1.603; 2.78), (1.593; 3.42), (1.552; 0.66), (1.547; 0.64), (1.506; 3.51), (1.496; 2.94), (1.493; 3.69), (1.492; 3.64), (1.489; 3.28), (1.486; 3.10), (1.471; 2.08), (1.454; 0.32), (1.449; 0.48), (1.447; 0.43), (1.444; 0.38), (1.436; 0.65), (1.430; 0.34), (1.403; 1.59), (1.396; 0.51), (1.388; 0.42), (1.385; 0.43), (1.382; 0.44), (1.381; 0.40), (1.378; 0.40), (1.242; 0.87), (1.224; 1.69), (1.207; 0.80), (1.196; 0.37), (1.178; 0.95), (1.171; 4.18), (1.161; 1.00), (1.153; 8.80), (1.143; 2.71), (1.135; 4.15), (1.126; 4.82), (1.108; 2.15), (−0.000; 0.82)
Ex. 154:
(7.826; 0.40), (7.424; 4.66), (7.423; 4.56), (7.094; 3.28), (6.887; 0.62), (6.838; 0.43), (5.689; 2.65), (3.908; 0.65), (3.891; 0.74), (3.769; 4.05), (3.578; 0.46), (3.568; 2.51), (3.441; 0.61), (3.222; 0.36), (3.118; 63.28), (3.061; 0.42), (2.885; 14.73), (2.838; 3.02), (2.673; 0.43), (2.499; 5.21), (2.494; 10.85), (2.490; 15.35), (2.485; 10.78), (2.480; 5.19), (2.267; 0.44), (2.190; 16.00), (2.167; 2.49), (1.627; 2.05), (1.613; 3.17), (1.609; 3.28), (1.607; 3.71), (1.605; 3.73), (1.602; 2.86), (1.592; 3.52), (1.551; 0.66), (1.547; 0.67), (1.506; 3.57), (1.496; 2.95), (1.493; 3.76), (1.492; 3.73), (1.489; 3.41), (1.486; 3.25), (1.471; 2.04), (1.258; 0.45), (1.241; 0.60), (1.212; 9.17), (1.195; 9.13), (1.186; 4.59), (1.169; 3.35), (1.064; 0.47), (1.047; 0.47), (−0.000; 1.83)
Ex. 158:
(7.626; 1.54), (7.008; 0.50), (6.987; 2.44), (6.726; 2.94), (3.402; 0.47), (3.384; 1.22), (3.367; 1.22), (3.349; 0.49), (3.118; 183.97), (2.944; 10.55), (2.527; 0.98), (2.511; 0.73), (2.506; 1.00), (2.498; 12.45), (2.493; 25.49), (2.489; 35.76), (2.484; 24.99), (2.479; 11.92), (2.412; 16.00), (2.368; 1.07), (2.340; 2.65), (2.298; 0.46), (2.143; 9.91), (2.125; 1.50), (2.118; 0.93), (2.109; 8.15), (2.041; 0.32), (1.158; 4.45), (1.140; 9.78), (1.122; 4.30), (−0.000; 3.35)
Ex. 159:
(7.917; 0.36), (7.827; 4.39), (7.823; 1.66), (7.811; 1.68), (7.807; 4.90), (7.680; 0.58), (7.664; 1.81), (7.637; 0.52), (7.404; 0.35), (7.376; 3.67), (7.356; 3.47), (7.304; 0.42), (7.283; 0.63), (7.262; 0.34), (7.212; 0.47), (7.194; 3.73), (7.178; 0.45), (6.906; 0.48), (6.792; 3.71), (5.689; 2.01), (3.821; 2.05), (3.818; 1.13), (3.782; 1.19), (3.567; 0.50), (3.511; 0.34), (3.501; 1.89), (3.416; 1.42), (3.399; 1.38), (3.383; 1.35), (3.303; 0.33), (3.269; 5.72), (3.241; 0.63), (3.219; 0.39), (3.211; 0.41), (3.203; 0.48), (3.155; 1.35), (3.115; 833.97), (2.960; 11.25), (2.670; 0.44), (2.667; 0.49), (2.662; 0.87), (2.657; 1.20), (2.652; 0.92), (2.648; 0.42), (2.526; 4.84), (2.510; 3.92), (2.506; 5.46), (2.497; 64.75), (2.493; 131.61), (2.488; 184.17), (2.483; 128.15), (2.479; 60.79), (2.463; 1.09), (2.407; 1.40), (2.388; 11.92), (2.362; 1.35), (2.349; 1.28), (2.328; 0.46), (2.325; 0.46), (2.320; 0.85), (2.315; 1.14), (2.310; 0.84), (2.305; 0.47), (2.210; 1.58), (2.188; 12.26), (2.176; 12.04), (2.126; 1.36), (2.096; 0.59), (2.063; 0.69), (2.040; 0.52), (2.037; 0.76), (1.404; 16.00), (1.361; 0.42), (1.245; 0.79), (1.169; 5.25), (1.151; 11.58), (1.133; 5.09), (0.008; 0.67), (−0.000; 18.65), (−0.008; 0.53)
Ex. 160:
(12.833; 0.34), (7.827; 3.31), (7.807; 3.71), (7.652; 4.23), (7.412; 0.38), (7.376; 2.97), (7.356; 2.72), (7.304; 0.34), (7.196; 2.92), (6.789; 3.08), (4.046; 0.38), (4.029; 0.42), (3.768; 0.35), (3.435; 0.33), (3.412; 0.33), (3.283; 1.03), (3.269; 1.81), (3.241; 0.51), (3.213; 1.60), (3.199; 0.63), (3.115; 1384.18), (3.062; 0.71), (3.036; 0.57), (3.023; 0.47), (2.983; 13.63), (2.945; 0.38), (2.666; 0.63), (2.662; 1.25),

-continued (2.657; 1.95), (2.652; 1.39), (2.648; 0.71), (2.526; 7.79), (2.510; 5.98), (2.506; 8.24), (2.497; 105.56),
(2.493; 217.28), (2.488; 305.85), (2.483; 214.46), (2.479; 103.10), (2.428; 0.65), (2.410; 1.36), (2.388; 9.64),
(2.368; 0.88), (2.363; 0.74), (2.348; 0.53), (2.324; 0.69), (2.320; 1.43), (2.315; 1.86), (2.310; 1.34),
(2.210; 0.39), (2.187; 9.69), (2.177; 9.76), (2.041; 0.94), (2.037; 1.34), (1.974; 1.90), (1.404; 16.00),
(1.360; 0.53), (1.298; 0.44), (1.260; 0.43), (1.252; 0.57), (1.245; 1.00), (1.195; 0.56), (1.177; 1.10),
(1.159; 0.53), (0.008; 0.81), (−0.000; 23.68), (−0.009; 0.73)
Ex. 161:
(7.829; 4.80), (7.825; 1.69), (7.813; 1.77), (7.809; 5.36), (7.804; 0.92), (7.769; 5.56), (7.581; 0.51),
(7.466; 4.43), (7.464; 4.40), (7.384; 3.74), (7.383; 4.25), (7.363; 3.92), (7.361; 3.29), (7.097; 6.72),
(6.884; 0.47), (6.820; 0.49), (5.689; 3.91), (3.950; 0.33), (3.798; 0.32), (3.766; 3.03), (3.269; 2.71),
(3.160; 0.49), (3.121; 299.73), (3.050; 0.34), (3.006; 6.72), (2.942; 2.78), (2.658; 0.33), (2.527; 0.64),
(2.511; 0.85), (2.507; 1.25), (2.498; 17.55), (2.494; 36.11), (2.489; 50.80), (2.484; 35.48), (2.480; 16.95),
(2.407; 0.62), (2.390; 13.55), (2.362; 0.67), (2.228; 0.35), (2.210; 16.00), (2.166; 1.82), (1.404; 0.32), (−0.000; 3.41)
Ex. 162:
(7.829; 5.32), (7.825; 2.16), (7.813; 2.10), (7.809; 5.75), (7.804; 1.21), (7.461; 4.54), (7.459; 4.58),
(7.383; 4.33), (7.363; 3.99), (7.361; 3.47), (7.110; 3.43), (6.882; 0.78), (6.821; 0.67), (5.689; 5.86),
(3.797; 0.34), (3.765; 5.19), (3.269; 2.24), (3.117; 316.25), (3.075; 0.33), (2.892; 15.66), (2.881; 1.61),
(2.830; 4.00), (2.658; 0.40), (2.527; 0.75), (2.511; 1.01), (2.506; 1.48), (2.498; 22.34), (2.493; 46.25),
(2.489; 65.35), (2.484; 45.91), (2.479; 22.10), (2.433; 0.46), (2.409; 0.68), (2.404; 0.62), (2.390; 13.93),
(2.362; 0.61), (2.320; 0.34), (2.315; 0.42), (2.226; 0.84), (2.208; 16.00), (2.163; 3.07), (1.243; 0.50),
(1.218; 9.83), (1.201; 9.79), (1.182; 4.60), (1.165; 4.25), (−0.000; 5.07)
Ex. 163:
(7.611; 1.57), (6.907; 2.56), (6.693; 2.49), (3.397; 0.48), (3.379; 1.26), (3.361; 1.30), (3.344; 0.51),
(3.107; 86.05), (2.939; 9.68), (2.526; 0.88), (2.510; 0.73), (2.497; 11.71), (2.492; 23.10), (2.487; 31.80),
(2.483; 22.37), (2.478; 10.91), (2.271; 1.11), (2.264; 14.53), (2.126; 9.81), (2.123; 9.71), (2.062; 16.00),
(2.040; 0.70), (1.155; 3.59), (1.138; 7.62), (1.120; 3.44), (−0.000; 2.55)
Ex. 164:
(7.665; 0.43), (7.159; 0.88), (6.784; 0.49), (3.203; 3.08), (3.111; 151.98), (2.985; 4.49), (2.662; 0.37),
(2.657; 0.55), (2.652; 0.38), (2.526; 2.42), (2.510; 1.48), (2.505; 1.99), (2.497; 28.90), (2.492; 60.04),
(2.488; 84.71), (2.483; 58.81), (2.478; 27.74), (2.319; 0.39), (2.315; 0.55), (2.310; 0.43), (2.305; 0.64),
(2.288; 0.68), (2.271; 0.50), (2.164; 4.15), (2.136; 4.33), (2.037; 0.57), (1.404; 1.93), (1.364; 0.72),
(1.361; 1.43), (1.343; 0.55), (1.317; 0.43), (1.303; 16.00), (1.292; 0.82), (1.263; 0.49), (1.252; 2.95),
(1.244; 0.65), (1.230; 0.78), (1.199; 0.73), (0.953; 0.39), (0.935; 0.36), (0.854; 0.41), (0.834; 0.33),
(0.817; 7.48), (0.809; 0.80), (0.800; 7.31), (0.792; 0.56), (0.780; 1.37), (0.774; 0.40), (0.763; 1.32),
(0.757; 0.38), (−0.000; 6.28)
Ex. 165:
(12.831; 0.38), (7.701; 0.44), (7.142; 1.40), (6.767; 1.25), (3.865; 0.48), (3.809; 0.34), (3.602; 0.34),
(3.303; 0.56), (3.285; 0.38), (3.275; 0.35), (3.260; 0.34), (3.246; 0.54), (3.241; 0.48), (3.209; 0.57),
(3.202; 0.59), (3.117; 1622.47), (3.068; 0.56), (2.863; 7.90), (2.849; 0.37), (2.842; 1.01), (2.695; 0.44),
(2.667; 0.75), (2.662; 1.53), (2.657; 2.13), (2.653; 1.56), (2.648; 0.78), (2.575; 0.38), (2.527; 9.85),
(2.510; 5.50), (2.506; 7.90), (2.498; 118.35), (2.493; 247.34), (2.488; 350.36), (2.483; 244.06),
(2.479; 115.60), (2.324; 0.80), (2.320; 1.66), (2.315; 2.31), (2.310; 1.38), (2.305; 0.98), (2.299; 0.34),
(2.288; 0.72), (2.271; 0.54), (2.226; 0.34), (2.156; 4.63), (2.134; 4.75), (2.116; 0.82), (2.041; 0.96),
(2.037; 1.88), (2.015; 0.69), (1.974; 0.52), (1.901; 0.68), (1.762; 0.41), (1.419; 1.05), (1.404; 7.77),
(1.361; 0.96), (1.302; 16.00), (1.269; 0.47), (1.259; 0.57), (1.245; 0.94), (1.235; 0.61), (1.230; 0.44),
(1.203; 6.61), (1.194; 4.00), (1.191; 2.44), (1.186; 6.70), (1.175; 1.59), (1.055; 0.35), (1.042; 0.36),
(0.950; 1.68), (0.933; 1.55), (0.895; 1.04), (0.854; 0.40), (0.840; 0.32), (0.817; 7.41), (0.800; 7.36),
(0.773; 0.36), (−0.000; 11.73), (−0.009; 0.44)
Ex. 166:
(7.975; 0.76), (7.660; 0.34), (7.150; 0.86), (6.772; 0.56), (3.865; 0.80), (3.399; 0.64), (3.382; 0.61),
(3.303; 0.49), (3.239; 0.36), (3.203; 0.54), (3.112; 739.13), (2.956; 2.65), (2.695; 0.39), (2.666; 0.57),
(2.662; 1.30), (2.657; 1.78), (2.652; 1.25), (2.648; 0.72), (2.526; 8.00), (2.510; 4.72), (2.505; 6.29),
(2.497; 95.29), (2.492; 199.03), (2.488; 282.19), (2.483; 196.71), (2.478; 93.30), (2.324; 0.68), (2.319; 1.33),
(2.315; 1.76), (2.310; 1.27), (2.305; 1.04), (2.288; 0.58), (2.271; 0.43), (2.159; 4.09), (2.135; 4.26),
(2.041; 0.52), (2.037; 1.57), (2.025; 0.33), (1.900; 0.41), (1.419; 0.82), (1.364; 0.67), (1.361; 1.18),
(1.315; 0.42), (1.303; 16.00), (1.292; 0.89), (1.245; 0.86), (1.206; 0.34), (1.197; 1.80), (1.164; 1.85),
(1.146; 3.77), (1.128; 1.64), (0.952; 0.85), (0.934; 0.92), (0.895; 0.77), (0.874; 0.32), (0.854; 0.38),
(0.838; 0.36), (0.817; 7.32), (0.800; 7.32), (0.774; 0.34), (0.008; 0.49), (−0.000; 20.20), (−0.008; 0.69)
Ex. 167:
(7.411; 0.78), (7.409; 0.74), (7.074; 0.71), (3.580; 0.36), (3.563; 0.36), (3.204; 2.05), (3.156; 1.67),
(3.115; 20.10), (2.972; 0.82), (2.498; 1.73), (2.493; 3.53), (2.489; 4.92), (2.484; 3.44), (2.479; 1.65),
(2.188; 2.76), (1.403; 16.00), (1.358; 5.76), (1.228; 0.40), (1.211; 0.84), (1.193; 0.40), (1.170; 0.73),
(1.152; 1.54), (1.135; 0.71)
Ex. 168:
(7.641; 0.37), (7.179; 0.84), (7.178; 0.84), (6.768; 1.22), (5.689; 3.32), (3.396; 0.33), (3.378; 0.33),
(3.111; 55.34), (2.952; 2.12), (2.526; 0.58), (2.510; 0.48), (2.497; 3.85), (2.493; 8.13), (2.493; 16.52),
(2.488; 23.07), (2.483; 16.11), (2.478; 7.69), (2.134; 3.10), (1.415; 2.15), (1.409; 2.22), (1.402; 16.00),
(1.397; 1.37), (1.392; 0.55), (1.367; 1.65), (1.363; 0.52), (1.323; 2.03), (1.319; 1.18), (1.309; 15.25),
(1.261; 0.42), (1.243; 0.87), (1.163; 1.25), (1.145; 2.61), (1.127; 1.15), (−0.000; 2.97)
Ex. 169:
(7.390; 0.43), (7.367; 0.48), (6.947; 0.46), (6.925; 0.44), (3.115; 165.73), (2.978; 1.23), (2.960; 0.49),
(2.526; 1.20), (2.510; 0.67), (2.506; 0.91), (2.497; 14.14), (2.493; 29.56), (2.488; 41.92), (2.483; 29.21),
(2.479; 13.84), (2.366; 3.11), (2.207; 0.61), (1.415; 0.94), (1.404; 16.00), (1.394; 3.82), (1.366; 0.70),
(1.172; 1.05), (1.164; 0.32), (1.155; 2.36), (1.147; 0.61), (1.137; 1.02), (−0.000; 1.92)
Ex. 170:
(7.974; 1.01), (7.770; 0.94), (7.720; 1.66), (7.718; 2.43), (7.715; 1.61), (7.699; 1.80), (7.696; 2.68),
(7.693; 1.74), (7.544; 1.32), (7.542; 2.36), (7.540; 1.20), (7.522; 2.10), (7.519; 3.85), (7.517; 1.90),
(7.457; 1.96), (7.454; 1.94), (7.441; 2.13), (7.438; 1.94), (7.435; 1.24), (7.431; 1.09), (7.419; 1.37),
(7.416; 1.27), (7.381; 4.42), (7.379; 4.24), (7.173; 1.90), (7.170; 1.84), (7.157; 1.71), (7.154; 1.67), -continued (7.151; 1.80), (7.149; 1.67), (7.135; 1.57), (7.133; 1.48), (7.084; 4.25), (6.885; 0.82), (3.952; 1.63),
(3.766; 5.63), (3.422; 1.12), (3.408; 1.19), (3.381; 0.87), (3.362; 0.58), (3.343; 0.58), (3.298; 0.96),
(3.112; 404.20), (2.979; 6.03), (2.921; 2.55), (2.866; 0.67), (2.719; 0.97), (2.718; 0.99), (2.688; 1.05),
(2.661; 0.88), (2.657; 1.21), (2.652; 0.97), (2.526; 5.51), (2.510; 3.31), (2.505; 4.68), (2.497; 66.62),
(2.493; 138.34), (2.488; 195.09), (2.483; 135.49), (2.478; 63.91), (2.319; 0.81), (2.315; 1.15), (2.310; 0.83),
(2.199; 16.00), (2.165; 3.34), (2.037; 1.02), (1.419; 0.68), (1.245; 1.59), (1.178; 5.25), (1.160; 11.29),
(1.143; 6.18), (1.124; 2.92), (1.111; 0.61), (1.106; 1.35), (1.094; 0.91), (1.076; 0.54), (0.856; 0.65),
(0.008; 0.54), (−0.000; 16.49), (−0.008; 0.55)
Ex. 171:
(7.760; 4.60), (7.719; 1.19), (7.716; 2.01), (7.714; 1.42), (7.697; 1.45), (7.695; 2.13), (7.692; 1.55),
(7.582; 0.37), (7.544; 1.05), (7.542; 1.90), (7.540; 1.11), (7.522; 1.61), (7.519; 3.11), (7.517; 1.76),
(7.457; 1.51), (7.454; 1.62), (7.441; 1.76), (7.438; 1.61), (7.435; 0.95), (7.431; 1.01), (7.419; 1.13),
(7.416; 1.10), (7.382; 3.47), (7.380; 3.57), (7.173; 1.50), (7.170; 1.49), (7.157; 1.38), (7.155; 1.40),
(7.151; 1.39), (7.149; 1.48), (7.135; 1.31), (7.133; 1.27), (7.078; 5.38), (6.883; 0.33), (6.821; 0.34),
(3.766; 2.03), (3.298; 0.94), (3.259; 0.83), (3.144; 0.66), (3.113; 485.36), (3.003; 7.17), (2.942; 1.84),
(2.927; 0.34), (2.666; 0.35), (2.662; 0.67), (2.657; 0.90), (2.652; 0.66), (2.648; 0.36), (2.526; 4.04),
(2.510; 2.26), (2.506; 3.20), (2.497; 48.65), (2.493; 100.98), (2.488; 142.81), (2.483; 99.36), (2.478; 47.10),
(2.320; 0.63), (2.315; 0.85), (2.310; 0.60), (2.199; 13.62), (2.166; 1.27), (2.041; 0.39), (2.037; 0.79),
(1.419; 0.47), (1.404; 16.00), (1.245; 0.39), (−0.000; 10.97)
Ex. 172:
(7.721; 1.26), (7.718; 2.43), (7.716; 2.72), (7.713; 2.28), (7.699; 1.28), (7.696; 2.45), (7.694; 2.84),
(7.692; 2.39), (7.542; 2.02), (7.539; 2.40), (7.537; 1.89), (7.519; 3.26), (7.517; 3.72), (7.515; 3.06),
(7.457; 1.35), (7.454; 1.86), (7.450; 1.27), (7.441; 1.50), (7.438; 1.99), (7.434; 1.73), (7.416; 1.30),
(7.377; 4.92), (7.374; 4.85), (7.172; 1.29), (7.170; 2.00), (7.168; 1.94), (7.154; 1.83), (7.152; 2.07),
(7.149; 2.11), (7.146; 1.71), (7.133; 1.64), (7.130; 1.51), (7.087; 4.01), (3.952; 1.28), (3.948; 1.32),
(3.765; 3.23), (3.763; 2.75), (3.761; 3.00), (3.112; 178.57), (3.109; 171.29), (3.108; 193.08), (2.890; 14.89),
(2.831; 2.72), (2.828; 2.64), (2.637; 2.34), (2.635; 2.21), (2.526; 2.06), (2.524; 1.80), (2.522; 2.16),
(2.506; 3.03), (2.497; 30.17), (2.493; 79.89), (2.488; 127.99), (2.486; 84.07), (2.483; 123.87), (2.479; 74.95),
(2.474; 25.83), (2.197; 16.00), (2.195; 15.87), (2.162; 2.63), (1.243; 1.99), (1.216; 13.23), (1.200; 13.05),
(1.183; 3.98), (1.179; 3.68), (1.166; 3.63), (1.162; 3.41), (1.157; 3.63), (1.155; 3.05), (1.153; 3.30),
(1.140; 3.24), (1.138; 2.81), (1.136; 3.11), (1.071; 1.40), (1.068; 1.38), (1.054; 1.52), (1.050; 1.45), (−0.000;
6.84), (−0.002; 5.45), (−0.004; 6.33)
Ex. 173:
(7.974; 1.55), (7.745; 0.83), (7.739; 0.79), (7.520; 5.43), (7.351; 1.92), (7.333; 3.73), (7.330; 3.08),
(7.319; 1.86), (7.315; 4.35), (7.288; 2.00), (7.279; 4.10), (7.275; 6.37), (7.271; 2.81), (7.258; 3.59),
(7.245; 3.18), (7.228; 1.61), (7.225; 1.87), (7.196; 0.92), (6.989; 3.53), (4.418; 0.90), (4.400; 2.25),
(4.383; 2.37), (4.365; 0.76), (4.250; 0.76), (4.232; 0.72), (4.161; 1.70), (3.426; 0.95), (3.413; 1.78),
(3.381; 1.23), (3.269; 1.08), (3.250; 1.08), (3.233; 0.87), (3.215; 0.83), (3.166; 22.11), (3.111; 1221.20),
(3.087; 8.67), (2.974; 4.15), (2.866; 1.45), (2.719; 1.86), (2.666; 1.17), (2.662; 2.63), (2.657; 3.27),
(2.652; 2.47), (2.647; 1.10), (2.526; 5.76), (2.510; 8.74), (2.505; 12.39), (2.497; 175.14), (2.492; 360.65),
(2.488; 508.88), (2.483; 355.12), (2.478; 168.88), (2.324; 1.08), (2.319; 2.02), (2.314; 3.27), (2.310; 2.36),
(2.305; 0.96), (2.206; 0.78), (2.138; 16.00), (2.041; 1.93), (2.037; 0.70), (1.625; 11.63), (1.608; 11.62),
(1.594; 1.36), (1.584; 0.69), (1.562; 4.74), (1.544; 5.00), (1.498; 0.73), (1.246; 0.93), (1.235; 1.82),
(1.173; 4.58), (1.155; 9.73), (1.137; 4.34), (1.112; 0.89), (1.094; 1.71), (1.076; 0.99), (1.015; 0.79),
(0.008; 2.23), (−0.000; 72.76), (−0.008; 2.32)
Ex. 174:
(7.641; 0.51), (7.351; 0.43), (7.335; 0.75), (7.332; 0.98), (7.330; 0.78), (7.319; 0.37), (7.314; 1.07),
(7.276; 0.82), (7.273; 1.55), (7.267; 0.37), (7.263; 0.55), (7.258; 0.61), (7.255; 0.85), (7.247; 0.35),
(7.242; 0.59), (7.125; 1.19), (6.752; 1.19), (4.393; 0.60), (4.375; 0.61), (3.388; 0.41), (3.371; 0.41),
(3.109; 96.50), (2.947; 3.59), (2.510; 0.61), (2.505; 0.91), (2.497; 13.78), (2.492; 28.45), (2.487; 40.10),
(2.483; 28.02), (2.478; 13.38), (2.144; 3.84), (2.113; 3.87), (1.621; 3.30), (1.603; 3.29), (1.404; 16.00),
(1.158; 1.69), (1.140; 3.74), (1.123; 1.62), (−0.000; 0.43)
Ex. 175:
(11.849; 0.63), (10.248; 0.66), (7.973; 0.71), (7.911; 0.70), (7.909; 0.80), (7.831; 0.85), (7.811; 0.63),
(7.808; 0.75), (7.757; 1.00), (7.741; 0.85), (7.718; 2.67), (7.715; 1.86), (7.699; 1.99), (7.697; 2.99),
(7.694; 1.92), (7.573; 0.63), (7.551; 0.74), (7.539; 2.40), (7.519; 2.30), (7.516; 3.71), (7.455; 1.97),
(7.452; 2.81), (7.448; 5.05), (7.439; 2.11), (7.436; 2.34), (7.430; 2.23), (7.417; 1.11), (7.414; 1.44),
(7.165; 1.57), (7.163; 1.79), (7.149; 1.77), (7.143; 1.80), (7.141; 1.78), (7.128; 1.26), (7.028; 3.02),
(3.884; 1.10), (3.839; 0.64), (3.744; 1.10), (3.440; 0.91), (3.419; 1.26), (3.411; 1.28), (3.393; 1.19),
(3.340; 0.75), (3.298; 0.65), (3.272; 0.68), (3.252; 0.69), (3.239; 0.62), (3.231; 0.90), (3.109; 2010.72),
(2.987; 5.65), (2.666; 1.64), (2.661; 3.40), (2.657; 4.58), (2.652; 3.05), (2.647; 1.54), (2.526; 3.96),
(2.510; 11.03), (2.505; 15.41), (2.497; 240.75), (2.492; 499.42), (2.488; 706.32), (2.483; 494.74),
(2.478; 237.33), (2.439; 1.06), (2.433; 0.73), (2.324; 1.35), (2.319; 2.85), (2.314; 4.43), (2.310; 3.09),
(2.305; 1.34), (2.184; 16.00), (2.040; 4.12), (2.037; 1.25), (1.900; 1.46), (1.404; 0.74), (1.245; 1.96),
(1.186; 5.21), (1.168; 12.02), (1.150; 5.75), (−0.000; 6.07)
Ex. 176:
(7.517; 5.53), (7.351; 1.67), (7.347; 0.67), (7.335; 2.94), (7.333; 3.83), (7.331; 2.96), (7.320; 1.60),
(7.315; 4.22), (7.308; 1.32), (7.289; 2.13), (7.279; 3.78), (7.275; 6.40), (7.271; 3.04), (7.261; 3.06),
(7.257; 3.56), (7.249; 2.60), (7.245; 3.68), (7.229; 1.70), (7.225; 1.90), (7.221; 1.51), (7.210; 0.85),
(7.202; 0.82), (7.196; 1.13), (6.994; 3.45), (5.690; 1.62), (4.418; 0.69), (4.401; 2.34), (4.383; 2.23),
(4.365; 0.76), (4.249; 0.73), (4.231; 0.84), (4.161; 4.10), (3.956; 0.50), (3.839; 0.76), (3.828; 0.56),
(3.795; 0.73), (3.413; 0.68), (3.387; 0.56), (3.381; 0.52), (3.166; 25.69), (3.118; 795.61), (2.886; 15.90),
(2.662; 0.96), (2.657; 1.30), (2.653; 0.91), (2.648; 0.52), (2.527; 1.32), (2.510; 3.49), (2.506; 5.01),
(2.498; 73.33), (2.493; 150.78), (2.488; 212.37), (2.484; 148.61), (2.479; 71.15), (2.386; 0.53), (2.320; 0.96),
(2.315; 1.33), (2.310; 0.95), (2.224; 0.45), (2.205; 0.90), (2.199; 0.52), (2.139; 16.00), (2.041; 4.89),
(1.625; 11.68), (1.612; 3.20), (1.607; 11.90), (1.594; 2.00), (1.585; 0.58), (1.562; 5.43), (1.544; 5.46),
(1.397; 0.52), (1.360; 0.50), (1.303; 0.58), (1.263; 0.84), (1.245; 1.32), (1.213; 8.18), (1.196; 8.10),
(0.008; 0.53), (−0.000; 16.24), (−0.008; 0.52)

Ex. 177:
(7.630; 4.61), (7.118; 3.30), (6.754; 3.48), (3.191; 0.65), (3.117; 494.33), (2.971; 16.00), (2.662; 0.36), (2.658; 0.54), (2.653; 0.34), (2.527; 2.01), (2.511; 1.50), (2.506; 2.09), (2.498; 28.44), (2.493; 58.64), (2.488; 82.70), (2.484; 57.62), (2.479; 27.47), (2.320; 0.37), (2.315; 0.53), (2.310; 0.42), (2.151; 11.14), (2.136; 11.08), (2.076; 0.49), (2.040; 1.03), (1.507; 0.70), (1.482; 14.83), (1.404; 7.03), (1.190; 1.16), (1.179; 3.47), (1.173; 3.52), (1.163; 1.37), (0.826; 1.60), (0.816; 4.28), (0.810; 4.54), (0.799; 1.28), (−0.000; 6.08)
Ex. 178:
(7.689; 0.73), (7.114; 2.86), (6.759; 2.84), (3.191; 0.41), (3.112; 616.25), (2.860; 16.00), (2.662; 0.66), (2.657; 0.89), (2.652; 0.68), (2.647; 0.35), (2.639; 0.38), (2.526; 3.35), (2.510; 2.42), (2.505; 3.42), (2.497; 48.08), (2.493; 98.76), (2.488; 138.90), (2.483; 96.91), (2.478; 46.17), (2.319; 0.67), (2.315; 0.83), (2.310; 0.64), (2.305; 0.38), (2.148; 9.59), (2.138; 9.66), (2.076; 0.43), (2.040; 0.89), (2.037; 0.40), (1.507; 0.39), (1.482; 12.86), (1.404; 0.63), (1.245; 0.71), (1.239; 0.41), (1.201; 13.15), (1.184; 13.28), (1.179; 4.47), (1.174; 3.35), (1.163; 1.30), (1.157; 0.69), (1.140; 0.48), (0.826; 1.42), (0.815; 3.73), (0.810; 3.93), (0.799; 1.11), (0.008; 0.71), (−0.000; 19.60), (−0.008; 0.55)
Ex. 179:
(8.006; 0.42), (7.642; 1.55), (7.235; 0.75), (7.217; 0.72), (7.175; 0.53), (7.170; 0.85), (7.152; 0.61), (7.150; 0.62), (7.128; 0.40), (7.116; 3.58), (6.757; 3.51), (3.408; 0.58), (3.389; 1.27), (3.371; 1.28), (3.354; 0.55), (3.287; 0.39), (3.269; 1.33), (3.251; 1.78), (3.233; 1.09), (3.215; 0.35), (3.191; 0.54), (3.156; 0.38), (3.150; 0.45), (3.115; 291.69), (2.970; 0.46), (2.949; 10.98), (2.908; 0.50), (2.888; 2.68), (2.866; 2.75), (2.734; 2.21), (2.733; 2.22), (2.720; 3.62), (2.718; 3.64), (2.658; 0.35), (2.527; 1.34), (2.511; 0.91), (2.506; 1.33), (2.498; 19.34), (2.493; 40.00), (2.488; 56.43), (2.484; 39.33), (2.479; 18.74), (2.315; 0.39), (2.310; 0.35), (2.306; 0.37), (2.298; 3.59), (2.150; 11.91), (2.137; 11.93), (2.040; 0.64), (2.037; 0.33), (1.507; 0.44), (1.482; 16.00), (1.245; 0.58), (1.191; 1.37), (1.179; 3.84), (1.174; 3.85), (1.163; 1.98), (1.160; 5.48), (1.142; 11.53), (1.124; 5.17), (1.112; 1.72), (1.094; 3.11), (1.077; 1.53), (1.033; 0.82), (1.015; 1.57), (0.997; 0.86), (0.857; 0.34), (0.826; 1.82), (0.816; 4.73), (0.810; 5.00), (0.799; 1.51), (−0.000; 9.66)
Ex. 180:
(7.696; 0.33), (7.138; 1.33), (6.765; 1.29), (3.114; 218.52), (2.862; 7.43), (2.526; 0.98), (2.510; 0.64), (2.506; 0.90), (2.497; 13.92), (2.493; 28.90), (2.488; 40.89), (2.483; 28.63), (2.479; 13.72), (2.155; 4.35), (2.137; 4.41), (2.040; 0.72), (1.839; 0.43), (1.820; 1.53), (1.802; 1.60), (1.783; 0.49), (1.353; 16.00), (1.203; 6.04), (1.186; 5.98), (0.770; 1.75), (0.752; 3.99), (0.733; 1.64), (−0.000; 6.70)
Ex. 181:
(7.647; 0.60), (7.140; 1.34), (6.762; 1.35), (3.391; 0.50), (3.374; 0.50), (3.115; 141.90), (2.951; 4.19), (2.527; 0.69), (2.510; 0.52), (2.506; 0.72), (2.498; 9.65), (2.493; 19.79), (2.488; 27.79), (2.484; 19.35), (2.479; 9.20), (2.156; 4.45), (2.136; 4.44), (1.839; 0.47), (1.820; 1.56), (1.802; 1.61), (1.783; 0.50), (1.409; 0.53), (1.404; 2.69), (1.353; 16.00), (1.161; 1.95), (1.144; 4.24), (1.126; 1.86), (0.770; 1.79), (0.752; 3.99), (0.733; 1.65), (−0.000; 3.59)
Ex. 182:
(9.864; 0.55), (7.645; 1.96), (7.352; 0.98), (7.350; 1.62), (7.346; 0.75), (7.333; 2.85), (7.331; 4.12), (7.329; 3.05), (7.319; 1.54), (7.314; 4.91), (7.312; 3.88), (7.288; 3.51), (7.284; 5.60), (7.278; 1.22), (7.267; 3.71), (7.255; 1.40), (7.249; 2.38), (7.243; 0.67), (7.231; 0.94), (7.133; 4.69), (6.761; 4.43), (5.689; 3.14), (4.278; 1.06), (4.124; 11.84), (3.652; 0.40), (3.615; 0.95), (3.406; 0.75), (3.389; 1.80), (3.371; 1.81), (3.354; 0.73), (3.187; 0.59), (3.159; 0.73), (3.117; 547.06), (2.949; 14.61), (2.662; 0.49), (2.657; 0.68), (2.652; 0.47), (2.527; 0.63), (2.510; 1.53), (2.506; 2.24), (2.498; 34.73), (2.493; 71.76), (2.488; 101.30), (2.484; 70.75), (2.479; 33.83), (2.320; 0.43), (2.315; 0.59), (2.310; 0.42), (2.146; 16.00), (2.128; 15.98), (2.040; 0.62), (1.404; 3.92), (1.245; 0.41), (1.158; 6.92), (1.141; 15.22), (1.123; 6.67), (0.008; 0.71), (−0.000; 21.56), (−0.008; 0.66)
Ex. 183:
(7.635; 1.81), (7.142; 1.30), (6.760; 1.35), (3.112; 185.90), (2.974; 6.34), (2.526; 0.98), (2.510; 0.70), (2.506; 0.95), (2.497; 13.69), (2.493; 28.23), (2.488; 39.79), (2.483; 27.77), (2.479; 13.22), (2.157; 4.41), (2.135; 4.38), (1.839; 0.46), (1.820; 1.57), (1.801; 1.61), (1.783; 0.52), (1.409; 0.58), (1.404; 2.52), (1.353; 16.00), (1.246; 0.35), (0.770; 1.79), (0.751; 3.96), (0.733; 1.66), (−0.000; 5.44)
Ex. 184:
(7.377; 0.36), (7.356; 0.36), (7.354; 0.36), (6.960; 0.36), (6.928; 0.36), (3.426; 0.35), (3.405; 0.45), (3.113; 31.33), (2.972; 0.94), (2.497; 3.68), (2.493; 7.66), (2.488; 10.85), (2.483; 7.62), (2.479; 3.66), (2.168; 2.30), (1.413; 1.00), (1.404; 2.03), (1.399; 16.00), (1.358; 0.37), (1.328; 0.88), (1.325; 0.97), (1.170; 0.80), (1.152; 1.68), (1.134; 0.77), (−0.000; 0.56)
Ex. 185:
(7.882; 0.46), (7.752; 4.69), (7.428; 3.91), (7.066; 4.91), (3.220; 0.33), (3.204; 1.52), (3.116; 396.81), (2.996; 7.13), (2.657; 0.56), (2.527; 0.66), (2.497; 33.26), (2.493; 65.15), (2.488; 88.94), (2.484; 64.01), (2.316; 0.49), (2.311; 0.39), (2.191; 14.75), (2.153; 0.41), (2.041; 0.48), (1.990; 0.47), (1.972; 1.43), (1.953; 1.92), (1.936; 2.33), (1.918; 1.92), (1.900; 0.72), (1.737; 0.65), (1.719; 2.11), (1.700; 2.42), (1.683; 2.12), (1.665; 1.67), (1.646; 0.55), (1.492; 0.40), (1.474; 0.43), (1.404; 5.78), (1.366; 0.77), (1.304; 15.24), (1.249; 0.73), (1.198; 0.47), (1.069; 3.45), (0.928; 0.47), (0.825; 0.53), (0.817; 0.35), (0.806; 1.03), (0.788; 0.50), (0.754; 7.70), (0.735; 16.00), (0.717; 7.09), (0.704; 0.72), (−0.000; 0.93)
Ex. 186:
(7.766; 0.50), (7.426; 3.06), (7.424; 3.01), (7.072; 2.82), (3.404; 0.74), (3.204; 1.27), (3.151; 0.44), (3.117; 160.04), (2.972; 3.43), (2.949; 0.42), (2.511; 0.53), (2.506; 0.78), (2.498; 11.35), (2.493; 23.34), (2.489; 32.83), (2.484; 22.84), (2.479; 10.83), (2.191; 11.27), (2.151; 0.43), (1.990; 0.36), (1.972; 1.22), (1.953; 1.53), (1.937; 1.83), (1.918; 1.63), (1.900; 0.51), (1.737; 0.53), (1.719; 1.90), (1.700; 2.19), (1.683; 1.77), (1.665; 1.54), (1.646; 0.47), (1.404; 10.11), (1.367; 0.75), (1.304; 13.80), (1.249; 0.46), (1.198; 0.59), (1.170; 3.12), (1.152; 6.64), (1.135; 3.04), (0.928; 0.62), (0.754; 7.10), (0.736; 16.00), (0.717; 6.57), (0.704; 0.68), (−0.000; 1.17)
Ex. 187:
(7.820; 0.37), (7.422; 3.15), (7.421; 3.40), (7.077; 2.70), (3.204; 1.54), (3.118; 202.03), (2.882; 11.66), (2.857; 0.74), (2.511; 0.54), (2.498; 13.26), (2.493; 27.64), (2.489; 39.59), (2.484; 28.78), (2.479; 14.52), (2.189; 12.64), (2.148; 0.63), (1.990; 0.37), (1.972; 1.30), (1.953; 1.70), (1.936; 1.99), (1.918; 1.77), (1.899; 0.56), (1.737; 0.56), (1.718; 1.98), (1.700; 2.32), (1.683; 1.87), (1.665; 1.61), (1.646; 0.51), (1.404; 11.08), (1.367; 0.78), (1.304; 14.54), (1.249; 0.68), (1.210; 7.81), (1.194; 8.04), (1.181; 1.32), (1.166; 0.37), (0.946; 0.37), (0.928; 0.75), (0.909; 0.34), (0.754; 7.25), (0.736; 16.00), (0.717; 6.94), (0.704; 0.93), (0.686; 0.40), (−0.000; 0.85)
Ex. 188:
(7.634; 4.20), (7.149; 2.87), (6.760; 3.12), (3.204; 0.97), (3.114; 283.48), (2.973; 14.33), (2.947; 1.39), (2.657; 0.39), (2.526; 1.65), (2.510; 1.18), (2.506; 1.65), (2.497; 22.90), (2.493; 47.19), (2.488; 66.59), (2.483; 46.44), (2.479; 22.12), (2.319; 0.41), (2.315; 0.49), (2.159; 9.80), (2.129; 9.58), (2.117; 0.73), (2.016; 0.52), (1.987; 0.37), (1.968; 1.27), (1.949; 1.51), (1.933; 1.80), (1.914; 1.60), (1.895; 0.49), (1.733; 0.61), (1.714; 1.91), (1.696; 2.17), (1.679; 1.80), (1.661; 1.55), (1.642; 0.52), (1.404; 14.46), (1.361; 0.84), (1.297; 13.73), (1.249; 0.40), (1.186; 0.85), (0.933; 0.45), (0.915; 0.97), (0.896; 0.46), (0.817; 0.33), (0.800; 0.32), (0.754; 7.13), (0.736; 16.00), (0.717; 6.54), (0.704; 0.43), (−0.000; 3.35)
Ex. 189:
(7.649; 1.26), (7.235; 0.47), (7.217; 0.47), (7.170; 0.54), (7.148; 3.07), (6.765; 2.83), (3.567; 1.81), (3.408; 0.52), (3.392; 1.09), (3.375; 1.11), (3.356; 0.54), (3.204; 1.47), (3.114; 284.98), (2.952; 9.19), (2.662; 0.34), (2.657; 0.45), (2.653; 0.34), (2.526; 1.90), (2.510; 1.38), (2.506; 1.87), (2.497; 25.60), (2.493; 52.71), (2.488; 74.31), (2.483; 51.77), (2.479; 24.58), (2.320; 0.47), (2.315; 0.61), (2.310; 0.37), (2.298; 2.20), (2.158; 9.78), (2.130; 9.69), (1.987; 0.35), (1.974; 0.35), (1.968; 1.26), (1.950; 1.55), (1.933; 1.83), (1.914; 1.61), (1.896; 0.49), (1.733; 0.59), (1.715; 1.90), (1.696; 2.18), (1.679; 1.77), (1.661; 1.53), (1.642; 0.53), (1.361; 0.89), (1.297; 13.85), (1.249; 0.61), (1.187; 0.34), (1.162; 4.38), (1.144; 9.67), (1.126; 4.23), (0.915; 0.34), (0.817; 0.35), (0.800; 0.32), (0.754; 7.09), (0.736; 16.00), (0.717; 6.60), (0.704; 0.63), (−0.000; 4.82)
Ex. 190:
(8.138; 0.39), (7.888; 0.44), (7.868; 0.43), (7.695; 0.72), (7.145; 2.66), (6.766; 2.70), (6.639; 0.35), (3.907; 4.05), (3.806; 0.40), (3.428; 0.35), (3.204; 4.25), (3.114; 485.09), (2.862; 15.93), (2.839; 2.00), (2.662; 0.51), (2.657; 0.79), (2.652; 0.51), (2.526; 2.77), (2.510; 1.90), (2.506; 2.66), (2.497; 39.35), (2.493; 81.56), (2.488; 115.23), (2.483; 80.57), (2.479; 38.62), (2.320; 0.63), (2.315; 0.84), (2.310; 0.57), (2.157; 9.23), (2.130; 9.13), (2.114; 1.40), (2.040; 0.67), (2.037; 0.37), (2.018; 1.11), (1.987; 0.38), (1.968; 1.23), (1.950; 1.44), (1.942; 0.35), (1.933; 1.72), (1.914; 1.53), (1.896; 0.48), (1.733; 0.72), (1.714; 1.80), (1.696; 2.02), (1.679; 1.64), (1.661; 1.50), (1.642; 0.63), (1.404; 16.00), (1.361; 1.01), (1.297; 13.00), (1.249; 1.44), (1.225; 0.36), (1.215; 0.35), (1.203; 13.00), (1.186; 14.78), (1.173; 2.26), (0.933; 0.96), (0.915; 2.02), (0.896; 0.93), (0.854; 0.33), (0.817; 0.38), (0.800; 0.42), (0.754; 6.65), (0.736; 14.99), (0.723; 1.52), (0.717; 6.22), (0.704; 1.83), (0.694; 0.42), (0.686; 0.81), (−0.000; 9.43)
Ex. 191:
(7.738; 0.44), (7.515; 4.25), (7.398; 0.36), (7.392; 3.19), (7.386; 1.26), (7.376; 1.54), (7.370; 5.61), (7.364; 0.86), (7.317; 0.71), (7.311; 4.53), (7.306; 1.36), (7.295; 1.03), (7.289; 2.70), (6.994; 2.73), (4.145; 7.76), (3.401; 0.67), (3.188; 0.44), (3.117; 303.18), (2.973; 3.42), (2.658; 0.41), (2.527; 0.43), (2.511; 1.12), (2.506; 1.55), (2.498; 22.27), (2.493; 45.91), (2.488; 64.63), (2.484; 45.14), (2.479; 21.53), (2.315; 0.41), (2.154; 12.31), (1.404; 16.00), (1.173; 3.54), (1.155; 7.51), (1.137; 3.40), (−0.000; 3.10)
Ex. 192:
(7.729; 1.91), (7.541; 1.76), (6.996; 1.49), (3.204; 0.60), (3.115; 115.14), (3.002; 2.05), (2.977; 0.54), (2.946; 0.46), (2.527; 0.61), (2.511; 0.45), (2.506; 0.63), (2.498; 8.92), (2.493; 18.40), (2.488; 25.92), (2.484; 18.06), (2.479; 8.61), (2.155; 5.31), (2.047; 0.36), (1.969; 0.58), (1.951; 0.72), (1.934; 0.85), (1.915; 0.76), (1.717; 0.91), (1.699; 1.04), (1.682; 0.83), (1.664; 0.73), (1.404; 16.00), (1.365; 0.33), (1.302; 6.50), (1.196; 0.52), (0.909; 0.57), (0.758; 3.36), (0.739; 7.52), (0.721; 3.11), (−0.000; 1.49)
Ex. 193:
(7.743; 0.43), (7.539; 3.79), (7.001; 2.60), (5.747; 0.35), (3.848; 0.38), (3.732; 0.65), (3.398; 1.02), (3.204; 2.32), (3.155; 0.56), (3.113; 252.98), (2.977; 3.35), (2.953; 0.64), (2.928; 0.43), (2.657; 0.37), (2.526; 1.34), (2.510; 1.01), (2.506; 1.43), (2.497; 19.44), (2.493; 39.87), (2.488; 56.07), (2.483; 39.09), (2.479; 18.65), (2.315; 0.40), (2.156; 11.45), (2.141; 0.36), (2.085; 0.42), (2.078; 0.33), (2.048; 0.74), (1.988; 0.38), (1.969; 1.23), (1.951; 1.59), (1.934; 1.89), (1.916; 1.67), (1.897; 0.51), (1.736; 0.61), (1.718; 1.95), (1.699; 2.25), (1.683; 1.82), (1.664; 1.60), (1.645; 0.53), (1.404; 12.21), (1.365; 0.71), (1.302; 14.00), (1.249; 0.89), (1.229; 0.36), (1.196; 1.14), (1.177; 3.45), (1.159; 7.33), (1.146; 1.23), (1.141; 3.44), (1.132; 0.53), (1.128; 0.65), (0.928; 0.55), (0.909; 1.16), (0.890; 0.51), (0.821; 0.34), (0.758; 7.18), (0.740; 16.00), (0.721; 6.67), (0.705; 1.08), (0.686; 0.56), (−0.000; 6.24)
Ex. 194:
(7.549; 0.60), (3.155; 0.34), (3.118; 73.82), (2.989; 0.57), (2.506; 0.41), (2.498; 5.90), (2.493; 12.16), (2.489; 17.10), (2.484; 11.91), (2.479; 5.66), (2.282; 2.55), (1.414; 16.00), (1.358; 0.48), (1.181; 0.48), (1.164; 0.95), (1.146; 0.46), (−0.000; 0.40)
Ex. 195:
(8.006; 0.33), (7.648; 1.20), (7.145; 2.76), (6.764; 2.79), (3.700; 0.65), (3.408; 0.52), (3.392; 1.05), (3.374; 1.10), (3.357; 0.53), (3.343; 0.43), (3.287; 0.41), (3.269; 1.11), (3.251; 1.45), (3.233; 0.96), (3.214; 0.38), (3.205; 0.38), (3.116; 382.47), (3.091; 2.42), (2.951; 8.57), (2.927; 0.45), (2.900; 0.61), (2.866; 2.20), (2.720; 2.88), (2.718; 2.92), (2.662; 0.35), (2.657; 0.54), (2.653; 0.36), (2.527; 0.51), (2.511; 1.36), (2.506; 1.99), (2.498; 28.76), (2.493; 59.41), (2.488; 83.75), (2.484; 58.58), (2.479; 28.04), (2.320; 0.41), (2.315; 0.64), (2.310; 0.42), (2.232; 0.73), (2.218; 0.73), (2.212; 0.78), (2.205; 0.80), (2.188; 0.65), (2.178; 0.73), (2.156; 9.21), (2.141; 9.21), (2.119; 0.48), (2.065; 0.38), (2.016; 0.37), (1.590; 0.97), (1.569; 1.36), (1.559; 1.50), (1.543; 1.38), (1.536; 1.43), (1.497; 0.32), (1.480; 0.60), (1.464; 0.73), (1.452; 0.80), (1.422; 1.91), (1.415; 1.85), (1.404; 1.53), (1.397; 1.22), (1.335; 0.53), (1.323; 16.00), (1.293; 0.74), (1.264; 0.38), (1.245; 0.65), (1.162; 4.12), (1.144; 8.99), (1.131; 0.85), (1.127; 3.99), (1.116; 0.70), (1.112; 1.48), (1.094; 2.53), (1.076; 1.25), (1.033; 0.69), (1.015; 1.27), (0.997; 0.67), (−0.000; 4.22),
Ex. 196:
(7.722; 2.23), (7.523; 2.19), (7.351; 0.70), (7.347; 0.36), (7.332; 1.38), (7.315; 1.61), (7.310; 0.72), (7.288; 0.74), (7.275; 2.40), (7.269; 1.27), (7.257; 1.39), (7.249; 1.07), (7.245; 1.42), (7.229; 0.67), (7.225; 0.70), (7.214; 0.46), (7.196; 0.48), (6.984; 1.81), (4.419; 0.33), (4.400; 0.93), (4.383; 0.94), (4.366; 0.35), (4.249; 0.34), (4.232; 0.39), (3.166; 11.39), (3.158; 1.00), (3.117; 818.41), (2.997; 2.31), (2.667; 0.52), (2.662; 1.02), (2.657; 1.53), (2.652; 1.14), (2.648; 0.52), (2.526; 1.30), (2.510; 3.90), (2.506; 5.50), (2.497; 81.32), (2.493; 167.32), (2.488; 236.16), (2.483; 165.54), (2.479; 79.20), (2.324; 0.50), (2.320; 0.94), (2.315; 1.46), (2.310; 1.04), (2.306; 0.52), (2.137; 6.41), (2.064; 0.38), (2.041; 6.45), (1.625; 4.67), (1.617; 0.70), (1.607; 4.71), (1.562; 2.35), (1.544; 2.35), (1.404; 16.00), (1.244; 0.69), (0.008; 0.64), (−0.000; 18.63), (−0.008; 0.59)

-continued

Ex. 197:
(7.636; 3.99), (7.147; 2.82), (6.760; 3.02), (3.343; 0.39), (3.205; 0.62), (3.187; 0.46), (3.163; 0.77),
(3.118; 793.27), (2.974; 13.78), (2.948; 0.85), (2.667; 0.36), (2.662; 0.59), (2.658; 0.89), (2.653; 0.66),
(2.648; 0.34), (2.533; 0.38), (2.527; 1.55), (2.511; 2.56), (2.506; 3.74), (2.498; 48.58), (2.493; 99.04),
(2.488; 138.55), (2.484; 97.00), (2.479; 46.61), (2.454; 0.37), (2.320; 0.62), (2.315; 0.89), (2.310; 0.62),
(2.233; 0.78), (2.211; 0.82), (2.201; 0.83), (2.189; 0.67), (2.177; 0.75), (2.157; 9.51), (2.141; 9.41),
(2.121; 0.47), (2.040; 0.34), (2.037; 0.32), (1.590; 0.99), (1.569; 1.41), (1.560; 1.59), (1.543; 1.42),
(1.536; 1.47), (1.479; 0.58), (1.463; 0.76), (1.454; 0.72), (1.450; 0.75), (1.419; 1.98), (1.414; 1.93),
(1.404; 13.69), (1.323; 16.00), (1.293; 0.63), (1.245; 0.42), (−0.000; 4.84)
Ex. 198:
(7.696; 0.72), (7.142; 2.88), (6.766; 2.84), (5.689; 1.04), (3.701; 0.95), (3.205; 0.38), (3.161; 0.35),
(3.114; 307.19), (3.083; 0.75), (2.863; 15.70), (2.840; 0.50), (2.815; 0.70), (2.657; 0.43), (2.639; 0.37),
(2.526; 0.68), (2.510; 1.18), (2.506; 1.75), (2.497; 23.99), (2.493; 49.14), (2.488; 69.02), (2.483; 48.50),
(2.479; 23.43), (2.320; 0.33), (2.315; 0.50), (2.310; 0.35), (2.233; 0.77), (2.210; 0.81), (2.203; 0.86),
(2.178; 0.71), (2.155; 9.56), (2.142; 9.58), (2.117; 0.38), (2.067; 0.52), (2.017; 0.40), (1.590; 0.98),
(1.569; 1.43), (1.559; 1.53), (1.543; 1.47), (1.536; 1.46), (1.479; 0.59), (1.463; 0.77), (1.451; 0.78),
(1.439; 1.08), (1.422; 1.97), (1.414; 1.88), (1.404; 6.01), (1.323; 16.00), (1.292; 0.61), (1.264; 0.39),
(1.203; 12.87), (1.187; 12.84), (1.177; 1.60), (1.160; 1.24), (1.157; 0.93), (1.140; 0.71), (1.110; 1.08), (−0.000;
5.29)
Ex. 199:
(7.418; 1.48), (7.416; 1.42), (7.072; 1.33), (3.879; 0.52), (3.408; 0.90), (3.203; 0.45), (3.152; 2.18),
(3.127; 335.58), (2.972; 1.67), (2.512; 0.70), (2.507; 1.06), (2.499; 12.32), (2.494; 24.69), (2.489; 34.26),
(2.485; 24.01), (2.480; 11.59), (2.189; 5.34), (2.172; 0.40), (1.842; 0.47), (1.824; 1.59), (1.805; 1.68),
(1.787; 0.56), (1.404; 9.63), (1.359; 16.00), (1.311; 1.72), (1.281; 1.00), (1.209; 0.45), (1.170; 1.43),
(1.152; 3.03), (1.134; 1.39), (0.769; 1.82), (0.751; 3.99), (0.737; 0.44), (0.732; 1.68), (0.719; 0.51), (−0.000;
1.34)
Ex. 200:
(7.975; 0.51), (7.415; 1.45), (7.414; 1.47), (7.078; 1.12), (3.227; 0.40), (3.209; 0.53), (3.187; 0.82),
(3.119; 950.66), (3.074; 0.81), (3.052; 0.36), (2.882; 4.86), (2.667; 0.38), (2.662; 0.67), (2.658; 0.89),
(2.653; 0.63), (2.527; 0.83), (2.511; 2.84), (2.498; 49.99), (2.493; 100.69), (2.489; 140.05), (2.484; 98.36),
(2.479; 47.59), (2.320; 0.65), (2.315; 0.77), (2.311; 0.58), (2.188; 5.23), (2.040; 0.70), (1.842; 0.49),
(1.824; 1.57), (1.805; 1.59), (1.787; 0.50), (1.404; 4.63), (1.359; 16.00), (1.245; 0.37), (1.210; 3.29),
(1.194; 3.20), (0.769; 1.83), (0.751; 4.02), (0.732; 1.57), (−0.000; 4.68)
Ex. 201:
(7.751; 1.81), (7.420; 1.46), (7.419; 1.40), (7.065; 2.05), (3.879; 0.52), (3.408; 0.56), (3.203; 2.04),
(3.187; 0.52), (3.118; 541.58), (2.996; 2.35), (2.662; 0.39), (2.658; 0.58), (2.653; 0.43), (2.527; 0.50),
(2.511; 1.77), (2.498; 30.89), (2.493; 62.13), (2.488; 86.35), (2.484; 60.56), (2.479; 29.26), (2.320; 0.33),
(2.315; 0.53), (2.310; 0.34), (2.189; 5.42), (2.171; 0.40), (2.040; 0.43), (1.842; 0.50), (1.824; 1.61),
(1.805; 1.75), (1.786; 0.66), (1.404; 5.94), (1.359; 16.00), (1.309; 1.58), (1.281; 0.99), (0.769; 1.81),
(0.750; 4.01), (0.732; 1.69), (0.718; 0.42), (−0.000; 3.35)
Ex. 202:
(7.719; 1.02), (7.605; 0.41), (7.159; 5.56), (6.799; 1.19), (6.776; 0.50), (3.443; 0.45), (3.434; 0.48),
(3.347; 41.17), (3.324; 1.19), (2.991; 1.24), (2.921; 3.18), (2.522; 0.39), (2.519; 0.44), (2.510; 8.78),
(2.507; 18.73), (2.504; 25.54), (2.501; 18.52), (2.498; 8.47), (2.150; 10.04), (2.128; 16.00), (1.145; 1.48),
(1.135; 3.09), (1.124; 2.35), (0.000; 0.96)
Ex. 203:
(7.617; 1.10), (6.956; 2.15), (6.705; 1.77), (6.490; 4.76), (3.809; 0.32), (3.576; 0.42), (3.507; 0.37),
(3.493; 0.45), (3.449; 0.55), (3.435; 0.54), (3.400; 0.50), (3.382; 1.18), (3.365; 1.16), (3.346; 0.48),
(3.269; 0.34), (3.251; 0.62), (3.233; 0.32), (3.193; 0.41), (3.187; 0.41), (3.114; 524.65), (2.943; 8.40),
(2.888; 0.73), (2.866; 0.43), (2.790; 0.96), (2.732; 0.64), (2.719; 0.61), (2.662; 0.52), (2.657; 0.73),
(2.652; 0.51), (2.526; 1.18), (2.510; 1.93), (2.506; 2.67), (2.497; 40.67), (2.493; 83.48), (2.488; 117.80),
(2.483; 82.05), (2.479; 38.98), (2.365; 0.75), (2.340; 1.28), (2.320; 0.52), (2.315; 0.73), (2.310; 0.51),
(2.272; 16.00), (2.140; 7.85), (2.124; 1.46), (2.115; 7.76), (2.040; 0.41), (1.244; 1.53), (1.158; 3.82),
(1.140; 8.20), (1.122; 3.72), (1.112; 0.35), (1.094; 0.49), (−0.000; 6.01)
Ex. 204:
(3.150; 4.89), (2.498; 4.36), (2.493; 8.98), (2.489; 12.65), (2.484; 8.85), (2.479; 4.25), (2.254; 2.39),
(1.410; 16.00), (1.266; 0.45), (1.248; 0.95), (1.231; 0.43), (−0.000; 0.81)
Ex. 205:
(7.819; 2.51), (7.818; 2.97), (7.815; 2.84), (7.814; 2.71), (7.747; 5.60), (7.647; 0.68), (7.645; 0.89),
(7.626; 6.13), (7.624; 6.20), (7.622; 5.74), (7.617; 5.14), (7.609; 5.56), (7.601; 0.83), (7.596; 0.86),
(7.035; 4.42), (5.688; 0.58), (3.734; 1.29), (3.264; 1.55), (3.115; 184.56), (3.012; 6.22), (2.954; 1.18),
(2.511; 0.64), (2.506; 0.95), (2.498; 13.02), (2.493; 26.60), (2.489; 37.32), (2.484; 26.12), (2.479; 12.52),
(2.218; 16.00), (2.086; 0.77), (2.041; 0.65), (1.974; 0.89), (1.404; 2.01), (1.178; 0.52), (−0.000; 8.53)
Ex. 206:
(7.822; 2.70), (7.820; 3.07), (7.817; 2.96), (7.816; 2.81), (7.764; 0.58), (7.752; 0.50), (7.646; 0.95),
(7.627; 6.42), (7.625; 6.38), (7.622; 5.99), (7.618; 5.18), (7.610; 5.62), (7.602; 0.92), (7.597; 0.88),
(7.584; 0.38), (7.040; 3.55), (5.689; 2.47), (4.283; 0.76), (3.730; 0.85), (3.608; 0.46), (3.408; 0.94),
(3.392; 0.78), (3.375; 0.50), (3.264; 0.66), (3.218; 0.44), (3.208; 0.32), (3.185; 0.44), (3.114; 434.61),
(3.089; 3.36), (2.987; 4.50), (2.924; 0.60), (2.662; 0.48), (2.657; 0.73), (2.653; 0.54), (2.526; 0.99),
(2.510; 2.28), (2.506; 3.42), (2.497; 38.98), (2.493; 78.00), (2.488; 107.98), (2.483; 75.43), (2.479; 36.08),
(2.319; 0.61), (2.315; 0.75), (2.310; 0.50), (2.219; 16.00), (2.084; 0.47), (2.041; 1.05), (1.404; 0.74),
(1.252; 0.32), (1.246; 0.36), (1.184; 4.59), (1.166; 9.76), (1.148; 4.65), (1.130; 0.58), (−0.000; 6.79)
Ex. 207:
(7.820; 1.14), (7.819; 1.29), (7.816; 1.23), (7.815; 1.18), (7.646; 0.34), (7.626; 2.38), (7.625; 2.32),
(7.622; 2.15), (7.618; 1.83), (7.605; 2.13), (7.597; 0.38), (7.045; 1.25), (3.730; 0.47), (3.115; 61.73),
(3.091; 1.10), (2.901; 6.21), (2.837; 0.41), (2.498; 5.89), (2.493; 11.86), (2.489; 16.46), (2.484; 11.52),
(2.479; 5.56), (2.220; 5.77), (1.404; 16.00), (1.224; 3.10), (1.207; 3.05), (1.188; 0.53), (1.171; 0.43), (−0.000;
0.88)

-continued

Ex. 208:
(7.906; 0.91), (7.652; 0.99), (7.135; 2.27), (6.764; 1.67), (4.162; 0.59), (3.392; 1.17), (3.377; 1.14),
(3.357; 0.68), (3.328; 0.37), (3.307; 0.36), (3.295; 0.38), (3.290; 0.40), (3.273; 0.52), (3.251; 0.45),
(3.197; 1.12), (3.191; 0.78), (3.181; 0.89), (3.107; 519.73), (2.952; 6.23), (2.657; 1.48), (2.613; 0.35),
(2.607; 0.40), (2.586; 0.48), (2.558; 0.60), (2.526; 2.25), (2.497; 91.30), (2.492; 167.52), (2.489; 196.22),
(2.487; 214.71), (2.485; 152.58), (2.483; 149.15), (2.426; 0.33), (2.418; 0.33), (2.315; 1.30), (2.153; 7.95),
(2.136; 8.14), (2.122; 0.58), (2.077; 16.00), (2.048; 1.10), (1.902; 0.39), (1.792; 0.85), (1.759; 3.19),
(1.742; 3.53), (1.711; 1.11), (1.688; 0.33), (1.406; 5.29), (1.404; 6.73), (1.246; 0.86), (1.162; 2.55),
(1.144; 4.99), (1.126; 2.31), (0.897; 0.33), (0.879; 0.35), (0.002; 8.93), (−0.000; 11.64)
Ex. 209:
(19.480; 0.77), (15.923; 0.74), (15.320; 0.90), (12.236; 0.71), (9.884; 0.85), (7.698; 0.87), (7.135; 1.78),
(6.766; 1.08), (5.689; 1.43), (4.161; 2.76), (3.418; 0.80), (3.311; 0.75), (3.274; 0.85), (3.250; 1.07),
(3.229; 1.20), (3.196; 1.89), (3.108; 1514.66), (3.033; 0.83), (2.864; 5.96), (2.657; 3.53), (2.603; 0.73),
(2.578; 0.91), (2.572; 1.05), (2.543; 1.86), (2.526; 4.62), (2.495; 222.36), (2.492; 387.67), (2.491; 395.63),
(2.487; 534.60), (2.483; 392.69), (2.478; 201.96), (2.317; 2.71), (2.314; 3.36), (2.153; 6.98), (2.138; 7.90),
(2.117; 2.52), (2.103; 1.44), (2.076; 16.00), (2.048; 3.00), (1.974; 0.84), (1.917; 0.75), (1.785; 1.19),
(1.754; 4.24), (1.740; 4.41), (1.402; 1.54), (1.296; 0.80), (1.279; 0.77), (1.259; 1.09), (1.246; 2.02),
(1.217; 0.86), (1.203; 8.05), (1.187; 8.15), (1.171; 0.81), (1.152; 0.76), (0.894; 0.77), (0.854; 0.81), (−0.000;
22.93), (−0.002; 21.28)
Ex. 210:
(7.817; 1.58), (7.816; 1.73), (7.813; 1.70), (7.812; 1.62), (7.673; 0.90), (7.646; 0.81), (7.626; 3.42),
(7.625; 3.20), (7.618; 2.78), (7.613; 2.45), (7.597; 0.52), (7.592; 0.62), (7.221; 2.27), (6.809; 1.95),
(3.813; 0.34), (3.489; 0.32), (3.420; 0.41), (3.404; 0.86), (3.387; 0.86), (3.369; 0.41), (3.218; 0.37),
(3.112; 126.35), (2.964; 6.71), (2.670; 0.33), (2.526; 0.80), (2.510; 1.09), (2.497; 16.71), (2.493; 33.19),
(2.488; 45.75), (2.483; 31.98), (2.478; 15.33), (2.194; 8.04), (2.185; 7.80), (1.404; 16.00), (1.171; 3.14),
(1.153; 6.94), (1.135; 3.02), (−0.000; 3.15)
Ex. 211:
(7.816; 1.24), (7.813; 1.21), (7.655; 2.43), (7.647; 0.61), (7.646; 0.61), (7.626; 2.46), (7.625; 2.37),
(7.617; 2.03), (7.613; 1.86), (7.597; 0.39), (7.592; 0.46), (7.220; 1.77), (6.801; 1.88), (3.264; 0.97),
(3.113; 161.82), (3.089; 1.12), (2.984; 8.03), (2.526; 0.78), (2.510; 0.97), (2.505; 1.48), (2.497; 16.57),
(2.493; 33.12), (2.488; 45.89), (2.483; 32.17), (2.479; 15.50), (2.192; 5.98), (2.184; 5.91), (1.404; 16.00), (−0.000;
3.80)
Ex. 212:
(7.816; 2.23), (7.812; 2.17), (7.811; 2.13), (7.717; 0.75), (7.646; 0.94), (7.626; 4.27), (7.625; 4.24),
(7.617; 3.56), (7.613; 3.27), (7.597; 0.72), (7.592; 0.83), (7.217; 3.01), (6.809; 2.74), (5.689; 1.08),
(3.813; 0.44), (3.489; 0.33), (3.112; 192.28), (2.875; 16.00), (2.657; 0.32), (2.526; 0.79), (2.510; 0.86),
(2.497; 19.73), (2.493; 40.14), (2.488; 56.18), (2.483; 39.82), (2.479; 19.61), (2.315; 0.34), (2.194; 10.15),
(2.183; 10.08), (1.211; 13.05), (1.195; 12.93), (−0.000; 7.00)
Ex. 213:
(7.634; 3.36), (7.134; 2.68), (6.757; 2.83), (4.161; 1.08), (3.197; 2.34), (3.186; 0.42), (3.112; 441.24),
(3.088; 5.89), (3.004; 0.46), (2.973; 12.76), (2.948; 0.33), (2.848; 0.55), (2.836; 0.50), (2.666; 0.40),
(2.661; 0.65), (2.657; 0.88), (2.652; 0.67), (2.647; 0.40), (2.548; 0.37), (2.526; 2.17),
(2.510; 3.25), (2.497; 49.77), (2.493; 98.30), (2.488; 135.48), (2.483; 94.80), (2.478; 45.67), (2.319; 0.59),
(2.315; 0.86), (2.310; 0.61), (2.305; 0.35), (2.153; 9.04), (2.134; 9.04), (2.076; 16.00), (2.049; 1.20),
(2.040; 1.33), (2.032; 1.16), (1.974; 0.47), (1.789; 0.85), (1.758; 3.28), (1.740; 3.52), (1.711; 1.26),
(1.404; 3.30), (1.361; 0.47), (1.263; 0.43), (1.245; 0.98), (1.230; 0.39), (1.165; 0.46), (0.857; 0.35),
(0.008; 0.80), (−0.000; 17.59), (−0.008; 0.57)
Ex. 214:
(17.722; 0.54), (7.975; 1.49), (7.667; 2.40), (7.466; 2.72), (7.464; 2.72), (7.443; 4.00), (7.370; 3.40),
(7.352; 3.88), (7.347; 2.16), (7.330; 2.57), (7.183; 3.73), (7.171; 5.16), (7.166; 3.38), (6.804; 4.66),
(3.869; 0.56), (3.683; 0.60), (3.669; 0.57), (3.587; 0.55), (3.573; 0.58), (3.551; 0.62), (3.526; 0.56),
(3.508; 0.57), (3.473; 0.56), (3.435; 1.00), (3.420; 1.28), (3.405; 2.39), (3.386; 2.22), (3.368; 1.32),
(3.335; 0.81), (3.309; 0.88), (3.278; 1.07), (3.269; 1.36), (3.257; 1.12), (3.250; 1.28), (3.232; 1.45),
(3.115; 2215.50), (3.054; 0.76), (2.963; 15.70), (2.866; 0.76), (2.719; 0.86), (2.662; 2.28), (2.657; 3.28),
(2.653; 2.12), (2.592; 0.63), (2.573; 0.98), (2.562; 1.29), (2.526; 7.57), (2.510; 10.39), (2.497; 177.91),
(2.493; 355.94), (2.488; 494.72), (2.483; 349.83), (2.479; 171.14), (2.421; 0.50), (2.325; 1.02), (2.319; 2.13),
(2.315; 2.98), (2.310; 2.20), (2.306; 1.05), (2.182; 15.45), (2.163; 15.18), (2.041; 2.63), (1.404; 16.00),
(1.296; 1.11), (1.263; 0.70), (1.245; 1.26), (1.173; 6.18), (1.155; 14.17), (1.137; 6.35), (1.110; 0.79),
(1.094; 0.66), (−0.000; 18.87)
Ex. 215:
(7.641; 3.48), (7.170; 2.55), (6.775; 2.75), (3.230; 1.32), (3.120; 11.19), (2.976; 11.69), (2.526; 0.40),
(2.510; 0.57), (2.497; 9.37), (2.493; 18.50), (2.488; 25.49), (2.483; 17.86), (2.479; 8.63), (2.289; 0.65),
(2.160; 9.62), (2.156; 9.43), (2.040; 0.42), (1.775; 0.68), (1.760; 15.97), (1.721; 0.75), (1.712; 1.27),
(1.705; 16.00), (1.695; 0.62), (1.682; 0.41), (1.658; 0.61), (1.641; 0.36), (1.628; 0.34), (1.404; 5.17), (−0.000;
2.50)
Ex. 216:
(7.657; 1.05), (7.170; 2.54), (6.781; 2.44), (3.814; 0.64), (3.472; 0.64), (3.395; 0.97), (3.377; 0.99),
(3.361; 0.43), (3.230; 0.41), (3.111; 92.00), (2.955; 7.35), (2.526; 0.63), (2.510; 0.83), (2.497; 13.71),
(2.493; 27.09), (2.488; 37.37), (2.483; 26.20), (2.478; 12.67), (2.172; 0.73), (2.158; 13.46), (2.114; 0.39),
(1.760; 15.97), (1.705; 16.00), (1.695; 0.97), (1.641; 0.71), (1.404; 0.85), (1.163; 3.38), (1.146; 7.25),
(1.128; 3.25), (−0.000; 6.07)
Ex. 217:
(7.823; 2.63), (7.819; 2.68), (7.771; 4.77), (7.740; 0.88), (7.735; 0.93), (7.654; 1.33), (7.633; 4.84),
(7.621; 3.71), (7.616; 3.39), (7.600; 1.02), (7.595; 1.12), (7.556; 0.48), (7.550; 0.47), (7.535; 1.03),
(7.530; 1.04), (7.505; 1.58), (7.491; 3.86), (7.489; 3.93), (7.108; 5.67), (5.688; 0.35), (4.283; 0.36),
(3.952; 0.41), (3.766; 1.26), (3.264; 16.00), (3.164; 0.61), (3.110; 393.19), (3.087; 4.31), (3.062; 0.56),
(3.007; 6.63), (2.942; 1.39), (2.662; 0.56), (2.657; 0.70), (2.652; 0.52), (2.526; 1.60), (2.510; 2.60),
(2.497; 39.26), (2.493; 77.20), (2.488; 106.07), (2.483; 74.65), (2.479; 36.33), (2.319; 0.49), (2.315; 0.65),
(2.310; 0.43), (2.215; 14.11), (2.165; 0.82), (2.040; 0.61), (1.974; 0.46), (1.404; 2.40), (1.110; 0.33), (−0.000;
4.24),

-continued

Ex. 218:
(10.786; 0.56), (8.143; 3.62), (8.123; 4.12), (8.001; 0.62), (7.981; 0.89), (7.953; 4.79), (7.933; 3.63),
(7.876; 0.82), (7.853; 0.81), (7.755; 4.22), (7.603; 4.67), (7.042; 3.81), (4.731; 0.56), (3.866; 1.66),
(3.753; 1.00), (3.565; 0.55), (3.555; 0.64), (3.500; 1.76), (3.420; 0.61), (3.392; 0.93), (3.377; 0.66),
(3.357; 2.12), (3.343; 0.75), (3.293; 7.33), (3.269; 0.97), (3.260; 1.11), (3.254; 1.13), (3.247; 1.24),
(3.238; 1.18), (3.181; 2.56), (3.111; 1698.04), (3.050; 1.84), (3.016; 7.04), (2.954; 0.58), (2.666; 1.39),
(2.662; 2.92), (2.657; 3.79), (2.652; 2.74), (2.648; 1.61), (2.610; 0.61), (2.567; 1.13), (2.526; 8.72),
(2.510; 13.01), (2.497; 217.48), (2.493; 431.78), (2.488; 595.52), (2.483; 418.44), (2.479; 202.77),
(2.319; 2.66), (2.315; 3.77), (2.310; 2.73), (2.257; 0.60), (2.227; 16.00), (2.201; 0.57), (2.188; 0.65),
(2.161; 1.08), (2.153; 0.67), (2.145; 0.64), (2.098; 1.07), (2.040; 0.93), (1.404; 2.56), (1.361; 0.66),
(1.296; 0.72), (1.245; 0.97), (0.895; 0.82), (0.016; 0.64), (0.008; 2.50), (−0.000; 65.07), (−0.008; 2.59)
Ex. 219:
(8.188; 0.46), (8.144; 4.28), (8.123; 5.26), (7.975; 1.19), (7.955; 5.79), (7.934; 4.63), (7.913; 0.51),
(7.890; 0.63), (7.854; 0.51), (7.836; 0.47), (7.625; 1.84), (7.218; 0.50), (7.177; 0.51), (7.106; 0.95),
(7.091; 1.19), (3.928; 0.78), (3.872; 0.56), (3.866; 1.75), (3.822; 1.45), (3.772; 0.45), (3.744; 0.45),
(3.577; 1.12), (3.526; 0.45), (3.500; 1.64), (3.429; 0.46), (3.401; 0.54), (3.383; 0.61), (3.370; 0.56),
(3.333; 0.70), (3.322; 0.76), (3.305; 0.91), (3.293; 0.93), (3.283; 0.89), (3.211; 1.92), (3.117; 1747.30),
(2.922; 10.36), (2.761; 0.56), (2.672; 0.86), (2.662; 2.17), (2.658; 2.65), (2.653; 2.11), (2.648; 1.18),
(2.637; 1.18), (2.609; 0.49), (2.595; 0.45), (2.564; 0.80), (2.546; 1.73), (2.527; 6.30), (2.511; 9.48),
(2.498; 158.60), (2.493; 315.79), (2.488; 435.90), (2.484; 306.74), (2.479; 149.56), (2.414; 0.45),
(2.390; 0.46), (2.320; 1.88), (2.315; 2.96), (2.310; 1.91), (2.299; 0.63), (2.237; 16.00),
(2.159; 1.17), (2.150; 1.29), (1.404; 15.37), (1.296; 0.99), (1.281; 1.36), (1.264; 1.58), (1.234; 9.75),
(1.217; 9.49), (1.157; 1.78), (1.140; 1.66), (1.072; 0.82), (1.064; 1.23), (1.054; 0.79), (1.049; 1.06),
(0.895; 0.58), (−0.000; 31.72), (−0.008; 1.35), (−1.983; 0.47)
Ex. 220:
(8.143; 3.36), (8.123; 3.93), (8.003; 0.35), (7.974; 0.78), (7.953; 4.56), (7.933; 3.41), (7.854; 0.41),
(7.832; 0.34), (7.768; 0.62), (7.762; 0.60), (7.599; 5.23), (7.174; 0.32), (7.042; 3.59), (6.875; 0.44),
(6.757; 0.36), (3.929; 0.42), (3.866; 1.17), (3.730; 1.60), (3.573; 0.35), (3.500; 1.26), (3.475; 0.40),
(3.420; 1.11), (3.412; 1.14), (3.369; 0.65), (3.354; 0.85), (3.332; 0.41), (3.323; 0.45), (3.304; 0.47),
(3.293; 1.63), (3.269; 0.65), (3.251; 0.79), (3.244; 0.90), (3.233; 0.64), (3.112; 682.09), (3.088; 28.28),
(3.028; 0.37), (2.989; 4.67), (2.924; 0.88), (2.866; 0.52), (2.718; 0.77), (2.670; 1.65), (2.662; 1.25),
(2.657; 1.60), (2.652; 1.26), (2.648; 0.74), (2.590; 0.48), (2.526; 3.83), (2.510; 6.03), (2.497; 93.94),
(2.493; 186.87), (2.488; 258.35), (2.483; 182.04), (2.479; 88.41), (2.319; 1.12), (2.315; 1.78), (2.310; 1.13),
(2.227; 16.00), (2.160; 0.83), (2.083; 0.87), (2.040; 0.35), (1.974; 0.32), (1.404; 7.85), (1.296; 0.41),
(1.270; 0.32), (1.243; 0.53), (1.186; 4.57), (1.168; 9.46), (1.150; 4.43), (1.130; 0.93), (1.112; 0.67),
(1.094; 0.58), (1.076; 0.33), (1.061; 0.47), (1.043; 0.98), (1.025; 0.48), (0.928; 0.49), (0.895; 0.45),
(0.008; 1.02), (−0.000; 29.95), (−0.009; 1.25)
Ex. 221:
(7.654; 0.93), (7.133; 2.25), (6.768; 1.78), (3.853; 0.55), (3.811; 0.84), (3.426; 0.87), (3.409; 0.48),
(3.393; 1.02), (3.377; 1.03), (3.365; 0.42), (3.361; 0.45), (3.197; 1.11), (3.193; 0.63), (3.175; 1.26),
(3.158; 1.78), (3.141; 1.96), (3.111; 205.10), (2.975; 0.37), (2.954; 7.07), (2.657; 0.37), (2.526; 1.66),
(2.510; 1.33), (2.497; 21.63), (2.493; 42.66), (2.488; 58.76), (2.483; 41.35), (2.479; 20.15), (2.315; 0.40),
(2.211; 0.40), (2.156; 8.72), (2.143; 8.30), (2.126; 0.34), (2.111; 0.59), (1.974; 0.40), (1.404; 1.89),
(1.296; 16.00), (1.279; 15.62), (1.232; 0.54), (1.215; 0.59), (1.211; 1.01), (1.194; 0.95), (1.177; 0.33),
(1.163; 3.15), (1.145; 6.62), (1.127; 2.94), (−0.000; 2.63)
Ex. 222:
(8.146; 3.37), (8.125; 4.06), (7.953; 4.46), (7.933; 3.56), (7.784; 2.79), (7.485; 3.76), (7.120; 2.51),
(3.895; 0.38), (3.498; 0.36), (3.293; 0.35), (3.207; 0.40), (3.196; 0.45), (3.112; 384.48), (3.012; 6.98),
(2.662; 0.77), (2.657; 1.02), (2.652; 0.75), (2.527; 2.38), (2.510; 3.68), (2.497; 57.99), (2.493; 114.59),
(2.488; 158.02), (2.484; 111.19), (2.479; 54.11), (2.324; 0.35), (2.320; 0.67), (2.315; 1.03), (2.310; 0.69),
(2.306; 0.38), (2.218; 16.00), (2.041; 0.82), (0.008; 0.70), (−0.000; 16.40), (−0.008; 0.59)
Ex. 223:
(8.146; 3.54), (8.125; 4.11), (7.975; 1.00), (7.954; 4.38), (7.933; 3.57), (7.867; 0.39), (7.847; 0.47),
(7.835; 0.48), (7.821; 0.33), (7.478; 4.25), (7.126; 2.56), (3.170; 1.09), (3.112; 533.83), (3.028; 0.33),
(2.896; 14.38), (2.662; 1.10), (2.657; 1.43), (2.652; 1.04), (2.648; 0.58), (2.526; 3.40), (2.510; 5.30),
(2.497; 89.14), (2.493; 177.70), (2.488; 246.93), (2.483; 174.62), (2.479; 85.64), (2.319; 1.06), (2.315; 1.54),
(2.310; 1.12), (2.214; 16.00), (2.041; 1.65), (1.404; 15.42), (1.296; 0.44), (1.220; 9.94), (1.204; 9.70),
(0.008; 0.83), (−0.000; 23.30), (−0.008; 1.01)
Ex. 224:
(8.146; 3.44), (8.125; 4.23), (7.953; 4.53), (7.933; 3.70), (7.796; 0.74), (7.482; 4.01), (7.123; 2.40),
(3.790; 0.38), (3.421; 1.20), (3.351; 0.32), (3.269; 0.32), (3.244; 0.50), (3.207; 0.42), (3.112; 376.62),
(2.986; 5.10), (2.666; 0.46), (2.662; 0.77), (2.657; 1.09), (2.653; 0.83), (2.648; 0.45), (2.526; 2.61),
(2.510; 4.14), (2.497; 62.71), (2.493; 123.95), (2.488; 171.53), (2.483; 120.61), (2.479; 58.55), (2.324; 0.33),
(2.319; 0.80), (2.315; 1.06), (2.310; 0.74), (2.306; 0.45), (2.216; 16.00), (2.041; 2.02), (1.404; 2.35),
(1.243; 0.37), (1.181; 4.24), (1.163; 8.85), (1.145; 4.10), (0.008; 0.92), (−0.000; 21.10), (−0.008; 0.75)
Ex. 225:
(7.823; 1.30), (7.819; 1.35), (7.654; 0.64), (7.634; 2.15), (7.621; 1.73), (7.616; 1.44), (7.600; 0.41),
(7.485; 1.82), (7.120; 1.39), (3.209; 0.41), (3.156; 0.70), (3.103; 449.95), (3.079; 5.59), (2.893; 5.95),
(2.661; 1.04), (2.656; 1.40), (2.651; 0.88), (2.647; 0.51), (2.526; 3.19), (2.509; 4.98), (2.497; 81.05),
(2.492; 161.42), (2.487; 223.05), (2.483; 157.77), (2.478; 77.41), (2.433; 0.52), (2.319; 0.95), (2.314; 1.41),
(2.309; 0.90), (2.214; 6.15), (2.040; 0.81), (1.404; 16.00), (1.296; 0.36), (1.290; 0.50), (1.273; 0.48),
(1.246; 0.44), (1.218; 4.00), (1.202; 3.96), (1.183; 0.46), (−0.000; 14.97), (−0.008; 0.68)
Ex. 226:
(7.975; 0.49), (7.730; 3.42), (7.523; 3.15), (6.997; 2.84), (3.765; 0.56), (3.217; 0.51), (3.211; 0.55),
(3.198; 1.08), (3.183; 1.88), (3.166; 3.02), (3.129; 627.79), (3.063; 0.51), (3.000; 3.39), (2.941; 0.66),
(2.663; 0.78), (2.658; 1.06), (2.654; 0.76), (2.648; 0.47), (2.563; 0.34), (2.527; 4.43), (2.511; 3.43),
(2.498; 57.09), (2.493; 112.84), (2.489; 155.53), (2.484; 109.56), (2.480; 53.08), (2.320; 0.73), (2.316; 0.93),
(2.311; 0.68), (2.181; 0.49), (2.166; 10.14), (2.043; 0.82), (2.038; 0.48), (1.975; 0.50), (1.403; 6.63),
(1.299; 16.00), (1.281; 15.57), (1.243; 0.36), (−0.000; 8.02),

Ex. 227:
(7.518; 3.08), (7.019; 0.33), (7.008; 1.96), (3.779; 0.39), (3.735; 0.46), (3.198; 1.46), (3.191; 0.64),
(3.183; 1.54), (3.166; 2.43), (3.149; 3.62), (3.128; 433.40), (2.889; 8.89), (2.663; 0.58), (2.658; 0.64),
(2.653; 0.45), (2.527; 3.08), (2.511; 2.17), (2.498; 39.83), (2.493; 80.13), (2.489; 111.51), (2.484; 79.39),
(2.480; 39.11), (2.325; 0.35), (2.320; 0.49), (2.316; 0.69), (2.311; 0.51), (2.168; 9.74), (2.088; 0.35),
(2.043; 0.48), (1.975; 0.58), (1.403; 5.54), (1.299; 16.00), (1.282; 15.93), (1.253; 0.48), (1.231; 1.03),
(1.215; 5.10), (1.199; 5.12), (1.177; 1.14), (1.159; 0.43), (−0.000; 5.22)
Ex. 228:
(7.750; 0.36), (7.520; 3.04), (7.001; 2.05), (3.765; 0.77), (3.730; 0.68), (3.405; 0.70), (3.342; 0.36),
(3.228; 0.42), (3.223; 0.42), (3.218; 0.49), (3.198; 1.42), (3.183; 1.70), (3.166; 2.69), (3.131; 506.13),
(2.975; 2.42), (2.923; 0.48), (2.918; 0.51), (2.663; 0.43), (2.658; 0.61), (2.654; 0.43), (2.528; 2.71),
(2.511; 2.01), (2.498; 34.73), (2.494; 69.29), (2.489; 96.23), (2.484; 68.22), (2.480; 33.39), (2.320; 0.47),
(2.316; 0.60), (2.311; 0.41), (2.185; 0.41), (2.182; 0.36), (2.167; 9.71), (2.084; 0.43), (1.403; 6.01),
(1.299; 16.00), (1.282; 15.72), (1.231; 0.56), (1.214; 0.53), (1.175; 2.53), (1.158; 5.13), (1.140; 2.67),
(1.129; 0.51), (1.122; 0.48), (−0.000; 2.48)
Ex. 229:
(7.638; 2.69), (7.136; 2.37), (6.761; 2.35), (3.433; 0.35), (3.426; 0.32), (3.375; 0.34), (3.251; 0.45),
(3.231; 0.49), (3.197; 1.70), (3.193; 1.01), (3.175; 1.84), (3.158; 3.05), (3.124; 524.98), (3.093; 1.19),
(2.974; 10.44), (2.662; 0.93), (2.658; 1.10), (2.653; 0.81), (2.527; 5.23), (2.511; 4.07), (2.498; 67.16),
(2.493; 133.57), (2.489; 184.94), (2.484; 130.78), (2.479; 63.80), (2.458; 1.01), (2.320; 0.85), (2.315; 1.26),
(2.310; 0.81), (2.155; 8.56), (2.141; 8.30), (2.123; 0.49), (2.120; 0.36), (2.038; 0.47), (1.404; 0.99),
(1.295; 16.00), (1.278; 15.42), (1.246; 0.35), (1.231; 0.61), (1.214; 0.78), (−0.000; 13.10), (−0.008; 0.66)
Ex. 230:
(7.737; 3.26), (7.565; 3.04), (7.012; 2.71), (3.230; 0.54), (3.107; 60.80), (3.005; 4.06), (2.526; 0.39),
(2.510; 0.62), (2.497; 9.63), (2.492; 19.03), (2.488; 26.18), (2.483; 18.46), (2.478; 9.02), (2.182; 10.05),
(1.765; 15.96), (1.710; 16.00), (1.404; 4.32), (−0.000; 1.90),
Ex. 231:
(7.777; 0.44), (7.444; 2.54), (7.091; 2.23), (3.409; 0.68), (3.230; 0.61), (3.180; 1.52), (3.111; 241.83),
(2.974; 2.82), (2.662; 0.46), (2.657; 0.67), (2.652; 0.47), (2.526; 1.53), (2.510; 2.33), (2.497; 36.33),
(2.493; 72.24), (2.488; 99.71), (2.483; 70.12), (2.478; 34.08), (2.319; 0.43), (2.315; 0.59), (2.310; 0.40),
(2.193; 9.31), (1.767; 15.55), (1.712; 16.00), (1.660; 1.30), (1.242; 0.43), (1.224; 0.57), (1.172; 2.40),
(1.154; 5.06), (1.136; 2.39), (0.008; 0.49), (−0.000; 13.15), (−0.008; 0.58)
Ex. 232:
(7.440; 2.52), (7.439; 2.51), (7.097; 1.92), (3.885; 0.36), (3.230; 1.78), (3.111; 127.90), (3.088; 4.14),
(2.886; 8.33), (2.657; 0.34), (2.526; 0.82), (2.510; 1.26), (2.497; 19.39), (2.493; 38.54), (2.488; 53.21),
(2.483; 37.42), (2.479; 18.19), (2.315; 0.35), (2.192; 9.16), (1.767; 15.25), (1.712; 16.00), (1.694; 0.40),
(1.658; 0.86), (1.640; 0.33), (1.404; 1.18), (1.239; 0.34), (1.212; 5.58), (1.196; 5.48), (0.008; 0.34), (−0.000;
8.38), (−0.008; 0.32)
Ex. 233:
(7.702; 0.57), (7.165; 2.24), (6.780; 2.21), (3.814; 0.96), (3.471; 0.93), (3.230; 0.62), (3.106; 174.89),
(2.865; 10.62), (2.657; 0.36), (2.526; 1.62), (2.510; 1.20), (2.497; 19.55), (2.492; 38.64), (2.488; 53.04),
(2.483; 37.30), (2.478; 18.23), (2.315; 0.41), (2.173; 0.79), (2.158; 16.00), (2.114; 0.61), (2.040; 0.34),
(1.760; 12.44), (1.705; 12.46), (1.695; 1.24), (1.658; 0.34), (1.641; 0.99), (1.404; 0.67), (1.205; 8.79),
(1.188; 8.68), (−0.000; 5.65)
Ex. 234:
(12.828; 0.46), (7.975; 1.02), (7.750; 2.94), (7.407; 2.48), (7.393; 0.38), (7.168; 0.42), (7.111; 0.39),
(7.066; 2.95), (6.384; 0.40), (4.747; 0.39), (3.773; 0.40), (3.618; 0.44), (3.383; 0.48), (3.373; 0.41),
(3.334; 0.49), (3.317; 0.52), (3.263; 1.00), (3.248; 0.90), (3.231; 1.09), (3.220; 1.12), (3.197; 4.01),
(3.192; 2.77), (3.175; 4.10), (3.122; 1905.53), (3.059; 1.23), (3.035; 1.03), (2.998; 4.64), (2.977; 1.12),
(2.945; 0.54), (2.888; 0.45), (2.751; 0.40), (2.734; 0.47), (2.663; 1.43), (2.658; 1.73), (2.653; 1.31),
(2.648; 0.86), (2.636; 0.45), (2.606; 0.44), (2.578; 0.46), (2.527; 9.35), (2.511; 6.46), (2.498; 105.41),
(2.493; 209.47), (2.489; 289.11), (2.484; 203.66), (2.479; 99.51), (2.416; 0.57), (2.406; 0.45), (2.320; 1.25),
(2.316; 1.62), (2.311; 1.42), (2.188; 9.72), (2.132; 0.44), (2.128; 0.54), (2.040; 1.45), (2.037; 1.16),
(1.901; 0.42), (1.404; 0.74), (1.315; 0.41), (1.299; 16.00), (1.282; 15.58), (1.269; 0.46), (1.245; 0.59),
(1.232; 1.36), (1.215; 1.29), (0.895; 0.74), (−0.000; 5.88)
Ex. 235:
(16.307; 0.32), (7.974; 0.39), (7.851; 0.32), (7.831; 0.41), (7.814; 0.44), (7.787; 0.34), (7.403; 2.68),
(7.094; 0.34), (7.077; 2.00), (3.765; 0.88), (3.347; 0.38), (3.341; 0.34), (3.307; 0.32), (3.276; 0.38),
(3.269; 0.35), (3.225; 0.58), (3.208; 0.80), (3.197; 3.01), (3.192; 1.86), (3.175; 2.19), (3.158; 2.71),
(3.117; 899.06), (3.056; 0.52), (3.035; 0.35), (3.028; 0.35), (3.018; 0.39), (2.882; 8.63), (2.831; 0.49),
(2.674; 0.34), (2.662; 0.93), (2.657; 1.27), (2.653; 0.94), (2.570; 0.37), (2.527; 6.63), (2.510; 4.21),
(2.497; 75.84), (2.493; 152.22), (2.488; 211.63), (2.484; 150.09), (2.479; 73.87), (2.406; 0.46), (2.365; 0.33),
(2.356; 0.32), (2.325; 0.59), (2.320; 1.02), (2.315; 1.33), (2.310; 1.02), (2.306; 0.79), (2.257; 0.36),
(2.204; 0.46), (2.186; 9.46), (2.163; 0.63), (2.130; 0.34), (2.037; 0.83), (1.900; 0.49), (1.404; 2.16),
(1.364; 0.40), (1.299; 16.00), (1.282; 15.73), (1.243; 0.53), (1.232; 1.55), (1.210; 6.01), (1.194; 5.92),
(1.166; 0.73), (0.895; 0.39), (−0.000; 13.93)
Ex. 236:
(7.975; 1.36), (7.768; 0.44), (7.406; 2.50), (7.074; 1.93), (3.776; 0.86), (3.413; 0.76), (3.407; 0.84),
(3.395; 0.83), (3.230; 0.43), (3.210; 0.81), (3.197; 2.42), (3.192; 1.71), (3.175; 2.25), (3.158; 2.64),
(3.151; 2.94), (3.122; 676.64), (3.043; 0.40), (3.035; 0.39), (3.018; 0.32), (2.972; 3.09), (2.944; 0.53),
(2.662; 0.58), (2.658; 0.75), (2.527; 3.70), (2.511; 2.64), (2.498; 43.26), (2.493; 85.50), (2.489; 117.33),
(2.484; 82.20), (2.479; 39.68), (2.325; 0.33), (2.320; 0.54), (2.315; 0.71), (2.311; 0.48), (2.207; 0.40),
(2.187; 9.53), (2.041; 0.50), (2.037; 0.41), (1.404; 1.13), (1.363; 0.35), (1.299; 16.00), (1.282; 15.70),
(1.277; 1.61), (1.232; 1.87), (1.215; 1.86), (1.193; 0.36), (1.170; 2.54), (1.152; 5.23), (1.134; 2.59), (−0.000;
4.09)
Ex. 237:
(7.696; 0.65), (7.127; 2.66), (6.764; 2.49), (3.853; 1.11), (3.811; 1.29), (3.426; 1.10), (3.197; 1.53),
(3.193; 0.60), (3.189; 0.43), (3.175; 1.24), (3.158; 1.86), (3.140; 2.80), (3.122; 145.97), (2.862; 12.90),
(2.527; 0.94), (2.511; 0.61), (2.498; 12.39), (2.494; 24.97), (2.489; 34.74), (2.484; 24.77), (2.480; 12.32),
(2.211; 0.70), (2.153; 8.87), (2.143; 8.85), (2.127; 0.57), (2.111; 0.83), (1.404; 0.47), (1.300; 4.04), (1.296; 16.00), (1.283; 4.14), (1.279; 15.66), (1.254; 0.35), (1.232; 0.89), (1.215; 1.29), (1.211; 2.06), (1.203; 10.92), (1.194; 2.58), (1.186; 10.75), (−0.000; 0.90)
Ex. 238:
(7.562; 3.08), (7.022; 2.04), (3.856; 0.82), (3.737; 0.50), (3.441; 0.70), (3.230; 6.25), (3.183; 0.57), (3.120; 463.44), (2.893; 9.45), (2.662; 0.42), (2.658; 0.62), (2.653; 0.53), (2.527; 3.11), (2.511; 2.08), (2.498; 37.76), (2.493; 75.32), (2.488; 104.30), (2.484; 73.69), (2.479; 36.09), (2.320; 0.50), (2.315; 0.72), (2.310; 0.47), (2.183; 9.76), (2.143; 0.48), (2.089; 0.37), (2.041; 0.66), (1.764; 15.55), (1.737; 0.34), (1.709; 16.00), (1.694; 0.93), (1.682; 0.40), (1.658; 3.03), (1.640; 0.75), (1.404; 2.97), (1.218; 5.05), (1.201; 5.16), (1.178; 0.67), (−0.000; 5.18)
Ex. 239:
(7.840; 1.21), (7.738; 1.39), (7.731; 1.55), (7.726; 0.71), (7.715; 2.18), (7.709; 1.54), (7.702; 4.44), (7.693; 1.50), (7.678; 1.37), (7.554; 0.13), (7.471; 0.82), (7.464; 0.74), (7.450; 1.31), (7.443; 1.18), (7.428; 0.73), (7.422; 0.66), (7.088; 1.19), (7.062; 0.56), (6.891; 0.25), (4.288; 0.16), (4.038; 0.28), (4.020; 0.25), (3.850; 0.14), (3.729; 0.86), (3.496; 0.17), (3.479; 0.43), (3.462; 0.45), (3.444; 0.22), (3.424; 0.53), (3.409; 0.38), (3.392; 0.94), (3.373; 1.38), (3.347; 1.29), (3.324; 423.49), (3.300; 7.93), (3.282; 0.30), (3.273; 0.64), (3.267; 2.04), (3.225; 0.12), (3.216; 0.18), (3.032; 1.79), (2.958; 4.19), (2.680; 0.20), (2.675; 0.45), (2.671; 0.62), (2.666; 0.44), (2.602; 0.13), (2.524; 1.88), (2.519; 2.66), (2.511; 33.85), (2.506; 74.07), (2.501; 103.23), (2.497; 73.75), (2.492; 33.43), (2.460; 0.20), (2.456; 0.21), (2.451; 0.23), (2.446; 0.23), (2.333; 0.46), (2.328; 0.65), (2.324; 0.47), (2.217; 8.71), (2.080; 0.57), (2.074; 0.39), (1.988; 1.11), (1.398; 2.28), (1.234; 0.16), (1.192; 0.39), (1.182; 1.06), (1.175; 1.02), (1.164; 2.61), (1.157; 1.09), (1.146; 1.98), (1.127; 0.55), (1.121; 0.41), (1.102; 0.16), (0.890; 0.30), (0.008; 0.26), (−0.000; 9.13), (−0.009; 0.29)
Ex. 240:
(7.892; 1.71), (7.737; 1.48), (7.731; 1.54), (7.715; 2.74), (7.709; 1.65), (7.697; 4.41), (7.693; 1.97), (7.677; 1.48), (7.471; 0.95), (7.464; 0.85), (7.450; 1.41), (7.443; 1.31), (7.428; 0.79), (7.422; 0.77), (7.095; 1.65), (7.063; 0.36), (6.887; 0.09), (5.755; 0.08), (4.674; 0.09), (4.658; 0.14), (4.642; 0.10), (4.288; 0.35), (4.038; 0.09), (3.886; 0.18), (3.879; 0.09), (3.869; 0.40), (3.852; 0.55), (3.836; 0.40), (3.819; 0.17), (3.728; 0.36), (3.429; 0.64), (3.382; 0.15), (3.329; 630.49), (3.306; 6.87), (3.280; 0.99), (3.267; 1.05), (3.230; 0.18), (3.219; 0.08), (3.060; 0.16), (2.920; 1.16), (2.882; 6.46), (2.822; 0.09), (2.680; 0.17), (2.675; 0.38), (2.671; 0.54), (2.666; 0.41), (2.662; 0.18), (2.601; 0.08), (2.524; 1.39), (2.520; 1.95), (2.511; 27.25), (2.506; 61.88), (2.502; 88.23), (2.497; 64.37), (2.493; 29.73), (2.452; 0.28), (2.437; 0.12), (2.376; 0.08), (2.338; 0.19), (2.333; 0.39), (2.329; 0.55), (2.324; 0.42), (2.319; 0.21), (2.218; 8.61), (2.141; 0.08), (2.080; 0.21), (2.073; 0.30), (1.988; 0.37), (1.398; 2.40), (1.227; 5.94), (1.210; 6.00), (1.192; 0.48), (1.175; 1.49), (1.159; 1.26), (1.058; 0.08), (1.041; 0.08), (0.890; 0.25), (0.008; 0.19), (−0.000; 7.06), (−0.008; 0.22)
Ex. 241:
(7.908; 7.36), (7.907; 8.63), (7.904; 8.19), (7.903; 8.07), (7.870; 3.64), (7.758; 1.65), (7.687; 2.87), (7.686; 3.13), (7.666; 13.44), (7.665; 13.06), (7.657; 10.97), (7.653; 9.91), (7.637; 2.43), (7.632; 2.84), (7.558; 10.68), (7.556; 10.67), (7.181; 4.10), (7.145; 1.73), (6.903; 0.45), (4.056; 1.05), (4.038; 3.16), (4.021; 3.18), (4.003; 1.08), (3.765; 2.47), (3.496; 0.45), (3.479; 1.19), (3.461; 1.27), (3.444; 0.62), (3.434; 1.82), (3.408; 1.05), (3.390; 2.82), (3.372; 3.03), (3.351; 3.18), (3.334; 1009.29), (3.304; 1.35), (3.293; 0.80), (3.284; 2.01), (3.217; 0.47), (3.029; 4.90), (2.953; 12.09), (2.676; 0.48), (2.672; 0.71), (2.667; 0.53), (2.542; 3.10), (2.525; 1.97), (2.521; 2.70), (2.512; 36.65), (2.507; 82.46), (2.503; 116.56), (2.498; 84.08), (2.493; 38.30), (2.458; 0.37), (2.454; 0.38), (2.334; 0.53), (2.329; 0.72), (2.325; 0.53), (2.211; 16.00), (2.167; 1.44), (2.074; 0.78), (1.989; 14.95), (1.193; 4.37), (1.175; 11.60), (1.157; 10.50), (1.141; 4.88), (1.119; 1.52), (1.113; 1.30), (1.095; 0.40), (−0.000; 9.20)
Ex. 242:
(7.712; 0.38), (7.706; 0.41), (7.428; 2.92), (7.424; 1.22), (7.407; 3.88), (7.386; 0.33), (7.369; 0.50), (7.348; 0.60), (7.256; 3.72), (7.251; 1.40), (7.239; 1.38), (7.234; 3.00), (7.183; 2.93), (7.172; 0.65), (7.151; 0.39), (6.784; 1.31), (3.912; 0.33), (3.901; 0.40), (3.300; 280.44), (3.231; 0.71), (3.149; 3.03), (3.120; 0.37), (3.026; 0.52), (2.933; 1.41), (2.673; 0.55), (2.669; 0.69), (2.664; 0.69), (2.539; 3.46), (2.504; 69.11), (2.500; 84.92), (2.496; 59.32), (2.424; 0.31), (2.403; 0.32), (2.331; 0.54), (2.326; 0.66), (2.322; 0.54), (2.152; 7.46), (2.115; 8.18), (2.088; 0.56), (2.069; 0.61), (2.049; 0.43), (1.787; 0.81), (1.709; 1.17), (1.689; 15.00), (1.655; 0.50), (1.648; 0.62), (1.634; 2.36), (1.416; 0.57), (1.398; 5.89), (1.236; 0.31), (1.153; 1.83), (1.135; 3.45), (1.118; 1.78), (1.092; 0.32), (−0.000; 10.60), (−0.008; 0.57)
Ex. 243:
(7.869; 3.47), (7.756; 1.64), (7.742; 4.70), (7.735; 5.12), (7.733; 4.81), (7.720; 5.46), (7.717; 5.60), (7.713; 5.65), (7.711; 5.86), (7.696; 4.69), (7.651; 0.36), (7.569; 0.46), (7.558; 10.12), (7.556; 10.22), (7.468; 2.77), (7.461; 2.53), (7.446; 4.48), (7.440; 4.21), (7.425; 2.47), (7.419; 2.35), (7.413; 0.33), (7.181; 3.98), (7.145; 1.72), (6.903; 1.78), (6.853; 0.50), (3.856; 0.43), (3.765; 9.54), (3.496; 0.45), (3.490; 0.42), (3.478; 1.35), (3.461; 1.18), (3.440; 2.22), (3.407; 1.04), (3.390; 4.40), (3.372; 4.14), (3.340; 1445.28), (3.289; 0.89), (3.286; 1.08), (3.267; 1.76), (3.240; 0.58), (3.231; 0.39), (3.225; 0.37), (3.216; 1.99), (3.029; 4.85), (3.003; 0.61), (2.953; 11.92), (2.905; 0.71), (2.871; 0.34), (2.677; 0.61), (2.672; 0.84), (2.667; 0.63), (2.663; 0.44), (2.542; 3.54), (2.525; 2.35), (2.521; 3.33), (2.512; 43.82), (2.507; 97.21), (2.503; 137.21), (2.498; 99.50), (2.494; 45.80), (2.334; 0.65), (2.330; 0.89), (2.325; 0.69), (2.305; 0.43), (2.212; 16.00), (2.167; 5.60), (2.074; 0.75), (2.052; 0.41), (1.989; 0.47), (1.397; 3.15), (1.259; 0.45), (1.241; 0.95), (1.234; 0.35), (1.223; 0.40), (1.177; 3.09), (1.159; 7.12), (1.141; 4.90), (1.112; 3.24), (1.095; 1.33), (−0.000; 4.23)
Ex. 244:
(7.920; 4.35), (7.743; 4.90), (7.736; 4.86), (7.733; 4.47), (7.720; 5.11), (7.718; 5.24), (7.714; 5.18), (7.711; 5.27), (7.696; 4.40), (7.555; 9.11), (7.553; 8.99), (7.468; 2.76), (7.461; 2.50), (7.447; 4.17), (7.440; 3.86), (7.425; 2.45), (7.419; 2.28), (7.192; 5.28), (7.141; 0.92), (6.901; 0.63), (3.898; 0.42), (3.881; 1.01), (3.864; 1.39), (3.856; 0.79), (3.848; 1.03), (3.831; 0.49), (3.764; 3.74), (3.428; 1.23), (3.366; 0.69), (3.328; 1146.89), (3.306; 2.17), (3.297; 1.12), (3.291; 1.20), (3.278; 3.48), (3.267; 1.05), (3.262; 0.39), (3.099; 0.47), (2.917; 2.73), (2.874; 16.00), (2.815; 0.76), (2.676; 0.78), (2.671; 1.12), (2.666; 1.12), (2.631; 0.69), (2.630; 0.66), (2.541; 4.86), (2.524; 2.80), (2.520; 3.86), (2.511; 56.47), (2.507; 128.66), (2.502; 183.64), (2.497; 133.68), (2.493; 61.52), (2.461; 0.60), (2.457; 0.71), (2.452; 0.79), (2.447; 0.71), (2.338; 0.43), (2.333; 0.86), (2.329; 1.15), (2.324; 0.88), (2.319; 0.40), (2.212; 15.60),

-continued (2.166; 2.02), (2.074; 1.40), (2.051; 0.48), (1.989; 0.43), (1.398; 7.25), (1.282; 0.41), (1.266; 0.50),
(1.222; 14.81), (1.205; 15.17), (1.170; 3.87), (1.154; 3.53), (1.146; 2.54), (1.130; 1.39), (1.061; 0.46),
(1.044; 0.49), (0.889; 0.38), (−0.000; 8.40)

Ex. 245:
(13.487; 1.79), (13.482; 2.37), (13.478; 2.03), (12.662; 13.70), (12.594; 0.49), (7.816; 3.52), (7.743; 1.37),
(7.736; 1.53), (7.732; 1.50), (7.720; 1.68), (7.717; 1.78), (7.714; 1.73), (7.711; 1.80), (7.695; 1.50),
(7.561; 3.39), (7.559; 3.42), (7.468; 0.93), (7.461; 0.90), (7.447; 1.50), (7.440; 1.36), (7.425; 0.78),
(7.419; 0.78), (7.156; 4.94), (3.856; 0.74), (3.765; 1.30), (3.427; 4.39), (3.392; 0.63), (3.377; 3.05),
(3.375; 1.25), (3.366; 1.51), (3.327; 3345.37), (3.289; 4.60), (3.280; 2.13), (3.277; 2.30), (3.266; 5.53),
(3.226; 0.89), (3.203; 0.50), (3.175; 0.49), (3.168; 0.48), (3.050; 4.97), (3.033; 0.48), (2.966; 5.02),
(2.680; 1.22), (2.675; 2.49), (2.670; 3.49), (2.666; 2.58), (2.661; 1.23), (2.601; 0.80), (2.597; 0.66),
(2.541; 16.00), (2.537; 3.04), (2.524; 10.33), (2.519; 14.24), (2.511; 180.60), (2.506; 400.82),
(2.501; 562.29), (2.497; 402.43), (2.492; 182.84), (2.442; 0.51), (2.338; 1.09), (2.333; 2.39), (2.328; 3.48),
(2.324; 2.57), (2.319; 1.16), (2.305; 0.46), (2.210; 9.52), (2.167; 0.86), (2.073; 9.25), (2.051; 1.13),
(1.398; 1.11), (1.292; 1.03), (1.235; 1.11), (1.108; 0.58), (1.091; 1.06), (1.073; 0.73), (1.055; 0.51),
(0.890; 1.45), (0.008; 0.84), (−0.000; 28.64), (−0.009; 0.79)

Ex. 246:
(7.738; 0.61), (7.654; 0.30), (7.637; 0.34), (7.633; 0.36), (7.566; 0.92), (7.562; 0.93), (7.545; 1.64),
(7.527; 1.07), (7.486; 0.35), (7.470; 1.78), (7.466; 1.49), (7.451; 2.07), (7.259; 3.69), (7.241; 2.23),
(7.220; 1.96), (7.113; 1.24), (7.094; 2.14), (7.076; 1.01), (6.838; 0.42), (6.819; 1.69), (3.871; 15.00),
(3.776; 0.33), (3.708; 0.37), (3.703; 0.31), (3.696; 0.31), (3.635; 0.34), (3.615; 0.37), (3.594; 0.33),
(3.570; 0.37), (3.529; 0.49), (3.513; 0.46), (3.476; 0.89), (3.456; 1.12), (3.317; 1395.59), (3.228; 0.42),
(3.226; 0.39), (3.025; 0.32), (2.947; 2.03), (2.670; 1.14), (2.572; 0.57), (2.559; 0.73), (2.540; 4.62),
(2.505; 142.62), (2.501; 151.37), (2.416; 0.31), (2.331; 1.02), (2.187; 12.57), (2.176; 10.22), (2.069; 0.76),
(2.049; 0.61), (1.398; 2.69), (1.293; 0.36), (1.236; 0.49), (1.162; 2.69), (1.144; 4.88), (1.127; 2.37),
(1.107; 0.33), (0.890; 0.37), (−0.000; 10.65)

Ex. 247:
(8.080; 0.59), (7.798; 1.02), (7.563; 0.81), (7.560; 0.85), (7.551; 1.05), (7.549; 1.25), (7.548; 1.27),
(7.547; 1.10), (7.537; 0.94), (7.534; 1.02), (7.468; 1.55), (7.465; 1.52), (7.456; 1.79), (7.453; 1.56),
(7.270; 3.39), (7.242; 1.91), (7.229; 1.76), (7.109; 1.07), (7.108; 1.04), (7.096; 1.97), (7.095; 1.90),
(7.084; 0.98), (7.082; 0.94), (6.834; 1.08), (3.872; 16.00), (3.852; 0.40), (3.842; 0.66), (3.830; 0.61),
(3.819; 0.42), (3.816; 0.37), (3.811; 0.90), (3.801; 0.48), (3.776; 0.49), (3.357; 371.04), (3.337; 0.38),
(3.334; 0.39), (3.246; 0.81), (2.888; 0.54), (2.853; 3.48), (2.763; 1.54), (2.762; 1.53), (2.630; 3.11),
(2.629; 3.03), (2.616; 0.40), (2.543; 1.43), (2.525; 0.82), (2.522; 1.09), (2.519; 1.25), (2.510; 22.98),
(2.507; 48.66), (2.504; 66.06), (2.501; 47.31), (2.498; 21.21), (2.388; 0.39), (2.210; 0.55), (2.187; 9.27),
(2.174; 5.35), (2.116; 0.54), (1.397; 1.57), (1.208; 3.53), (1.197; 3.77), (1.162; 0.88), (1.142; 4.79),
(1.131; 4.59), (1.057; 1.71), (1.045; 1.70), (0.000; 1.83)

Ex. 248:
(7.906; 3.84), (7.884; 3.79), (7.832; 1.28), (7.721; 0.64), (7.652; 3.60), (7.141; 3.99), (7.119; 3.51),
(7.112; 0.68), (7.096; 0.37), (7.069; 1.53), (7.047; 0.77), (3.844; 15.00), (3.818; 0.38), (3.477; 0.87),
(3.467; 0.96), (3.387; 3.91), (3.320; 73.02), (3.315; 102.30), (3.309; 485.92), (3.255; 0.64), (3.215; 0.38),
(3.070; 0.31), (3.030; 1.95), (3.009; 0.58), (2.958; 3.91), (2.674; 0.60), (2.539; 6.04), (2.505; 69.18),
(2.500; 73.18), (2.328; 0.50), (2.210; 9.74), (2.069; 0.53), (2.049; 0.31), (1.398; 3.00), (1.235; 0.36),
(1.180; 1.94), (1.164; 3.31), (1.147; 2.34), (0.016; 0.87), (0.011; 1.47), (−0.000; 9.89)

Ex. 249:
(7.685; 2.16), (7.568; 0.37), (7.564; 0.40), (7.550; 0.48), (7.547; 0.57), (7.545; 0.58), (7.543; 0.54),
(7.529; 0.46), (7.524; 0.51), (7.471; 0.77), (7.466; 0.78), (7.452; 0.92), (7.448; 0.78), (7.267; 1.74),
(7.242; 0.93), (7.222; 0.82), (7.113; 0.53), (7.111; 0.50), (7.095; 0.94), (7.093; 0.90), (7.076; 0.47),
(7.074; 0.42), (6.810; 1.75), (3.872; 8.00), (3.801; 0.25), (3.428; 0.20), (3.369; 0.20), (3.327; 188.63),
(3.288; 0.25), (3.277; 0.34), (3.245; 0.59), (3.020; 0.94), (2.949; 0.95), (2.689; 0.19), (2.675; 0.16),
(2.671; 0.23), (2.666; 0.17), (2.541; 0.86), (2.524; 0.68), (2.519; 0.97), (2.511; 12.45), (2.506; 27.17),
(2.502; 37.92), (2.497; 27.28), (2.493; 12.65), (2.333; 0.21), (2.329; 0.26), (2.324; 0.18), (2.185; 4.79),
(2.174; 4.81), (1.398; 2.90), (−0.000; 1.06)

Ex. 250:
(7.714; 0.57), (7.226; 5.03), (7.189; 0.47), (6.908; 0.46), (6.799; 2.05), (4.057; 0.35), (4.040; 0.99),
(4.022; 0.98), (4.004; 0.36), (3.813; 2.36), (3.443; 0.81), (3.404; 0.76), (3.339; 2.08), (3.309; 157.08),
(3.285; 4.29), (3.232; 5.94), (2.934; 2.12), (2.540; 0.70), (2.523; 1.16), (2.510; 15.12), (2.505; 27.81),
(2.501; 35.88), (2.497; 24.31), (2.492; 11.35), (2.381; 0.69), (2.365; 2.50), (2.348; 2.57), (2.332; 0.89),
(2.267; 0.46), (2.262; 0.40), (2.251; 0.63), (2.244; 1.14), (2.225; 1.55), (2.207; 1.60), (2.188; 1.39),
(2.158; 13.31), (2.136; 2.75), (2.127; 15.00), (2.070; 0.35), (1.987; 4.28), (1.717; 1.05), (1.698; 1.40),
(1.680; 1.32), (1.661; 0.99), (1.300; 10.42), (1.283; 10.03), (1.265; 1.68), (1.248; 1.81), (1.245; 1.30),
(1.228; 1.13), (1.193; 1.25), (1.176; 2.46), (1.158; 2.38), (1.153; 3.01), (1.135; 5.82), (1.117; 2.92),
(0.821; 4.24), (0.802; 9.36), (0.784; 4.03), (0.778; 1.25), (0.759; 1.59), (0.754; 0.92), (0.740; 0.76), (−0.000; 4.96)

Ex. 251:
(7.910; 0.58), (7.903; 3.28), (7.897; 1.05), (7.885; 1.22), (7.880; 3.37), (7.726; 0.62), (7.709; 0.46),
(7.704; 0.50), (7.234; 2.63), (7.136; 3.41), (7.131; 1.06), (7.114; 1.17), (7.114; 3.04), (7.041; 0.39),
(7.018; 0.35), (6.814; 1.04), (3.843; 15.00), (3.819; 1.57), (3.807; 1.87), (3.800; 1.15), (3.698; 0.53),
(3.498; 0.79), (3.457; 0.65), (3.304; 123.83), (3.281; 16.36), (2.973; 0.58), (2.943; 1.08), (2.940; 1.07),
(2.674; 0.57), (2.669; 0.72), (2.664; 0.67), (2.539; 1.57), (2.522; 3.07), (2.509; 42.15), (2.504; 78.17),
(2.500; 101.51), (2.496; 68.95), (2.491; 32.39), (2.331; 0.63), (2.327; 0.73), (2.322; 0.49), (2.249; 0.71),
(2.210; 1.03), (2.183; 7.84), (2.172; 6.98), (2.138; 0.38), (2.121; 0.92), (2.089; 0.55), (2.070; 0.37),
(2.062; 0.72), (2.049; 0.34), (1.398; 1.56), (1.236; 0.37), (1.160; 1.60), (1.142; 3.18), (1.124; 1.63),
(1.106; 0.40), (1.101; 0.32), (1.083; 0.45), (0.890; 0.36), (−0.000; 7.92)

Ex. 252:
(7.781; 5.27), (7.726; 1.94), (7.719; 2.06), (7.711; 1.95), (7.704; 2.22), (7.695; 3.44), (7.692; 6.54),
(7.674; 2.21), (7.643; 0.55), (7.636; 0.63), (7.620; 0.61), (7.614; 0.63), (7.573; 0.51), (7.557; 0.64),
(7.551; 0.71), (7.536; 0.74), (7.465; 1.21), (7.458; 1.15), (7.444; 2.03), (7.437; 1.92), (7.422; 1.07),
(7.416; 0.97), (7.387; 0.40), (7.381; 0.43), (7.366; 0.61), (7.359; 0.64), (7.338; 0.41), (7.066; 4.57),
(5.747; 0.58), (3.850; 0.43), (3.733; 1.09), (3.469; 0.50), (3.440; 0.54), (3.402; 0.80), (3.348; 5.15),

-continued (3.309; 2464.30), (3.286; 126.16), (3.266; 18.00), (3.195; 0.79), (3.179; 0.73), (3.167; 0.63), (3.137; 0.59),
(3.091; 0.47), (3.054; 7.34), (2.972; 7.54), (2.891; 0.38), (2.674; 2.17), (2.669; 2.81), (2.665; 2.14),
(2.627; 0.40), (2.607; 0.45), (2.539; 5.86), (2.523; 11.25), (2.509; 161.17), (2.505; 299.79), (2.500; 388.93),
(2.496; 263.39), (2.491; 123.33), (2.384; 0.39), (2.345; 0.38), (2.332; 2.14), (2.327; 2.75), (2.323; 1.97),
(2.238; 0.44), (2.216; 15.00), (2.143; 0.46), (2.082; 1.09), (2.069; 1.22), (2.049; 0.99), (1.987; 0.37),
(1.908; 0.77), (1.409; 2.61), (1.404; 2.08), (1.398; 6.96), (1.292; 0.41), (1.237; 0.70), (0.890; 1.45),
(0.008; 1.34), (−0.000; 28.61), (−0.008; 1.06)
Ex. 253:
(7.913; 0.42), (7.906; 3.19), (7.901; 1.13), (7.889; 1.59), (7.884; 4.72), (7.647; 3.20), (7.148; 0.43),
(7.141; 3.33), (7.136; 1.12), (7.124; 1.08), (7.119; 3.17), (7.112; 0.39), (7.076; 1.29), (7.065; 0.35),
(7.043; 0.36), (3.862; 0.50), (3.845; 15.00), (3.833; 0.70), (3.818; 0.79), (3.311; 164.40), (3.288; 8.52),
(3.269; 1.37), (2.918; 0.82), (2.883; 4.52), (2.763; 0.54), (2.633; 1.01), (2.631; 0.99), (2.540; 0.40),
(2.523; 0.77), (2.510; 11.20), (2.506; 20.84), (2.501; 27.11), (2.497; 18.49), (2.492; 8.78), (2.211; 8.04),
(1.398; 1.71), (1.227; 4.42), (1.211; 4.50), (1.178; 1.05), (1.161; 0.90), (1.148; 1.73), (1.131; 1.58),
(1.062; 0.61), (1.046; 0.61), (−0.000; 1.33)
Ex. 254:
(7.913; 0.40), (7.906; 3.23), (7.901; 1.07), (7.889; 1.15), (7.884; 3.50), (7.876; 0.42), (7.777; 3.20),
(7.653; 3.42), (7.148; 0.44), (7.141; 3.41), (7.136; 1.13), (7.124; 1.08), (7.119; 3.18), (7.111; 0.40),
(7.053; 2.75), (3.845; 15.00), (3.818; 0.63), (3.316; 264.58), (3.292; 11.50), (3.269; 1.41), (3.248; 0.53),
(3.052; 4.03), (2.970; 4.09), (2.540; 0.50), (2.523; 0.93), (2.510; 13.24), (2.506; 24.64), (2.501; 31.98),
(2.497; 21.64), (2.493; 10.12), (2.209; 8.68), (1.398; 1.77), (−0.000; 1.76)
Ex. 255:
(7.914; 0.33), (7.906; 3.21), (7.901; 1.09), (7.889; 1.13), (7.884; 3.57), (7.877; 0.50), (7.860; 0.79),
(7.749; 0.56), (7.515; 2.67), (7.514; 2.63), (7.158; 0.85), (7.150; 0.70), (7.142; 3.57), (7.137; 1.38),
(7.125; 1.42), (7.120; 3.44), (3.845; 15.00), (3.818; 1.22), (3.461; 0.36), (3.404; 0.39), (3.388; 0.80),
(3.370; 0.87), (3.350; 0.76), (3.309; 319.77), (3.286; 19.90), (3.215; 1.08), (3.025; 1.00), (2.952; 2.40),
(2.674; 0.32), (2.670; 0.39), (2.665; 0.34), (2.540; 0.85), (2.523; 1.58), (2.510; 22.85), (2.505; 42.61),
(2.501; 55.42), (2.496; 37.59), (2.492; 17.67), (2.332; 0.30), (2.328; 0.41), (2.205; 5.44), (1.398; 1.37),
(1.246; 0.49), (1.175; 0.84), (1.158; 1.80), (1.141; 1.37), (−0.000; 4.35)
Ex. 256:
(7.906; 3.84), (7.901; 1.24), (7.889; 1.19), (7.884; 3.44), (7.877; 0.36), (7.512; 2.65), (7.170; 1.24),
(7.150; 0.56), (7.142; 3.43), (7.137; 1.17), (7.125; 1.25), (7.120; 3.27), (7.113; 0.41), (3.874; 0.37),
(3.845; 15.00), (3.765; 0.37), (3.305; 368.22), (3.282; 15.93), (2.913; 0.66), (2.874; 3.71), (2.762; 0.65),
(2.674; 0.34), (2.669; 0.47), (2.665; 0.35), (2.632; 1.21), (2.631; 1.22), (2.539; 1.23), (2.523; 1.90),
(2.509; 26.87), (2.505; 49.95), (2.500; 64.90), (2.496; 44.02), (2.491; 20.68), (2.332; 0.34), (2.327; 0.44),
(2.322; 0.34), (2.218; 0.51), (2.205; 5.06), (2.069; 0.53), (1.398; 1.54), (1.222; 3.71), (1.205; 3.85),
(1.172; 1.01), (1.159; 0.87), (1.148; 2.30), (1.131; 1.96), (1.062; 0.75), (1.045; 0.73), (−0.000; 6.49)
Ex. 257:
(7.914; 0.38), (7.906; 3.25), (7.901; 1.11), (7.889; 1.12), (7.884; 3.56), (7.877; 0.44), (7.809; 2.45),
(7.518; 2.55), (7.149; 0.53), (7.142; 4.08), (7.138; 3.71), (7.125; 1.17), (7.120; 3.27), (7.113; 0.44),
(3.845; 15.00), (3.304; 163.19), (3.280; 6.34), (3.270; 1.15), (3.049; 3.24), (2.966; 3.31), (2.670; 0.32),
(2.539; 0.79), (2.523; 1.23), (2.509; 17.21), (2.505; 31.98), (2.500; 41.51), (2.496; 28.31), (2.492; 13.37),
(2.205; 8.78), (1.987; 0.52), (1.398; 3.65), (−0.000; 4.52)
Ex. 258:
(7.816; 1.68), (7.702; 0.80), (7.660; 5.73), (7.054; 1.81), (7.031; 0.81), (6.890; 0.35), (3.859; 0.41),
(3.730; 1.58), (3.711; 0.82), (3.568; 0.30), (3.469; 1.01), (3.452; 1.10), (3.422; 0.93), (3.381; 2.57),
(3.363; 3.17), (3.310; 1095.29), (3.286; 53.70), (3.232; 7.41), (3.021; 2.30), (2.949; 5.51), (2.930; 0.47),
(2.674; 0.86), (2.670; 1.19), (2.665; 0.89), (2.539; 2.57), (2.505; 134.74), (2.500; 170.81), (2.496; 117.83),
(2.383; 0.71), (2.367; 2.24), (2.351; 2.34), (2.332; 1.35), (2.327; 1.27), (2.322; 0.96), (2.279; 0.32),
(2.267; 0.53), (2.259; 0.83), (2.250; 0.63), (2.236; 0.95), (2.218; 1.22), (2.200; 1.32), (2.181; 1.13),
(2.150; 15.00), (2.080; 1.20), (2.069; 0.72), (2.049; 0.37), (1.908; 0.57), (1.719; 0.95), (1.700; 1.29),
(1.681; 1.16), (1.663; 0.87), (1.398; 3.34), (1.303; 9.05), (1.286; 8.82), (1.265; 2.04), (1.248; 2.02),
(1.236; 0.64), (1.230; 0.49), (1.174; 1.69), (1.156; 3.88), (1.139; 3.34), (1.122; 1.51), (1.104; 0.45),
(0.890; 0.63), (0.827; 3.75), (0.808; 8.27), (0.790; 3.59), (0.777; 1.01), (0.758; 1.84), (0.746; 0.72),
(0.739; 0.89), (0.727; 0.34), (−0.000; 9.81)
Ex. 259:
(7.762; 5.33), (7.661; 5.35), (7.037; 4.74), (3.858; 0.42), (3.731; 0.92), (3.713; 0.62), (3.469; 0.38),
(3.439; 0.60), (3.421; 0.82), (3.411; 0.76), (3.319; 888.49), (3.296; 46.03), (3.232; 6.56), (3.045; 7.31),
(3.013; 0.45), (2.962; 7.46), (2.671; 0.69), (2.540; 1.34), (2.506; 81.53), (2.501; 103.21), (2.497; 72.71),
(2.383; 0.63), (2.367; 2.12), (2.350; 2.22), (2.333; 1.11), (2.328; 0.86), (2.323; 0.63), (2.267; 0.45),
(2.258; 0.69), (2.250; 0.56), (2.237; 0.92), (2.218; 1.20), (2.200; 1.30), (2.181; 1.07), (2.149; 15.00),
(2.080; 0.73), (2.069; 0.33), (1.737; 0.30), (1.718; 0.94), (1.700; 1.24), (1.681; 1.16), (1.663; 0.88),
(1.644; 0.30), (1.398; 2.81), (1.303; 8.56), (1.286; 8.34), (1.265; 1.81), (1.248; 1.80), (1.236; 0.49),
(1.229; 0.45), (0.890; 0.31), (0.827; 3.66), (0.808; 7.89), (0.790; 3.47), (0.777; 0.95), (0.758; 1.56),
(0.746; 0.61), (0.740; 0.78), (0.729; 0.34), (−0.000; 3.82)
Ex. 260:
(7.845; 1.87), (7.734; 0.83), (7.519; 6.53), (7.143; 2.00), (7.127; 0.56), (7.110; 0.84), (5.747; 0.42),
(4.021; 0.30), (3.779; 1.29), (3.607; 0.50), (3.590; 0.52), (3.568; 0.37), (3.468; 1.09), (3.450; 1.17),
(3.408; 1.17), (3.395; 1.53), (3.380; 2.60), (3.363; 2.98), (3.308; 659.72), (3.284; 22.95), (3.232; 2.52),
(3.177; 2.16), (3.019; 2.66), (2.986; 0.53), (2.982; 0.53), (2.944; 6.60), (2.674; 0.64), (2.670; 0.85),
(2.665; 0.69), (2.562; 0.42), (2.539; 1.82), (2.509; 52.09), (2.505; 94.50), (2.500; 120.27), (2.496; 83.59),
(2.390; 0.94), (2.374; 3.33), (2.358; 3.40), (2.341; 1.08), (2.332; 0.71), (2.327; 0.87), (2.323; 0.64),
(2.263; 0.40), (2.244; 0.75), (2.235; 1.39), (2.216; 2.01), (2.191; 15.00), (2.162; 0.81), (2.069; 0.83),
(1.987; 1.10), (1.742; 0.39), (1.723; 1.38), (1.704; 1.88), (1.686; 1.76), (1.667; 1.30), (1.649; 0.39),
(1.398; 3.68), (1.304; 13.32), (1.287; 13.03), (1.265; 1.91), (1.249; 1.79), (1.237; 0.91), (1.219; 1.15),
(1.201; 0.60), (1.193; 0.45), (1.174; 1.52), (1.169; 2.17), (1.151; 5.00), (1.133; 4.14), (0.816; 5.59),
(0.798; 12.17), (0.779; 5.80), (0.760; 1.37), (0.741; 0.64), (−0.000; 6.25), (−0.008; 0.34)
Ex. 261:
(8.079; 0.81), (7.927; 0.36), (7.892; 3.13), (7.720; 0.65), (7.514; 7.27), (7.152; 3.44), (7.105; 0.64),
(6.901; 0.63), (3.886; 0.44), (3.867; 0.85), (3.852; 1.28), (3.836; 1.24), (3.819; 0.74), (3.803; 0.33), -continued (3.765; 3.19), (3.572; 0.41), (3.408; 0.36), (3.306; 391.72), (3.282; 20.77), (3.232; 2.52), (2.906; 1.96),
(2.866; 10.86), (2.822; 1.25), (2.762; 2.38), (2.674; 0.50), (2.667; 0.83), (2.632; 4.37), (2.540; 1.21),
(2.505; 61.59), (2.500; 76.83), (2.496; 52.59), (2.390; 1.06), (2.374; 3.56), (2.358; 3.67), (2.342; 1.19),
(2.332; 0.59), (2.327; 0.67), (2.323; 0.50), (2.266; 0.32), (2.251; 0.58), (2.243; 0.97), (2.236; 1.48),
(2.217; 2.09), (2.191; 15.00), (2.168; 2.82), (2.070; 0.48), (1.742; 0.48), (1.723; 1.52), (1.704; 2.05),
(1.686; 1.89), (1.667; 1.42), (1.649; 0.48), (1.398; 5.47), (1.304; 14.41), (1.287; 13.96), (1.265; 1.00),
(1.248; 1.33), (1.214; 10.97), (1.198; 11.44), (1.163; 3.68), (1.148; 8.63), (1.131; 6.51), (1.062; 2.65),
(1.056; 0.66), (1.045; 2.64), (1.039; 0.60), (0.817; 6.01), (0.798; 12.73), (0.779; 5.55), (0.758; 0.70),
(0.740; 0.32), (−0.000; 4.59)
Ex. 262:
(7.794; 2.84), (7.524; 3.92), (7.123; 2.77), (3.568; 0.37), (3.408; 0.44), (3.378; 0.53), (3.307; 398.91),
(3.286; 10.96), (3.232; 4.63), (3.042; 5.72), (3.003; 0.56), (2.958; 5.79), (2.674; 0.48), (2.669; 0.62),
(2.665; 0.48), (2.560; 0.32), (2.539; 1.34), (2.505; 67.42), (2.500; 85.22), (2.496; 59.21), (2.390; 0.65),
(2.374; 2.22), (2.357; 2.28), (2.341; 0.74), (2.332; 0.54), (2.327; 0.63), (2.323; 0.44), (2.267; 0.31),
(2.250; 0.49), (2.244; 0.42), (2.234; 1.02), (2.216; 1.48), (2.191; 15.00), (2.180; 1.45), (2.161; 0.46),
(2.069; 0.46), (1.742; 0.30), (1.722; 0.97), (1.704; 1.29), (1.686; 1.19), (1.667; 0.89), (1.398; 3.01),
(1.304; 9.00), (1.287; 8.76), (1.265; 1.22), (1.248; 1.16), (0.816; 3.86), (0.797; 8.27), (0.779; 3.78),
(0.758; 1.03), (0.739; 0.46), (−0.000; 4.24)
Ex. 263:
(7.865; 0.89), (7.754; 0.41), (7.524; 3.25), (7.510; 2.96), (7.506; 1.78), (7.497; 3.35), (7.459; 1.53),
(7.454; 1.55), (7.452; 1.52), (7.173; 1.18), (7.167; 1.81), (7.162; 1.79), (7.156; 1.14), (7.150; 1.00),
(7.144; 0.99), (7.134; 0.59), (4.040; 0.30), (3.834; 15.00), (3.822; 1.15), (3.806; 0.86), (3.790; 0.72),
(3.767; 1.47), (3.478; 0.49), (3.462; 0.50), (3.406; 0.56), (3.390; 1.03), (3.372; 1.13), (3.309; 203.18),
(3.285; 17.37), (3.226; 0.43), (3.027; 1.20), (2.954; 2.93), (2.540; 0.68), (2.510; 18.71), (2.505; 33.19),
(2.501; 41.42), (2.497; 27.90), (2.208; 6.14), (2.170; 1.03), (1.987; 1.18), (1.193; 0.42), (1.175; 1.57),
(1.158; 2.39), (1.142; 1.75), (1.117; 0.76), (−0.000; 2.40)
Ex. 264:
(7.739; 0.52), (7.595; 4.58), (7.576; 5.02), (7.249; 5.08), (7.205; 4.95), (7.185; 4.49), (6.842; 2.25),
(3.461; 0.50), (3.394; 0.84), (3.356; 1.16), (3.308; 251.06), (3.284; 26.87), (3.249; 0.32), (2.955; 2.23),
(2.675; 0.37), (2.670; 0.48), (2.665; 0.44), (2.540; 0.93), (2.510; 28.47), (2.506; 51.15), (2.501; 64.36),
(2.497; 43.84), (2.333; 0.39), (2.328; 0.47), (2.323; 0.35), (2.190; 13.75), (2.155; 15.00), (1.398; 7.66),
(1.166; 3.80), (1.148; 7.82), (1.131; 3.69), (−0.000; 4.58)
Ex. 265:
(7.798; 0.75), (7.596; 5.50), (7.576; 5.89), (7.246; 5.23), (7.205; 5.86), (7.186; 5.37), (6.849; 1.98),
(3.837; 0.48), (3.809; 0.55), (3.409; 0.33), (3.395; 0.44), (3.311; 538.81), (3.287; 39.43), (2.870; 7.50),
(2.675; 0.49), (2.670; 0.65), (2.666; 0.53), (2.633; 0.50), (2.540; 1.29), (2.523; 2.59), (2.510; 38.16),
(2.506; 70.70), (2.501; 91.35), (2.497; 62.01), (2.493; 29.07), (2.333; 0.55), (2.328; 0.66), (2.324; 0.49),
(2.318; 0.30), (2.189; 13.28), (2.155; 15.00), (2.124; 0.35), (2.070; 0.47), (1.398; 10.40), (1.209; 5.75),
(1.194; 6.24), (1.148; 1.17), (1.131; 0.89), (1.063; 0.35), (1.045; 0.35), (0.890; 0.31), (0.008; 0.31), (−0.000;
6.82)
Ex. 266:
(7.691; 6.50), (7.596; 5.15), (7.577; 5.76), (7.251; 5.06), (7.206; 5.66), (7.186; 5.23), (6.835; 5.27),
(3.310; 600.14), (3.287; 43.52), (3.216; 0.34), (3.013; 2.57), (2.985; 2.36), (2.973; 2.57), (2.967; 2.59),
(2.679; 0.34), (2.675; 0.58), (2.670; 0.76), (2.666; 0.56), (2.540; 1.59), (2.523; 3.03), (2.510; 42.66),
(2.506; 79.18), (2.501; 102.35), (2.497; 69.65), (2.492; 32.78), (2.332; 0.59), (2.328; 0.73), (2.324; 0.52),
(2.319; 0.32), (2.189; 15.00), (2.154; 14.95), (2.070; 0.42), (1.398; 11.01), (0.890; 0.32), (−0.000; 6.24)
Ex. 267:
(7.868; 1.42), (7.697; 0.33), (7.656; 3.46), (7.472; 0.34), (7.183; 0.44), (7.061; 1.42), (6.885; 0.32),
(3.859; 1.73), (3.839; 0.49), (3.822; 0.37), (3.729; 1.27), (3.422; 0.74), (3.297; 110.79), (3.274; 5.03),
(3.232; 2.01), (2.910; 0.90), (2.874; 4.94), (2.826; 0.49), (2.669; 0.35), (2.539; 0.95), (2.522; 1.36),
(2.509; 21.22), (2.504; 39.68), (2.500; 51.51), (2.495; 35.49), (2.491; 17.01), (2.384; 0.42), (2.367; 1.40),
(2.351; 1.46), (2.335; 0.57), (2.326; 0.43), (2.322; 0.32), (2.256; 0.32), (2.238; 0.63), (2.219; 0.75),
(2.201; 0.78), (2.182; 0.68), (2.151; 9.25), (2.081; 0.93), (1.719; 0.57), (1.700; 0.76), (1.682; 0.74),
(1.663; 0.56), (1.398; 15.00), (1.303; 5.70), (1.286; 5.54), (1.265; 0.64), (1.246; 1.00), (1.229; 1.36),
(1.220; 4.90), (1.203; 5.03), (1.170; 1.47), (1.154; 1.17), (0.827; 2.32), (0.809; 5.07), (0.790; 2.21),
(0.777; 0.42), (0.766; 0.49), (0.758; 0.66), (0.747; 0.85), (0.729; 0.39), (−0.000; 4.66)
Ex. 268:
(7.822; 0.68), (7.806; 0.90), (7.801; 0.65), (7.783; 0.66), (7.489; 3.41), (7.467; 5.10), (7.394; 3.80),
(7.376; 4.24), (7.371; 2.60), (7.354; 2.86), (7.227; 3.09), (7.217; 5.36), (7.199; 3.87), (6.853; 1.00),
(6.827; 0.84), (4.204; 0.60), (3.993; 0.69), (3.907; 0.67), (3.882; 0.79), (3.864; 0.92), (3.843; 1.06),
(3.826; 1.04), (3.799; 1.34), (3.775; 0.67), (3.751; 0.70), (3.727; 0.74), (3.698; 0.75), (3.689; 0.85),
(3.676; 1.00), (3.667; 0.70), (3.645; 0.78), (3.639; 0.81), (3.627; 0.86), (3.614; 0.94), (3.602; 0.92),
(3.598; 1.06), (3.582; 1.05), (3.561; 1.13), (3.556; 1.12), (3.501; 1.88), (3.501; 1.62), (3.494; 1.63),
(3.480; 1.68), (3.454; 1.97), (3.429; 2.49), (3.416; 3.06), (3.401; 3.82), (3.389; 4.87), (3.312; 4328.58),
(3.288; 176.73), (3.228; 1.36), (2.877; 7.14), (2.674; 3.24), (2.670; 4.57), (2.665; 3.33), (2.647; 0.62),
(2.540; 9.04), (2.523; 20.07), (2.509; 266.05), (2.505; 489.53), (2.501; 630.79), (2.496; 433.53),
(2.492; 206.91), (2.438; 0.93), (2.332; 3.16), (2.327; 4.56), (2.323; 2.94), (2.188; 12.86), (2.160; 15.00),
(2.069; 5.65), (2.049; 0.63), (1.987; 0.75), (1.398; 1.16), (1.292; 0.61), (1.212; 8.11), (1.199; 8.44),
(0.890; 1.10), (0.854; 0.60), (0.008; 1.48), (−0.000; 31.14)
Ex. 269:
(7.691; 2.76), (7.486; 2.68), (7.465; 4.05), (7.464; 3.97), (7.392; 3.15), (7.375; 3.66), (7.370; 2.21),
(7.352; 2.71), (7.225; 4.62), (7.215; 3.99), (7.214; 4.05), (7.198; 3.14), (7.196; 3.12), (6.828; 3.03),
(3.424; 0.32), (3.411; 0.41), (3.393; 0.74), (3.382; 0.76), (3.376; 1.04), (3.371; 0.90), (3.307; 1289.41),
(3.284; 72.87), (3.200; 0.60), (3.181; 0.54), (3.151; 0.46), (3.139; 0.41), (3.125; 0.37), (3.098; 0.36),
(3.013; 2.75), (2.996; 2.65), (2.975; 2.71), (2.903; 0.35), (2.890; 0.35), (2.679; 0.76), (2.674; 1.28),
(2.669; 1.68), (2.665; 1.30), (2.604; 0.42), (2.576; 0.65), (2.539; 3.20), (2.523; 7.26), (2.509; 94.75),
(2.505; 175.75), (2.500; 228.34), (2.496; 156.14), (2.492; 73.75), (2.356; 0.31), (2.332; 1.19), (2.327; 1.53),
(2.322; 1.16), (2.301; 0.32), (2.185; 14.99), (2.155; 15.00), (2.069; 2.42), (1.987; 0.32), (1.398; 6.20),
(1.253; 0.32), (1.236; 0.65), (1.109; 0.37), (1.091; 0.59), (1.073; 0.37), (0.890; 0.38), (0.008; 1.50), (−0.000;
29.53), (−0.008; 0.94)

-continued

Ex. 270:
(7.910; 0.43), (7.902; 3.23), (7.897; 1.10), (7.885; 1.17), (7.880; 3.48), (7.873; 0.42), (7.726; 1.15),
(7.704; 1.22), (7.681; 3.03), (7.235; 2.66), (7.205; 0.94), (7.136; 3.40), (7.131; 1.20), (7.119; 1.09),
(7.114; 3.17), (7.106; 0.38), (7.040; 1.25), (7.018; 1.16), (6.925; 0.95), (6.807; 2.62), (3.843; 15.00),
(3.819; 4.53), (3.807; 5.62), (3.708; 0.33), (3.498; 1.96), (3.375; 0.63), (3.339; 2.23), (3.308; 402.32),
(3.284 10.77), (3.013; 1.38), (2.953; 1.45), (2.674; 0.38), (2.670; 0.50), (2.665; 0.37), (2.539; 1.02),
(2.523; 2.22), (2.509; 28.10), (2.505; 52.18), (2.500; 67.62), (2.496; 46.50), (2.492; 22.05), (2.332; 0.38),
(2.327; 0.49), (2.323; 0.35), (2.210; 3.00), (2.183; 8.23), (2.172; 8.13), (2.151; 0.35), (2.121; 2.99),
(2.069; 0.49), (1.398; 6.57), (−0.000; 2.78)
Ex. 271:
(7.505; 2.84), (7.496; 1.62), (7.492; 2.44), (7.455; 1.49), (7.451; 1.48), (7.243; 2.65), (7.164; 0.77),
(7.157; 0.81), (7.154; 0.80), (7.150; 0.71), (7.146; 0.91), (7.141; 0.73), (7.134; 0.67), (6.822; 1.03),
(3.831; 15.00), (3.395; 0.40), (3.310; 255.35), (3.286; 8.20), (2.982; 0.55), (2.944; 1.15), (2.540; 0.46),
(2.523; 1.14), (2.510; 15.58), (2.505; 28.81), (2.501; 37.35), (2.496; 25.42), (2.492; 12.03), (2.188; 8.24),
(2.176; 7.20), (2.070; 0.41), (1.162; 1.71), (1.144; 3.34), (1.126; 1.59), (−0.000; 1.71)
Ex. 272:
(7.910; 0.45), (7.903; 3.22), (7.898; 1.09), (7.886; 1.18), (7.881; 3.43), (7.873; 0.40), (7.789; 0.43),
(7.727; 1.03), (7.722; 0.38), (7.710; 0.41), (7.705; 1.09), (7.229; 2.73), (7.205; 0.85), (7.143; 0.50),
(7.136; 3.40), (7.130; 1.14), (7.118; 1.14), (7.113; 3.12), (7.106; 0.36), (7.040; 1.09), (7.035; 0.37),
(7.023; 0.36), (7.018; 1.00), (6.926; 0.85), (6.821; 0.96), (3.843; 15.00), (3.819; 4.20), (3.807; 5.07),
(3.498; 1.65), (3.303; 111.27), (3.280; 1.52), (2.862; 3.42), (2.540; 0.33), (2.523; 0.93), (2.509; 13.13),
(2.505; 24.30), (2.501; 31.36), (2.496; 21.48), (2.492; 10.29), (2.210; 2.71), (2.185; 8.02), (2.172; 6.88),
(2.147; 0.31), (2.121; 2.60), (1.398; 13.12), (1.205; 2.82), (1.191; 3.14), (−0.000; 2.78)
Ex. 273:
(7.667; 4.35), (7.231; 4.67), (6.793; 4.12), (3.812; 0.60), (3.477; 0.38), (3.447; 0.53), (3.428; 0.54),
(3.371; 1.73), (3.306; 556.35), (3.232; 4.74), (3.007; 2.61), (2.945; 2.60), (2.674; 0.83), (2.669; 1.17),
(2.665; 0.84), (2.539; 1.99), (2.522; 4.81), (2.509; 69.58), (2.505; 130.08), (2.500; 170.60), (2.496; 118.38),
(2.491; 57.65), (2.440; 0.42), (2.380; 0.82), (2.364; 2.58), (2.348; 2.69), (2.331; 1.66), (2.327; 1.45),
(2.322; 0.99), (2.318; 0.62), (2.284; 0.30), (2.262; 0.38), (2.242; 1.08), (2.223; 1.49),
(2.205; 1.51), (2.187; 1.32), (2.158; 14.90), (2.126; 15.00), (2.085; 0.49), (2.069; 0.90), (1.908; 0.31),
(1.735; 0.35), (1.716; 1.01), (1.697; 1.42), (1.679; 1.33), (1.661; 1.00), (1.642; 0.32), (1.398; 12.20),
(1.300; 10.69), (1.283; 10.43), (1.265; 1.37), (1.248; 1.40), (1.237; 0.59), (1.228; 0.55), (1.106; 0.39),
(0.890; 0.39), (0.820; 4.27), (0.802; 9.60), (0.783; 4.17), (0.758; 1.15), (0.739; 0.56), (0.008; 0.43), (−0.000;
14.42)
Ex. 274:
(7.802; 2.88), (7.515; 2.65), (7.513; 2.72), (7.129; 3.98), (3.430; 0.37), (3.330; 233.68), (3.308; 0.43),
(3.233; 6.89), (3.043; 3.81), (2.957; 3.90), (2.541; 0.93), (2.525; 0.51), (2.520; 0.71), (2.511; 9.43),
(2.507; 21.40), (2.502; 30.49), (2.497; 22.09), (2.493; 10.07), (2.188; 7.81), (2.187; 7.83), (2.153; 0.44),
(2.074; 0.32), (1.765; 13.11), (1.710; 16.00), (1.655; 3.10), (1.424; 0.93), (1.398; 1.17), (−0.000; 1.79)
Ex. 275:
(7.826; 1.43), (7.712; 0.71), (7.657; 4.79), (7.062; 1.42), (7.036; 0.66), (4.221; 0.34), (3.469; 0.52),
(3.452; 0.53), (3.429; 0.83), (3.401; 0.44), (3.383; 1.24), (3.365; 1.87), (3.329; 511.53), (3.290; 0.59),
(3.279; 0.99), (3.178; 0.57), (3.024; 2.13), (2.949; 4.98), (2.675; 0.37), (2.671; 0.55), (2.666; 0.39),
(2.541; 2.01), (2.524; 1.70), (2.519; 2.40), (2.511; 28.91), (2.506; 62.53), (2.502; 87.07), (2.497; 62.76),
(2.493; 29.15), (2.333; 0.40), (2.329; 0.57), (2.324; 0.39), (2.179; 10.73), (2.073; 0.59), (1.761; 15.94),
(1.734; 0.44), (1.706; 16.00), (1.689; 0.37), (1.679; 0.44), (1.656; 0.59), (1.398; 1.70), (1.174; 1.42),
(1.157; 3.06), (1.138; 2.14), (1.119; 0.59), (−0.000; 2.66)
Ex. 276:
(7.768; 0.87), (7.224; 4.93), (7.191; 1.03), (6.908; 0.93), (6.806; 1.82), (6.675; 0.39), (3.842; 0.52),
(3.813; 4.87), (3.785; 0.43), (3.702; 2.54), (3.572; 0.40), (3.446; 0.99), (3.424; 0.66), (3.391; 0.87),
(3.307; 1038.24), (3.284; 8.89), (3.232; 3.03), (2.889; 0.95), (2.853; 6.27), (2.813; 1.08), (2.790; 0.68),
(2.674; 1.24), (2.669; 1.59), (2.630; 0.35), (2.539; 2.56), (2.522; 7.38), (2.509; 91.13), (2.505; 166.01),
(2.500; 212.69), (2.496; 149.36), (2.442; 0.62), (2.429; 0.42), (2.381; 0.80), (2.365; 2.56), (2.348; 2.66),
(2.332; 1.90), (2.327; 1.67), (2.323; 1.29), (2.261; 0.54), (2.243; 1.35), (2.224; 1.71), (2.207; 1.68),
(2.188; 1.47), (2.157; 12.73), (2.137; 5.07), (2.127; 15.00), (2.119; 4.67), (2.095; 0.45), (2.069; 1.70),
(2.065; 2.08), (2.026; 0.32), (2.006; 0.48), (1.991; 0.60), (1.971; 0.55), (1.948; 0.49), (1.717; 1.09),
(1.698; 1.45), (1.680; 1.35), (1.661; 1.01), (1.643; 0.35), (1.399; 14.99), (1.351; 0.43), (1.336; 0.36),
(1.300; 9.83), (1.283; 9.44), (1.265; 1.04), (1.245; 2.69), (1.228; 2.73), (1.199; 5.59), (1.183; 6.35),
(1.155; 2.98), (1.132; 0.81), (1.057; 0.52), (1.039; 0.42), (0.821; 4.12), (0.802; 8.85), (0.784; 3.96),
(0.754; 1.51), (0.734; 0.72), (−0.000; 13.85)
Ex. 277:
(7.833; 1.32), (7.719; 0.61), (7.588; 5.65), (7.512; 2.45), (7.491; 3.57), (7.490; 3.50), (7.410; 2.72),
(7.392; 3.12), (7.387; 1.85), (7.370; 2.33), (7.239; 3.40), (7.221; 2.68), (7.086; 1.52),
(7.061; 0.75), (3.482; 0.65), (3.465; 0.70), (3.452; 0.49), (3.430; 0.42), (3.422; 0.46), (3.407; 0.84),
(3.392; 1.59), (3.374; 1.93), (3.311; 1019.79), (3.187; 0.36), (3.031; 1.97), (2.962; 4.51), (2.679; 0.50),
(2.674; 0.83), (2.670; 1.06), (2.665; 0.87), (2.540; 1.88), (2.523; 4.87), (2.510; 62.00), (2.505; 114.23),
(2.501; 147.93), (2.496; 102.19), (2.492; 49.56), (2.332; 0.78), (2.327; 1.05), (2.323; 0.77), (2.183; 15.00),
(2.069; 1.10), (1.398; 2.39), (1.235; 0.34), (1.182; 1.77), (1.165; 3.53), (1.149; 2.19), (−0.000; 4.24)
Ex. 278:
(7.840; 0.66), (7.637; 2.59), (7.613; 2.09), (7.594; 2.26), (7.228; 2.23), (7.209; 2.05), (7.098; 0.72),
(7.074; 0.35), (3.485; 0.31), (3.468; 0.34), (3.394; 0.77), (3.375; 0.92), (3.309; 559.54), (3.286; 5.36),
(3.033; 0.95), (2.964; 2.17), (2.891; 0.45), (2.732; 0.35), (2.674; 0.43), (2.670; 0.59), (2.665; 0.43),
(2.540; 0.70), (2.523; 2.54), (2.509; 33.15), (2.505; 60.97), (2.501; 78.52), (2.496; 53.98), (2.492; 25.86),
(2.332; 0.43), (2.327; 0.56), (2.323; 0.42), (2.183; 6.62), (2.069; 0.59), (1.987; 0.34), (1.398; 15.00),
(1.183; 0.77), (1.175; 0.85), (1.167; 1.61), (1.157; 1.01), (1.150; 1.03), (−0.000; 1.27)
Ex. 279:
(7.894; 2.25), (7.718; 0.43), (7.633; 5.85), (7.612; 4.88), (7.593; 5.33), (7.227; 5.26), (7.208; 4.83),
(7.105; 2.33), (7.075; 0.49), (3.870; 0.58), (3.854; 0.76), (3.837; 0.58), (3.729; 0.62), (3.310; 393.82),
(3.287; 3.23), (2.921; 1.46), (2.889; 7.95), (2.675; 0.39), (2.670; 0.51), (2.666; 0.38), (2.540; 0.64),
(2.524; 2.33), (2.510; 28.80), (2.506; 53.00), (2.501; 68.19), (2.497; 46.89), (2.493; 22.37), (2.333; 0.37),

-continued (2.328; 0.49), (2.324; 0.36), (2.185; 15.00), (2.082; 0.45), (2.070; 0.51), (1.398; 7.69), (1.231; 7.86),
(1.215; 8.03), (1.184; 2.01), (1.169; 1.67), (−0.000; 0.72)
Ex. 280:
(7.889; 1.96), (7.710; 0.39), (7.585; 5.62), (7.513; 2.57), (7.491; 3.78), (7.410; 2.74), (7.392; 3.21),
(7.387; 1.91), (7.370; 2.34), (7.239; 3.48), (7.222; 2.84), (7.096; 2.04), (7.065; 0.46), (3.869; 0.59),
(3.852; 0.75), (3.835; 0.60), (3.395; 0.44), (3.311; 579.08), (2.918; 1.44), (2.888; 7.66), (2.674; 0.53),
(2.670; 0.68), (2.666; 0.50), (2.566; 0.60), (2.540; 1.19), (2.523; 3.22), (2.510; 38.96), (2.506; 71.34),
(2.501; 91.92), (2.497; 63.82), (2.493; 30.88), (2.332; 0.50), (2.328; 0.62), (2.323; 0.48), (2.185; 15.00),
(2.070; 0.60), (1.398; 6.99), (1.230; 7.74), (1.213; 7.85), (1.183; 1.85), (1.168; 1.49), (−0.000; 4.48)
Ex. 281:
(7.779; 5.40), (7.589; 5.52), (7.514; 2.29), (7.491; 3.48), (7.410; 2.49), (7.392; 2.92), (7.387; 1.71),
(7.370; 2.11), (7.240; 3.16), (7.222; 2.59), (7.069; 4.61), (3.309; 435.94), (3.286; 3.21), (3.054; 5.87),
(2.975; 5.94), (2.675; 0.39), (2.670; 0.52), (2.666; 0.38), (2.540; 0.87), (2.523; 2.36), (2.510; 30.29),
(2.506; 55.67), (2.501; 71.67), (2.497; 49.42), (2.492; 23.67), (2.333; 0.37), (2.328; 0.50), (2.323; 0.38),
(2.182; 15.00), (2.070; 0.48), (1.398; 8.28), (−0.000; 3.12)
Ex. 282:
(7.787; 1.28), (7.638; 1.33), (7.612; 1.05), (7.593; 1.15), (7.227; 1.13), (7.208; 1.04), (7.082; 1.09),
(3.307; 82.40), (3.283; 0.84), (3.056; 1.49), (2.977; 1.51), (2.523; 0.49), (2.510; 6.23), (2.506; 11.46),
(2.501; 14.76), (2.497; 10.16), (2.492; 4.85), (2.183; 3.51), (1.398; 15.00), (−0.000; 0.42)
Ex. 283:
(8.185; 0.62), (7.744; 0.54), (7.721; 2.47), (7.715; 4.31), (7.699; 4.73), (7.693; 4.58), (7.678; 2.46),
(7.658; 0.32), (7.644; 0.35), (7.459; 1.30), (7.453; 1.22), (7.438; 2.31), (7.432; 2.06), (7.417; 1.20),
(7.410; 1.11), (7.269; 3.33), (7.249; 0.47), (7.231; 0.36), (7.181; 0.36), (7.162; 0.35), (6.831; 1.27),
(4.143; 0.69), (4.125; 0.73), (3.683; 0.37), (3.655; 0.34), (3.457; 0.67), (3.444; 0.77), (3.440; 0.84),
(3.427; 0.87), (3.409; 0.98), (3.378; 1.69), (3.375; 1.78), (3.308; 1186.03), (3.285; 16.71), (3.214; 0.68),
(3.165; 0.43), (3.137; 0.36), (3.131; 0.36), (3.111; 0.35), (3.102; 0.33), (3.072; 0.33), (3.050; 0.33),
(2.947; 2.21), (2.913; 0.46), (2.871; 0.45), (2.718; 0.58), (2.674; 1.23), (2.670; 1.50), (2.665; 1.21),
(2.522; 7.05), (2.509; 92.00), (2.505; 165.38), (2.500; 208.86), (2.496; 143.21), (2.332; 1.22), (2.327; 1.54),
(2.323; 1.13), (2.300; 1.56), (2.226; 0.36), (2.221; 0.38), (2.194; 15.00), (2.182; 12.33), (2.069; 1.17),
(1.987; 0.46), (1.398; 9.67), (1.237; 0.52), (1.229; 1.18), (1.211; 1.81), (1.193; 1.06), (1.163; 2.92),
(1.145; 5.54), (1.128; 2.82), (1.086; 0.41), (1.074; 0.36), (1.056; 0.78), (1.039; 0.46), (0.891; 0.42),
(0.008; 0.53), (−0.000; 9.20), (−0.008; 0.35)
Ex. 284:
(7.123; 0.36), (7.110; 0.49), (5.747; 0.38), (3.514; 0.32), (3.489; 0.36), (3.303; 1370.46), (3.280; 19.83),
(3.190; 0.49), (3.175; 0.65), (3.158; 1.19), (3.141; 1.48), (3.124; 1.09), (3.107; 0.58), (3.077; 0.78),
(3.058; 0.68), (2.984; 1.37), (2.925; 0.35), (2.678; 1.03), (2.673; 1.92), (2.669; 2.59), (2.664; 1.93),
(2.624; 0.33), (2.522; 11.92), (2.509; 150.99), (2.504; 277.07), (2.500; 357.04), (2.495; 246.08),
(2.491; 119.06), (2.370; 0.37), (2.363; 0.33), (2.331; 2.24), (2.326; 2.88), (2.322; 2.01), (2.277; 0.34),
(2.256; 0.36), (2.227; 0.45), (2.203; 0.48), (2.160; 4.04), (2.134; 4.98), (2.069; 1.37), (2.035; 0.37),
(2.015; 0.36), (1.987; 0.60), (1.907; 0.44), (1.399; 0.66), (1.264; 0.68), (1.242; 15.00), (1.224; 14.47),
(1.212; 0.91), (1.192; 0.34), (1.174; 0.35), (1.106; 1.18), (0.890; 0.57), (0.008; 0.59), (−0.000; 13.64), (−0.008; 0.65)
Ex. 285:
(7.749; 0.39), (7.069; 2.85), (6.754; 1.32), (6.549; 0.50), (5.746; 0.39), (4.651; 0.35), (4.645; 0.35),
(4.039; 0.63), (4.021; 0.62), (3.810; 0.33), (3.790; 0.31), (3.540; 0.33), (3.513; 0.36), (3.494; 0.44),
(3.480; 0.53), (3.473; 0.51), (3.439; 0.73), (3.311; 1646.60), (3.288; 25.24), (3.218; 0.45), (3.192; 0.32),
(3.172; 0.62), (3.155; 1.14), (3.138; 1.46), (3.121; 1.02), (3.103; 0.40), (2.909; 0.52), (2.887; 0.46),
(2.846; 4.23), (2.674; 1.36), (2.670; 1.79), (2.665; 1.31), (2.523; 8.40), (2.509; 108.23), (2.505; 197.06),
(2.500; 252.25), (2.496; 175.31), (2.492; 86.50), (2.431; 0.59), (2.332; 1.44), (2.327; 1.89), (2.323; 1.37),
(2.253; 1.03), (2.214; 0.56), (2.201; 0.47), (2.140; 7.82), (2.121; 8.66), (2.069; 0.86), (1.987; 2.48),
(1.398; 1.31), (1.251; 2.67), (1.240; 15.00), (1.223; 14.41), (1.212; 1.74), (1.193; 4.35), (1.175; 4.99),
(1.157; 1.66), (1.107; 0.99), (0.890; 0.48), (−0.000; 2.94)
Ex. 286:
(7.072; 2.58), (6.748; 1.22), (4.039; 0.40), (4.021; 0.42), (3.308; 1577.08), (3.284; 24.88), (3.172; 0.66),
(3.155; 1.19), (3.138; 1.54), (3.121; 1.15), (3.104; 0.54), (2.986; 0.52), (2.931; 1.24), (2.678; 0.80),
(2.674; 1.42), (2.669; 1.90), (2.665; 1.39), (2.660; 0.74), (2.522; 8.76), (2.509; 110.26), (2.505; 200.92),
(2.500; 258.03), (2.496; 175.51), (2.491; 83.75), (2.331; 1.65), (2.327; 2.11), (2.322; 1.48), (2.318; 0.76),
(2.252; 0.63), (2.227; 0.33), (2.216; 0.42), (2.208; 0.33), (2.200; 0.33), (2.141; 7.64), (2.120; 8.26),
(2.069; 0.91), (2.034; 0.38), (2.015; 0.37), (1.987; 1.71), (1.398; 2.49), (1.264; 0.70), (1.254; 1.62),
(1.251; 1.84), (1.240; 15.00), (1.229; 2.53), (1.223; 14.13), (1.212; 1.09), (1.201; 0.45), (1.193; 0.70),
(1.184; 0.43), (1.175; 1.15), (1.166; 0.37), (1.157; 0.84), (1.149; 2.12), (1.132; 4.02), (1.114; 1.95),
(0.008; 0.53), (−0.000; 12.46), (−0.008; 0.55)
Ex. 287:
(7.793; 0.79), (7.682; 0.37), (7.422; 3.66), (7.006; 0.92), (6.991; 0.58), (3.452; 0.72), (3.441; 0.82),
(3.415; 0.94), (3.326; 1401.71), (3.241; 0.88), (3.219; 0.60), (3.193; 0.52), (3.188; 0.49), (3.181; 0.77),
(3.164; 1.33), (3.147; 1.71), (3.129; 1.24), (3.112; 0.67), (3.013; 1.32), (2.980; 0.40), (2.942; 2.91),
(2.675; 0.71), (2.671; 0.87), (2.666; 0.73), (2.541; 3.57), (2.524; 4.16), (2.510; 46.92), (2.506; 85.61),
(2.501; 109.81), (2.497; 74.92), (2.493; 35.43), (2.338; 0.33), (2.333; 0.57), (2.328; 0.77), (2.324; 0.56),
(2.147; 10.08), (2.069; 1.04), (2.050; 0.52), (1.398; 0.38), (1.245; 15.00), (1.228; 14.69), (1.205; 0.39),
(1.187; 0.41), (1.168; 1.06), (1.151; 2.20), (1.135; 1.54), (0.008; 0.50), (−0.000; 8.67)
Ex. 288:, (7.221; 2.26), (6.809; 0.77), (4.057; 0.31), (4.039; 0.97), (4.022; 0.97), (4.004; 0.33),
(3.306; 130.00), (2.933; 1.02), (2.540; 0.31), (2.509; 9.27), (2.505; 16.66), (2.501; 21.21), (2.496; 14.85),
(2.152; 15.00), (1.987; 4.29), (1.978; 0.35), (1.398; 0.98), (1.193; 1.20), (1.175; 2.36), (1.157; 1.84),
(1.154; 1.34), (1.136; 2.38), (1.118; 1.22), (−0.000; 1.32)
Ex. 289:
(7.692; 0.43), (7.068; 3.16), (6.749; 1.97), (3.300; 166.39), (3.186; 0.48), (3.169; 1.07), (3.152; 1.44),
(3.135; 1.15), (3.120; 0.63), (2.935; 1.93), (2.673; 0.34), (2.669; 0.43), (2.539; 2.35), (2.504; 45.99),
(2.500; 58.02), (2.496; 41.11), (2.332; 0.33), (2.327; 0.43), (2.323; 0.33), (2.142; 11.17), (2.119; 4.97),
(2.113; 9.33), (2.049; 0.31), (1.293; 0.56), (1.268; 0.62), (1.237; 15.00), (1.220; 14.51), (1.200; 1.55),
(1.184; 0.62), (1.149; 3.06), (1.132; 6.12), (1.114; 3.13), (−0.000; 7.06)

-continued

Ex. 290:
(7.854; 1.25), (7.735; 0.67), (7.574; 5.59), (7.248; 0.46), (7.230; 0.43), (7.180; 0.52), (7.162; 0.44),
(6.866; 1.53), (6.851; 0.86), (3.806; 14.39), (3.788; 0.30), (3.477; 0.62), (3.459; 0.60), (3.441; 0.31),
(3.410; 0.47), (3.393; 1.08), (3.375; 1.10), (3.357; 0.52), (3.303; 51.05), (3.034; 2.11), (2.961; 4.17),
(2.509; 8.08), (2.505; 14.57), (2.500; 18.52), (2.496; 12.92), (2.338; 15.00), (2.300; 2.14), (1.189; 1.45),
(1.171; 2.97), (1.162; 1.90), (1.154; 1.72), (−0.000; 4.53),
Ex. 291:
(7.863; 1.31), (7.749; 0.62), (7.448; 5.05), (7.248; 0.62), (7.230; 0.57), (7.181; 0.69), (7.162; 0.58),
(6.862; 1.74), (3.806; 14.95), (3.477; 0.53), (3.460; 0.56), (3.409; 0.49), (3.391; 1.13), (3.374; 1.15),
(3.356; 0.56), (3.309; 79.21), (3.285; 2.36), (3.033; 1.91), (2.955; 4.28), (2.510; 6.12), (2.505; 11.09),
(2.501; 14.18), (2.497; 9.96), (2.338; 15.00), (2.300; 2.83), (1.187; 1.25), (1.169; 2.84), (1.151; 2.11),
(1.130; 0.63), (−0.000; 2.43)
Ex. 292:
(7.685; 0.72), (7.631; 0.52), (7.607; 0.61), (7.591; 0.57), (7.577; 0.67), (7.557; 0.60), (7.337; 1.63),
(7.318; 4.39), (7.300; 4.95), (7.267; 6.07), (7.250; 4.46), (7.232; 2.94), (7.217; 1.34), (7.193; 0.56),
(7.074; 4.91), (6.748; 2.44), (4.153; 0.65), (4.086; 0.56), (4.062; 10.08), (3.485; 0.60), (3.470; 0.76),
(3.455; 0.95), (3.414; 1.67), (3.306; 1794.57), (3.216; 1.82), (3.147; 1.06), (3.121; 0.74), (3.105; 0.73),
(3.099; 0.70), (3.081; 0.77), (3.062; 0.52), (2.994; 0.84), (2.981; 1.12), (2.929; 2.87), (2.875; 0.54),
(2.733; 0.56), (2.718; 0.52), (2.695; 0.70), (2.674; 2.17), (2.669; 2.64), (2.665; 2.22), (2.637; 0.68),
(2.626; 0.60), (2.539; 14.79), (2.504; 284.22), (2.500; 358.38), (2.496; 253.42), (2.430; 1.33), (2.405; 0.93),
(2.393; 0.79), (2.332; 2.19), (2.327; 2.67), (2.322; 2.05), (2.292; 0.56), (2.268; 0.61), (2.256; 0.74),
(2.245; 0.55), (2.207; 1.25), (2.197; 0.75), (2.183; 1.32), (2.176; 1.47), (2.164; 1.30), (2.152; 1.20),
(2.135; 13.93), (2.110; 15.00), (2.069; 2.09), (2.049; 1.17), (2.008; 0.97), (1.987; 0.55), (1.972; 0.86),
(1.399; 0.79), (1.352; 1.11), (1.297; 0.63), (1.292; 0.59), (1.260; 0.82), (1.236; 1.73), (1.146; 3.91),
(1.128; 7.34), (1.111; 3.70), (−0.000; 13.79)
Ex. 293:
(7.744; 0.33), (7.695; 0.50), (7.668; 0.46), (7.647; 0.38), (7.637; 0.36), (7.607; 0.36), (7.590; 0.34),
(7.573; 0.33), (7.390; 5.80), (7.386; 2.53), (7.369; 8.79), (7.293; 7.95), (7.272; 5.14), (7.081; 2.37),
(6.757; 0.89), (4.069; 12.66), (4.039; 0.71), (3.997; 0.39), (3.625; 0.35), (3.603; 0.40), (3.592; 0.39),
(3.582; 0.42), (3.558; 0.51), (3.516; 0.66), (3.302; 2097.70), (3.191; 1.24), (3.147; 0.85), (3.093; 0.56),
(3.082; 0.54), (3.056; 0.55), (3.046; 0.55), (3.035; 0.64), (2.938; 2.98), (2.908; 1.01), (2.849; 0.36),
(2.839; 0.38), (2.815; 0.37), (2.801; 0.41), (2.783; 0.40), (2.768; 0.42), (2.760; 0.45), (2.752; 0.39),
(2.728; 0.46), (2.701; 0.63), (2.673; 2.88), (2.669; 3.67), (2.664; 2.74), (2.626; 0.83), (2.539; 11.91),
(2.504; 382.45), (2.500; 474.05), (2.496; 335.40), (2.364; 0.76), (2.331; 2.88), (2.326; 3.56), (2.298; 0.62),
(2.272; 0.52), (2.226; 0.59), (2.210; 0.56), (2.196; 0.69), (2.180; 1.15), (2.142; 12.45), (2.114; 15.00),
(2.069; 8.86), (2.049; 0.80), (2.024; 0.35), (1.987; 0.67), (1.977; 0.35), (1.399; 0.44), (1.293; 0.49),
(1.270; 0.35), (1.237; 1.34), (1.151; 4.07), (1.134; 6.56), (1.117; 3.36), (1.081; 0.38), (0.890; 0.81),
(0.854; 0.36), (−0.000; 21.60), (−0.020; 0.37)
Ex. 294:
(7.708; 0.56), (7.179; 4.86), (6.779; 2.17), (3.304; 385.60), (3.205; 0.38), (3.195; 1.53), (3.181; 0.31),
(2.931; 2.17), (2.890; 0.42), (2.876; 0.55), (2.869; 0.85), (2.860; 0.59), (2.849; 0.92), (2.840; 1.54),
(2.832; 0.90), (2.820; 0.57), (2.811; 0.85), (2.803; 0.47), (2.669; 0.73), (2.664; 0.54), (2.539; 4.31),
(2.509; 41.30), (2.504; 72.28), (2.500; 90.39), (2.496; 62.77), (2.434; 0.36), (2.331; 0.53), (2.327; 0.71),
(2.322; 0.53), (2.146; 13.67), (2.135; 15.00), (2.085; 0.30), (2.069; 0.87), (2.049; 0.45), (1.942; 1.66),
(1.912; 1.89), (1.814; 1.73), (1.805; 1.44), (1.781; 1.96), (1.707; 0.88), (1.682; 0.85), (1.676; 0.97),
(1.573; 0.66), (1.565; 0.66), (1.541; 1.68), (1.533; 1.66), (1.511; 1.77), (1.503; 1.75), (1.480; 0.78),
(1.472; 0.73), (1.412; 0.81), (1.398; 2.14), (1.380; 1.74), (1.357; 1.21), (1.349; 1.72), (1.318; 0.69),
(1.292; 0.31), (1.255; 0.64), (1.246; 0.48), (1.233; 0.78), (1.224; 1.11), (1.215; 0.70), (1.200; 0.60),
(1.193; 0.93), (1.185; 0.59), (1.151; 3.15), (1.133; 5.85), (1.116; 2.91), (−0.000; 1.85)
Ex. 295:
(7.660; 5.57), (7.181; 4.83), (6.773; 4.84), (3.309; 805.43), (3.285; 16.14), (3.195; 1.62), (3.177; 0.39),
(3.168; 0.36), (3.063; 0.33), (3.001; 2.76), (2.944; 2.78), (2.877; 0.57), (2.869; 0.89), (2.860; 0.63),
(2.848; 0.92), (2.840; 1.57), (2.831; 0.96), (2.819; 0.61), (2.811; 0.87), (2.803; 0.52), (2.674; 0.81),
(2.669; 1.02), (2.665; 0.82), (2.539; 2.41), (2.509; 57.71), (2.505; 102.41), (2.500; 129.23), (2.496; 90.66),
(2.331; 0.76), (2.327; 0.96), (2.322; 0.76), (2.147; 15.00), (2.134; 14.87), (2.069; 0.48), (2.049; 0.38),
(1.940; 1.65), (1.908; 2.01), (1.813; 1.74), (1.806; 1.43), (1.781; 1.96), (1.707; 0.88), (1.676; 0.98),
(1.571; 0.65), (1.564; 0.65), (1.541; 1.69), (1.534; 1.64), (1.510; 1.75), (1.503; 1.77), (1.480; 0.79),
(1.472; 0.77), (1.411; 0.83), (1.398; 1.97), (1.380; 1.72), (1.356; 1.22), (1.348; 1.71), (1.324; 0.56),
(1.317; 0.68), (1.255; 0.64), (1.246; 0.48), (1.231; 0.77), (1.224; 1.08), (1.216; 0.67), (1.202; 0.56),
(1.192; 0.96), (0.890; 0.40), (−0.000; 8.29)
Ex. 296:
(7.766; 0.81), (7.176; 4.81), (6.786; 1.88), (3.808; 0.54), (3.304; 498.91), (3.280; 12.69), (3.195; 2.09),
(2.850; 6.85), (2.832; 1.52), (2.820; 0.80), (2.811; 0.97), (2.803; 0.58), (2.673; 0.73), (2.669; 0.87),
(2.665; 0.69), (2.539; 1.96), (2.504; 84.85), (2.500; 106.38), (2.496; 74.95), (2.332; 0.67), (2.327; 0.82),
(2.322; 0.65), (2.146; 13.18), (2.135; 15.00), (2.069; 0.43), (2.049; 0.32), (1.941; 1.68), (1.908; 1.97),
(1.813; 1.76), (1.806; 1.49), (1.781; 1.97), (1.707; 0.93), (1.675; 1.00), (1.572; 0.67), (1.565; 0.69),
(1.541; 1.72), (1.534; 1.62), (1.511; 1.78), (1.504; 1.76), (1.479; 0.82), (1.472; 0.79), (1.412; 0.91),
(1.398; 4.45), (1.388; 1.34), (1.381; 1.82), (1.356; 1.31), (1.349; 1.79), (1.324; 0.59), (1.317; 0.73),
(1.255; 0.78), (1.224; 1.71), (1.194; 6.21), (1.183; 6.40), (0.890; 0.33), (−0.000; 7.08), (−0.008; 0.37)
Ex. 297:
(7.786; 0.31), (7.326; 1.31), (6.982; 0.38), (6.828; 1.54), (3.372; 0.43), (3.353; 0.53), (3.303; 88.40),
(3.010; 0.44), (2.940; 1.03), (2.539; 0.39), (2.504; 17.94), (2.500; 22.31), (2.496; 16.28), (2.142; 3.91),
(1.250; 15.00), (1.166; 0.47), (1.150; 0.91), (1.134; 0.61), (−0.000; 2.82)
Ex. 298:
(7.195; 3.16), (7.167; 0.67), (6.899; 0.77), (6.798; 1.37), (6.666; 1.27), (6.551; 1.00), (6.418; 1.27),
(4.677; 3.65), (4.650; 0.98), (4.558; 3.59), (4.530; 0.84), (3.852; 0.64), (3.808; 3.28), (3.706; 3.05),
(3.697; 6.06), (3.515; 0.68), (3.495; 0.83), (3.443; 2.87), (3.309; 1493.77), (3.218; 3.23), (3.174; 1.49),
(3.121; 0.77), (3.013; 0.68), (2.945; 0.85), (2.930; 0.94), (2.913; 0.75), (2.891; 0.77), (2.851; 4.31),
(2.829; 0.89), (2.808; 2.14), (2.802; 5.49), (2.787; 6.26), (2.674; 2.36), (2.669; 3.00), (2.665; 2.28),
(2.647; 0.67), (2.576; 1.62), (2.539; 10.01), (2.505; 307.88), (2.500; 381.06), (2.496; 267.32), (2.332; 2.35), (2.327; 2.80), (2.323; 2.22), (2.202; 0.70), (2.174; 1.18), (2.150; 10.22), (2.142; 11.84), (2.132; 8.14),
(2.101; 5.11), (2.085; 1.64), (2.069; 3.20), (2.062; 4.18), (2.049; 1.40), (2.026; 4.76), (2.001; 0.77),
(1.987; 1.00), (1.724; 0.94), (1.431; 1.88), (1.417; 15.00), (1.413; 14.41), (1.370; 0.80), (1.366; 0.76),
(1.341; 3.57), (1.337; 3.58), (1.256; 0.70), (1.237; 1.33), (1.193; 4.54), (1.184; 5.06), (1.166; 7.20),
(1.159; 7.59), (1.150; 6.24), (1.143; 6.22), (1.068; 1.06), (1.057; 5.97), (1.041; 5.73), (1.018; 0.71),
(0.890; 0.89), (0.008; 3.37), (−0.000; 52.10)

Ex. 299:
(7.668; 3.51), (7.200; 2.99), (7.166; 0.61), (6.898; 0.61), (6.784; 3.05), (6.763; 0.42), (6.682; 0.30),
(5.567; 0.40), (4.676; 3.56), (4.649; 0.77), (4.558; 3.60), (4.530; 0.76), (3.852; 0.33), (3.808; 2.54),
(3.705; 1.91), (3.443; 1.89), (3.405; 0.54), (3.395; 0.66), (3.382; 1.15), (3.368; 2.34), (3.339; 9.68),
(3.307; 983.95), (3.218; 2.69), (3.101; 0.59), (3.047; 0.70), (3.004; 2.06), (2.940; 3.31), (2.855; 0.36),
(2.815; 0.33), (2.800; 0.33), (2.784; 0.34), (2.754; 0.32), (2.731; 0.33), (2.674; 1.31), (2.669; 1.59),
(2.665; 1.30), (2.626; 0.49), (2.609; 0.55), (2.604; 0.57), (2.539; 5.39), (2.509; 89.50), (2.504; 156.91),
(2.500; 196.63), (2.496; 136.19), (2.393; 0.48), (2.331; 1.29), (2.327; 1.58), (2.322; 1.23), (2.286; 0.41),
(2.253; 0.56), (2.225; 0.44), (2.201; 0.54), (2.151; 11.32), (2.140; 10.01), (2.116; 2.35), (2.106; 2.42),
(2.085; 0.49), (2.069; 1.59), (2.065; 1.84), (2.049; 0.95), (1.908; 0.44), (1.472; 0.35), (1.428; 1.69),
(1.417; 15.00), (1.413; 14.35), (1.370; 0.80), (1.366; 0.75), (1.341; 3.32), (1.337; 3.18), (1.235; 0.47),
(0.890; 0.54), (−0.000; 30.14), (−0.008; 1.16)

Ex. 300:
(7.694; 0.37), (7.072; 2.95), (6.826; 0.34), (6.749; 1.45), (3.510; 0.32), (3.309; 942.06), (3.212; 0.60),
(3.190; 0.51), (3.173; 0.69), (3.155; 1.28), (3.138; 1.58), (3.121; 1.20), (3.104; 0.58), (2.933; 1.56),
(2.674; 0.93), (2.669; 1.12), (2.665; 0.94), (2.622; 0.32), (2.539; 3.89), (2.509; 67.32), (2.505; 119.09),
(2.500; 150.56), (2.496; 106.01), (2.442; 0.59), (2.332; 0.86), (2.327; 1.07), (2.322; 0.84), (2.166; 0.33),
(2.141; 8.67), (2.120; 9.29), (2.069; 0.70), (1.975; 0.45), (1.409; 0.42), (1.293; 0.41), (1.264; 0.87),
(1.240; 15.00), (1.223; 14.31), (1.197; 0.32), (1.149; 2.37), (1.132; 4.42), (1.114; 2.11), (1.086; 0.72),
(1.070; 0.70), (−0.000; 4.33)

Ex. 301:
(7.198; 3.11), (6.898; 0.50), (6.792; 1.34), (4.676; 3.49), (4.650; 0.61), (4.558; 3.59), (4.531; 0.52),
(3.808; 2.00), (3.701; 1.93), (3.668; 1.28), (3.603; 0.57), (3.582; 0.55), (3.556; 0.64), (3.532; 0.76),
(3.518; 0.96), (3.496; 1.00), (3.468; 1.57), (3.442; 2.92), (3.316; 1238.52), (3.219; 2.51), (3.179; 1.31),
(3.146; 0.87), (3.135; 0.87), (3.104; 0.69), (3.079; 0.78), (3.070; 0.71), (3.064; 0.64), (3.047; 0.54),
(3.037; 0.55), (2.931; 2.24), (2.908; 2.98), (2.731; 0.52), (2.694; 0.51), (2.675; 1.66), (2.670; 2.05),
(2.639; 0.62), (2.627; 0.61), (2.594; 0.86), (2.540; 11.27), (2.505; 218.30), (2.501; 270.28), (2.497; 188.30),
(2.384; 0.63), (2.372; 0.87), (2.349; 0.56), (2.328; 2.17), (2.323; 1.68), (2.299; 0.60), (2.290; 0.72),
(2.276; 0.71), (2.246; 1.13), (2.206; 2.91), (2.150; 9.81), (2.141; 11.40), (2.126; 2.47), (2.099; 3.53),
(2.069; 2.26), (2.063; 1.97), (2.048; 1.39), (2.039; 3.13), (2.016; 0.71), (1.429; 2.19), (1.417; 15.00),
(1.413; 14.72), (1.399; 2.99), (1.371; 0.57), (1.341; 2.26), (1.337; 2.22), (1.325; 1.20), (1.292; 0.79),
(1.236; 0.86), (1.152; 2.43), (1.134; 4.59), (1.112; 4.22), (1.094; 1.98), (1.084; 1.44), (1.066; 2.02),
(1.048; 1.08), (0.890; 0.65), (−0.000; 8.39)

Ex. 302:
(7.782; 0.55), (7.764; 0.59), (7.429; 2.99), (7.407; 3.75), (7.401; 0.86), (7.256; 3.75), (7.234; 2.97),
(7.181; 2.54), (6.797; 1.03), (3.919; 0.55), (3.854; 0.50), (3.839; 0.57), (3.829; 0.55), (3.807; 0.87),
(3.781; 0.60), (3.714; 0.54), (3.708; 0.60), (3.515; 0.50), (3.489; 0.61), (3.481; 0.58), (3.470; 0.70),
(3.450; 0.88), (3.414; 1.14), (3.408; 1.28), (3.299; 1075.79), (3.225; 1.02), (3.214; 0.80), (3.211; 0.77),
(3.196; 0.56), (3.149; 1.03), (2.852; 3.76), (2.809; 0.73), (2.695; 0.61), (2.668; 2.78), (2.664; 2.32),
(2.631; 1.27), (2.622; 0.76), (2.602; 0.95), (2.569; 1.85), (2.539; 14.59), (2.504; 298.33), (2.500; 370.44),
(2.496; 262.21), (2.428; 1.43), (2.399; 0.96), (2.345; 0.77), (2.331; 2.22), (2.326; 2.68), (2.313; 0.74),
(2.224; 0.75), (2.209; 0.51), (2.185; 0.69), (2.174; 0.80), (2.153; 7.29), (2.116; 8.27), (2.088; 0.99),
(2.076; 0.87), (2.069; 2.20), (2.049; 1.06), (1.865; 0.52), (1.787; 1.54), (1.741; 0.74), (1.736; 0.66),
(1.689; 15.00), (1.646; 0.67), (1.633; 0.97), (1.612; 0.66), (1.459; 0.81), (1.398; 0.76), (1.292; 0.84),
(1.250; 0.64), (1.236; 1.43), (1.184; 4.32), (1.148; 2.03), (1.131; 1.56), (1.102; 0.82), (1.062; 0.78),
(1.045; 0.70), (0.890; 0.60), (−0.000; 30.42)

Ex. 303:
(11.174; 0.53), (7.797; 1.01), (7.686; 0.59), (7.418; 3.18), (7.010; 1.21), (5.747; 0.43), (3.957; 0.41),
(3.946; 0.45), (3.831; 0.47), (3.612; 0.40), (3.554; 0.45), (3.545; 0.44), (3.537; 0.50), (3.444; 1.53),
(3.422; 1.68), (3.304; 1613.40), (3.282; 27.72), (3.202; 1.46), (3.197; 1.47), (3.178; 1.81), (3.161; 2.06),
(3.144; 1.66), (3.129; 0.99), (3.116; 0.75), (3.098; 1.16), (3.080; 0.77), (3.061; 0.95), (3.045; 2.76),
(3.012; 2.02), (2.989; 1.14), (2.942; 3.99), (2.730; 0.40), (2.674; 2.32), (2.669; 2.92), (2.664; 2.36),
(2.539; 6.40), (2.504; 300.32), (2.500; 372.84), (2.496; 263.85), (2.331; 2.18), (2.327; 2.75), (2.322; 2.19),
(2.301; 0.39), (2.212; 0.50), (2.198; 0.81), (2.166; 0.46), (2.139; 10.01), (2.120; 0.71), (2.105; 0.51),
(2.069; 1.41), (2.004; 1.00), (1.987; 0.62), (1.454; 1.06), (1.436; 1.03), (1.414; 0.40), (1.398; 0.66),
(1.392; 0.93), (1.373; 0.95), (1.365; 0.72), (1.353; 0.69), (1.347; 0.69), (1.318; 0.65), (1.311; 1.26),
(1.294; 1.39), (1.278; 1.12), (1.260; 1.85), (1.243; 15.00), (1.226; 14.72), (1.217; 6.11), (1.211; 3.54),
(1.200; 6.31), (1.194; 3.10), (1.183; 2.30), (1.167; 2.45), (1.151; 4.23), (1.127; 6.18), (1.110; 4.61),
(1.023; 1.23), (1.006; 1.24)

Ex. 304:
(7.799; 1.13), (7.683; 0.81), (7.425; 0.62), (7.418; 0.80), (7.382; 3.48), (7.007; 1.32), (3.945; 1.02),
(3.810; 0.75), (3.750; 0.56), (3.734; 0.62), (3.719; 0.65), (3.707; 0.64), (3.689; 0.69), (3.683; 0.72),
(3.660; 1.28), (3.647; 0.80), (3.633; 0.87), (3.628; 0.95), (3.624; 0.97), (3.601; 1.07), (3.586; 1.04),
(3.560; 1.08), (3.524; 1.39), (3.510; 1.58), (3.308; 4331.04), (3.218; 3.72), (3.194; 3.01), (3.176; 3.04),
(3.159; 2.35), (3.145; 1.75), (3.058; 0.90), (3.045; 1.04), (3.014; 2.10), (2.990; 0.88), (2.967; 1.10),
(2.942; 4.37), (2.899; 0.60), (2.708; 0.83), (2.674; 4.37), (2.669; 5.63), (2.664; 4.73), (2.539; 12.51),
(2.504; 591.21), (2.500; 740.17), (2.496; 525.85), (2.393; 1.59), (2.388; 1.39), (2.346; 1.34), (2.331; 4.31),
(2.327; 5.43), (2.323; 4.34), (2.303; 0.86), (2.288; 0.87), (2.253; 0.68), (2.213; 0.74), (2.199; 1.15),
(2.146; 2.06), (2.139; 3.12), (2.129; 9.93), (2.069; 7.21), (2.050; 0.68), (2.000; 0.61), (1.762; 0.73),
(1.352; 0.78), (1.297; 1.11), (1.289; 1.13), (1.259; 1.33), (1.243; 4.49), (1.231; 15.00), (1.214; 13.28),
(1.204; 2.72), (1.188; 2.03), (1.151; 3.98), (1.137; 2.75), (1.108; 1.01), (1.101; 0.63), (1.072; 0.79),
(1.054; 0.79), (0.891; 1.03), (−0.000; 7.06)

Ex. 305:
(13.752; 0.60), (11.911; 0.58), (9.906; 0.59), (7.670; 1.20), (7.429; 3.24), (7.407; 3.43), (7.389; 0.76),
(7.371; 0.75), (7.256; 3.60), (7.234; 3.15), (7.190; 1.37), (7.178; 0.73), (7.169; 0.87), (7.149; 0.70),
(6.782; 1.13), (3.840; 0.60), (3.707; 0.70), (3.659; 0.74), (3.625; 0.71), (3.571; 0.68), (3.569; 0.85),
(3.557; 0.81), (3.547; 0.87), (3.536; 0.79), (3.524; 0.90), (3.503; 1.00), (3.481; 1.13), (3.438; 1.69),
(3.300; 1976.66), (3.218; 1.65), (3.182; 1.15), (3.148; 2.09), (3.121; 0.75), (3.106; 0.62), (3.099; 0.60),
(3.079; 0.64), (3.039; 1.09), (3.007; 1.78), (2.966; 1.70), (2.954; 1.95), (2.946; 1.99), (2.891; 0.68),
(2.855; 0.58), (2.805; 0.61), (2.777; 0.63), (2.759; 0.61), (2.694; 1.19), (2.669; 4.57), (2.618; 1.33),
(2.614; 1.57), (2.602; 1.92), (2.539; 22.42), (2.504; 503.02), (2.500; 597.25), (2.373; 0.97), (2.327; 4.38),
(2.258; 0.61), (2.225; 0.65), (2.213; 0.59), (2.156; 6.50), (2.117; 7.04), (2.080; 0.80), (2.069; 2.72),
(2.050; 1.26), (1.773; 0.70), (1.763; 0.74), (1.740; 3.20), (1.689; 15.00), (1.667; 0.75), (1.653; 0.67),
(1.634; 1.34), (1.398; 0.80), (1.352; 0.88), (1.292; 1.05), (1.236; 2.20), (0.892; 0.77), (0.869; 0.62),
(0.854; 0.68), (0.834; 0.81), (−0.000; 33.65)
Ex. 306:
(7.795; 1.04), (7.683; 0.54), (7.423; 3.56), (7.007; 1.21), (6.986; 0.69), (6.948; 0.39), (3.798; 0.32),
(3.567; 0.30), (3.449; 0.84), (3.431; 0.67), (3.371; 1.91), (3.354; 2.36), (3.303; 309.83), (3.280; 12.04),
(3.201; 0.55), (3.181; 0.75), (3.163; 1.29), (3.146; 1.60), (3.129; 1.21), (3.116; 0.72), (3.060; 0.31),
(3.012; 2.25), (2.941; 3.90), (2.910; 0.39), (2.669; 0.76), (2.664; 0.65), (2.582; 0.46), (2.538; 1.88),
(2.504; 76.63), (2.500; 90.90), (2.327; 0.69), (2.322; 0.58), (2.299; 0.38), (2.147; 10.87), (2.109; 0.37),
(2.099; 0.40), (2.080; 0.31), (2.069; 1.21), (1.999; 0.68), (1.987; 0.51), (1.949; 0.32), (1.551; 0.32),
(1.457; 0.49), (1.438; 0.54), (1.398; 4.38), (1.369; 0.44), (1.360; 0.42), (1.350; 0.38), (1.313; 0.79),
(1.308; 0.92), (1.289; 1.53), (1.271; 1.49), (1.267; 1.35), (1.245; 15.00), (1.228; 14.69), (1.204; 1.90),
(1.187; 1.78), (1.167; 2.43), (1.150; 3.66), (1.134; 2.66), (1.083; 0.31), (1.072; 0.85), (1.055; 0.85), (−0.000;
4.69)
Ex. 307:
(7.706; 0.56), (7.163; 4.58), (6.777; 2.09), (3.409; 0.78), (3.301; 251.63), (3.277; 11.21), (3.196; 0.45),
(2.929; 2.14), (2.673; 0.47), (2.669; 0.58), (2.665; 0.47), (2.539; 1.32), (2.504; 58.03), (2.500; 71.76),
(2.496; 50.55), (2.331; 0.44), (2.326; 0.55), (2.208; 0.54), (2.196; 1.06), (2.188; 1.16), (2.175; 1.88),
(2.164; 1.68), (2.145; 13.98), (2.136; 15.00), (2.069; 0.30), (1.398; 0.61), (1.149; 2.96), (1.132; 5.64),
(1.114; 2.86), (1.085; 0.97), (1.073; 2.02), (1.066; 3.28), (1.059; 1.91), (1.052; 2.00), (1.046; 2.92),
(1.039; 1.52), (1.025; 0.72), (1.015; 1.66), (1.007; 3.51), (1.002; 2.96), (0.995; 3.25), (0.989; 2.41),
(0.976; 0.83), (−0.000; 2.47)
Ex. 308:
(7.664; 6.01), (7.177; 4.60), (6.774; 4.78), (3.348; 117.50), (3.324; 6.24), (3.197; 0.38), (3.011; 3.23),
(2.931; 3.26), (2.525; 0.41), (2.522; 0.52), (2.518; 0.52), (2.510; 12.27), (2.507; 26.41), (2.503; 35.90),
(2.500; 25.62), (2.497; 11.62), (2.200; 0.41), (2.192; 0.92), (2.186; 0.93), (2.184; 0.64), (2.178; 1.80),
(2.173; 0.53), (2.170; 1.01), (2.165; 0.94), (2.157; 0.57), (2.144; 13.50), (2.134; 13.43), (2.077; 0.61),
(1.397; 2.43), (1.079; 0.77), (1.071; 1.88), (1.067; 2.88), (1.061; 1.63), (1.058; 1.79), (1.053; 2.68),
(1.048; 1.06), (1.024; 0.34), (1.008; 1.19), (1.003; 2.80), (1.000; 1.94), (0.998; 2.23), (0.995; 3.00),
(0.990; 2.41), (0.983; 0.73), (−0.000; 7.59)
Ex. 309:
(7.768; 0.72), (7.162; 4.10), (6.789; 1.46), (3.808; 0.59), (3.306; 295.49), (3.282; 10.40), (3.196; 0.66),
(2.851; 6.06), (2.674; 0.38), (2.669; 0.49), (2.539; 0.88), (2.505; 47.54), (2.500; 59.62), (2.496; 42.75),
(2.430; 0.37), (2.327; 0.52), (2.225; 0.33), (2.208; 0.56), (2.196; 1.01), (2.188; 1.16), (2.185; 1.02),
(2.176; 1.80), (2.163; 1.70), (2.145; 12.97), (2.138; 15.00), (2.104; 0.50), (2.069; 0.35), (1.398; 1.82),
(1.233; 0.48), (1.195; 5.32), (1.181; 5.83), (1.131; 0.66), (1.086; 0.89), (1.080; 0.86), (1.073; 1.93),
(1.066; 3.21), (1.059; 1.95), (1.053; 2.03), (1.046; 2.94), (1.039; 1.61), (1.025; 0.76), (1.015; 1.64),
(1.007; 3.44), (1.002; 2.96), (0.995; 3.24), (0.989; 2.42), (0.977; 0.84), (−0.000; 0.79)
Ex. 310:
(7.793; 3.20), (7.792; 3.27), (7.772; 3.61), (7.770; 3.49), (7.655; 3.08), (7.653; 3.01), (7.637; 3.28),
(7.635; 3.01), (7.230; 3.66), (7.151; 2.53), (7.134; 2.74), (7.130; 2.69), (7.112; 2.26), (6.858; 1.23),
(3.482; 0.51), (3.306; 269.22), (3.284; 5.28), (2.967; 2.68), (2.675; 0.42), (2.670; 0.51), (2.666; 0.41),
(2.540; 1.15), (2.505; 49.88), (2.501; 61.32), (2.497; 43.15), (2.332; 0.39), (2.328; 0.53), (2.188; 13.39),
(2.149; 15.00), (2.070; 0.48), (1.398; 1.94), (1.172; 3.74), (1.154; 7.28), (1.136; 3.54), (−0.000; 0.38)
Ex. 311:
(7.793; 2.67), (7.791; 2.70), (7.771; 2.90), (7.769; 2.80), (7.688; 6.27), (7.653; 2.70), (7.651; 2.66),
(7.635; 2.91), (7.633; 2.70), (7.216; 5.01), (7.149; 2.40), (7.131; 2.56), (7.127; 2.52), (7.109; 2.13),
(6.819; 5.18), (3.305; 176.16), (3.281; 3.82), (3.007; 2.91), (2.971; 2.89), (2.670; 0.35), (2.540; 0.79),
(2.506; 33.86), (2.501; 41.64), (2.497; 29.12), (2.328; 0.34), (2.181; 15.00), (2.142; 14.97), (1.398; 4.24), (−0.000;
0.92)
Ex. 312:
(7.794; 3.48), (7.792; 3.50), (7.772; 3.29), (7.770; 3.12), (7.652; 2.85), (7.650; 2.80), (7.635; 3.11),
(7.633; 2.88), (7.212; 5.11), (7.148; 2.43), (7.131; 2.61), (7.127; 2.56), (7.109; 2.16), (6.831; 2.30),
(3.824; 0.45), (3.809; 0.44), (3.304; 175.95), (3.281; 4.16), (2.868; 8.30), (2.674; 0.30), (2.670; 0.38),
(2.540; 0.85), (2.505; 37.42), (2.501; 45.92), (2.497; 32.22), (2.332; 0.32), (2.328; 0.40), (2.180; 13.64),
(2.144; 15.00), (2.071; 0.45), (1.398; 3.33), (1.208; 6.60), (1.194; 6.89), (1.148; 0.62), (1.131; 0.32), (−0.000;
0.98)
Ex. 313:
(7.774; 0.39), (7.651; 1.86), (7.237; 0.47), (7.071; 2.62), (6.746; 1.90), (4.039; 0.38), (3.535; 0.56),
(3.518; 0.59), (3.503; 0.63), (3.466; 0.83), (3.443; 1.04), (3.422; 1.25), (3.403; 1.78), (3.304; 1571.27),
(3.187; 1.57), (3.170; 1.93), (3.152; 2.05), (3.135; 1.65), (3.118; 1.01), (3.104; 0.76), (3.094; 0.64),
(3.086; 0.71), (3.077; 0.96), (3.055; 0.70), (3.036; 0.82), (2.978; 2.17), (2.957; 2.13), (2.931; 1.58),
(2.871; 0.43), (2.828; 0.44), (2.798; 0.45), (2.786; 0.38), (2.762; 0.44), (2.747; 0.46), (2.717; 0.48),
(2.694; 0.71), (2.674; 2.18), (2.669; 2.54), (2.664; 2.03), (2.644; 0.70), (2.612; 0.94), (2.606; 1.05),
(2.592; 1.25), (2.562; 2.32), (2.539; 7.94), (2.504; 256.50), (2.500; 314.88), (2.496; 223.28), (2.417; 1.22),
(2.385; 0.88), (2.332; 2.09), (2.326; 2.37), (2.299; 0.59), (2.289; 0.59), (2.272; 0.56), (2.258; 0.54),
(2.229; 0.48), (2.203; 1.47), (2.164; 1.76), (2.143; 9.21), (2.113; 9.31), (2.069; 2.44), (2.028; 0.54), (2.019; 0.48), (1.987; 1.51), (1.410; 0.38), (1.399; 0.53), (1.381; 0.45), (1.367; 0.39), (1.268; 0.72), (1.244; 4.52), (1.237; 15.00), (1.227; 4.85), (1.220; 13.57), (1.193; 0.83), (1.175; 0.89), (1.157; 0.52), (1.107; 1.70), (0.889; 0.38), (−0.000; 15.10).

In the $^1$H-NMR (DMSO, 400 MHz) of examples 49, 52 and 56, the septuplet for CH(Me)$_2$ was not detected.

The logP values were measured in accordance with EEC Directive 79/831 Annex V.A8 by HPLC (High Performance Liquid Chromatography) on reversed-phase columns (C18), using the method below:

[a] The determination was carried out in the acidic range at pH 2.3 using the mobile phases 0.1% aqueous phosphoric acid and acetonitrile linear gradient from 10% acetonitrile to 95% acetonitrile.

[b] The LC-MS determination in the acidic range was carried out at pH 2.7 using the mobile phases 0.1% aqueous formic acid and acetonitrile (comprising 0.1% formic acid) linear gradient from 10% acetonitrile to 95% acetonitrile

[c] The LC-MS determination in the neutral range was carried out at pH 7.8 using the mobile phases 0.001 molar ammonium bicarbonate solution and acetonitrile linear gradient from 10% acetonitrile to 95% acetonitrile.

Calibration was carried out using unbranched alkan-2-ones (having 3 to 16 carbon atoms) with known logP values (determination of the logP values by the retention times using linear interpolation between two successive alkanones).

Unless indicated otherwise, the chemical NMR shifts 6 in ppm were measured at 400 MHz in the solvent DMSOd$_6$ using the internal standard tetramethylsilane.

*: the septuplet for CH(CH$_3$)$_2$ was not shown.
**: recorded in the solvent CD$_3$CN Signal splitting is described by the abbreviations below:
s=Singlet; d=Doublet; t=Triplet; q=Quadruplet; m=Multiplet

SYNTHESIS EXAMPLES

Preparation of N'-{4-[(3-tert-butyl-4-cyanoisothiazol-5-yl)oxy]-2,5-dimethylphenyl}-N-propyl-N-methylimidoformamide (Ex. No. 4)

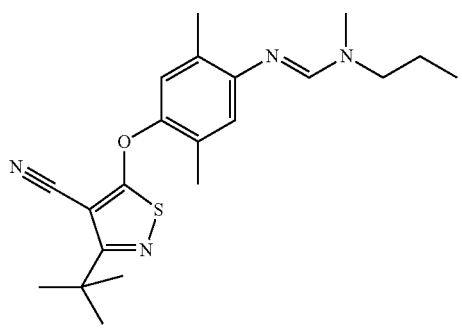

10 mg of para-toluenesulphonic acid are added to a solution of 0.40 g (1.32 mmol) of 5-(4-amino-2,5-dimethylphenoxy)-3-tert-butylisothiazole-4-carbonitrile in 20 ml of methyl orthoformate, and the mixture is heated at reflux for 2 h. The volatile components are then removed under reduced pressure, the residue is dissolved in 20 ml of dichloromethane and 194 mg (2.65 mmol) of propylmethylamine are added, and the reaction mixture is stirred at room temperature for 16 h. The reaction mixture is then freed from the solvent under reduced pressure.

Purification by column chromatography on alumina using cyclohexane/ethyl acetate gives 0.60 g (1.32 mmol, 99% of theory) of N'-{4-[(3-tert-butyl-4-cyanoisothiazol-5-yl)oxy]-2,5-dimethylphenyl}-N-propyl-N-methylimidoformamide of logP(HCO$_2$H)=2.19.

Preparation of 5-(4-amino-2,5-dimethylphenoxy)-3-tert-butylisothiazole-4-carbonitrile

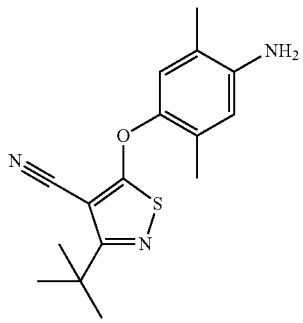

A suspension of 5.0 g (24.9 mmol) of 3-tert-butyl-5-chloroisothiazole-4-carbonitrile, 3.41 g (24.9 mmol) of 2,5-dimethyl-4-hydroxyaniline and 5.51 g (39.86 mmol) of potassium carbonate in 100 ml of DMF is heated under reflux for 6 h. After cooling, the reaction mixture is poured onto ice-water. After extraction with dichloromethane, the combined organic phases are dried over Na$_2$SO$_4$ and freed from the solvent under reduced pressure.

Purification by column chromatography on silica gel using cyclohexane/ethyl acetate gives 5.9 g (19.6 mmol, 79% of theory) of 5-(4-amino-2,5-dimethylphenoxy)-3-(4-chlorobenzyl)isothiazole-4-carbonitrile.

Preparation of 3-tert-butyl-5-chloroisothiazole-4-carbonitrile

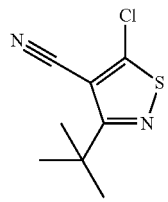

At 0° C., 1.48 g (22.0 mmol) of sodium nitrite are added to a suspension of 1.30 g (7.0 mmol) of 5-amino-3-tert-butyl-isothiazole-4-carbonitrile in 55 ml of conc. hydrochloric acid. The reaction mixture is stirred at 0° C. for 1 h and at room temperature for 2 h. The reaction mixture is then neutralized by addition of sodium hydroxide solution. After the addition of water, the mixture is extracted with methyl t-butyl ether and the combined organic phases are dried over Na$_2$SO$_4$ and freed from the solvent under reduced pressure.

This gives 0.7 g (3.50 mmol, 47% of theory) of 3-tert-butyl-5-chloroisothiazole-4-carbonitrile.

Preparation of
5-amino-3-tert-butylisothiazole-4-carbonitrile

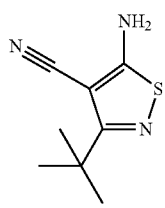

At 0° C., 1.16 g (1.1 mmol) of an aqueous hydrogen peroxide solution (35%) are added dropwise to a suspension of 1.50 g (8.0 mmol) of (2E)-3-amino-2-cyano-4,4-dimethyl-pent-2-enthioamide in 15 ml of methanol. The reaction mixture is heated under reflux for 2 h. After cooling, the reaction mixture is poured onto ice-water and extracted with dichloromethane. The combined organic phases are dried over $Na_2SO_4$ and freed from the solvent under reduced pressure.

This gives 1.30 g (7.17 mmol, 90% of theory) of 5-amino-3-tert-butylisothiazole-4-carbonitrile of $logP(HCO_2H)$ =2.40.

Preparation of (2E)-3-amino-2-cyano-4,4-dimethyl-pent-2-enthioamide

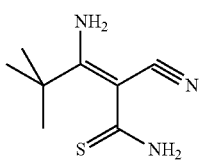

With cooling, 1.52 g (4.50 mmol) of hydrogen sulphide are introduced as a gas into a mixture of 1.6 g (1.40 mmol) of (1-amino-2,2-dimethylpropylidene)propanedinitrile, 1.41 g (1.40 mmol) of triethylamine and 2.21 g (2.80 mmol) of pyridine. For 1 h, nitrogen is then passed through the reaction mixture, and the reaction mixture is then added to ice-water and extracted with dichloromethane. The combined organic phases are dried over $Mg_2SO_4$ and freed from the solvent under reduced pressure.

Purification by column chromatography on silica gel using heptane/ethyl acetate gives 1.5 g (0.82 mmol, 56% of theory) of 5-(4-amino-2,5-dimethylphenoxy)-3-(4-chlorobenzyl) isothiazole-4-carbonitrile.

Preparation of
(1-amino-2,2-dimethylpropylidene)propanedinitrile

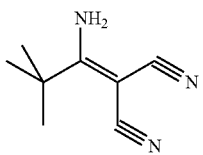

Until the reaction has gone to completion, a total of 7.74 g (45.5 mmol) of ammonia are introduced into a solution of 54 g (33.2 mmol) of (1-methoxy-2,2-dimethylpropylidene)propanedinitrile in 200 ml of ethanol, whereupon a yellow solid precipitates, and the mixture is stirred at room temperature for another 2 h. The mixture is then filtered and the solid is washed with cold ethanol and dried under reduced pressure.

This gives 24.2 g (16.2 mmol, 49% of theory) of (1-amino-2,2-dimethylpropylidene)propanedinitrile.

Concentration of the mother liquor gives a further 9.3 g (6.2 mmol, 19% of theory) of (1-amino-2,2-dimethylpropylidene)propanedinitrile.

Preparation of (1-methoxy-2,2-dimethylpropylidene) propanedinitrile

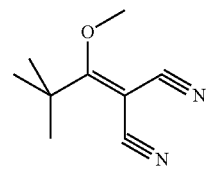

34 g (26.6 mmol) of dimethyl sulphate, dissolved in 45 ml of dioxane, are added to a solution of 4.0 g (2.70 mmol) of (1-hydroxy-2,2-dimethylpropylidene)propanedinitrile in 7 ml of water. 24.6 g (29.3 mmol) of sodium bicarbonate are then added, and the reaction mixture is heated at 85° C. for 2 h. After cooling to room temperature, 100 ml of water are added and the mixture is extracted with diethyl ether. The combined organic phases are dried over $Mg_2SO_4$ and freed from the solvent under reduced pressure.

This gives 3.2 g (2.0 mmol, 50% pure, 37% of theory) of (1-methoxy-2,2-dimethylpropylidene)propanedinitrile.

Preparation of (1-hydroxy-2,2-dimethylpropylidene) propanedinitrile

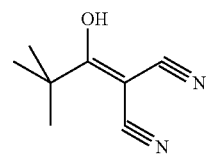

Under protective gas, 182 g (1.5 mol) of trimethylacetyl chloride, dissolved in 100 ml of tetrahydrofuran, are, at 0° C., added dropwise over a period of 2 h to a solution of 100 g (1.5 mol) of malononitrile and 306 g (3.0 mol) of triethylamine in 1 l of tetrahydrofuran. The reaction mixture is then stirred at 0° C. for another 1 h and filtered, and the solid obtained is washed with tetrahydrofuran. The combined filtrates are added to ice-water and adjusted to pH=3 using semiconcentrated sulphuric acid. The mixture is then extracted with chloroform. The combined organic phases are dried over $Mg_2SO_4$ and freed from the solvent under reduced pressure. The residue obtained is taken up in diethyl ether, the organic is washed with 25% strength sulphuric acid and water and once more dried over $Mg_2SO_4$ and freed from the solvent under reduced pressure.

This gives 227 g (1.51 mol, 100% of theory) of (1-hydroxy-2,2-dimethylpropylidene)propane dinitrile.

Preparation of N'-(4-{[3-(4-chlorobenzyl)-4-cyanoisothiazol-5-yl]oxy}-2,5-dimethylphenyl)-N-ethyl-N-methylimidoformamide (Ex. No. 27)

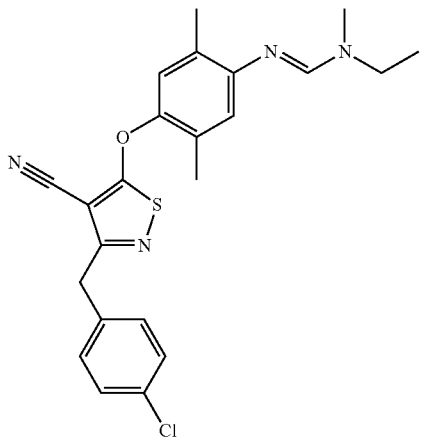

A solution of 1.80 g (4.87 mmol) of 5-(4-amino-2,5-dimethylphenoxy)-3-(4-chlorobenzyl)isothiazole-4-carbonitrile and 0.91 g (6.8 mmol) of N-(dimethoxymethyl)-N-methylethanamine in 60 ml of toluene is stirred at 80° C. for 22 h. Another 0.91 g (6.8 mmol) of N-(dimethoxymethyl)-N-methylethanamine is added, and the solution is then stirred for a further 22 h.

After cooling, the reaction mixture is freed from the solvent under reduced pressure.

Purification by column chromatography on alumina using hexane/ethyl acetate gives 0.18 g (0.41 mmol, 8% of theory) of N-(4-{[3-(4-chlorobenzyl)-4-cyanoisothiazol-5-yl]oxy}-2,5-dimethylphenyl)-N-ethyl-N-methylimidoformamide of logP(HCO$_2$H)=2.39.

Preparation of 5-(4-amino-2,5-dimethylphenoxy)-3-(4-ehlorobenzyl)isothiazole-4-earbonitrile

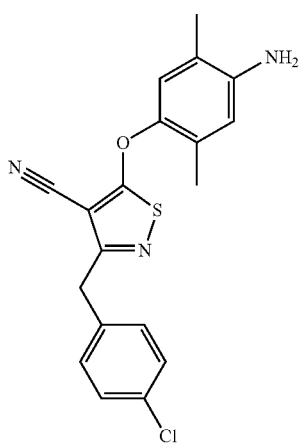

A suspension of 3.90 g (14.49 mmol) of 5-chloro-3-(4-chlorobenzyl)isothiazole-4-carbonitrile, 1.99 g (14.49 mmol) of 2,5-dimethyl-4-hydroxyaniline and 3.20 g (23.18 mmol) of potassium carbonate in 20 ml of DMF is heated under reflux for 6 h. After cooling, the reaction mixture is poured onto ice-water. After extraction with dichloromethane, the combined organic phases are dried over Na$_2$SO$_4$ and freed from the solvent under reduced pressure.

Purification by column chromatography on silica gel using hexane/ethyl acetate gives 1.70 g (4.6 mmol, 29% of theory) of 5-(4-amino-2,5-dimethylphenoxy)-3-(4-chlorobenzyl)isothiazole-4-carbonitrile of logP(HCO$_2$H)=4.03.

Preparation of 5-chloro-3-(4-chlorobenzyl)isothiazole-4-carbonitrile

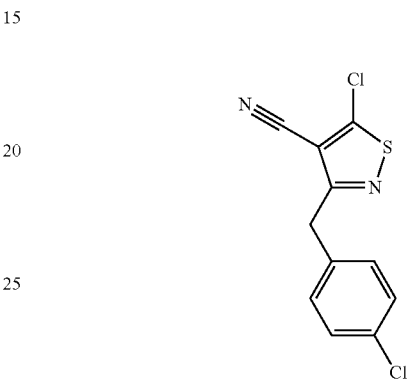

At 0° C., 4.14 g (60.07 mmol) of sodium nitrite are added to a suspension of 5.00 g (20.0 mmol) of 5-amino-3-(4-chlorobenzyl)isothiazole-4-carbonitrile in 80 ml of conc. hydrochloric acid. The reaction mixture is stirred at 0° C. for 1 h and at room temperature for 2 h. The reaction mixture is then neutralized by addition of aqueous sodium hydroxide solution. After the addition of water, the mixture is extracted with methyl t-butyl ether and the combined organic phases are dried over Na$_2$SO$_4$ and freed from the solvent under reduced pressure.

This gives 3.90 g (14.49 mmol, 54% of theory) of 5-chloro-3-(4-chlorobenzyl)isothiazole-4-carbonitrile of logP(HCO$_2$H)=3.87.

Preparation of 5-amino-3-(4-chlorobenzyl)isothiazole-4-carbonitrile

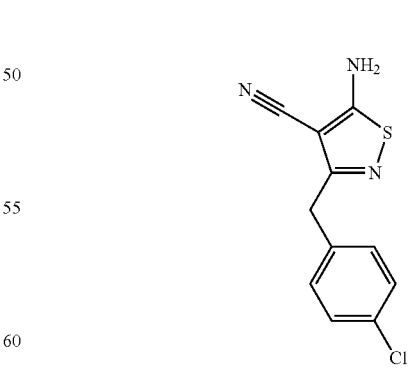

At 0° C., 2.70 g (27.8 mmol) of an aqueous hydrogen peroxide solution (35%) are added dropwise to a suspension of 7.00 g (20.6 mmol) of 3-amino-4-(4-chlorophenyl)-2-cyanobut-2-enthioamide in 80 ml of methanol. The reaction mixture is heated under reflux for 2 h. After cooling, the reaction mixture is added to ice-water and extracted with dichloromethane. The combined organic phases are dried over Na$_2$SO$_4$ and freed from the solvent under reduced pressure.

This gives 5.00 g (20.0 mmol, 97% of theory) of 5-amino-3-(4-chlorobenzyl)isothiazole-4-carbonitrile of logP(HCO$_2$H)=2.40.

Preparation of 3-amino-4-(4-chlorophenyl)-2-cyanobut-2-enthioamide

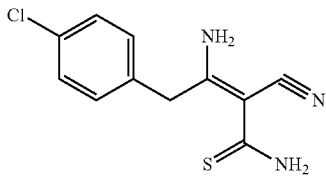

3-amino-4-(4-chlorophenyl)-2-cyanobut-2-enthioamide can be prepared analogously to 3-amino-2-cyano-4-(4-nitrophenyl)but-2-enthioamide (Bioorganic & Medicinal Chemistry Letters, 2006, 4326-4330).

Preparation of N'-{2,5-dimethyl-4-[(3-phenylisothiazol-5-yl)oxy]phenyl}-N-ethyl-N-methylimidoformamide (Ex. No. 43)

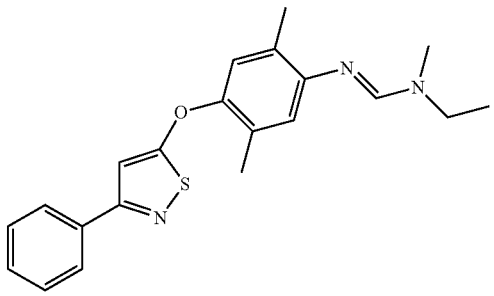

A solution of 0.40 g (1.35 mmol) of 2,5-dimethyl-4-[(3-phenylisothiazol-5-yl)oxy]aniline and 0.25 g (1.9 mmol) of N-(dimethoxymethyl)-N-methylethanamine in 10 ml of toluene is stirred at 80° C. for 22 h. Another 0.25 g (1.9 mmol) of N-(dimethoxymethyl)-N-methylethanamine are added, and the mixture is then stirred for a further 22 h. After cooling, the reaction mixture is freed from the solvent under reduced pressure.

Purification by column chromatography on alumina using hexane/ethyl acetate gives 0.23 g (0.63 mmol, 45% of theory) of N'-{2,5-dimethyl-4-[(3-phenylisothiazol-5-yl)oxy]phenyl}-N-ethyl-N-methylimidoformamide of logP(HCO$_2$H)=2.11.

Preparation of 2,5-dimethyl-4-[(3-phenylisothiazol-5-yl)oxy]aniline

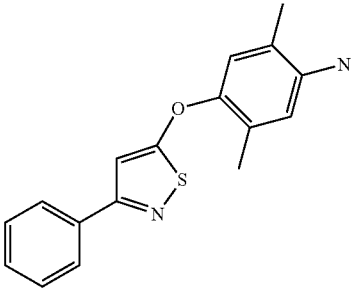

0.34 g (8.43 mmol) of sodium hydride (60% in mineral oil) is added to a solution of 2,5-dimethyl-4-hydroxyaniline in 15 ml of DMF, and the reaction mixture is stirred at room temperature for 2 h. A solution of 1.50 g (7.67 mmol) of 5-chloro-3-phenylisothiazole in 5 ml of DMF is added dropwise to the reaction mixture. The reaction mixture is then stirred at 100° C. for 3 h. After cooling, the reaction mixture is added to ice-water and extracted with ethyl acetate. The combined organic phases are dried over Na$_2$SO$_4$ and freed from the solvent under reduced pressure.

This gives 3.00 g (10.1 mmol, 80% of theory) of 2,5-dimethyl-4-[(3-phenylisothiazol-5-yl)oxy]aniline of logP(HCO$_2$H)=3.60.

Preparation of 5-chloro-3-phenylisothiazole

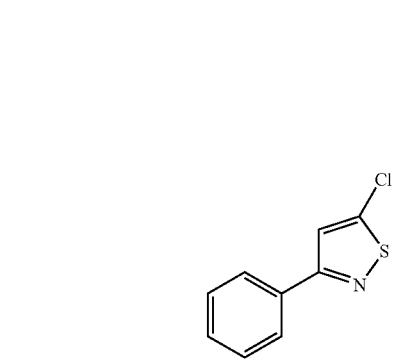

9.15 g (68.1 mmol) of copper dichloride and 7.02 g (68.1 mmol) of t-butyl nitrite are initially charged in 140 ml of acetonitrile. At 60° C., 8.00 g (45.4 mmol) of 3-phenylisothiazol-5-amine are added a little at a time to this suspension. The reaction mixture is then stirred at 80° C. for 1 h. After cooling, semiconcentrated hydrochloric acid is added and the reaction mixture is extracted with dichloromethane. The combined organic phases are dried over Na$_2$SO$_4$ and freed from the solvent under reduced pressure.

Purification by column chromatography on silica gel using hexane/ethyl acetate gives 5.10 g (26.1 mmol, 55% of theory) of 5-chloro-3-phenylisothiazole of logP(HCO₂H)=3.82.

Preparation of 3-phenylisothiazol-5-amine

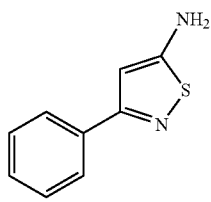

3-phenylisothiazol-5-amine can be prepared according to JACS, 1994, 2292-2300.

Preparation of N'-{4-[(4-chloro-3-phenylisothiazol-5-yl)oxy]-2,5-dimethylphenyl}-N-ethyl-N-methylimidoformamide (Ex. No. 48)

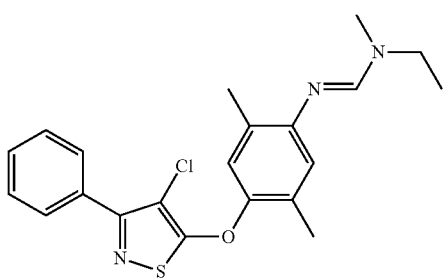

At room temperature, 483 mg (3.63 mmol) of N-(dimethoxymethyl)-N-methylethanamine are added to a solution of 600 mg (1.81 mmol) of 4-[(4-chloro-3-phenyl-isothiazol-5-yl)oxy]-2,5-dimethylaniline in 8 ml of toluene. The reaction mixture is stirred at 60° C. for 24 hours. After cooling, the solvent is removed under pressure. The residue is filtered through alumina (neutral, activated) using petroleum ether/ethyl acetate (9/1). This gives 607 mg (1.52 mmol, 84% of theory) of N'-{4-[(4-chloro-3-phenylisothiazol-5-yl)oxy]-2,5-dimethylphenyl}-N-ethyl-N-methylimidoformamide of logP(HCO₂H)=2.25.

Preparation of 4-[(4(4-chloro-3-phenylisothiazol-5-yl)oxy]-2,5-dimethylaniline

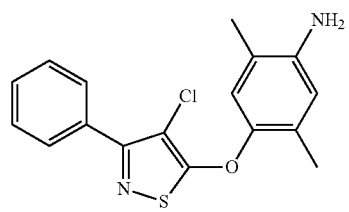

A suspension of 300 mg (1.30 mmol) of 4,5-dichloro-3-phenylisothiazole, 179 mg (1.30 mmol) of 4-amino-2,5-dimethylbenzene and 680 mg (2.08 mmol) of caesium carbonate in 5 ml of N,N-dimethylformamide is stirred at 150° C. for 4 hours. After cooling, the reaction mixture is diluted with water and extracted with dichloromethane. The combined organic phases are dried over Na₂SO₄. The mixture is then filtered and concentrated under reduced pressure. The residue is purified by column chromatography on silica gel using cyclohexane/ethyl acetate (3/1). This gives 310 mg (0.94 mmol, 72% of theory) of 4-[(4-chloro-3-phenylisothiazol-5-yl)oxy]-2,5-dimethylaniline of logP(HCO₂H)=4.22.

Preparation of 4,5-dichloro-3-phenylisothiazole

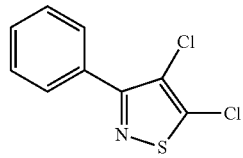

At room temperature, 6.60 g (64.1 mmol) of tert-butyl nitrite are added to a suspension of 8.61 g (64.1 mmol) of copper dichloride in 150 ml of acetonitrile. At 60° C., 9.00 g (42.7 mmol) of 4-chloro-3-phenylisothiazol-5-amine are then added a little at a time. After the addition has ended, the reaction mixture is heated to 80° C. and stirred at this temperature for another hour. After cooling, the reaction mixture is added to semiconcentrated hydrochloric acid and extracted with dichloromethane. The combined organic phases are dried over Na₂SO₄. The mixture is then filtered and concentrated under reduced pressure. The residue is purified by column chromatography on silica gel using cyclohexane/ethyl acetate (9/1). This gives 3.68 g (16 mmol, 37% of theory) of 4,5-dichloro-3-phenylisothiazole of logP(HCO₂H) =4.44.

Preparation of 4-chloro-3-phenylisothiazol-5-amine

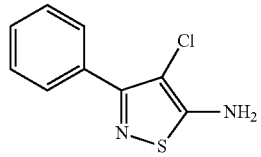

At room temperature, 7.19 g (53.9 mmol) of 1-chloropyr-rolidine-2,5-dione are added a little at a time to a solution of 9.50 g (53.9 mmol) of 3-phenylisothiazol-5-amine (*J. Am. Chem. Soc.* 1994, 116(6), 2292-2300) in 100 ml of acetonitrile. The reaction mixture is stirred at room temperature for 24 hours. The acetonitrile is removed under reduced pressure. The residue is purified by column chromatography on silica gel using cyclohexane/ethyl acetate (3/1). This gives 9.10 g (43.1 mmol, 80% of theory) of 4-chloro-3-phenylisothiazol-5-amine of logP(HCO$_2$H)=2.21.

Preparation of N'-{4-[(4-bromo-3-phenylisothiazol-5-yl)oxy]-5-chloro-2-methylphenyl}-N-ethyl-N-methylimidoformamide (Ex. No. 54)

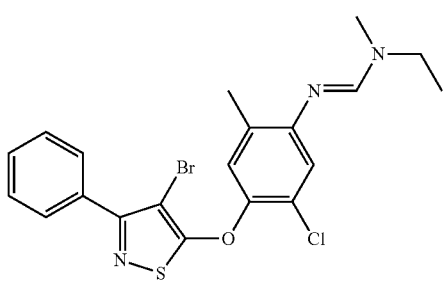

At room temperature, 108 mg (0.809 mmol) of N-(dimethoxymethyl)-N-methylethanamine are added to a solution of 160 mg (0.404 mmol) of 4-[(4-bromo-3-phenyl-isothiazol-5-yl)oxy]-5-chloro-2-methylaniline in 8 ml of toluene. The reaction mixture is stirred at 60° C. for 24 hours. After cooling, the solvent is removed under pressure. The residue is filtered through alumina (neutral, activated) using petroleum ether/ethyl acetate (9/1). This gives 171 mg (0.37 mmol, 91% of theory) of N'-{4-[(4-bromo-3-phenylisothiazol-5-yl)oxy]-5-chloro-2-methylphenyl}-N-ethyl-N-methylimidoformamide of logP(HCO$_2$H)=2.26.

Preparation of 4[(4-bromo-3-phenylisothiazol-5-yl)oxy]-5-chloro-2-methylaniline

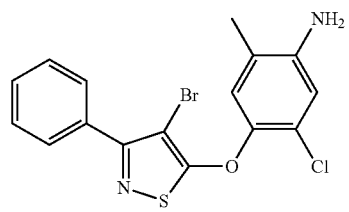

A suspension of 580 mg (1.86 mmol) of 4-bromo-5-chloro-3-phenylisothiazole, 293 mg (1.86 mmol) of 4-amino-2-chloro-5-methylbenzene and 969 mg (2.97 mmol) of caesium carbonate in 5 ml of N,N-dimethylformamide is stirred at 150° C. for 4 hours. After cooling, the reaction mixture is diluted with water and extracted with dichloromethane. The combined organic phases are dried over Na$_2$SO$_4$. The mixture is then filtered and concentrated under reduced pressure. The residue is purified by column chromatography on silica gel using cyclohexane/ethyl acetate (3/1). This gives 517 mg (1.3 mmol, 70% of theory) of 4-[(4-bromo-3-phenylisothiazol-5-yl)oxy]-5-chloro-2-methylaniline of logP(HCO$_2$H)=4.41.

Preparation of 4-bromo-5-chloro-3-phenylisothiazole

At room temperature, 2.91 g (28.2 mmol) of tert-butyl nitrite are added to a suspension of 3.79 g (28.2 mmol) of copper dichloride in 70 ml of acetonitrile. At 60° C., 4.80 g (18.8 mmol) of 4-bromo-3-phenylisothiazol-5-amine are then added a little at a time. After the addition has ended, the reaction mixture is heated to 80° C. and stirred at this temperature for another hour. After cooling, the reaction mixture is added to semiconcentrated hydrochloric acid and extracted with dichloromethane. The combined organic phases are dried over Na$_2$SO$_4$. The mixture is then filtered and concentrated under reduced pressure. The residue is purified by column chromatography on silica gel using cyclohexane/ethyl acetate (9/1). This gives 3.05 g (11.1 mmol, 59% of theory) of 4-bromo-5-chloro-3-phenylisothiazole of logP(HCO$_2$H)=4.41.

Preparation of 4-bromo-3-phenylisothiazol-5-amine

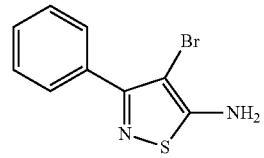

At room temperature, 10.09 g (56.7 mmol) of 1-brompyrrolidine-2,5-dione are added a little at a time to a solution of 10.00 g (56.7 mmol) of 3-phenylisothiazol-5-amine (*J. Am. Chem. Soc.* 1994, 116(6), 2292-2300) in 100 ml of acetonitrile. The reaction mixture is stirred at room temperature for 24 hours. The acetonitrile is removed under pressure. The residue is purified by column chromatography on silica gel using cyclohexane/ethyl acetate (3/1). This gives 14.10 g (55 mmol, 97% of theory) of 4-bromo-3-phenylisothiazol-5-amine of logP(HCO$_2$H)=2.26.

BIOLOGICAL EXAMPLES

Example 1

*Sphaerotheca* Test (Cucumber)/protective

Solvent: 49 parts by weight of N,N-dimethylformamide
Emulsifier: 1 part by weight of alkylaryl polyglycol ether (polyoxyethylene(16) tristearyl phenyl ether)

To produce a suitable preparation of active compound, one part by weight of active compound is mixed with the stated amounts of solvent and emulsifier, and the concentrate is diluted with water to the desired concentration.

To test for protective activity, young cucumber plants are sprayed with the active compound preparation at the stated application rate. One day after the treatment, the plants are inoculated with a spore suspension of *Sphaerotheca fuliginea*. The plants are then placed in a greenhouse at 70% relative atmospheric humidity and a temperature of 23° C.

Evaluation is carried out 7 days after the inoculation. 0% means an efficacy which corresponds to that of the control, whereas an efficacy of 100% means that no infection is observed.

In this test, the compounds according to the invention below, Nos. 1, 3, 4, 5, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 50, 53, 56, 57, 58, 59, 60, 61, 62, 65, 66, 67, 68, 69, 71, 72, 73, 74, 75, 76, 77, 78, 79, 80, 81, 83, 84, 85, 86, 89, 90, 91, 92, 94, 95, 97, 98, 99, 100, 101, 102, 103, 104, 105, 112, 113, 114, 115, 116, 117, 118, 119, 120, 121, 122, 123, 124, 125, 126, 127, 129, 130, 131, 132, 133, 134, 135, 136, 137, 138, 139, 140, 141, 142, 143, 144, 145, 146, 147, 148, 149, 150, 151, 152, 153, 154, 158, 159, 160, 161, 161, 162, 163, 166, 167, 168, 169, 174, 175, 179, 181, 182, 184, 190, 191, 194, 195, 203, 204, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 243, 244, 245, 246, 247, 248, 249, 250, 251, 253, 254, 255, 256, 257, 258, 259, 260, 261, 262, 263, 265, 267, 268, 270, 271, 272, 273, 274, 275, 283, 284, 285, 286, 287, 288, 290, 291, 292, 293, 294, 295, 296, 297, 298 and 299 from Table 1, show, at an active compound concentration of 500 ppm, an efficacy of 70% or more.

Example 2

*Puccinia* Test (Wheat)/protective

Solvent: 49 parts by weight of N,N-dimethylformamide
Emulsifier: 1 part by weight of alkylaryl polyglycol ether (polyoxyethylene(16) tristearyl phenyl ether)

To produce a suitable preparation of active compound, one part by weight of active compound is mixed with the stated amounts of solvent and emulsifier, and the concentrate is diluted with water to the desired concentration.

To test for protective activity, young wheat plants are sprayed with the active compound preparation at the stated application rate. One day after the treatment, the plants are inoculated with a spore suspension of *Puccinia recondita* and then remain at 100% rel humidity and 22° C. for 48 h. The plants then remain at 80% rel. atmospheric humidity and a temperature of 20° C.

Evaluation is carried out 7-9 days after the inoculation. 0% means an efficacy which corresponds to that of the control, whereas an efficacy of 100% means that no infection is observed.

In this test, the compounds according to the invention below, Nos. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 64, 65, 66, 67, 68, 69, 70, 71, 72, 73, 74, 75, 76, 77, 78, 79, 80, 81, 82, 83, 84, 85, 86, 89, 90, 91, 92, 93, 94, 95, 97, 98, 99, 100, 101, 102, 103, 104, 105, 112, 113, 114, 115, 116, 117, 118, 119, 120, 121, 122, 123, 124, 125, 126, 127, 129, 130, 131, 132, 133, 134, 135, 136, 137, 138, 139, 140, 141, 142, 143, 144, 145, 146, 147, 148, 149, 150, 151, 152, 153, 154, 158, 159, 160, 161, 162, 163, 166, 167, 168, 169, 174, 175, 179, 181, 182, 184, 190, 191, 194, 195, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 243, 244, 245, 246, 247, 248, 249, 250, 251, 252, 253, 254, 255, 256, 257, 258, 259, 260, 261, 262, 263, 264, 266, 267, 268, 269, 270, 271, 272, 273, 274, 275, 276, 277, 278, 279, 280, 281, 283, 284, 285, 286, 287, 290, 291, 292, 293, 294, 295, 296, 297, 298 and 299 from Table 1, show, at an active compound concentration of 500 ppm, an efficacy of 70% or more.

Example 3

*Botrytis* Test (Bean)/protective

Solvents: 24.5 parts by weight of acetone 24.5 parts by weight of dimethylacetamide
Emulsifier: 1 part by weight of alkylaryl polyglycol ether (polyoxyethylene(16) tristearyl phenyl ether)

To produce a suitable preparation of active compound, one part by weight of active compound is mixed with the stated amounts of solvents and emulsifier, and the concentrate is diluted with water to the desired concentration.

To test for protective activity, young plants are sprayed with the active compound preparation at the stated application rate. After the spray coating has dried on, two small pieces of agar colonized by *Botrytis cinerea* are placed onto each leaf. The inoculated plants are placed in a dark chamber at about 20° C. and 100% relative atmospheric humidity.

The size of the infected areas on the leaves is evaluated two days after the inoculation. 0% means an efficacy which corresponds to that of the control, whereas an efficacy of 100% means that no infection is observed.

In this test, the compounds according to the invention below, Nos. 5, 6, 7, 8, 10, 11, 12, 13, 14, 15, 16, 17, 20, 21, 22, 23, 24, 25, 26, 27, 28, 31, 32, 33, 34, 37, 40, 42, 43, 48, 50, 53, 56, 58, 64, 65, 66, 67, 68, 69, 70, 71, 72, 76, 77, 78, 79, 80, 81, 83, 84, 86, 89, 95, 97, 98, 99, 100, 101, 103, 104, 105, 108, 112, 113, 114, 116, 121, 122, 123, 124, 125, 126, 127, 129, 130, 132, 139, 153, 159, 165, 166, 167, 168, 174, 177, 178, 179, 180, 181, 182, 183, 184, 185, 186, 188, 189, 190, 191, 195, 197, 198, 199, 200, 201, 208, 209, 210, 211, 212, 213, 215, 216, 221, 227, 228, 229, 231, 233, 236, 237, 243, 246, 249 and 270 from Table 1, show, at an active compound concentration of 250 ppm, an efficacy of 70% or more.

Example 4

*Uromyces* Test (Bean)/protective

Solvents: 24.5 parts by weight of acetone 24.5 parts by weight of dimethylacetamide
Emulsifier: 1 part by weight of alkylaryl polyglycol ether (polyoxyethylene(16) tristearyl phenyl ether)

To produce a suitable preparation of active compound, one part by weight of active compound is mixed with the stated amounts of solvents and emulsifier, and the concentrate is diluted with water to the desired concentration.

To test for protective activity, young plants are sprayed with the active compound preparation at the stated application rate. After the spray coating has dried on, the plants are inoculated with an aqueous spore suspension of the bean rust pathogen *Uromyces appendiculatus* and then remain at about 20° C. and 100% relative atmospheric humidity in an integration cabin for one day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

In this test, the compounds according to the invention below, Nos. 1, 3, 4, 5, 6, 7, 8, 10, 12, 13, 14, 15, 16, 17, 18, 19, 20, 21, 22, 23, 24, 25, 26, 27, 31, 32, 33, 34, 37, 40, 42, 43, 48, 50, 53, 58, 59, 64, 65, 66, 67, 68, 69, 70, 71, 72, 73, 74, 75, 76, 77, 78, 79, 80, 81, 83, 84, 89, 95, 98, 99, 100, 100, 101, 103, 105, 108, 112, 113, 116, 117, 118, 122, 123, 124, 125, 127, 129, 130, 132, 139, 153, 159, 163, 163, 165, 166, 167, 174, 177, 178, 179, 180, 181, 182, 183, 184, 186, 188, 189, 190, 191, 195, 197, 198, 199, 200, 201, 203, 204, 208, 209, 210, 211, 212, 213, 215, 216, 221, 227, 228, 229, 231, 233, 236, 237, 243, 246, 249 and 270 from Table 1, show, at an active compound concentration of 10 ppm, an efficacy of 70% or more.

Example 5

*Leptosphaeria nodorum* Test (Wheat)/protective

Solvent: 49 parts by weight of N,N-dimethylacetamide
Emulsifier: 1 part by weight of alkylaryl polyglycol ether (polyoxyethylene(16) tristearyl phenyl ether)

To produce a suitable preparation of active compound, one part by weight of active compound is mixed with the stated amounts of solvent and emulsifier, and the concentrate is diluted with water to the desired concentration.

To test for protective activity, young plants are sprayed with the active compound preparation at the stated application rate. After the spray coating has dried on, the plants are sprayed with spores of a spore suspension of *Leptosphaeria nodorum*. The plants remain at 20° C. and 100% relative atmospheric humidity in an incubation cabin for 48 hours.

The plants are placed in a greenhouse at a temperature of about 22° C. and a relative atmospheric humidity of about 80%.

Evaluation is carried out 8 days after the inoculation. 0% means an efficacy which corresponds to that of the control, whereas an efficacy of 100% means that no infection is observed.

In this test, the compounds according to the invention below, Nos. 1, 4, 5, 6, 8, 10, 22, 25, 27, 32, 34, 43, 48, 59, 64, 65, 66, 67, 68, 70, 72, 74, 78, 80, 81, 83, 84, 87, 98, 99, 100, 103, 119, 122, 123, 124, 145, 163, 166, 167, 169, 174, 179, 181, 182, 184, 189, 193, 195, 199, 202, 203, 221 and 246 from Table 1, show, at an active compound concentration of 500 ppm, an efficacy of 70% or more.

Example 6

*Septoria tritici* Test (Wheat)/protective

Solvent: 49 parts by weight of N,N-dimethylacetamide
Emulsifier: 1 part by weight of alkylaryl polyglycol ether (polyoxyethylene(16) tristearyl phenyl ether)

To produce a suitable preparation of active compound, one part by weight of active compound is mixed with the stated amounts of solvent and emulsifier, and the concentrate is diluted with water to the desired concentration.

To test for protective activity, young plants are sprayed with the active compound preparation at the stated application rate. After the spray coating has dried on, the plants are sprayed with a spore suspension of *Septoria tritici*. The plants remain at 20° C. and 100% relative atmospheric humidity in an incubation cabin for 48 hours. The plants are then placed under a translucent hood at 15° C. and 100% relative atmospheric humidity for a further 60 hours.

The plants are placed in a greenhouse at a temperature of about 15° C. and a relative atmospheric humidity of 80%.

Evaluation is carried out 21 days after the inoculation. 0% means an efficacy which corresponds to that of the control, whereas an efficacy of 100% means that no infection is observed.

In this test, the compounds according to the invention below, Nos. 1, 4, 5, 6, 8, 10, 12, 14, 15, 16, 18, 20, 21, 22, 24, 25, 27, 28, 31, 32, 34, 37, 43, 48, 58, 59, 64, 65, 66, 67, 68, 69, 70, 71, 72, 73, 74, 75, 78, 79, 80, 81, 83, 84, 86, 87, 89, 95, 97, 98, 99, 100, 100, 101, 102, 103, 104, 105, 107, 112, 113, 116, 117, 118, 119, 120, 120, 121, 122, 123, 124, 125, 126, 129, 130, 139, 142, 147, 153, 153, 154, 158, 159, 162, 163, 165, 166, 167, 174, 175, 178, 179, 180, 181, 182, 183, 184, 185, 186, 187, 188, 189, 190, 191, 193, 193, 194, 195, 197, 198, 199, 200, 202, 203, 207, 208, 209, 210, 212, 213, 214, 215, 216, 219, 220, 221, 223, 227, 229, 233, 234, 236, 237, 238, 241, 246, 248, 250, 251, 253, 255, 256, 261, 262, 263, 265, 267, 271, 272, 273, 274, 275, 277, 283, 284, 285, 286 and 287 from Table 1, show, at an active compound concentration of 500 ppm, an efficacy of 70% or more.

Example 7

*Pyrenophora teres* test (barley)/protective

Solvent: 49 parts by weight of N,N-dimethylacetamide
Emulsifier: 1 part by weight of alkylaryl polyglycol ether (polyoxyethylene(16) tristearyl phenyl ether)

To produce a suitable preparation of active compound, one part by weight of active compound is mixed with the stated amounts of solvent and emulsifier, and the concentrate is diluted with water to the desired concentration.

To test for protective activity, young plants are sprayed with the active compound preparation at the stated application rate. After the spray coating has dried on, the plants are sprayed with a spore suspension of *Pyrenophora teres*. The plants remain at 20° C. and 100% relative atmospheric humidity in an incubation cabin for 48 hours.

The plants are placed in a greenhouse at a temperature of about 20° C. and a relative atmospheric humidity of about 80%.

Evaluation is carried out 8 days after the inoculation. 0% means an efficacy which corresponds to that of the control, whereas an efficacy of 100% means that no infection is observed.

In this test, the compounds according to the invention below, Nos. 1, 3, 4, 5, 6, 8, 10, 12, 14, 15, 16, 18, 22, 25, 26, 27, 32, 37, 40, 43, 46, 48, 58, 59, 62, 64, 65, 66, 67, 68, 70, 72, 73, 74, 75, 78, 79, 80, 81, 83, 84, 86, 87, 89, 91, 95, 97, 98, 99, 100, 101, 102, 103, 105, 107, 112, 113, 116, 117, 118, 119, 120, 121, 123, 124, 125, 129, 130, 132, 136, 139, 142, 147, 153, 154, 155, 158, 160, 162, 163, 165, 166, 167, 174, 175, 178, 179, 180, 181, 182, 183, 186, 187, 188, 189, 190, 193, 197, 198, 199, 200, 201, 202, 203, 207, 210, 214, 215, 216, 220, 221, 224, 228, 229, 231, 233, 236, 237, 239, 241, 243, 246, 248, 251, 255, 260, 263, 271, 272, 274, 275, 283, 284, 285, 286 and 287 from Table 1, show, at an active compound concentration of 500 ppm, an efficacy of 70% or more.

Example 8

Phakopsora Test (Soya Beans)/protective

Solvent: 28.5 parts by weight of acetone
Emulsifier: 1.5 parts by weight of alkylaryl polyglycol ether (polyoxyethylene(16) tristearyl phenyl ether)

To produce a suitable preparation of active compound, one part by weight of active compound is mixed with the stated amount of solvent, and the concentrate is diluted with water and the stated amount of emulsifier to the desired concentration.

To test for protective activity, young rice plants are sprayed with the active compound preparation at the stated application rate. One day after the treatment, the plants are inoculated with an aqueous spore suspension of *Phakopsora pachyrhizi*. The plants are then placed in a greenhouse at 80% relative atmospheric humidity and 20° C.

Evaluation is carried out 11 days after the inoculation. 0% means an efficacy which corresponds to that of the control, whereas an efficacy of 100% means that no infection is observed.

In this test, the compounds according to the invention below, Nos. 1, 3, 5, 10, 12, 13, 14, 15, 16, 17, 18, 19, 22, 24, 27, 31, 32, 33, 43, 48 and 59 from Table 1, show, at an active compound concentration of 100 ppm, an efficacy of 80% or more.

Example 9

Pyricularia Test (Rice)/protective

Solvent: 28.5 parts by weight of acetone
Emulsifier: 1.5 parts by weight of alkylaryl polyglycol ether To produce a suitable preparation of active compound, one part by weight of active compound is mixed with the stated amount of solvent, and the concentrate is diluted with water and the stated amount of emulsifier to the desired concentration.

To test for protective activity, young rice plants are sprayed with the active compound preparation at the stated application rate. One day after the treatment, the plants are inoculated with an aqueous spore suspension of *Pyricularia oryzae*. The plants are then placed in a greenhouse at 100% relative atmospheric humidity and 25° C.

Evaluation is carried out 7 days after the inoculation. 0% means an efficacy which corresponds to that of the control, whereas an efficacy of 100% means that no infection is observed.

In this test, the compound according to the invention below, No. 6 from Table 1, shows, at an active compound concentration of 250 ppm, an efficacy of 80% or more.

Example 10

Cochliobolus Test (Rice)/protective

Solvent: 28.5 parts by weight of acetone
Emulsifier: 1.5 parts by weight of alkylaryl polyglycol ether To produce a suitable preparation of active compound, one part by weight of active compound is mixed with the stated amount of solvent, and the concentrate is diluted with water and the stated amount of emulsifier to the desired concentration.

To test for protective activity, young rice plants are sprayed with the active compound preparation at the stated application rate. One day after the treatment, the plants are inoculated with an aqueous spore suspension of *Cochliobolus miyabeanus*. The plants are then placed in a greenhouse at 100% relative atmospheric humidity and 25° C.

Evaluation is carried out 4 days after the inoculation. 0% means an efficacy which corresponds to that of the control, whereas an efficacy of 100% means that no infection is observed.

In this test, the compound according to the invention below, No. 6 from Table 1, shows, at an active compound concentration of 250 ppm, an efficacy of 80% or more.

The invention claimed is:
1. Isothiazolyloxyphenylamidines of the formula (I)

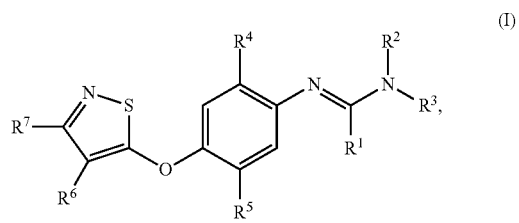

in which
$R^1$ is selected from the group consisting of hydrogen; straight-chain or branched $C_{1-12}$-alkyl, $C_{2-12}$-alkenyl, $C_{2-12}$-alkinyl and cyclic $C_{3-8}$-alkyl, $C_{4-8}$-alkenyl and $C_{4-8}$-alkinyl groups, where in the ring systems of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR$_2$', where R' is hydrogen or a $C_{1-12}$-alkyl group and X is a halogen atom selected from the group consisting of F, Cl, Br and I;

$R^2$ is selected from the group consisting of straight-chain and branched $C_{1-12}$-alkyl, $C_{2-12}$-alkenyl, $C_{2-12}$-alkinyl, cyclic $C_{3-8}$-alkyl, $C_{4-8}$-alkenyl, $C_{4-8}$-alkinyl or $C_{5-18}$-aryl, $C_{7-19}$-aralkyl and $C_{7-19}$-alkaryl groups, where in the ring systems of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR$_2$', where R' and X have the above meanings;

$R^3$ is selected from the group consisting of —CN, —SH, —SR'', —OR'', —(C=O)—R'', where R'' has the above meanings; straight-chain and branched $C_{1-12}$-alkyl, $C_{2-12}$-alkenyl, $C_{2-12}$-alkinyl, cyclic $C_{3-8}$-alkyl, $C_{4-8}$-alkenyl, $C_{4-8}$-alkinyl and $C_{5-18}$-aryl, $C_{7-19}$-aralkyl and $C_{7-19}$-alkaryl groups, where in the ring systems of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR$_2$', wherein R' and X have the above meanings; or in which $R^2$ and $R^3$,
$R^2$ and $R^1$ or R$^1$ and R$^3$ together with the atoms to which they are attached or with further atoms selected from the group consisting of C, N, O, P and S may form a four- to seven-membered ring which may be substituted by R', OR', SR', NR'$_2$, SiR'$_3$ groups, where R' has the above meanings;

R$^4$ is selected from the group consisting of hydrogen, —X, —CN, —SH, —SR", —OR", —(C=O)—R", where R" has the above meanings; straight-chain and branched C$_{1-12}$-alkyl, C$_{2-12}$-alkenyl, C$_{2-12}$-alkinyl, cyclic C$_{3-8}$-alkyl, C$_{4-8}$-alkenyl, C$_{4-8}$-alkinyl or C$_{5-18}$-aryl, C$_{7-19}$-aralkyl or C$_{7-19}$-alkaryl groups, where in the ring systems of all of the cyclic groups mentioned above one or more carbon atoms may be replaced by heteroatoms selected from the group consisting of C, N, O, P and S and all of the groups mentioned above may be substituted by one or more groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide (—CONR$_2$') groups, where R' and X have the above meanings;

R$^5$ is selected from the group consisting of hydrogen, —X, —CN, —SH, —SR", —OR", —(C=O)—R", where R" has the above meanings; straight-chain and branched C$_{1-12}$-alkyl, C$_{2-12}$-alkenyl, C$_{2-12}$-alkinyl, cyclic C$_{3-8}$-alkyl, C$_{4-8}$-alkenyl, C$_{4-8}$-alkinyl or C$_{5-18}$-aryl, C$_{7-19}$-aralkyl or C$_{7-19}$-alkaryl groups, where in the ring systems of all of the cyclic groups mentioned above one or more carbon atoms may be replaced by heteroatoms selected from the group consisting of C, N, O, P and S and all of the groups mentioned above may be substituted by one or more groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide (—CONR$_2$') groups, where R' and X have the above meanings;

R$^6$ is selected from the group consisting of hydrogen, halogen (—X), alkoxy (—OR'), thioether or mercapto (—SR'), amino (—NR'$_2$), nitro (—NO$_2$), silyl (—SiR'$_3$), carboxyl (—COOR'), cyano (—CN) and amide (—CONR$_2$') groups, straight-chain and branched C$_{1-12}$-alkyl, C$_{2-12}$-alkenyl, C$_{2-12}$-alkinyl, cyclic C$_{3-12}$-alkyl, C$_{4-12}$-alkenyl, C$_{4-12}$-alkinyl or C$_{5-18}$-aryl, C$_{7-19}$-aralkyl or C$_{7-19}$-alkaryl groups, where in the ring system of all of the cyclic groups mentioned above one or more carbon atoms may be replaced by heteroatoms selected from the group consisting of C, N, O, P and S and all of the groups mentioned above may be substituted by one or more groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide (—CONR$_2$') groups, where R' and X have the above meanings;

R$^7$ is selected from the group consisting of hydrogen, straight-chain and branched C$_{1-12}$-alkyl, C$_{2-12}$-alkenyl, C$_{2-12}$-alkinyl, cyclic C$_{3-12}$-alkyl, C$_{4-12}$-alkenyl, C$_{4-12}$-alkinyl or C$_{5-18}$-aryl, C$_{7-19}$-aralkyl or C$_{7-19}$-alkaryl groups, where in the ring system of all the cyclic groups mentioned above one or more carbon atoms may be replaced by heteroatoms selected from the group consisting of C, N, O, P and S and all of the groups mentioned above may be substituted by one or more groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide (—CONR$_2$') groups, where R' and X have the above meanings;

R$^6$ and R$^7$ together with the atoms to which they are attached or with further atoms selected from the group consisting of C, N, O, P and S may form a four- to seven-membered ring which may be substituted by R'—, X—, —OR', —SR', —NR'$_2$, —SiR'$_3$, —COOR', —CN and NR$_2$'CO— groups, where R' and X have the above meanings;

or their salts, N-oxides, metal complexes and their stereoisomers.

2. Isothiazolyloxyphenylamidines of the formula (I) according to claim 1, where

R$^1$ is selected from the group consisting of hydrogen, a mercapto group (—SH) and C$_{1-8}$-alkyl groups;

R$^2$ is selected from straight-chain and branched C$_{1-8}$-alkyl groups;

R$^3$ is selected from straight-chain, branched and alicyclic C$_{1-8}$-alkyl groups;

or in which

R$^2$ and R$^3$ together with the nitrogen atom to which they are attached or with further atoms selected from the group consisting of N and O may form a five- or six-membered ring which may be substituted by one or more C$_{1-12}$-alkyl groups;

R$^4$ is selected from the group consisting of halogen atoms, straight-chain and branched C$_{1-12}$-alkyl groups and C$_{1-5}$-haloalkyl groups;

R$^5$ is selected from the group consisting of halogen atoms, straight-chain and branched C$_{1-12}$-alkyl groups and C$_{1-5}$-haloalkyl groups;

R$^6$ is selected from the group consisting of hydrogen, halogen atoms, cyano and straight-chain C$_{1-8}$-alkyl groups;

R$^7$ is selected from the group consisting of hydrogen, straight-chain and branched C$_{1-12}$-alkyl groups and phenyl groups, wherein the phenyl groups may be substituted by halogen atoms and/or by straight-chain or branched C$_{1-12}$-alkyl groups;

R$^6$ and R$^7$ together with the atoms to which they are attached form a fused-on five- or six-membered ring which may have one, two or three unsaturated bonds;

or their salts, N-oxides, metal complexes and their stereoisomers.

3. Isothiazolyloxyphenylamidines of the formula (I) according to claim 1 or 2 in which R$^1$ is selected from the group consisting of hydrogen, mercapto and methyl;

R$^2$ is selected from the group consisting of methyl and ethyl;

R$^3$ is selected from the group consisting of methyl, ethyl and isopropyl; or where R$^2$ and R$^3$ together with the nitrogen atom to which they are attached form a piperidyl, piperidinyl, pyrrolidyl, pyrrolidinyl or 2,6-dimethylmorpholinyl radical;

R$^4$ is selected from the group consisting of a Cl atom and a methyl group;

R$^5$ is selected from the group consisting of a Cl-atom and a methyl group;

R$^6$ is selected from the group consisting of hydrogen, halogen atoms and a cyano group;

R$^7$ is selected from the group consisting of tert-butyl, ethyl, phenyl and benzyl groups, where the phenyl groups may be substituted in the 3- or 4-position by halogen atoms or by a tert-butyl or methyl group;

R$^6$ and R$^7$ together with the atoms to which they are attached may form a phenyl ring;

or their salts, N-oxides, metal complexes and their stereoisomers.

4. Isothiazolyloxyphenylamidine according to claim 1 selected from the group consisting of N'-{4-[(4-cyano-3-ethyl-1,2-thiazol-5-yl)oxy]-2,5-dimethylphenyl}-N-ethyl-N-methylimidoformamide (1), 5-(2,5-dimethyl-4-{[(E)-piperidin-1-ylmethylidene]amino}phenoxy)-3-ethyl-1,2-thiazole-4-carbonitrile (2), N'-{4-[(4-cyano-3-ethyl-1,2-thiazol-5-yl)oxy]-2,5-dimethylphenyl}-N-methyl-N-propylimidoformamide (3), N'-{4-[(3-tert-butyl-4-cyano-1,2-thiazol-5-yl)oxy]-2,5-dimethylphenyl}-N-methyl-N-propylimidoformamide (4), N'-{4-[(3-tert-butyl-4-cyano-1,2-thiazol-5-yl)oxy]-2,5-dimethylphenyl}-N-methyl-N-prop-2-en-1-ylimidoformamide (5), N'-{4-[(3-tert-butyl-4-cyano-1,2-thiazol-5-yl)oxy]-2,5-dimethylphenyl}-N-ethyl-N-methylimidoformamide (6), 3-tert-butyl-5-(2,5-dimethyl-4-{[(E)-piperidin-1-ylmethylidene]amino}phenoxy)-1,2-thiazole-4-carbonitrile (7), N'-{4-[(3-tert-butyl-4-cyano-1,2-thiazol-5-yl)oxy]-2,5-dimethylphenyl}-N,N-dimethylimidoformamide (8), N'-{2-chloro-4-[(4-cyano-3-ethyl-1,2-thiazol-5-yl)oxy]-5-methylphenyl}-N-ethyl-N-methylimidoformamide (9), N'-{4-[(3-tert-butyl-4-cyano-1,2-thiazol-5-yl)oxy]-2-chloro-5-methylphenyl}-N-ethyl-N-methylimidoformamide (10), N'-{5-chloro-4-[(4-cyano-3-phenyl-1,2-thiazol-5-yl)oxy]-2-methylphenyl}-N,N-dimethylimidoformamide (11), N'-{5-chloro-4-[(4-cyano-3-phenyl-1,2-thiazol-5-yl)oxy]-2-methylphenyl}-N-ethyl-N-methylimidoformamide (12), N'-{5-chloro-4-[(4-cyano-3-phenyl-1,2-thiazol-5-yl)oxy]-2-methylphenyl}-N-methyl-N-propylimidoformamide (13), N'-{4-[(4-cyano-3-phenyl-1,2-thiazol-5-yl)oxy]-2,5-dimethylphenyl}-N,N-dimethylimidoformamide (14), N'-{4-[(4-cyano-3-phenyl-1,2-thiazol-5-yl)oxy]-2,5-dimethylphenyl}-N-ethyl-N-methylimidoformamide (15), N'-{4-[(4-cyano-3-phenyl-1,2-thiazol-5-yl)oxy]-2,5-dimethylphenyl}-N-methyl-N-propylimidoformamide (16), N'-{2-chloro-4-[(4-cyano-3-phenyl-1,2-thiazol-5-yl)oxy]-5-methylphenyl}-N,N-dimethylimidoformamide (17), N'-{2-chloro-4-[(4-cyano-3-phenyl-1,2-thiazol-5-yl)oxy]-5-methylphenyl}-N-ethyl-N-methylimidoformamide (18), N'-{2-chloro-4-[(4-cyano-3-phenyl-1,2-thiazol-5-yl)oxy]-5-methylphenyl}-N-methyl-N-propylimidoformamide (19), 3-(4-chlorophenyl)-5-(2,5-dimethyl-4-{[(E)-piperidin-1-ylmethylidene]amino}phenoxy)-1,2-thiazole-4-carbonitrile (20), N'-(4-{[3-(4-chlorophenyl)-4-cyano-1,2-thiazol-5-yl]oxy}-2,5-dimethylphenyl)-N-methyl-N-propylimidoformamide (21), N'-(4-{[3-(4-chlorophenyl)-4-cyano-1,2-thiazol-5-yl]oxy}-2,5-dimethylphenyl)-N-ethyl-N-methylimidoformamide (22), N'-(4-{[3-(4-chlorophenyl)-4-cyano-1,2-thiazol-5-yl]oxy}-2,5-dimethylphenyl)-N,N-dimethylimidoformamide (23), N'-(4-{[4-cyano-3-(3-methylphenyl)-1,2-thiazol-5-yl]oxy}-2,5-dimethylphenyl)-N,N-dimethylimidoformamide (24), N'-(4-{[4-cyano-3-(3-methylphenyl)-1,2-thiazol-5-yl]oxy}-2,5-dimethylphenyl)-N-ethyl-N-methylimidoformamide (25), N'-(4-{[4-cyano-3-(3-methylphenyl)-1,2-thiazol-5-yl]oxy}-2,5-dimethylphenyl)-N-methyl-N-propylimidoformamide (26), N'-(4-{[3-(4-chlorobenzyl)-4-cyano-1,2-thiazol-5-yl]oxy}-2,5-dimethylphenyl)-N-ethyl-N-methylimidoformamide (27), N'-(4-{[3-(4-tert-butylphenyl)-4-cyano-1,2-thiazol-5-yl]oxy}-2,5-dimethylphenyl)-N-ethyl-N-methylimidoformamide (28), N'-(4-{[3-(4-tert-butyl-phenyl)-4-cyano-1,2-thiazol-5-yl]oxy}-2,5-dimethylphenyl)-N-methyl-N-propylimidoformamide (29), N'-(4-{[3-(4-tert-butylphenyl)-4-cyano-1,2-thiazol-5-yl]oxy}-2,5-dimethylphenyl)-N-methyl-N-prop-2-en-1-ylimidoformamide (30), N'-(4-{[4-cyano-3-(4-fluorophenyl)-1,2-thiazol-5-yl]oxy}-2,5-dimethylphenyl)-N,N-dimethylimidoformamide (31), N'-(4-{[4-cyano-3-(4-fluorophenyl)-1,2-thiazol-5-yl]oxy}-2,5-dimethylphenyl)-N-ethyl-N-methylimidoformamide (32), N'-(4-{[4-cyano-3-(4-fluorophenyl)-1,2-thiazol-5-yl]oxy}-2,5-dimethylphenyl)-N-methyl-N-propylimidoformamide (33), N'-{4-[(4-bromo-3-phenyl-1,2-thiazol-5-yl)oxy]-2,5-dimethylphenyl}-N-ethyl-N-methylimidoformamide (34), N'-(2-chloro-4-{[4-cyano-3-(4-fluorophenyl)-1,2-thiazol-5-yl]oxy}-5-methylphenyl)-N-methyl-N-propylimidoformamide (35), N'-(5-chloro-4-{[4-cyano-3-(4-fluorophenyl)-1,2-thiazol-5-yl]oxy}-2-methylphenyl)-N,N-dimethylimidoformamide (36), N'-(5-chloro-4-{[4-cyano-3-(4-fluorophenyl)-1,2-thiazol-5-yl]oxy}-2-methylphenyl)-N-ethyl-N-methylimidoformamide (37), N'-(5-chloro-4-{[4-cyano-3-(4-fluorophenyl)-1,2-thiazol-5-yl]oxy}-2-methylphenyl)-N-methyl-N-propylimidoformamide (38), N'-(5-chloro-4-{[4-cyano-3-(3-methylphenyl)-1,2-thiazol-5-yl]oxy}-2-methylphenyl)-N,N-dimethylimidoformamide (39), N'-(5-chloro-4-{[4-cyano-3-(3-methylphenyl)-1,2-thiazol-5-yl]oxy}-2-methylphenyl)-N-ethyl-N-methylimidoformamide (40), N'-(5-chloro-4-{[4-cyano-3-(3-methylphenyl)-1,2-thiazol-5-yl]oxy}-2-methylphenyl)-N-methyl-N-propylimidoformamide (41), N'-{2,5-dimethyl-4-[(3-phenyl-1,2-thiazol-5-yl)oxy]phenyl}-N,N-dimethylimidoformamide (42), N'-{2,5-dimethyl-4-[(3-phenyl-1,2-thiazol-5-yl)oxy]phenyl}-N-ethyl-N-methylimidoformamide (43), N'-{2,5-dimethyl-4-[(3-phenyl-1,2-thiazol-5-yl)oxy]phenyl}-N-methyl-N-propylimidoformamide (44), N'-{2-chloro-5-methyl-4-[(3-phenyl-1,2-thiazol-5-yl)oxy]phenyl}-N,N-dimethylimidoformamide (45), N'-{2-chloro-5-methyl-4-[(3-phenyl-1,2-thiazol-5-yl)oxy]phenyl}-N-ethyl-N-methylimidoformamide (46), N'-{2-chloro-5-methyl-4-[(3-phenyl-1,2-thiazol-5-yl)oxy]phenyl}-N-methyl-N-propylimidoformamide (47), N'-{4-[(4-chloro-3-phenyl-1,2-thiazol-5-yl)oxy]-2,5-dimethylphenyl}-N-ethyl-N-methylimidoformamide (48), N'-{4-[(4-chloro-3-phenyl-1,2-thiazol-5-yl)oxy]-2,5-dimethylphenyl}-N-methyl-N-propan-2-ylimidoformamide (49), 4-[(4-chloro-3-phenyl-1,2-thiazol-5-yl)oxy]-2,5-dimethyl-N-[(E)-piperidin-1-ylmethylidene]aniline (50), N'-{5-chloro-4-[(4-chloro-3-phenyl-1,2-thiazol-5-yl)oxy]-2-methylphenyl}-N-ethyl-N-methylimidoformamide (51), N'-{5-chloro-4-[(4-chloro-3-phenyl-1,2-thiazol-5-yl)oxy]-2-methylphenyl}-N-methyl-N-propan-2-ylimidoformamide (52), 5-chloro-4-[(4-chloro-3-phenyl-1,2-thiazol-5-yl)oxy]-2-methyl-N-[(E)-piperidin-1-ylmethylidene]aniline (53), N'-{4-[(4-bromo-3-phenyl-1,2-thiazol-5-yl)oxy]-5-chloro-2-methylphenyl}-N-ethyl-N-methylimidoformamide (54), N'-{4-[(4-bromo-3-phenyl-1,2-thiazol-5-yl)oxy]-5-chloro-2-methylphenyl}-N-methyl-N-propan-2-ylimidoformamide (55), 4-[(4-bromo-3-phenyl-1,2-thiazol-5-yl)oxy]-5-chloro-2-methyl-N-[(E)-piperidin-1-ylmethylidene]aniline (56), N'-(2-chloro-4-{[4-cyano-3-(4-fluorophenyl)-1,2-thiazol-5-yl]oxy}-5-methylphenyl)-N,N-dimethylimidoformamide (57), N'-(2-chloro-4-{[4-cyano-3-(4-fluorophenyl)-1,2-thiazol-5-yl]oxy}-5-methylphenyl)-N-ethyl-N-methylimidoformamide (58), N'-[4-(2,1-benzothiazol-3-yloxy)-2,5-dimethylphenyl]-N-ethyl-N-methylimidoformamide (59), N'-[4-(2,1-benzothiazol-3-yloxy)-2,5-dimethylphenyl]-N,N-dimethylimidoformamide (60), N'-[4-(2,1-benzothiazol-3-yloxy)-2,5-dimethylphenyl]-N-methyl-N-propylimidoformamide (61), 4-(2,1-benzothiazol-3-yloxy)-2,5-dimethyl-N-[(E)-piperidin-1-ylmethylidene]aniline (62), 4-(2,1-benzothiazol-3-yloxy)-2,5-dimethyl-N-[(E)-pyrrolidin-1-ylmethylidene]aniline (63), N'-{4-[(3-tert-butyl-4-chloro-1,2-thiazol-5-yl)oxy]-2,5-dimethylphenyl}-N-ethyl-N-methylimidoformamide (64), N'-{4-[(3-tert-butyl-4-chloro-1,2-thiazol-5-yl)oxy]-2,5-dimethylphenyl}-N- methyl-N-propan-2-ylimidoformamide (65), 4-[(3-tert-butyl-4-chloro-1,2-thiazol-5-yl)oxy]-2,5-dimethyl-N-[(E)-piperidin-1-ylmethylidene]aniline (66), N'-{4-[(3-tert-butyl-4-chloro-1,2-thiazol-5-yl)oxy]-2-chloro-5-methylphenyl}-N-ethyl-N-methylimidoformamide (67), N'-{4-[(3-tert-butyl-4-chloro-1,2-thiazol-5-yl)oxy]-2-chloro-5-methylphenyl}-N-methyl-N-propan-2-ylimidoformamide (68), 4-[(3-tert-butyl-4-chloro-1,2-thiazol-5-yl)oxy]-2-chloro-5-methyl-N-[(E)-piperidin-1-ylmethylidene]-aniline (69), N'-{4-[(3-tert-butyl-4-chloro-1,2-thiazol-5-yl)oxy]-5-chloro-2-methylphenyl}-N-ethyl-N-methylimidoformamide (70), N'-{4-[(3-tert-butyl-4-chloro-1,2-thiazol-5-yl)oxy]-5-chloro-2-methylphenyl}-N-methyl-N-propan-2-ylimidoformamide (71), 4-[(3-tert-butyl-4-chloro-1,2-thiazol-5-yl)oxy]-5-chloro-2-methyl-N-[(E)-piperidin-1-ylmethylidene]aniline (72), N'-{4-[(3-tert-butyl-1,2-thiazol-5-yl)oxy]-2,5-dimethylphenyl}-N,N-dimethylimidoformamide (73), N'-{4-[(3-tert-butyl-1,2-thiazol-5-yl)oxy]-2,5-dimethylphenyl}-N-ethyl-N-methylimidoformamide (74), N'-{4-[(3-tert-butyl-1,2-thiazol-5-yl)oxy]-2,5-dimethylphenyl}-N-methyl-N-propylimidoformamide (75), N'-(4-{[4-cyano-3-(3-fluorophenyl)-1,2-thiazol-5-yl]oxy}-2,5-dimethylphenyl)-N,N-dimethylimidoformamide (76), N'-(4-{[4-cyano-3-(3-fluorophenyl)-1,2-thiazol-5-yl]oxy}-2,5-dimethylphenyl)-N-methyl-N-propan-2-ylimidoformamide (77), N'-(4-{[4-cyano-3-(3-fluorophenyl)-1,2-thiazol-5-yl]oxy}-2,5-dimethylphenyl)-N-ethyl-N-methylimidoformamide (78), N'-(4-{[4-cyano-3-(2-methylphenyl)-1,2-thiazol-5-yl]oxy}-2,5-dimethylphenyl)-N,N-dimethylimidoformamide (79), N'-(4-{[4-cyano-3-(2-methylphenyl)-1,2-thiazol-5-yl]oxy}-2,5-dimethylphenyl)-N-methyl-N-propan-2-ylimidoformamide (80), N'-(4-{[4-cyano-3-(2-methylphenyl)-1,2-thiazol-5-yl]oxy}-2,5-dimethylphenyl)-N-ethyl-N-methylimidoformamide (81), N'-{[4(3-tert-butyl-4-cyano-1,2-thiazol-5-yl)oxy]-2,5-difluorophenyl}-N-ethyl-N-methylimidoformamide (82), N'-{4-[(4-chloro-3-methyl-1,2-thiazol-5-yl)oxy]-2,5-dimethylphenyl}-N-ethyl-N-methylimidoformamide (83), 4-[(4-chloro-3-methyl-1,2-thiazol-5-yl)oxy]-2,5-dimethyl-N-[(E)-piperidin-1-ylmethylidene]aniline (84), N'-{5-chloro-4-[(4-chloro-3-methyl-1,2-thiazol-5-yl)oxy]-2-methylphenyl}-N-ethyl-N-methylimidoformamide (85), 5-chloro-4-[(4-chloro-3-methyl-1,2-thiazol-5-yl)oxy]-2-methyl-N-[(E)-piperidin-1-ylmethylidene]-aniline (86), N'-{2-chloro-4-[(4-chloro-3-methyl-1,2-thiazol-5-yl)oxy]-5-methylphenyl}-N-ethyl-N-methylimidoformamide (87), 2-chloro-4-[(4-chloro-3-methyl-1,2-thiazol-5-yl)oxy]-5-methyl-N-[(E)-piperidin-1-ylmethylidene]aniline (88), N'-(2-chloro-4-{[4-cyano-3-(3-fluorophenyl)-1,2-thiazol-5-yl]oxy}-5-methylphenyl)-N-ethyl-N-methylimidoformamide (89), N'-(2-chloro-4-{[3-(2-chlorophenyl)-4-cyano-1,2-thiazol-5-yl]oxy}-5-methylphenyl)-N,N-dimethylimidoformamide (90), N'-(2-chloro-4-{[3-(2-chlorophenyl)-4-cyano-1,2-thiazol-5-yl]oxy}-5-methylphenyl)-N-ethyl-N-methylimidoformamide (91), N'-(2-chloro-4-{[3-(2-chlorophenyl)-4-cyano-1,2-thiazol-5-yl]oxy}-5-methylphenyl)-N-methyl-N-propan-2-ylimidoformamide (92), N'-(5-chloro-4-{[4-cyano-3-(2-methylphenyl)-1,2-thiazol-5-yl]oxy}-2-methylphenyl)-N,N-dimethylimidoformamide (93), N'-(5-chloro-4-{[4-cyano-3-(2-methylphenyl)-1,2-thiazol-5-yl]oxy}-2-methylphenyl)-N-methyl-N-propan-2-ylimidoformamide (94), N'-(5-chloro-4-{[4-cyano-3-(2-methylphenyl)-1,2-thiazol-5-yl]oxy}-2-methylphenyl)-N-ethyl-N-methylimidoformamide (95), N'-(4-{[4-cyano-3-(2,2-dimethylpropyl)-1,2-thiazol-5-yl]oxy}-2,5-dimethylphenyl)-N,N-dimethylimidoformamide (96), N'-(4-{[4-cyano-3-(2,2-dimethylpropyl)-1,2-thiazol-5-yl]oxy}-2,5-dimethylphenyl)-N-methyl-N-propan-2-ylimidoformamide (97), N'-(4-{[4-cyano-3-(2,2-dimethylpropyl)-1,2-thiazol-5-yl]oxy}-2,5-dimethylphenyl)-N-ethyl-N-methylimidoformamide (98), N'-(4-{[3-(1-chlorocyclopropyl)-4-cyano-1,2-thiazol-5-yl]oxy}-2,5-dimethylphenyl)-N,N-dimethylimidoformamide (99), N'-(4-{[3-(1-chlorocyclopropyl)-4-cyano-1,2-thiazol-5-yl]oxy}-2,5-dimethylphenyl)-N-ethyl-N-methylimidoformamide (100), N'-(4-{[3-(1-chlorocyclopropyl)-4-cyano-1,2-thiazol-5-yl]oxy}-2,5-dimethylphenyl)-N-methyl-N-propan-2-ylimidoformamide (101), N'-(5-chloro-4-{[4-cyano-3-(2,2-dimethylpropyl)-1,2-thiazol-5-yl]oxy}-2-methylphenyl)-N,N-dimethylimidoformamide (102), N'-{4-[(4-bromo-3-methyl-1,2-thiazol-5-yl)oxy]-2,5-dimethylphenyl}-N-ethyl-N-methylimidoformamide (103), N'-(2-chloro-4-{[4-cyano-3-(3-fluorophenyl)-1,2-thiazol-5-yl]oxy}-5-methylphenyl)-N,N-dimethylimidoformamide (104), N'-(2-chloro-4-{[4-cyano-3-(3-fluorophenyl)-1,2-thiazol-5-yl]oxy}-5-methylphenyl)-N-methyl-N-propan-2-ylimidoformamide (105), N'-{4-[(3-tert-butyl-4-cyano-1,2-thiazol-5-yl)oxy]-2,5-difluorophenyl}-N-methyl-N-propan-2-ylimidoformamide (106), 4-[(4-bromo-3-methyl-1,2-thiazol-5-yl)oxy]-2,5-dimethyl-N-[(E)-piperidin-1-ylmethylidene]aniline (107), N'-{4-[(4-bromo-3-methyl-1,2-thiazol-5-yl)oxy]-5-chloro-2-methylphenyl}-N-ethyl-N-methylimidoformamide (108), 4-[(4-bromo-3-methyl-1,2-thiazol-5-yl)oxy]-5-chloro-2-methyl-N-[(E)-piperidin-1-ylmethylidene]aniline (109), N'-{4-[(4-bromo-3-methyl-1,2-thiazol-5-yl)oxy]-2-chloro-5-methylphenyl}-N-ethyl-N-methylimidoformamide (110), 4-[(4-bromo-3-methyl-1,2-thiazol-5-yl)oxy]-2-chloro-5-methyl-N-[(E)-piperidin-1-ylmethylidene]aniline (111), N'-(5-chloro-4-{[4-cyano-3-(2,2-dimethylpropyl)-1,2-thiazol-5-yl]oxy}-2-methylphenyl)-N-methyl-N-propan-2-ylimidoformamide (112), N'-(5-chloro-4-{[4-cyano-3-(2,2-dimethylpropyl)-1,2-thiazol-5-yl]oxy}-2-methylphenyl)-N-ethyl-N-methylimidoformamide (113), N'-(5-chloro-4-{[4-cyano-3-(3-fluorophenyl)-1,2-thiazol-5-yl]oxy}-2-methylphenyl)-N,N-dimethylimidoformamide (114), N'-(2-chloro-4-{[4-cyano-3-(2-methylphenyl)-1,2-thiazol-5-yl]oxy}-5-methylphenyl)-N,N-dimethylimidoformamide (115), N'-(2-chloro-4-{[4-cyano-3-(2-methylphenyl)-1,2-thiazol-5-yl]oxy}-5-methylphenyl)-N-methyl-N-propan-2-ylimidoformamide (116), N'-(2-chloro-4-{[4-cyano-3-(2,2-dimethylpropyl)-1,2-thiazol-5-yl]oxy}-5-methylphenyl)-N,N-dimethylimidoformamide (117), N'-(2-chloro-4-{[4-cyano-3-(2,2-dimethylpropyl)-1,2-thiazol-5-yl]oxy}-5-methylphenyl)-N-methyl-N-propan-2-ylimidoformamide (118), N'-(2-chloro-4-{[4-cyano-3-(2,2-dimethylpropyl)-1,2-thiazol-5-yl]oxy}-5-methylphenyl)-N-ethyl-N-methylimidoformamide (119), N'-(4-{[4-cyano-3-(2-phenylpropan-2-yl)-1,2-thiazol-5-yl]oxy}-2,5-dimethylphenyl)-N,N-dimethylimidoformamide (120), N'-(4-{[4-cyano-3-(2-phenylpropan-2-yl)-1,2-thiazol-5-yl]oxy}-2,5-dimethylphenyl)-N-methyl-N-propan-2-ylimidoformamide (121), N'-(4-{[4-cyano-3-(2-phenylpropan-2-yl)-1,2-thiazol-5-yl]oxy}-2,5-dimethylphenyl)-N-ethyl-N-methylimidoformamide (122), N'-(4-{[3-(2-chlorophenyl)-4-cyano-1,2-thiazol-5-yl]oxy}-2,5-dimethylphenyl)-N,N-dimethylimidoformamide (123), N'-(4-{[3-(2-chlorophenyl)-4-cyano-1,2-thiazol-5-yl]oxy}-2,5-dimethylphenyl)-N-methyl-N-propan-2-ylimidoformamide (124), N'-(4-{[3-(2-chlorophenyl)-4-cyano-1,2-thiazol-5-yl]oxy}-2,5-dimethylphenyl)-N-ethyl-N-methylimidoformamide (125), N'-(5-chloro-4-{[3-(2-chlorophenyl)-4-cyano-1,2-thiazol-5-yl]oxy}-2-methylphenyl)-N,N-dimethylimidoformamide (126), N'-(4-{[4-cyano-3-(2-fluorophenyl)-1,2-thiazol-5-yl]oxy}-2,5-dimethylphenyl)-

N,N-dimethylimidoformamide (127), N'-(4-{[4-cyano-3-(2-fluorophenyl)-1,2-thiazol-5-yl]oxy}-2,5-dimethylphenyl)-N-methyl-N-propan-2-ylimidoformamide (128), N'-(4-{[4-cyano-3-(2-fluorophenyl)-1,2-thiazol-5-yl]oxy}-2,5-dimethylphenyl)-N-ethyl-N-methylimidoformamide (129), N'-(5-chloro-4-{[4-cyano-3-(3-fluorophenyl)-1,2-thiazol-5-yl]oxy}-2-methylphenyl)-N-ethyl-N-methylimidoformamide (130), N'-(2-chloro-4-{[4-cyano-3-(2-methylphenyl)-1,2-thiazol-5-yl]oxy}-5-methylphenyl)-N-ethyl-N-methylimidoformamide (131), N'-(5-chloro-4-{[3-(2-chlorophenyl)-4-cyano-1,2-thiazol-5-yl]oxy}-2-methylphenyl)-N-ethyl-N-methylimidoformamide (132), N'-(2-chloro-4-{[4-cyano-3-(2-fluorophenyl)-1,2-thiazol-5-yl]oxy}-5-methylphenyl)-N,N-dimethylimidoformamide (133), N'-(5-chloro-4-{[3-(2-chlorophenyl)-4-cyano-1,2-thiazol-5-yl]oxy}-2-methylphenyl)-N-methyl-N-propan-2-ylimidoformamide (134), N'-(2-chloro-4-{[4-cyano-3-(2-fluorophenyl)-1,2-thiazol-5-yl]oxy}-5-methylphenyl)-N-methyl-N-propan-2-ylimidoformamide (135), N'-(2-chloro-4-{[4-cyano-3-(2-fluorophenyl)-1,2-thiazol-5-yl]oxy}-5-methylphenyl)-N-ethyl-N-methylimidoformamide (136), N'-(5-chloro-4-{[4-cyano-3-(2-fluorophenyl)-1,2-thiazol-5-yl]oxy}-2-methylphenyl)-N,N-dimethylimidoformamide (137), N'-(5-chloro-4-{[4-cyano-3-(2-fluorophenyl)-1,2-thiazol-5-yl]oxy}-2-methylphenyl)-N-methyl-N-propan-2-ylimidoformamide (138), N'-(5-chloro-4-{[4-cyano-3-(2-fluorophenyl)-1,2-thiazol-5-yl]oxy}-2-methylphenyl)-N-ethyl-N-methylimidoformamide (139), N'-(2-chloro-4-{[3-(1-chlorocyclopropyl)-4-cyano-1,2-thiazol-5-yl]oxy}-5-methylphenyl)-N,N-dimethylimidoformamide (140), N'-(2-chloro-4-{[3-(1-chlorocyclopropyl)-4-cyano-1,2-thiazol-5-yl]oxy}-5-methylphenyl)-N-methyl-N-propan-2-ylimidoformamide (141), N'-(2-chloro-4-{[3-(1-chlorocyclopropyl)-4-cyano-1,2-thiazol-5-yl]oxy}-5-methylphenyl)-N-ethyl-N-methylimidoformamide (142), N'-(5-chloro-4-{[3-(1-chlorocyclopropyl)-4-cyano-1,2-thiazol-5-yl]oxy}-2-methylphenyl)-N,N-dimethylimidoformamide (143), ethyl 5-(2,5-dimethyl-4-{[(E)-piperidin-1-ylmethylidene]amino}phenoxy)-3-methyl-1,2-thiazole-4-carboxylate (144), ethyl 5-[4-({(E)-[ethyl(methyl)amino]methylidene}amino)-2,5-dimethylphenoxy]-3-methyl-1,2-thiazole-4-carboxylate (145), ethyl 5-[2,5-dimethyl-4-({(E)-[methyl(propan-2-yl)amino]methylidene}amino)phenoxy]-3-methyl-1,2-thiazole-4-carboxylate (146), ethyl 5-[5-chloro-4-({(E)-[ethyl(methyl)amino]methylidene}amino)-2-methylphenoxy]-3-methyl-1,2-thiazole-4-carboxylate (147), ethyl 5-[5-chloro-2-methyl-4-({(E)-[methyl(propan-2-yl)amino]methylidene}amino)phenoxy]-3-methyl-1,2-thiazole-4-carboxylate (148), ethyl 5-(2-chloro-5-methyl-4-{[(E)-piperidin-1-ylmethylidene]amino}phenoxy)-3-methyl-1,2-thiazole-4-carboxylate (149), ethyl 5-[2-chloro-4-({(E)-[ethyl(methyl)amino]methylidene}amino)-5-methylphenoxy]-3-methyl-1,2-thiazole-4-carboxylate (150), ethyl 5-[2-chloro-5-methyl-4-({(E)-[methyl(propan-2yl)amino]methylidene}amino)phenoxy]-3-methyl-1,2-thiazole-4-carboxylate (151), ethyl 5-(5-chloro-2-methyl-4-{[(E)-piperidin-1-ylmethylidene]amino}phenoxy)-3-methyl-1,2-thiazole-4-carboxylate (152), N'-(5-chloro-4-{[3-(1-chlorocyclopropyl)-4-cyano-1,2-thiazol-5-yl]oxy}-2-methylphenyl)-N-ethyl-N-methylimidoformamide (153), N'-(5-chloro-4-{[3-(1-chlorocyclopropyl)-4-cyano-1,2-thiazol-5-yl]oxy}-2-methylphenyl)-N-methyl-N-propan-2-ylimidoformamide (154), N-[(E)-({4-[(3-tert-butyl-4-cyano-1,2-thiazol-5-yl)oxy]-2,5-dimethylphenyl}imino)methyl]-N-methylethanaminium chloride (155), N-[(E)-({4-[(3-tert-butyl-4-cyano-1,2-thiazol-5-yl)oxy]-2,5-dimethylphenyl}imino)methyl]-N-methylethanaminium bromide (156), N'-{4-[(3-tert-butyl-4-cyano-1,2-thiazol-5-yl)oxy]-2,5-dimethylphenyl}-N-ethyl-N-methylimidoformamide-1,2-benzothiazol-3(2H)-one 1,1-dioxide (1:1) (157), N-ethyl-N'-{4-[(4-iodo-3-methyl-1,2-thiazol-5-yl)oxy]-2,5-dimethylphenyl}-N-methylimidoformamide (158), N'-(4-{[4-cyano-3-(4-methylphenyl)-1,2-thiazol-5-yl]oxy}-2,5-dimethylphenyl)-N-ethyl-N-methylimidoformamide (159), N'-(4-{[4-cyano-3-(4-methylphenyl)-1,2-thiazol-5-yl]oxy}-2,5-dimethylphenyl)-N,N-dimethylimidoformamide (160), N'-(5-chloro-4-{[4-cyano-3-(4-methylphenyl)-1,2-thiazol-5-yl]oxy}-2-methylphenyl)-N,N-dimethylimidoformamide (161), N'-(5-chloro-4-{[4-cyano-3-(4-methylphenyl)-1,2-thiazol-5-yl]oxy}-2-methylphenyl)-N-methyl-N-propan-2-ylimidoformamide (162), N'-{4-[(3,4-dimethyl-1,2-thiazol-5-yl)oxy]-2,5-dimethylphenyl}-N-ethyl-N-methylimidoformamide (163), N'-(4-{[4-cyano-3-(2,3-dimethylbutan-2-yl)-1,2-thiazol-5-yl]oxy}-2,5-dimethylphenyl)-N,N-dimethylimidoformamide (164), N'-(4-{[4-cyano-3-(2,3-dimethylbutan-2-yl)-1,2-thiazol-5-yl]oxy}-2,5-dimethylphenyl)-N-methyl-N-propan-2-ylimidoformamide (165), N'-(4-{[4-cyano-3-(2,3-dimethylbutan-2-yl)-1,2-thiazol-5-yl]oxy}-2,5-dimethylphenyl)-N-ethyl-N-methylimidoformamide (166), N'-{4-[(3-tert-butyl-4-cyano-1,2-thiazol-5-yl)oxy]-5-chloro-2-methylphenyl}-N-ethyl-N-methylimidoformamide (167), N'-{5-tert-butyl-4-[(3-tert-butyl-4-cyano-1,2-thiazol-5-yl)oxy]-2-methylphenyl}-N-ethyl-N-methylimidoformamide (168), N'-{5-bromo-4-[(3-tert-butyl-4-cyano-1,2-thiazol-5-yl)oxy]-2-methylphenyl}-N-ethyl-N-methylimidoformamide (169), N'-[4-(2,1-benzothiazol-3-yloxy)-5-chloro-2-methylphenyl]-N-ethyl-N-methylimidoformamide (170), N'-[4-(2,1-benzothiazol-3-yloxy)-5-chloro-2-methylphenyl]-N,N-dimethylimidoformamide (171), N'-[4-(2,1-benzothiazol-3-yloxy)-5-chloro-2-methylphenyl]-N-methyl-N-propan-2-ylimidoformamide (172), N'-(2-chloro-4-{[4-cyano-3-(1-phenylethyl)-1,2-thiazol-5-yl]oxy}-5-methylphenyl)-N-ethyl-N-methylimidoformamide (173), N'-(4-{[4-cyano-3-(1-phenylethyl)-1,2-thiazol-5-yl]oxy}-2,5-dimethylphenyl)-N-ethyl-N-methylimidoformamide (174), N'-[4-(2,1-benzothiazol-3-yloxy)-2-chloro-5-methylphenyl]-N-ethyl-N-methylimidoformamide (175), N-(2-chloro-4-{[4-cyano-3-(1-phenylethyl)-1,2-thiazol-5-yl]oxy}-5-methylphenyl)-N-methyl-N-propan-2-ylimidoformamide (176), N'-(4-{[4-cyano-3-(1-methylcyclopropyl)-1,2-thiazol-5-yl]oxy}-2,5-dimethylphenyl)-N,N-dimethylimidoformamide (177), N'-(4-{[4-cyano-3-(1-methylcyclopropyl)-1,2-thiazol-5-yl]oxy}-2,5-dimethylphenyl)-N-methyl-N-propan-2-ylimidoformamide (178), N'-(4-{[4-cyano-3-(1-methylcyclopropyl)-1,2-thiazol-5-yl]oxy}-2,5-dimethylphenyl)-N-ethyl-N-methylimidoformamide (179), N'-(4-{[4-cyano-3-(2-methylbutan-2-yl)-1,2-thiazol-5-yl]oxy}-2,5-dimethylphenyl)-N-methyl-N-propan-2-ylimidoformamide (180), N'-(4-{[4-cyano-3-(2-methylbutan-2-yl)-1,2-thiazol-5-yl]oxy}-2,5-dimethylphenyl)-N-ethyl-N-methylimidoformamide (181), N'-{4-[(3-benzyl-4-cyano-1,2-thiazol-5-yl)oxy]-2,5-dimethylphenyl}-N-ethyl-N-methylimidoformamide (182), N'-(4-{[4-cyano-3-(2-methylbutan-2-yl)-1,2-thiazol-5-yl]oxy}-2,5-dimethylphenyl)-N,N-dimethylimidoformamide (183), N'-{4-[(3-tert-butyl-4-cyano-1,2-thiazol-5-yl)oxy]-5-fluoro-2-methylphenyl}-N-ethyl-N-methylimidoformamide (184), N'-(5-chloro-4-{[4-cyano-3-(3-methylpentan-3-yl)-1,2-thiazol-5-yl]oxy}-2-methylphenyl)-N,N-dimethylimidoformamide (185), N'-(5-chloro-4-{[4-cyano-3-(3-methylpentan-3-yl)-1,2-thiazol-5-yl]oxy}-2-methylphenyl)-N-ethyl-N-methylimidoformamide (186), N'-(5-chloro-4-{[4-cyano-3-

(3-methylpentan-3-yl)-1,2-thiazol-5-yl]oxy}-2-methylphenyl)-N-methyl-N-propan-2-ylimidoformamide (187), N'-(4-{[4-cyano-3-(3-methylpentan-3-yl)-1,2-thiazol-5-yl]oxy}-2,5-dimethylphenyl)-N,N-dimethylimidoformamide (188), N'-(4-{[4-cyano-3-(3-methylpentan-3-yl)-1,2-thiazol-5-yl]oxy}-2,5-dimethylphenyl)-N-ethyl-N-methylimidoformamide (189), N'-(4-{[4-cyano-3-(3-methylpentan-3-yl)-1,2-thiazol-5-yl]oxy}-2,5-dimethylphenyl)-N-methyl-N-propan-2-ylimidoformamide (190), N'-(2-chloro-4-{[3-(4-chlorobenzyl)-4-cyano-1,2-thiazol-5-yl]oxy}-5-methylphenyl)-N-ethyl-N-methylimidoformamide (191), N'-(2-chloro-4-{[4-cyano-3-(3-methylpentan-3-yl)-1,2-thiazol-5-yl]oxy}-5-methylphenyl)-N,N-dimethylimidoformamide (192), N'-(2-chloro-4-{[4-cyano-3-(3-methylpentan-3-yl)-1,2-thiazol-5-yl]oxy}-5-methylphenyl)-N-ethyl-N-methylimidoformamide (193), N'-{4-[(3-tert-butyl-4-cyano-1,2-thiazol-5-yl)oxy]-5-cyano-2-methylphenyl}-N-ethyl-N-methylimidoformamide (194), N'-(4-{[4-cyano-3-(1-methylcyclohexyl)-1,2-thiazol-5-yl]oxy}-2,5-dimethylphenyl)-N-ethyl-N-methylimidoformamide (195), N'-(2-chloro-4-{[4-cyano-3-(1-phenylethyl)-1,2-thiazol-5-yl]oxy}-5-methylphenyl)-N,N-dimethylimidoformamide (196), N'-(4-{[4-cyano-3-(1-methylcyclohexyl)-1,2-thiazol-5-yl]oxy}-2,5-dimethylphenyl)-N,N-dimethylimidoformamide (197), N'-(4-{[4-cyano-3-(1-methylcyclohexyl)-1,2-thiazol-5-yl]oxy}-2,5-dimethylphenyl)-N-methyl-N-propan-2-ylimidoformamide (198), N'-(5-chloro-4-{[4-cyano-3-(2-methylbutan-2-yl)-1,2-thiazol-5-yl]oxy}-2-methylphenyl)-N-ethyl-N-methylimidoformamide (199), N'-(5-chloro-4-{[4-cyano-3-(2-methylbutan-2-yl)-1,2-thiazol-5-yl]oxy}-2-methylphenyl)-N-methyl-N-propan-2-ylimidoformamide (200), N'-(5-chloro-4-{[4-cyano-3-(2-methylbutan-2-yl)-1,2-thiazol-5-yl]oxy}-2-methylphenyl)-N,N-dimethylimidoformamide (201), N'-{4-[(3,4-dichloro-1,2-thiazol-5-yl)oxy]-2,5-dimethylphenyl}-N-ethyl-N-methylimidoformamide (202), N'-{2,5-dimethyl-4-[(3-methyl-1,2-thiazol-5-yl)oxy]phenyl}-N-ethyl-N-methylimidoformamide (203), N'-{4-[(3-tert-butyl-4-cyano-1,2-thiazol-5-yl)oxy]-2-chloro-5-methylphenyl}-N-ethyl-N-methylimidoformamide hydrochloride (1:1) (204), N'-(2-chloro-4-{[4-cyano-3-(2,4-dichlorophenyl)-1,2-thiazol-5-yl]oxy}-5-methylphenyl)-N,N-dimethylimidoformamide (205), N'-(2-chloro-4-{[4-cyano-3-(2,4-dichlorophenyl)-1,2-thiazol-5-yl]oxy}-5-methylphenyl)-N-ethyl-N-methylimidoformamide (206), N'-(2-chloro-4-{[4-cyano-3-(2,4-dichlorophenyl)-1,2-thiazol-5-yl]oxy}-5-methylphenyl)-N-methyl-N-propan-2-ylimidoformamide (207), N'-[4-({4-cyano-3-[(3S,5S,7S)-tricyclo-[3.3.1.1$^{3,7}$]dec-1-yl]-1,2-thiazol-5-yl}oxy)-2,5-dimethylphenyl]-N-ethyl-N-methylimidoformamide (208), N'-[4-({4-cyano-3-[(3S,5S,7S)-tricyclo[3.3.1.1$^{3,7}$]dec-1-yl]-1,2-thiazol-5-yl}oxy)-2,5-dimethylphenyl]-N-methyl-N-propan-2-ylimidoformamide (209), N'-(4-{[4-cyano-3-(2,4-dichlorophenyl)-1,2-thiazol-5-yl]oxy}-2,5-dimethylphenyl)-N-ethyl-N-methylimidoformamide (210), N'-(4-{[4-cyano-3-(2,4-dichlorophenyl)-1,2-thiazol-5-yl]oxy}-2,5-dimethylphenyl)-N,N-dimethylimidoformamide (211), N'-(4-{[4-cyano-3-(2,4-dichlorophenyl)-1,2-thiazol-5-yl]oxy}-2,5-dimethylphenyl)-N-methyl-N-propan-2-ylimidoformamide (212), N'-[4-({4-cyano-3-[(3S,5S,7S)-tricyclo[3.3.1.1$^{3,7}$]dec-1-yl]-1,2-thiazol-5-yl}oxy)-2,5-dimethylphenyl]-N,N-dimethylimidoformamide (213), N'-{4-[(4-chloro-2,1-benzothiazol-3-yl)oxy]-2,5-dimethylphenyl}-N-ethyl-N-methylimidoformamide (214), N'-(4-{[4-cyano-3-(2-fluoropropan-2-yl)-1,2-thiazol-5-yl]oxy}-2,5-dimethylphenyl)-N,N-dimethylimidoformamide (215), N'-(4-{[4-cyano-3-(2-fluoropropan-2-yl)-1,2-thiazol-5-yl]oxy}-2,5-dimethylphenyl)-N-ethyl-N-methylimidoformamide (216), N'-(5-chloro-4-{[4-cyano-3-(2,4-dichlorophenyl)-1,2-thiazol-5-yl]oxy}-2-methylphenyl)-N,N-dimethylimidoformamide (217), N'-[2-chloro-4-({4-cyano-3-[4-(trifluoromethyl)phenyl]-1,2-thiazol-5-yl}oxy)-5-methylphenyl]-N,N-dimethylimidoformamide (218), N'-[2-chloro-4-({4-cyano-3-[4-(trifluoromethyl)phenyl]-1,2-thiazol-5-yl}oxy)-5-methylphenyl]-N-methyl-N-propan-2-ylimidoformamide (219), N'-[2-chloro-4-({4-cyano-3-[4-(trifluoromethyl)phenyl]-1,2-thiazol-5-yl}oxy)-5-methylphenyl]-N-ethyl-N-methylimidoformamide (220), N'-(4-{[4-cyano-3-(propan-2-yl)-1,2-thiazol-5-yl]oxy}-2,5-dimethylphenyl)-N-ethyl-N-methylimidoformamide (221), N'-[5-chloro-4-({4-cyano-3-[4-(trifluoromethyl)phenyl]-1,2-thiazol-5-yl}oxy)-2-methylphenyl]-N,N-dimethylimidoformamide (222), N'-[5-chloro-4-({4-cyano-3-[4-(trifluoromethyl)phenyl]-1,2-thiazol-5-yl}oxy)-2-methylphenyl]-N-methyl-N-propan-2-ylimidoformamide (223), N'-[5-chloro-4-({4-cyano-3-[4-(trifluoromethyl)phenyl]-1,2-thiazol-5-yl}oxy)-2-methylphenyl]-N-ethyl-N-methylimidoformamide (224), N'-(5-chloro-4-{[4-cyano-3-(2,4-dichlorophenyl)-1,2-thiazol-5-yl]oxy}-2-methylphenyl)-N-methyl-N-propan-2-ylimidoformamide (225), N'-(2-chloro-4-{[4-cyano-3-(propan-2-yl)-1,2-thiazol-5-yl]oxy}-5-methylphenyl)-N,N-dimethylimidoformamide (226), N'-(2-chloro-4-{[4-cyano-3-(propan-2-yl)-1,2-thiazol-5-yl]oxy}-5-methylphenyl)-N-methyl-N-propan-2-ylimidoformamide (227), N'-(2-chloro-4-{[4-cyano-3-(propan-2-yl)-1,2-thiazol-5-yl]oxy}-5-methylphenyl)-N-ethyl-N-methylimidoformamide (228), N'-(4-{[4-cyano-3-(propan-2-yl)-1,2-thiazol-5-yl]oxy}-2,5-dimethylphenyl)-N,N-dimethylimidoformamide (229), N'-(2-chloro-4-{[4-cyano-3-(2-fluoropropan-2-yl)-1,2-thiazol-5-yl]oxy}-5-methylphenyl)-N,N-dimethylimidoformamide (230), N'-(5-chloro-4-{[4-cyano-3-(2-fluoropropan-2-yl)-1,2-thiazol-5-yl]oxy}-2-methylphenyl)-N-ethyl-N-methylimidoformamide (231), N'-(5-chloro-4-{[4-cyano-3-(2-fluoropropan-2-yl)-1,2-thiazol-5-yl]oxy}-2-methylphenyl)-N-methyl-N-propan-2-ylimidoformamide (232), N'-(4-{[4-cyano-3-(2-fluoropropan-2-yl)-1,2-thiazol-5-yl]oxy}-2,5-dimethylphenyl)-N-methyl-N-propan-2-ylimidoformamide (233), N'-(5-chloro-4-{[4-cyano-3-(propan-2-yl)-1,2-thiazol-5-yl]oxy}-2-methylphenyl)-N,N-dimethylimidoformamide (234), N'-(5-chloro-4-{[4-cyano-3-(propan-2-yl)-1,2-thiazol-5-yl]oxy}-2-methylphenyl)-N-methyl-N-propan-2-ylimidoformamide (235), N'-(5-chloro-4-{[4-cyano-3-(propan-2-yl)-1,2-thiazol-5-yl]oxy}-2-methylphenyl)-N-ethyl-N-methylimidoformamide (236), N'-(4-{[4-cyano-3-(propan-2-yl)-1,2-thiazol-5-yl]oxy}-2,5-dimethylphenyl)-N-methyl-N-propan-2-ylimidoformamide (237), N'-(2-chloro-4-{[4-cyano-3-(2-fluoropropan-2-yl)-1,2-thiazol-5-yl]oxy}-5-methylphenyl)-N-methyl-N-propan-2-ylimidoformamide (238), N'-(2-chloro-4-{[3-(2-chloro-4-fluorophenyl)-4-cyano-1,2-thiazol-5-yl]oxy}-5-methylphenyl)-N-ethyl-N-methylimidoformamide (239), N'-(2-chloro-4-{[3-(2-chloro-4-fluorophenyl)-4-cyano-1,2-thiazol-5-yl]oxy}-5-methylphenyl)-N-methyl-N-propan-2-ylimidoformamide (240), N'-(5-chloro-4-{[4-cyano-3-(2,4-dichlorophenyl)-1,2-thiazol-5-yl]oxy}-2-methylphenyl)-N-ethyl-N-methylimidoformamide (241), N'-[4-({3-[2-(4-chlorophenyl)propan-2-yl]-4-cyano-1,2-thiazol-5-yl}oxy)-2,5-dimethylphenyl]-N-ethyl-N-methylimidoformamide (242), N'-(5-chloro-4-{[3-(2-chloro-4-fluorophenyl)-4-cyano-1,2-thiazol-5-yl]oxy}-2-methylphenyl)-N-ethyl-N-methylimidoformamide (243), N'-(5-chloro-4-{[3-(2-chloro-4-fluorophenyl)-4-cyano-1,2-thiazol-5-yl]oxy}-2- methylphenyl)-N-methyl-N-propan-2-ylimidoformamide (244), N'-(5-chloro-4-{[3-(2-chloro-4-fluorophenyl)-4-cyano-1,2-thiazol-5-yl]oxy}-2-methylphenyl)-N,N-dimethylimidoformamide (245), N'-(4-{[4-cyano-3-(2-methoxyphenyl)-1,2-thiazol-5-yl]oxy}-2,5-dimethylphenyl)-N-ethyl-N-methylimidoformamide (246), N'-(4-{[4-cyano-3-(2-methoxyphenyl)-1,2-thiazol-5-yl]oxy}-2,5-dimethylphenyl)-N-methyl-N-propan-2-ylimidoformamide (247), N'-(2-chloro-4-{[4-cyano-3-(4-methoxyphenyl)-1,2-thiazol-5-yl]oxy}-5-methylphenyl)-N-ethyl-N-methylimidoformamide (248), N'-(4-{[4-cyano-3-(2-methoxyphenyl)-1,2-thiazol-5-yl]oxy}-2,5-dimethylphenyl)-N,N-dimethylimidoformamide (249), N'-(4-{[4-cyano-3-(2,2-dichloro-1-ethyl-3-methylcyclopropyl)-1,2-thiazol-5-yl]oxy}-2,5-dimethylphenyl)-N-ethyl-N-methylimidoformamide (250), N'-(4-{[4-cyano-3-(4-methoxyphenyl)-1,2-thiazol-5-yl]oxy}-2,5-dimethylphenyl)-N-ethyl-N-methylimidoformamide (251), N'-(2-chloro-4-{[3-(2-chloro-4-fluorophenyl)-4-cyano-1,2-thiazol-5-yl]oxy}-5-methylphenyl)-N,N-dimethylimidoformamide (252), N'-(2-chloro-4-{[4-cyano-3-(4-methoxyphenyl)-1,2-thiazol-5-yl]oxy}-5-methylphenyl)-N-methyl-N-propan-2-ylimidoformamide (253), N'-(2-chloro-4-{[4-cyano-3-(4-methoxyphenyl)-1,2-thiazol-5-yl]oxy}-5-methylphenyl)-N,N-dimethylimidoformamide (254), N'-(5-chloro-4-{[4-cyano-3-(4-methoxyphenyl)-1,2-thiazol-5-yl]oxy}-2-methylphenyl)-N-ethyl-N-methylimidoformamide (255), N'-(5-chloro-4-{[4-cyano-3-(4-methoxyphenyl)-1,2-thiazol-5-yl]oxy}-2-methylphenyl)-N-methyl-N-propan-2-ylimidoformamide (256), N'-(5-chloro-4-{[4-cyano-3-(4-methoxyphenyl)-1,2-thiazol-5-yl]oxy}-2-methylphenyl)-N,N-dimethylimidoformamide (257), N'-(2-chloro-4-{[4-cyano-3-(2,2-dichloro-1-ethyl-3-methylcyclopropyl)-1,2-thiazol-5-yl]oxy}-5-methylphenyl)-N-ethyl-N-methylimidoformamide (258), N'-(2-chloro-4-{[4-cyano-3-(2,2-dichloro-1-ethyl-3-methylcyclopropyl)-1,2-thiazol-5-yl]oxy}-5-methylphenyl)-N,N-dimethylimidoformamide (259), N'-(5-chloro-4-{[4-cyano-3-(2,2-dichloro-1-ethyl-3-methylcyclopropyl)-1,2-thiazol-5-yl]oxy}-2-methylphenyl)-N-ethyl-N-methylimidoformamide (260), N'-(5-chloro-4-{[4-cyano-3-(2,2-dichloro-1-ethyl-3-methylcyclopropyl)-1,2-thiazol-5-yl]oxy}-2-methylphenyl)-N-methyl-N-propan-2-yl-imidoformamide (261), N'-(5-chloro-4-{[4-cyano-3-(2,2-dichloro-1-ethyl-3-methylcyclopropyl)-1,2-thiazol-5-yl]oxy}-2-methylphenyl)-N,N-dimethylimidoformamide (262), N'-(5-chloro-4-{[4-cyano-3-(3-methoxyphenyl)-1,2-thiazol-5-yl]oxy}-2-methylphenyl)-N-ethyl-N-methylimidoformamide (263), N'-{4-[(4,7-dichloro-2,1-benzothiazol-3-yl)oxy]-2,5-dimethylphenyl}-N-ethyl-N-methylimidoformamide (264), N'-{4-[(4,7-dichloro-2,1-benzothiazol-3-yl)oxy]-2,5-dimethylphenyl}-N-methyl-N-propan-2-ylimidoformamide (265), N'-{4-[(4,7-dichloro-2,1-benzothiazol-3-yl)oxy]-2,5-dimethylphenyl}-N,N-dimethylimidoformamide (266), N'-(2-chloro-4-{[4-cyano-3-(2,2-dichloro-1-ethyl-3-methylcyclopropyl)-1,2-thiazol-5-yl]oxy}-5-methylphenyl)-N-methyl-N-propan-2-ylimidoformamide (267), N'-{4-[(4-chloro-2,1-benzothiazol-3-yl)oxy]-2,5-dimethylphenyl}-N-methyl-N-propan-2-ylimidoformamide (268), N'-{4-[(4-chloro-2,1-benzothiazol-3-yl)oxy]-2,5-dimethylphenyl}-N,N-dimethylimidoformamide (269), N'-(4-{[4-cyano-3-(4-methoxyphenyl)-1,2-thiazol-5-yl]oxy}-2,5-dimethylphenyl)-N,N-dimethylimidoformamide (270), N'-(4-{[4-cyano-3-(3-methoxyphenyl)-1,2-thiazol-5-yl]oxy}-2,5-dimethylphenyl)-N-methylimidoformamide (271), N'-(4-{[4-cyano-3-(4-methoxyphenyl)-1,2-thiazol-5-yl]oxy}-2,5-dimethylphenyl)-N-methyl-N-propan-2-ylimidoformamide (272), N'-(4-{[4-cyano-3-(2,2-dichloro-1-ethyl-3-methylcyclopropyl)-1,2-thiazol-5-yl]oxy}-2,5-dimethylphenyl)-N,N-dimethylimidoformamide (273), N'-(5-chloro-4-{[4-cyano-3-(2-fluoropropan-2-yl)-1,2-thiazol-5-yl]oxy}-2-methylphenyl)-N,N-dimethylimidoformamide (274), N'-(2-chloro-4-{[4-cyano-3-(2-fluoropropan-2-yl)-1,2-thiazol-5-yl]oxy}-5-methylphenyl)-N-ethyl-N-methylimidoformamide (275), N'-(4-{[4-cyano-3-(2,2-dichloro-1-ethyl-3-methylcyclopropyl)-1,2-thiazol-5-yl]oxy}-2,5-dimethylphenyl)-N-methyl-N-propan-2-ylimidoformamide (276), N'-{2-chloro-4-[(4-chloro-2,1-benzothiazol-3-yl)oxy]-5-methylphenyl}-N-ethyl-N-methylimidoformamide (277), N'-{2-chloro-4-[(4,7-dichloro-2,1-benzothiazol-3-yl)oxy]-5-methylphenyl}-N-ethyl-N-methylimidoformamide (278), N'-{2-chloro-4-[(4,7-dichloro-2,1-benzothiazol-3-yl)oxy]-5-methylphenyl}-N-methyl-N-propan-2-ylimidoformamide (279), N'-{2-chloro-4-[(4-chloro-2,1-benzothiazol-3-yl)oxy]-5-methylphenyl}-N-methyl-N-propan-2-ylimidoformamide (280), N'-{2-chloro-4-[(4-chloro-2,1-benzothiazol-3-yl)oxy]-5-methylphenyl}-N,N-dimethylimidoformamide (281), N'-{2-chloro-4-[(4,7-dichloro-2,1-benzothiazol-3-yl)oxy]-5-methylphenyl}-N,N-dimethylimidoformamide (282), N'-(4-{[3-(2-chloro-4-fluorophenyl)-4-cyano-1,2-thiazol-5-yl]oxy}-2,5-dimethylphenyl)-N-ethyl-N-methylimidoformamide (283), N'-(4-{[4-chloro-3-(propan-2-yl)-1,2-thiazol-5-yl]oxy}-2,5-dimethylphenyl)-N,N-dimethylimidoformamide (284), N'-(4-{[4-chloro-3-(propan-2-yl)-1,2-thiazol-5-yl]oxy}-2,5-dimethylphenyl)-N-methyl-N-propan-2-ylimidoformamide (285), N'-(4-{[4-chloro-3-(propan-2-yl)-1,2-thiazol-5-yl]oxy}-2,5-dimethylphenyl)-N-ethyl-N-methylimidoformamide (286), N'-(2-chloro-4-{[4-chloro-3-(propan-2-yl)-1,2-thiazol-5-yl]oxy}-5-methylphenyl)-N-ethyl-N-methylimidoformamide (287), N'-{4-[(3-bromo-4-cyano-1,2-thiazol-5-yl)oxy]-2,5-dimethylphenyl}-N-ethyl-N-methylimidoformamide (288), N'-(4-{[4-bromo-3-(propan-2-yl)-1,2-thiazol-5-yl]oxy}-2,5-dimethylphenyl)-N-ethyl-N-methylimidoformamide (289), N'-{2-bromo-4-[(4-chloro-3-methyl-1,2-thiazol-5-yl)oxy]-5-methoxyphenyl}-N-ethyl-N-methylimidoformamide (290), N'-{2-chloro-4-[(4-chloro-3-methyl-1,2-thiazol-5-yl)oxy]-5-methoxyphenyl}-N-ethyl-N-methylimidoformamide (291), N'-{4-[(3-benzyl-4-chloro-1,2-thiazol-5-yl)oxy]-2,5-dimethylphenyl}-N-ethyl-N-methylimidoformamide (292), N'-(4-{[4-chloro-3-(4-chlorobenzyl)-1,2-thiazol-5-yl]oxy}-2,5-dimethylphenyl)-N-ethyl-N-methylimidoformamide (293), N'-{4-[(4-cyano-3-cyclohexyl-1,2-thiazol-5-yl)oxy]-2,5-dimethylphenyl}-N-ethyl-N-methylimidoformamide (294), N'-{4-[(4-cyano-3-cyclohexyl-1,2-thiazol-5-yl)oxy]-2,5-dimethylphenyl}-N,N-dimethylimidoformamide (295), N'-{4-[(4-cyano-3-cyclohexyl-1,2-thiazol-5-yl)oxy]-2,5-dimethylphenyl}-N-methyl-N-propan-2-ylimidoformamide (296), N'-{4-[(3-tert-butyl-1,2-thiazol-5-yl)oxy]-2-chloro-5-methylphenyl}-N-ethyl-N-methylimidoformamide (297), N'-(4-{[4-cyano-3-(1-fluoro-2-methylpropan-2-yl)-1,2-thiazol-5-yl]oxy}-2,5-dimethylphenyl)-N-methyl-N-propan-2-ylimidoformamide (298), N'-(4-{[4-cyano-3-(1-fluoro-2-methylpropan-2-yl)-1,2-thiazol-5-yl]oxy}-2,5-dimethylphenyl)-N,N-dimethylimidoformamide (299), N'-(2,5-dimethyl-4-{[3-(propan-2-yl)-1,2-thiazol-5-yl]oxy}phenyl)-N-ethyl-N-methylimidoformamide (300), N'-(4-{[4-cyano-3-(1-fluoro-2-methylpropan-2-yl)-1,2-thiazol-5-yl]oxy}-2,5-dimethylphenyl)-N-ethyl-N-methylimidoformamide (301), N'-[4-({3-[2-(4-chlorophenyl)propan-2-yl]-4-cyano-1,2-thiazol-5-yl}oxy)-2,5-dimethylphenyl]-N-methyl-N-propan-2-ylimidoformamide (302), N'-(4-{[4-bromo-3-(propan-2-yl)-

1,2-thiazol-5-yl]oxy}-2-chloro-5-methylphenyl)-N-ethyl-N-methylimidoformamide (303), N'-(2-chloro-4-{[4-iodo-3-(propan-2-yl)-1,2-thiazol-5-yl]oxy}-5-methylphenyl)-N-ethyl-N-methylimidoformamide (304), N'-[4-({3-[2-(4-chlorophenyl)propan-2-yl]-4-cyano-1,2-thiazol-5-yl}oxy)-2,5-dimethylphenyl]-N,N-dimethylimidoformamide (305), N'-{2-chloro-4-[(4-cyano-3-cyclohexyl-1,2-thiazol-5-yl)oxy]-5-methylphenyl}-N-ethyl-N-methylimidoformamide (306), N'-{4-[(4-cyano-3-cyclopropyl-1,2-thiazol-5-yl)oxy]-2,5-dimethylphenyl}-N-ethyl-N-methylimidoformamide (307), N'-{4-[(4-cyano-3-cyclopropyl-1,2-thiazol-5-yl)oxy]-2,5-dimethylphenyl}-N,N-dimethylimidoformamide (308), N'-{4-[(4-cyano-3-cyclopropyl-1,2-thiazol-5-yl)oxy]-2,5-dimethylphenyl}-N-methyl-N-propan-2-ylimidoformamide (309), N'-{4-[(7-chloro-2,1-benzothiazol-3-yl)oxy]-2,5-dimethylphenyl}-N-ethyl-N-methylimidoformamide (310), N'-{4-[(7-chloro-2,1-benzothiazol-3-yl)oxy]-2,5-dimethylphenyl}-N,N-dimethylimidoformamide (311), N'-{4-[(7-chloro-2,1-benzothiazol-3-yl)oxy]-2,5-dimethylphenyl}-N-methyl-N-propan-2-ylimidoformamide (312), N'-(4-{[4-bromo-3-(propan-2-yl)-1,2-thiazol-5-yl]oxy}-2,5-dimethylphenyl)-N,N-dimethylimidoformamide (313) or their salts, N-oxides, metal complexes and their stereoisomers.

5. A composition for controlling unwanted microorganisms, comprising at least one isothiazolyloxyphenylamidine according to claim 1.

6. A method for controlling an unwanted microorganism, comprising applying an isothiazolyloxyphenylamidine according to claim 1 to the microorganism and/or its habitat.

* * * * *